US009803242B2

(12) United States Patent
Umansky et al.

(10) Patent No.: US 9,803,242 B2
(45) Date of Patent: Oct. 31, 2017

(54) MIRNA-BASED UNIVERSAL SCREENING TEST (UST)

(75) Inventors: Samuil R. Umansky, Princeton, NJ (US); Kira S. Sheinerman, New York, NY (US); Vladimir Tsivinsky, Sharon, MA (US)

(73) Assignee: DiamiR, LLC, Princeton, NJ (US)

( * ) Notice: Subject to any disclaimer, the term of this patent is extended or adjusted under 35 U.S.C. 154(b) by 252 days.

(21) Appl. No.: 14/112,684

(22) PCT Filed: Apr. 18, 2012

(86) PCT No.: PCT/US2012/034098
§ 371 (c)(1),
(2), (4) Date: Oct. 18, 2013

(87) PCT Pub. No.: WO2012/145409
PCT Pub. Date: Oct. 26, 2012

(65) Prior Publication Data
US 2014/0256562 A1  Sep. 11, 2014

Related U.S. Application Data

(60) Provisional application No. 61/476,591, filed on Apr. 18, 2011, provisional application No. 61/478,766, filed on Apr. 25, 2011, provisional application No. 61/546,431, filed on Oct. 12, 2011.

(51) Int. Cl.
*C12Q 1/68* (2006.01)
*C12P 19/34* (2006.01)
*C07H 21/02* (2006.01)

(52) U.S. Cl.
CPC ......... *C12Q 1/6883* (2013.01); *C12Q 1/6886* (2013.01); *C12Q 2600/112* (2013.01); *C12Q 2600/118* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 7,993,831 | B2 * | 8/2011 | Latham et al. ............... 435/6.12 |
| 8,486,626 | B2 * | 7/2013 | Umansky et al. ............. 435/6.1 |
| 8,632,967 | B2 | 1/2014 | Kuroda et al. |
| 8,648,017 | B2 | 2/2014 | Umansky et al. |
| 2007/0161004 | A1 | 7/2007 | Brown et al. |
| 2008/0171667 | A1 | 7/2008 | Brown et al. |
| 2009/0075258 | A1 | 3/2009 | Latham et al. |
| 2009/0081640 | A1 * | 3/2009 | Umansky et al. ................ 435/5 |
| 2009/0176723 | A1 | 7/2009 | Brown et al. |
| 2010/0151480 | A1 | 6/2010 | Taylor et al. |
| 2010/0167937 | A1 | 7/2010 | Goldknopf et al. |
| 2010/0167948 | A1 | 7/2010 | Krichevsky et al. |
| 2010/0184046 | A1 | 7/2010 | Klass et al. |
| 2010/0196426 | A1 | 8/2010 | Skog et al. |
| 2010/0216139 | A1 | 8/2010 | Galas et al. |
| 2010/0227908 | A1 | 9/2010 | Cairns et al. |
| 2010/0267804 | A1 | 10/2010 | Port et al. |
| 2010/0279292 | A1 | 11/2010 | Marsh et al. |
| 2010/0286044 | A1 | 11/2010 | Litman et al. |
| 2010/0323357 | A1 | 12/2010 | Nana-Sinkam et al. |
| 2011/0003704 | A1 | 1/2011 | Skog et al. |
| 2011/0053157 | A1 | 3/2011 | Skog et al. |
| 2011/0053158 | A1 | 3/2011 | Mambo et al. |
| 2011/0086348 | A1 | 4/2011 | Prasad et al. |
| 2011/0111976 | A1 | 5/2011 | Fare et al. |
| 2011/0117111 | A1 | 5/2011 | Kwon et al. |
| 2011/0117560 | A1 | 5/2011 | Spinale et al. |
| 2011/0143360 | A1 | 6/2011 | Kuroda et al. |
| 2011/0160285 | A1 | 6/2011 | Anderson et al. |
| 2011/0160290 | A1 * | 6/2011 | Tewari .................. 514/44 R |
| 2012/0034608 | A1 | 2/2012 | Zhou et al. |
| 2012/0093936 | A1 | 4/2012 | Lindenberg et al. |
| 2012/0184599 | A1 | 7/2012 | Marcet et al. |
| 2012/0252693 | A1 | 10/2012 | Umansky et al. |
| 2012/0270746 | A1 | 10/2012 | Kuroda et al. |
| 2013/0131194 | A1 | 5/2013 | Skog et al. |
| 2014/0120545 | A1 | 5/2014 | Umansky et al. |
| 2014/0170648 | A1 | 6/2014 | Kuroda et al. |
| 2014/0194319 | A1 | 7/2014 | Skog et al. |
| 2014/0194613 | A1 | 7/2014 | Skog et al. |
| 2014/0357507 | A1 | 12/2014 | Umansky et al. |

FOREIGN PATENT DOCUMENTS

| CN | 101942502 | 1/2011 |
| CN | 101962685 | 2/2011 |
| JP | 2010-536372 A | 12/2010 |
| WO | WO2005118806 | 12/2005 |

(Continued)

OTHER PUBLICATIONS

European Search Report dated Jan. 26, 2015, which issued during prosecution of European Application No. 12773705.4.
Hebert et al. "Alterations of the microRNA network cause neurodegenerative disease" 2009, Trends in Neurosciences, 32(4):199-206.
Cogswell, John P., et al., "Identification of miRNA Changes in Alzheimer's Disease Brain and CSF Yields Putative Biomarkers and Insights into Disease Pathways", Journal of Alzheimer's Disease, vol. 14, pp. 27-41, 2008.
Kosaka, Nobuyoshi, et al., "Circulating microRNA in body fluid: a new potential biomarker for cancer diagnosis and prognosis", Cancer Sci., vol. 101, pp. 2087-2092, 2010.
Laterza, Omar F., et al., "Plasma MicroRNAs as Diagnostically Sensitive and Specific Biomarkers of Tissue Injury", Clinical Chemistry, vol. 55:11, pp. 1-7, 2009.
Lugli, Giovanni, et al., "Expression of microRNAs and their precursors in synaptic fractions of adult mouse forebrain", Journal of Neurochemistry, vol. 106, pp. 650-661, 2008.

(Continued)

*Primary Examiner* — Richard Schnizer
(74) *Attorney, Agent, or Firm* — Troutman Sanders LLP

(57) ABSTRACT

Described are methods for early noninvasive or minimally invasive detection of pathological changes in organ systems/organs/tissues/cells by quantifying organ system-/organ-/tissue-/cells type-enriched miRNA in bodily fluids.

11 Claims, 75 Drawing Sheets

(56) References Cited

FOREIGN PATENT DOCUMENTS

| WO | WO2007073737 | 7/2007 |
|---|---|---|
| WO | WO2008153692 | 12/2008 |
| WO | WO2009009457 | 1/2009 |
| WO | WO2009012468 | 1/2009 |
| WO | WO2009015357 | 1/2009 |
| WO | WO2009025852 | 2/2009 |
| WO | WO2009036236 | 3/2009 |
| WO | WO2009070653 | 6/2009 |
| WO | 2009/100029 A1 | 8/2009 |
| WO | WO 2009/100029 | 8/2009 |
| WO | WO2009114681 | 9/2009 |
| WO | WO 2009/120877 | 10/2009 |
| WO | WO2009132273 | 10/2009 |
| WO | 2009/143379 A2 | 11/2009 |
| WO | WO 2009/133915 | 11/2009 |
| WO | WO2009143379 | 11/2009 |
| WO | WO2010054386 | 5/2010 |
| WO | WO 2011/015720 | 2/2011 |
| WO | WO2011057003 | 5/2011 |
| WO | WO2012145363 | 10/2012 |
| WO | 2013/036936 A1 | 3/2013 |
| WO | 2015/073972 A1 | 5/2015 |

OTHER PUBLICATIONS

Lugli, Giovanni, et al., "File S2. Entire list of measured human, rat and mouse microRNAs by microarray after filtering and normalization," Journal of Neurochemistry, vol. 106, 2008.

Maes, Olivier C., et al. "Methodology for Discovery of Alzheimer's Disease Blood-Based Biomarkers", J Gerontol A Biol Sci Med Sci, vol. 64A, pp. 636-645, 2009.

Maes, Olivier C., et al. MicroRNA: Implications for Alzheimer Disease and other Human CNS Disorders, Current Genomics, vol. 10, pp. 154-168, 2009.

Schratt, Gerhard M., et al., "A brain-specific microRNA regulates dendritic spine development", Nature, vol. 439, pp. 283-289, 2006.

Sempere, Lorenzo F, et al., "Expression profiling of mammalian microRNAs uncovers a subset of brain-expressed microRNAs with possible roles in murine and human neuronal differentiation", Genome Biology, vol. 5:R13, pp. R13.1-R13.11, 2004.

Wang, Wang-Xia, et al., "The Expression of MicroRNA miR-107 Decreases Early in Alzheimer's Disease and May Accelerate Disease Progression through Regulation of β-Site Amyloid Precursor Protein-Cleaving Enzyme 1", The Journal of Neuroscience, vol. 28, pp. 1213-1223, 2008.

International Search Report for International Appl. No. PCT/US2010/055495, dated Jun. 6, 2011.

International Preliminary Report on Patentability for International Appl. No. PCT/US2010/055495, dated May 8, 2012.

Adachi, Taichi, et al., Plasma MicroRNA 499 as a Biomarker of Acute Myocardial Infarction, Clinical Chemistry, vol. 56, No. 7, pp. 1183-1185, 2010.

Albert MS, et al., The diagnosis of mild cognitive impairment due to Alzheimer's disease: Recommendations from National Institute on Aging-Alzheimer's Association workgroups on diagnostic guidelines for Alzheimer's disease, Alzheimers Dement, vol. 7, pp. 270-279, 2011.

Backes, Christina, et al., A dictionary on microRNAs and their putative target pathways, Nucleic Acids Res, vol. 38, pp. 4476-4486, 2010.

Bak, Mads, et al., MicroRNA expression in the adult mouse central nervous system, RNA., vol. 14(3), pp. 432-444, 2008.

Bartel DP, MicroRNAs: target recognition and regulatory functions, Cell, vol. 136, pp. 215-233, 2009.

Bishop DL, et al., Axon branch removal at developing synapses by axosome shedding, Neuron, vol. 44, pp. 651-661, 2004.

Brase, Jan C., et al., Circulating miRNAs are correlated with tumor progression in prostate cancer, International Journal of Cancer, vol. 128(3), pp. 608-616, 2011.

Brase, Jan C., et al., Serum microRNAs as non-invasive biomarkers for cancer, Molecular Cancer, vol. 9, pp. 306-315, 2010.

Charras, Guillaume T., et al., Life and times of a cellular bleb, Biophys J., vol. 94(5), pp. 1836-1853, 2008.

Chen, Xi, Characterization of microRNAs in serum: a novel class of biomarkers for diagnosis of cancer and other diseases, Cell Research, vol. 18, pp. 997-1006, 2008.

Chim, Stephen S.C., et al., Detection and Characterization of Placental MicroRNAs in Maternal Plasma, Clinical Chemistry, vol. 54(3), pp. 482-490, 2008.

Eaton BA, et al., Synapse disassembly, Genes Dev., vol. 17, pp. 2075-2082, 2003.

Edbauer, D., et al., Regulation of synaptic structure and function by FMRP-associated microRNAs miR-125b and miR-132, Neuron, vol. 65(3), pp. 373-384, 2010.

Emery, VO., Alzheimer disease: are we intervening too late? J Neural Transm., vol. 118(9), pp. 1361-1378, 2011.

Fackler OT, Grosse R., Cell motility through plasma membrane blebbing, J Cell Biol., vol. 181(6), pp. 879-884, 2008.

Griffiths-Jones S., et al., miRBase: microRNA sequences, targets and gene nomenclature, Nucleic Acids Res., vol. 34, Database issue: D140-D144, 2006.

Hua Y-J., et al., Identification and target prediction of miRNAs specifically expressed in rat neural tissue, BMC Genomics, vol. 10, pp. 214-225, 2009.

Hunter, Melissa Piper, et al., Detection of microRNA Expression in Human Peripheral Blood Microvesicles, PLoS ONE, 3(11): e3694, 2008.

Ji, Xi, et al., Plasma miR-208 as a Biomarker of Myocardial Injury, Clinical Chemistry, vol. 55(11), pp. 1944-1949, 2009.

Koirala S, et al., Pruning an Axon Piece by Piece, Neuron, vol. 44, pp. 578-580, 2004.

Kosaka, Nobuyoshi, et al., Secretory Mechanisms and Intercellular Transfer of MicroRNAs in Living Cells, J Biol Chem., vol. 285(23), pp. 17442-17452, 2010.

Kye Mj, et al., Somatodendritic microRNAs identified by laser capture and multiplex RT-PCR, RNA, vol. 13, pp. 1224-1234, 2007.

Landgraf, Pablo, A Mammalian microRNA Expression Atlas Based on Small RNA Library Sequencing, Cell, vol. 129(7), pp. 1401-1414, 2007.

Lee EJ, et al., Systematic evaluation of microRNA processing patterns in tissues, cell lines, and tumors, RNA, vol. 14, pp. 35-42, 2008.

Liang Y, et al., Characterization of microRNA expression profiles in normal human tissues, BMC Genomics, vol. 8, pp. 166-185, 2007.

Liu, Da-Zhi, et al., Brain and blood microRNA expression profiling of ischemic stroke, intracerebral hemorrhage, and kainate seizures, J Cereb Blood Flow Metab. , advance online publication, 2009, doi:10.1038/jcbfm.2009.186, pp. 1-12.

Lodes, Michael J., et al., Detection of Cancer with Serum miRNAs on an Oligonucleotide Microarray. PLoS ONE, vol. 4(7): e6229, 2009.

Low LK, et al., Axon pruning: an essential step underlying the developmental plasticity of neuronal connections, Phil Trans R Soc B., vol. 361, pp. 1531-1544, 2006.

McKhann GM, et al., the diagnosis of dementia due to Alzheimer's disease: Recommendations from National Institute on Aging-Alzheimer's Association workgroups on diagnostic guidelines for Alzheimer's disease, Alzheimers Dement., vol. 7, pp. 263-269, 2011.

Miller G, Alzheimer's biomarker initiative hits its stride, Science, vol. 326, pp. 386-389, 2009.

Mitchell PS, et al., Circulating microRNAs as stable blood-based markers for cancer detection, Proc Natl Acad Sci USA, vol. 105, pp. 10513-10518, 2008.

Mitchell, Patrick S., et al., Circulating microRNAs as stable blood-based markers for cancer detection, Proc Natl Acad Sci USA, vol. 105(30): 10513-10518, 2008.

Natera-Naranjo, Orlangie, et al., Identification and quantitative analyses of microRNAs located in the distal axons of sympathetic neurons, RNA, vol. 16, pp. 1516-1529, 2010.

(56) References Cited

OTHER PUBLICATIONS

Olsen, Line, et al., MicroRNAs Show Mutually Exclusive Expression Patterns in the Brain of Adult Male Rats. PLoS ONE, vol. 4(10): e7225, 2009.
Peltier HJ, et al.. Normalization of microRNA expression levels in quantitative RT-PCR assays: identification of suitable reference RNA targets in normal and cancerous human solid tissues, RNA, vol. 14, pp. 844-852, 2008.
Ray S, et al., Classification and prediction of clinical Alzheimer's diagnosis based on plasma signaling proteins, Nat Med., vol. 13, pp. 1359-1362, 2007.
Satoh J-i, MicroRNAs and Their Therapeutic Potential for Human Diseases: Aberrant MicroRNA Expression in Alzheimer's Disease Brain, J Pharmacol Sci., vol. 114, pp. 269-275, 2010.
Schmand B, et al., Value of Neurophysiological Tests, Neuroimaging, and Biomarkers for Diagnosing Alzheimer's Disease in Younger and Older Age Cohorts, J Am Geriatr Soc., vol. 59, pp. 1705-1710, 2001.
Schratt, Gerhard, microRNAs at the synapse, Nature Reviews Neuroscience, vol. 10, pp. 842-849, 2009.
Skog J, et al., Glioblastoma microvesicles transport RNA and proteins that promote tumour growth and provide diagnostic biomarkers, Nat Cell Biol., vol. 10(12), pp. 1470-1476, 2008.
Sperling RA, et al., The diagnosis of dementia due to Alzheimer's disease: Recommendations from National Institute on Aging-Alzheimer's Association workgroups on diagnostic guidelines for Alzheimer's disease, Alzheimers Dement., vol. 7, pp. 280-292, 2011.
Wang, Guo-Kun, et al., Circulating microRNA: a novel potential biomarker for early diagnosis of acute myocardial infarction in humans, European Heart Journal, vol. 31, Issue 6, pp. 659-666, 2010.
Wang, Kai, et al., Circulating microRNAs, potential biomarkers for drug-induced liver injury, Proc Natl Acad Sci USA, vol. 106(11), pp. 4402-4407, 2009.
Yoshiyama Y, et al., Synapse Loss and Microglial Activation Precede Tangles in P301S Tauopathy Mouse Model, Neuron., vol. 53, pp. 337-351, 2007.
Braak, et al., Neuropathological staging of Alzheimer's related changes, Acta Neuropathol., vol. 82, pp. 239-259, 1991.
Geekiyanage, et al., Blood serum miRNA: Non-invasive biomarkers for Alzheimer's disease, Exp Neurol., vol. 235, pp. 491-496, 2012, ePub Dec. 1, 2011.
Hebert, et al., Loss of microRNA cluster miR-29a/b-1 in sporadic Alzheimer's disease correlates with increased BACEI/beta-secretase expression, Proc Natl Acad Sci USA, vol. 105, pp. 6415-6420, 2008.
International Search Report and Written Opinion of the International Searching Authority for International Application No. PCT/US12/34098, dated Jul. 17, 2012.
International Search Report and Written Opinion of the International Searching Authority for International Application No. PCT/US12/34025, dated Sep. 28, 2012.
Kemppainen, et al., MicroRNAs as biomarkers in blood and other biofluids, poster 2010? [Retrieved from the Internet Sep. 8, 2012: <http://www.asuragen.comipdfs/postersibiomarkers.pdf>].
McDonald, et al., Analysis of circulating microRNA: pre analytical and analytical challenges, Clin Chern., vol. 57, pp. 833-840, 2011.
Satoh, Molecular network of microRNA targets in Alzheimer's disease brains, Exp Neurol., vol. 235, pp. 436-446, 2012, ePub Sep. 16, 2011.
Schipper, et al., MicroRNA expression in Alzheimer blood mononuclear cells, Gene Regul. Syst. Bio., Vo., 1, pp. 263-274, 2007.
Yoo et al., Oxidative Stress Regulated Genes in Nigral Dopaminergic Neuronal Cells: Correlation with the Known Pathology in Parkinson's Disease, Molecular Brain Research, 2003, 110, 76-84.
European Search Report dated Oct. 30, 2014, which issued during prosecution of European Application No. 12774179.1.

European Communication pursuant to Article 94(3) EPC dated May 24, 2013, which issued during prosecution of European Application No. 10 779 376.2.
European Communication pursuant to Article 94(3) EPC dated Aug. 21, 2014, which issued during prosecution of European Application No. 10 779 376.2.
Gillardon, et al. "MicroRNA and proteome expression profiling in early-symptomatic α-synuclein(A30P)-transgenic mice" Proteomics Clinical Applications 2008, 2(5):697-705.
Sheinerman et al. "Universal screening test based on analysis of circulating organ-enriched microRNAs: a noval approach to diagnostic screening," Expert Rev. Mol. Diagn. 15(3), 329-338 (2015).
Chinese Office Action dated Jun. 2, 2015, which issued during prosecution of Chinese Application No. 201280030033.X.
Londin et al. "Analysis of 13 cell types reveals evidence for the expression of numerous novel primate- and tissue-specific microRNAs," PNAS, Feb. 2015 (E1106-E1115).
Sheinerman et al. "Analysis of organ-enriched micro-RNAs in plasma as an approach to development of Universal Screening Test: feasibility study," Journal of Translational Medicine 2013 11:304.
Sheinerman et al. "Plasma microRNA biomarkers for detection of mild cognitive impairment: biomarker validation study," Aging, Dec. 2013, vol. 5 No. 12, Dec. 2013 (925-938).
European Communication pursuant to Article 94(3) EPC dated Jun. 25, 2015, which issued during prosecution of European Application No. 12 774 179.1.
Sheinerman et al. "Early detection of neurodegenerative diseases, Cell Cycle," 12:1, Jan. 2013 (1-2).
Sheinerman et al. "Circulating cell-free microRNA as biomarkers for screening, diagnosis, and monitoring of neurode-generative diseases and other neurologic pathologies," Front.Cell.Neurosci. Sep. 2013, 7:150, pp. 1-10.
Chinese Office Action dated Jul. 23, 2014, which issued during prosecution of Chinese Application No. 201280030033.
Bredesen "mCiRNA-Synaptic Crystal Ball?," Aging, 2012, vol. 4 No. 11, pp. 732-733.
Chinese Office Action and Translation dated Aug. 5, 2015, which issued during prosecution of Chinese Application No. 201280030048.6.
Chinese Office Action dated Mar. 26, 2015, which issued during prosecution of Chinese Application No. 201280030048.6.
Chinese Office Action dated Nov. 24, 2015, which issued during prosecution of Chinese Application No. 201280030048.6.
European Communication pursuant to Article 94(3) EPC dated Nov. 6, 2015, which issued during prosecution of European Application No. 10779376.2.
Hua et al. "A Catalogue of Glioblastoma and Brain MicroRNAs Identified by Deep Sequencing," OMICS A Journal of Integrative Biology vol. 16, No. 12, 2012 (690-699).
International Search Report and Written Opinion of the International Searching Authority dated Apr. 28, 2015 issued during prosecution of International Application No. PCT/US2014/65959.
Sheinerman et al. "Plasma microRNA biomarkers for detection of mild cognitive impairment," Aging, vol. 4 No. 9, Sep. 2012 (590-605).
Supplementary Figures and Tables from Peltier et al (RNA (2008), 14:844-852) (the balance of the article is of record as citation C47 in the IDS of Oct. 18, 2013).
Lindner, Kirsten et al., "Circulating microRNAs: emerging biomarkers for diagnosis and prognosis in patients with gastrointestinal cancers", Clinical Science, 128, pp. 1-15, 2015.
European Communication pursuant to Article 94(3) EPC dated Jan. 5, 2016, which issued during prosecution of European Application No. 12773705.4.
Australian Office Acton Issued in Australian Patent Application No. 2012245628 dated Jun. 8, 2016, 6 pages.
Shingara, J. et al. "An optimized isotation and labang platform for accurate microRNA expression profiling", RNA (2005), vol. 11, p. 1461-1470.
Veerla, S. et al. "miRNA expression in urothelial carcinomas: important roles of miR-10a, miR-222, miR-125b, miR-7 and

(56) References Cited

OTHER PUBLICATIONS miR452 for lung stage and metastasis, and frequent homozygous losses of miR-31", International Journal of Cancer (2009), vol. 124, p. 2236-2242.

Xu, S. et al. "MicroRNA (miRNA) transcriptome of mouse retina and identification of a sensory organ-specific miRNA cluster", Journal of Biological Chemistry (2007), vol. 282, p. 25053-25066.

European Extended Search Report Issued in European Application No. EP16192259.6; dated Jan. 24, 2017, 8 pages.

Office Action issued in Japanese Patent Application No. 2014-506501 dated Mar. 16, 2016 (and English-language translation thereof), 15 pages.

* cited by examiner

MIRNA-BASED UNIVERSAL SCREENING TEST (UST)

CROSS-REFERENCE TO RELATED APPLICATIONS

This application is a U.S. National Phase application under 35 U.S.C. §371 of International Patent Application No. PCT/US2012/034098, filed Apr. 18, 2012 and published in English on Oct. 26, 2012 as WO 2012/145409 under PCT Article 21(2), and which claims priority from U.S. Provisional Application Ser. No. 61/476,591 filed on Apr. 18, 2011, U.S. Provisional Application Ser. No. 61/478,766 filed on Apr. 25, 2011, and U.S. Provisional Application Ser. No. 61/546,431 filed on Oct. 12, 2011, all of which are incorporated herein by reference in their entirety.

TECHNICAL FIELD OF INVENTION

The present invention describes methods for early non-invasive or minimally invasive detection of pathological changes in organ systems, particular organs, tissues, and/or cells by quantifying organ system/organ/tissue/cell type-enriched miRNA in bodily fluids.

BACKGROUND OF THE INVENTION

It is well accepted that the treatment of any disease is easier and more effective if an underlying pathology is diagnosed as early as possible. For some diseases early diagnosis (preferably before the appearance of clear clinical symptoms) is critically important because of pathology transition into a more advanced, sometimes irreversible, stage. For example, one of the major problems for drug development and treatment of Alzheimer's Disease and other neurodegenerative diseases is their late clinical manifestation and diagnosis due to high compensatory potentials of the brain. As a result, these diseases are usually diagnosed when many neurons are already dead and currently the best case scenario is the prevention of pathology worsening, not a real recovery. Cancer is another example, since treatment of the metastatic stage of the disease is much more problematic than the treatment of the primary tumor. There are many other pathologies of this kind, but again the treatment of any disease is more effective if it is diagnosed earlier.

There are several basic types of clinical tests: (i) genetic tests that help to predict predisposition to a particular disease; (ii) screening tests, which are applied to a large population for early detection of a disease, preferably prior to its clinical manifestation; (iii) diagnostic tests, which are applied when a person has clinical symptoms of a disease or when the pathology has been detected by a screening test; (iv) molecular predictive tests that should predict the disease outcome and drug sensitivity.

Screening tests are most important for the early detection of a disease. It is true not only for spontaneous diseases but also for genetically linked pathologies, for which high chances of getting a disease are predicted by genetic testing. Ideally, everybody should undergo regular screening for all possible life threatening and many other diseases. There have been numerous attempts to develop tests for early detection of various diseases and different screening tests are currently performed for specific risk groups. For example, periodic colonoscopy is recommended to people over 50 years old, Pap smears are recommended to women and the PSA test to men for early detection of the cervical and prostate cancer, respectively. A main advantage of these tests is their disease-specificity, but at the same time it is their serious disadvantage because each test addresses only one particular pathology. However, there are many hundreds of human diseases, and it is difficult to imagine that such specific screening tests would be developed for all of those pathologies. Moreover, even if specific tests for early detection of all human diseases have been developed, it is highly unlikely that such tests would be used for screening purposes, especially for relatively rare diseases due to economic factors. Because screening tests for each particular disease address large populations their specificity and positive predictive value (PPV) are very important. For example, if a screening test for a relatively common disease (1:10,000) is 100% sensitive and 99% specific, which is almost impossible to achieve, and 1 million people are screened, 100 cases would be detected correctly but about 10,000 people would receive false positive results. Obviously, such outcome would cause emotional distress for these people as well as significant financial consequences for additional tests.

SUMMARY OF THE INVENTION

As specified in the Background Section, above, there is a great need in the art for new screening tests. According to the current paradigm for screening test development and its clinical application, one of the main features of such test should be its high disease specificity. However, as mentioned above there are many hundreds of diseases and screening for each particular disease is principally impossible. The present invention proposes a significant paradigm shift: development and implementation of one or a small number of universal screening tests (USTs), which specifically detect a pathology of any particular organ system, organ, tissue and/or cell type, without diagnosing a particular disease. Such USTs should be performed periodically for any given subject for an early, preferably at clinically asymptomatic stage, and then more specific tests can be used for a more specific diagnosis. The USTs as described herein would improve disease diagnosis and treatment, and significantly decrease medical expenses. Also, the USTs as described herein would make tests for rare diseases more targeted since they will be applied to much smaller populations preselected by UST and, therefore, will be more economically practical.

Because UST will address a large population (preferably everyone), its first important feature is minimal invasiveness. The present invention proposes to register various physiological and pathological processes in particular organs, tissues and even cell types by analysis of respective biomarkers in bodily fluids that can be obtained by non-invasive or minimally invasive methods, such as, e.g., plasma/scrum, urine, or saliva. Secondly, UST cannot be based on the inducing factor or pathogenesis of diseases, since there are too many of them. Thirdly, to be widely used, UST should not be very expensive, which, in particular, means that it has to utilize a limited number of biomarker types that can be analyzed by the same technique.

Biomarkers used for UST should have a set of parameters that make them suitable for such type of a test:
1. Cell/tissue/organ-specificity or significant enrichment (e.g., at least 5 times higher concentration as compared to other cells/tissues/organs).
2. Ability to be secreted into extracellular space and to pass various barriers within the body.
3. Presence in detectable amounts in bodily fluids that can be obtained with minimal invasiveness.

4. Stability.
5. Detectability with high sensitivity and specificity at a relatively low cost.

The following classes of molecules can be of potential use for UST:
1. Proteins.
2. mRNA and mRNA fragments.
3. miRNA.
4. DNA fragments
5. DNA methylation.
6. Lipids.
7. Sugars.

However, some of these potential tissue-specific biomarkers have serious disadvantages, which make their use impractical or even impossible. For example, DNA methylation, lipids, and sugars are not sufficiently specific to differentiate between various tissue and cell types. Besides, DNA fragments appear in the extracellular space and in the bloodstream mainly from dying cells (Lichtenstein et al., Ann. New York Acad. Sci. 2001, 945:239-249) and, thus, circulating cell-free DNA cannot be used to detect pathology stages, which are not accompanied by cell death. Proteins and mRNA are better candidates for UST due to their higher tissue-specificity/enrichment (Diez-Roux et al., PLOS Biology. 2011, 9:e1000582). However, mRNA are large molecules, they are easily degraded by nucleases, and so only short fragments of these molecules appear in the bloodstream. This does not exclude their use as biomarkers for UST but makes test development more difficult. Proteins are good candidates but current methods for their detection are significantly less sensitive than nucleic acid detection techniques. Also, many proteins are large molecules and are not able to cross cellular membrane and other barriers.

The present invention proposes to use miRNA biomarkers in the UST for the following reasons: miRNA are small molecules, they can appear in the extracellular space, cross brain, kidney, and placenta barriers, appear in various bodily fluids, are stable, and existing methods for their analysis are very specific and sensitive. Most importantly, miRNA constitute a large class of diverse molecules with at least some miRNA being enriched in some organ systems, organs, tissues and/or cells, thus providing molecular markers for all parts of the body.

MicroRNA (miRNA) are a class of non-coding RNAs whose final product (mature miRNA) is an approximately 22 nt functional RNA molecule. They play important roles in the regulation of target genes by binding to complementary regions of messenger transcripts to repress their translation or regulate degradation (Griffiths-Jones Nucleic Acids Research, 2006, 34, Database issue: D140-D144). Frequently, one miRNA can target multiple mRNAs and one mRNA can be regulated by multiple miRNA targeting different regions of the 3' UTR. Once bound to an mRNA, miRNA can modulate gene expression and protein production by affecting mRNA translation and stability (e.g., Baek et al., Nature. 2008, 455:64; Selbach et al., Nature. 2008, 455:58; Ambros, Nature. 2004, 431:350-355; Bartel, Cell. 2004, 116:281-297; Cullen, Virus Research. 2004, 102:3-9; He et al. Nat. Rev. Genet. 2004, 5:522-531; and Ying et al., Gene. 2004, 342:25-28). There are other classes of less characterized small RNAs (reviewed in Kim, Mol. Cells, 2005, 19: 1-15). Many of miRNA are specific to or overexpressed in certain organs/tissues/cells (See, e.g., Hua et al., BMC Genomics 2009, 10:214; Liang et al., BMC Genomics. 2007, 8:166; Landgraf et al., Cell. 2007, 129: 1401-1414; Lee et al., RNA. 2008, 14:35-42). Due to their small size, miRNA can cross the blood-brain, kidney, and placental barriers into bodily fluids where they are sufficiently stable (Rosenfeld et al., Nature Biotech. 2008, 26:462-469; Mitchell et al., Proc. Natl. Acad. Sci. USA. 2008, 105: 10513-10518; Chen et al., Cell Res. 2008, 18:997-1006; Chim et al., Clin. Chem. 2008, 54:482-490; De Smaele et al., Brain Res. 2010, 1338:100-111; Fichtlscherer et al., Circ. Res. 2010, 107:677-684; Scholer et al., Exp. Hematol. 2010, 38:1126-1130). Analysis of cell/tissue-specific miRNA in bodily fluids was proposed for detection of in vivo cell death (U.S. Patent Pub. No 20090081640; Laterza et al., Clin Chem. 2009, 55:1977-1983). The increase of concentrations of circulating cell-free liver-enriched miRNA in the bloodstream has been demonstrated in several studies (Zhang et al., Clin Chem. 2010, 56:1830-1838; Xu et al., Mol Carcinogenesis. 2011, 50:136-142). For example, the levels of liver-enriched miRNA-122a go up in serum of patients with hepatitis and hepatocellular carcinomas, and the authors come to a conclusion that due to this non-specificity for a particular disease these miRNA cannot be used as biomarkers for HCC (Zhang et al., Clin Chem. 2010, 56:1830-1838; Li et al., Cancer Res. 2010, 70:9798-9807). On the contrary, the present invention demonstrates that such disease non-specificity of the organ/tissue/cell-enriched miRNA is a significant advantage when they are used as biomarkers for UST development.

Expression and concentrations of miRNA are regulated by various physiological and pathological signals. Some of miRNA are characteristic of a particular pathology, such as hypoxia (Loscalzo, J. Clin. Invest. 2010, 120: 3815-3817; Pocock, Pflugers Arch. 2011, 461:307-315), inflammation (Tili et al., Int. Rev. Immunol. 2009, 28:264-284; Davidson-Moncada et al., Ann. NY Acad. Sci. 2010, 1183:183-194; Roy and Sen, Physiol. Genomics. 2011, 43:557-565), or carcinogenesis (Budhu et al., J. Hematol. Oncol. 2010, 3:37; Zen and Zhang, Med. Res. Rev. 2012, 32:326-348). This phenomenon makes it reasonable to include such miRNA as biomarkers into the USTs of the invention. An increase of these miRNA concentrations in bodily fluids will indicate the presence of a respective general pathology in the body without localizing it to a particular organ, tissue or cell type. Generally speaking, this would be the same approach as proposed above for organ/tissue-enriched miRNA: organ/tissue-enriched miRNA will help to detect a pathology in a particular organ or tissue; on the other hand, miRNA characteristic of a particular general pathology will help to detect the presence of this pathology somewhere in the body without indicating a specific organ/tissue involved. A combined use of miRNA biomarkers which are enriched in an organ system, organ, tissue, and/or cell type, and miRNA biomarkers characteristic of a particular general pathology will provide a more precise diagnosis, namely the presence of a particular pathology in a particular organ or tissue or cell type. For example, increased concentrations of miRNA characteristic of hypoxia in plasma, combined with increased concentrations of miRNA enriched in the heart, will provide more specific diagnosis of heart ischemia obtained by the UST.

Thus, in one aspect, the present invention provides a method for detecting a pathology in any organ system in a subject, which method comprises:
a. measuring levels of miRNAs enriched in various organ systems in a bodily fluid sample collected from the subject;
b. measuring levels of preselected normalizer miRNAs in the same bodily fluid sample collected from the subject;
c. calculating the ratios of the levels of the miRNAs measured in steps (a) and (b);

d. comparing the ratios of the levels of the miRNAs calculated in step (c) with the corresponding control ratios, and
e. (i) identifying the subject as being afflicted with a pathology of a particular organ system when the ratios of the levels of the miRNAs enriched in said organ system to their respective miRNA normalizers calculated in step (c) are higher than the corresponding control ratios or (ii) identifying the subject as not being afflicted with a pathology of said organ system when the ratios of the levels of the miRNAs enriched in said organ system to their respective miRNA normalizers calculated in step (c) are not higher than the corresponding control ratios.

The invention also provides a method for detecting a pathology in an organ system in a subject, which method comprises:
a. measuring the level of at least one miRNA enriched in said organ system in a bodily fluid sample collected from the subject;
b. measuring the level of a normalizer miRNA in the same bodily fluid sample collected from the subject;
c. calculating the ratio of the levels of the miRNAs measured in steps (a) and (b);
d. comparing the ratio of the levels of the miRNAs calculated in step (c) with a corresponding control ratio, and
e. (i) identifying the subject as being afflicted with a pathology of said organ system when the ratio of the levels of the miRNAs calculated in step (c) is higher than the corresponding control ratio or (ii) identifying the subject as not being afflicted with a pathology of said organ system when the ratio of the levels of the miRNAs calculated in step (c) is not higher than the corresponding control ratio.

The normalizer miRNA useful in the above two methods can be, for example, ubiquitous miRNA, miRNA expressed in many organs but under-expressed in said organ system, or experimentally selected miRNA enriched in said organ system.

The control ratio of the levels of the miRNAs used in the above two methods can be a predetermined standard (e.g., determined using a population of control subjects [e.g., age-matched to the diagnosed subject] without pathologies of the respective organ system) or the ratio of the levels of the same mRNAs in a similarly processed bodily fluid sample from the same subject collected in the past.

In one embodiment, the above methods involve determining two or more miRNA ratios.

In one embodiment of the above methods, the miRNA enriched in an organ system is selected from miRNAs listed in Table 2, below.

In another embodiment of the above methods, the organ system is central nervous system and the miRNA/normalizer pairs are selected from those listed in Table 4, below.

In yet another embodiment of the above methods, the organ system is respiratory system and the miRNA/normalizer pairs are selected from those listed in Table 5, below.

In a further embodiment of the above methods, the organ system is gastrointestinal (GI) system and the miRNA/normalizer pairs are selected from those listed in Table 7, below.

In another aspect, the invention provides a method for detecting a pathology in any organ in a subject, which method comprises:
a. measuring levels of miRNAs enriched in various organs in a bodily fluid sample collected from the subject;
b. measuring levels of preselected normalizer miRNAs in the same bodily fluid sample collected from the subject;
c. calculating the ratios of the levels of the miRNAs measured in steps (a) and (b);
d. comparing the ratios of the levels of the miRNAs calculated in step (c) with the corresponding control ratios, and
e. (i) identifying the subject as being afflicted with a pathology of a particular organ when the ratios of the levels of the miRNAs enriched in said organ to their respective miRNA normalizers calculated in step (c) are higher than the corresponding control ratios or (ii) identifying the subject as not being afflicted with a pathology of said organ when the ratios of the levels of the miRNAs enriched in said organ to their respective miRNA normalizers calculated in step (c) are not higher than the corresponding control ratios.

The invention also provides a method for detecting a pathology in an organ in a subject, which method comprises:
a. measuring the level of at least one miRNA enriched in said organ in a bodily fluid sample collected from the subject;
b. measuring the level of a normalizer miRNA in the same bodily fluid sample collected from the subject;
c. calculating the ratio of the levels of the miRNAs measured in steps (a) and (b);
d. comparing the ratio of the levels of the miRNAs calculated in step (c) with a corresponding control ratio, and
e. (i) identifying the subject as being afflicted with a pathology of said organ when the ratio of the levels of the miRNAs calculated in step (c) is higher than the corresponding control ratio or (ii) identifying the subject as not being afflicted with a pathology of said organ when the ratio of the levels of the miRNAs calculated in step (c) is not higher than the corresponding control ratio.

The normalizer miRNA useful in the above two methods can be, for example, ubiquitous miRNA, miRNA expressed in many organs but under-expressed in said organ, or experimentally selected miRNA enriched in said organ.

The control ratio of the levels of the miRNAs used in the above two methods can be a predetermined standard (e.g., determined using a population of control subjects [e.g., age-matched to the diagnosed subject] without pathologies of the respective organ) or the ratio of the levels of the same mRNAs in a similarly processed bodily fluid sample from the same subject collected in the past.

In one embodiment, the above two methods involve determining two or more miRNA ratios.

In one embodiment of the above two methods, the miRNA enriched in an organ is selected from miRNAs listed in Tables 1 and 2, below.

In another embodiment of the above two methods, the organ is a gastrointestinal (GI) organ and the miRNA/normalizer pairs are selected from those listed in Table 9, below.

In another aspect, the invention provides a method for detecting a pathology in any tissue in a subject, which method comprises:
a. measuring levels of miRNAs enriched in various tissues in a bodily fluid sample collected from the subject;
b. measuring levels of normalizer miRNAs in the same bodily fluid sample collected from the subject;
c. calculating the ratios of the levels of the miRNAs measured in steps (a) and (b);
d. comparing the ratios of the levels of the miRNAs calculated in step (c) with the corresponding control ratios, and
e. (i) identifying the subject as being afflicted with a pathology of a particular tissue when the ratios of the levels of the miRNAs enriched in said tissue to their respective miRNA normalizers calculated in step (c) are higher than the corresponding control ratios or (ii) identifying the subject as not being afflicted with a pathology of said tissue when the ratios of the levels of the miRNAs enriched in said tissue to their respective miRNA normalizers calculated in step (c) are not higher than the corresponding control ratios.

The invention also provides a method for detecting a pathology in a tissue in a subject, which method comprises:
a. measuring the level of at least one miRNA enriched in said tissue in a bodily fluid sample collected from the subject;
b. measuring the level of a normalizer miRNA in the same bodily fluid sample collected from the subject;
c. calculating the ratio of the levels of the miRNAs measured in steps (a) and (b);
d. comparing the ratio of the levels of the miRNAs calculated in step (c) with a corresponding control ratio, and
e. (i) identifying the subject as being afflicted with a pathology of said tissue when the ratio of the levels of the miRNAs calculated in step (c) is higher than the corresponding control ratio or (ii) identifying the subject as not being afflicted with a pathology of said tissue when the ratio of the levels of the miRNAs calculated in step (c) is not higher than the corresponding control ratio.

The normalizer miRNA useful in the above two methods can be, for example, ubiquitous miRNA, miRNA expressed in many tissues but under-expressed in said tissue, or experimentally selected miRNA enriched in said tissue.

The control ratio of the levels of the miRNAs used in the above two methods can be a predetermined standard (e.g., determined using a population of control subjects [e.g., age-matched to the diagnosed subject] without pathologies of the respective tissue) or the ratio of the levels of the same mRNAs in a similarly processed bodily fluid sample from the same subject collected in the past.

In one embodiment, the above two methods involve determining two or more miRNA ratios.

In one embodiment of the above two methods, the miRNA enriched in a tissue is selected from miRNAs listed in Tables 1 and 2, below.

In another aspect, the invention provides a method for detecting a pathology in any cell type in a subject, which method comprises:
a. measuring levels of miRNAs enriched in various cell types in a bodily fluid sample collected from the subject;
b. measuring levels of normalizer miRNAs in the same bodily fluid sample collected from the subject;
c. calculating the ratios of the levels of the miRNAs measured in steps (a) and (b);
d. comparing the ratios of the levels of the miRNAs calculated in step (c) with the corresponding control ratios, and
e. (i) identifying the subject as being afflicted with a pathology of a particular cell type when the ratios of the levels of the miRNAs enriched in said cell type to their respective miRNA normalizers calculated in step (c) are higher than the corresponding control ratios or (ii) identifying the subject as not being afflicted with a pathology of said cell type when the ratios of the levels of the miRNAs enriched in said cell type to their respective miRNA normalizers calculated in step (c) are not higher than the corresponding control ratios.

The invention also provides a method for detecting a pathology in a cell type in a subject, which method comprises:
a. measuring the level of at least one miRNA enriched in said cell type in a bodily fluid sample collected from the subject;
b. measuring the level of a normalizer miRNA in the same bodily fluid sample collected from the subject;
c. calculating the ratio of the levels of the miRNAs measured in steps (a) and (b);
d. comparing the ratio of the levels of the miRNAs calculated in step (c) with a corresponding control ratio, and
e. (i) identifying the subject as being afflicted with a pathology of said cell type when the ratio of the levels of the miRNAs calculated in step (c) is higher than the corresponding control ratio or (ii) identifying the subject as not being afflicted with a pathology of said cell type when the ratio of the levels of the miRNAs calculated in step (c) is not higher than the corresponding control ratio.

The normalizer miRNA useful in the above two methods can be, for example, ubiquitous miRNA, miRNA expressed in many cell types but under-expressed in said cell type, or experimentally selected miRNA enriched in said cell type.

The control ratio of the levels of the miRNAs used in the above two methods can be a predetermined standard (e.g., determined using a population of control subjects [e.g., age-matched to the diagnosed subject] without pathologies of the respective cell type) or the ratio of the levels of the same mRNAs in a similarly processed bodily fluid sample from the same subject collected in the past.

In one embodiment, the above two methods involve determining two or more miRNA ratios.

In one embodiment of the above two methods, the miRNA enriched in a cell type is selected from miRNAs listed in Tables 1 and 2, below.

The above-described methods can be combined. For example, detecting a pathology of an organ system can be followed by determining the affected organ and/or tissue and/or cell type, etc.

Any of the above-described methods can also further comprise identifying whether the pathology is cancer or inflammation, which method comprises:
a. measuring the level of at least one miRNA associated with cancer in a bodily fluid sample collected from the subject;
b. measuring the level of at least one miRNA associated with inflammation in the same bodily fluid sample collected from the subject;
c. measuring the level of at least one miRNA enriched in the involved organ system, organ, tissue or cell type in the same bodily fluid sample collected from the subject;
d. measuring the level of at least one normalizer miRNA in the same bodily fluid sample collected from the subject;
e. calculating pair-wise ratios of the levels of the miRNAs measured in steps (a), (b), (c), and (d) (e.g., ratios a/b, a/c, aid, b/c, b/d, and c/d);
f. comparing the ratios of the levels of the miRNAs calculated in step (e) with the corresponding predetermined ratios characteristic of cancer and inflammation, and
g. (i) identifying that the pathology is cancer when the ratios of the levels of the miRNAs calculated in step (e) are in the predetermined range characteristic of cancer, or (ii) identifying that the pathology is inflammation when the ratios of the levels of the miRNAs calculated in step (e) are in the predetermined range characteristic of inflammation.

In one embodiment of the above method, the miRNAs associated with cancer and inflammation are selected from miRNAs listed in Table 3, below.

In one embodiment of the above method, the pathology relates to lung and the miRNA pairs are selected from those listed in Table 6, below.

In one embodiment of the above method, the pathology relates to gastrointestinal (GI) system and the miRNA pairs are selected from those listed in Table 8, below.

In one embodiment of the above method, the pathology relates to respiratory system or gastrointestinal (GI) system and the miRNA pairs are selected from those listed in Table 11, below.

A similar method can be applied to distinguishing cancer or inflammation from hypoxia.

Any of the above methods can be followed by administering a disease-specific diagnostic test to the subject.

Any of the above methods can be followed by administering a therapeutic treatment to the subject that has been diagnosed as having a pathology.

Any of the above methods can be followed by recruiting the subject in a clinical trial (this can apply to both subjects diagnosed as having a pathology and to subjects diagnosed as not having a pathology).

The above-described methods of the invention can be applied for detecting pathologies in any subject, including subjects who have no clinical symptoms indicative of a pathology of said organ system or organ or tissue or cell type.

In a separate aspect, the invention provides a method for identifying a compound useful for slowing down the progression or treating a pathology of an organ system or organ or tissue or cell type, which method comprises:

a. measuring the level of at least one miRNA enriched in said organ system or organ or tissue or cell type in one or more bodily fluid samples collected from a subject having said pathology of said organ system or organ or tissue or cell type, wherein said bodily fluid sample(s) is collected prior to administration of a test compound;

b. measuring the level of a normalizer miRNA in the same bodily fluid sample(s) from the subject collected prior to administration of the test compound;

c. calculating the ratio of the levels of the miRNAs measured in steps (a) and (b) for each of the bodily fluid samples collected from the subject prior to administration of the test compound;

d. measuring the level of the same miRNA as in step (a) in one or more bodily fluid samples collected from the subject following administration of the test compound;

e. measuring the level of the same normalizer miRNA as in step (b) in the same bodily fluid sample(s) collected from the subject following administration of the test compound;

f. calculating the ratio of the levels of the miRNAs measured in steps (d) and (c) for each of the bodily fluid samples collected from the subject following administration of the test compound;

g. comparing the ratio of the levels of the miRNAs calculated in steps (c) and (f), and h. (i) identifying that the test compound is useful for slowing down the progression or treating said pathology of said organ system or organ or tissue or cell type if the ratio of the levels of the miRNAs calculated in step (f) is lower than the ratio of the levels of the miRNAs calculated in step (c); (ii) identifying that the test compound is not useful for slowing down the progression or treating said pathology of said organ system or organ or tissue or cell type if the ratio of the levels of the miRNAs calculated in step (f) is not lower than the ratio of the levels of the miRNAs calculated in step (c).

In one embodiment of the above method, the pathology is cancer or inflammation or hypoxia, and miRNA is selected from miRNAs listed in Table 3, below.

In another aspect, the invention provides a method for determining toxicity of a compound (e.g., a compound being tested in a clinical trial) or environmental factor (e.g., allergen, smoking, UV, radiation, asbestos, etc.) to an organ system or organ or tissue or cell type in a subject free of pathologies of said organ system or organ or tissue or cell type, which method comprises:

a. measuring the level of at least one miRNA enriched in said organ system or organ or tissue or cell type in one or more bodily fluid samples collected from the subject before the subject has been exposed to the compound or environmental factor;

b. measuring the level of a normalizer miRNA in the same bodily fluid sample(s) collected from the subject before the subject has been exposed to the compound or environmental factor;

c. calculating the ratio of the levels of the miRNAs measured in steps (a) and (b) for each of the bodily fluid samples collected from the subject before the subject has been exposed to the compound or environmental factor;

d. measuring the level of the same miRNA enriched in said organ system or organ or tissue or cell type in one or more bodily fluid samples collected from the subject after the subject had been exposed to the compound or environmental factor;

e. measuring the level of the same normalizer miRNA in the same bodily fluid sample(s) collected from the subject after the subject had been exposed to the compound or environmental factor;

f. calculating the ratio of the levels of the miRNAs measured in steps (d) and (e) for each of the bodily fluid samples;

g. comparing the ratio of the levels of the miRNAs calculated in steps (c) and (f), and h. (i) identifying that the compound or environmental factor is not toxic to said organ system or organ or tissue or cell type if the ratio of the levels of the miRNAs calculated in step (f) is not higher than the ratio of the levels of the miRNAs calculated in step (c); (ii) identifying that the compound or environmental factor is toxic to said organ system or organ or tissue or cell type if the ratio of the levels of the miRNAs calculated in step (f) is higher than the ratio of the levels of the miRNAs calculated in step (c).

In one embodiment, the above two methods involve determining two or more miRNA ratios.

In one embodiment of the above two methods, the miRNA enriched in an organ system or organ or tissue or cell type is selected from miRNAs listed in Tables 1 and 2, below.

In one embodiment of the above two methods, the organ system is central nervous system and the miRNA/normalizer pairs are selected from those listed in Table 4, below.

In one embodiment of the above two methods, the organ system is respiratory system and the miRNA/normalizer pairs are selected from those listed in Table 5, below.

In one embodiment of the above two methods, the organ system is gastrointestinal (GI) system and the miRNA/normalizer pairs are selected from those listed in Table 7, below.

Each of the measuring steps in the above-described methods does not have to be performed in the specific order listed above.

Subjects used in the methods of the present invention include, e.g., humans, veterinary animals and experimental animal models of diseases. Non-limiting examples of biomarker miRNAs and normalizer miRNAs useful in the above-described methods of the present invention are provided, e.g., in Tables 1-11, below.

Non-limiting examples of bodily fluid samples which can be used in the methods of the invention include, e.g., urine, blood plasma and serum. If urine is used, it is preferred that the urine sample has been held in the bladder for less than 4 hours.

Non-limiting examples of methods for determining the level of miRNA in the methods of the invention include, e.g., hybridization, RT-PCR, and direct sequencing.

In some embodiments, the methods of the invention comprise (e.g., as an initial step) the step of collecting a bodily fluid sample from the subject.

In one embodiment (applicable to any of the above methods of the invention), the method also includes a step of reducing or eliminating degradation of miRNA. Non-limiting examples of useful methods for reducing or eliminating miRNA degradation include, e.g., adding an RNase inhibitor, treatment with guanidine chloride, treatment with guanidine isothiocyanate, treatment with N-lauroylsarcosine, treatment with sodium dodecyl sulphate (SDS), and a combination thereof.

In conjunction with the above diagnostic and screening methods, the present invention also provides various kits comprising one or more primer and/or probe sets specific for the detection of target miRNA. Such kits can further include primer and/or probe sets specific for the detection of normalizer miRNA. Non-limiting examples of primer or probe combinations in kits are as follows:

1. primers or probes specific for at least two miRNAs selected from the group consisting of miR-1, 22, 30a-3p, 30e-3p, 133a, 133b, 197, 208a, 208b, 221, 222, 302a, 302c, 367, 378, 499-5p, and 30e*.

2. primers or probes specific for at least two miRNAs selected from the group consisting of miR-1, 22, 95, 133a, 133b, 140, and 206.

3. primers or probes specific for at least two miRNAs selected from the group consisting of miR-15b, 18b, 21, 34b, 126, 135b, 142-3p, 142-5p, 146, 146b-5p, 155, 199b-5p, 200c, 205, 211, 223, 224, 302b, 375, 449a, 449b, 450b-5p, 486, 492, 522, 566, 5'74-3p, 620, 650, 766, and 886-5p.

4. primers or probes specific for at least two miRNAs selected from the group consisting of miR-34b, 135b, 146, 146b, 147b, 155, 199b-5p, 200b, 200c, 205, 219-5p, 223, 302b, and 375.

5. primers or probes specific for at least two miRNAs selected from the group consisting of miR-30e-3p, 122a, 130b, 136, 148a, 194, 376c, 455-3p, 518b, 616, 801, 885-5p, 17*, 30d*, and 194*.

6. primers or probes specific for at least two miRNAs selected from the group consisting of miR-10a, 10b, 30a-3p, 30c, 107, 135a, 135b, 184, 187, 190, 194, 196b, 200a, 204, 211, 324-5p, 489, 500, 501-5p, 502-3p, 502-5p, 503, 506, 508-3p, 508-5p, 509-3p, 509-5p, 510, 532-5p, 768-3p, 886-3p, 886-5p, 891a, 10b*, 30a*, 30c-2*, 30e*, 200a*, 200b*, 424*, and 500*.

7. primers or probes specific for at least two miRNAs selected from the group consisting of miR-Let-7g, 18, 23b, 26a, 26b, 27b, 28, 106b, 143, 145, 152, 218, 221, 223, 296, 374, 422b, and 451.

6. primers or probes specific for at least two miRNAs selected from the group consisting of miR-10b, 30, 99a, 139-3p, 139-5p, 193a-5p, 196a, 224, 335, 365, 378/378*, 422b, 494, 518d-3p, 642a-3p, 708, 10b*, and 335*.

7. primers or probes specific for at least two miRNAs selected from the group consisting of miR-let-7a, 10b, 26a, 30a-3p, 30a-5p, 125b, 126, 145, 146, 195, 196a-2, 196b, 205, 206, 335, 339-5p, 378, 516-5p, 517c, 519c, 520g, 520h, 525, and 1246.

8. primers or probes specific for at least two miRNAs selected from the group consisting of miR-Let-7a, let-7b, let-7c, 10b, l'7-3p, 26a, 100, 125a, 125b, 127, 195, 199a-5p, 202, 214, 298, 382, 503, 672, 741, 742, 883-3p, 199a*, and 202*.

9. primers or probes specific for at least two miRNAs selected from the group consisting of miR-10a, 10b, 31, 34b, 34c, 135a, 135b, 424, and 449.

10. primers or probes specific for at least two miRNAs selected from the group consisting of miR-Let-7c, 10b, 26a, 99a, 100, 125a-5p, 125b, 130a, 140, 143, 145, 195, 196b, 199b, 204, 214, 222, 939, and 199*.

11. primers or probes specific for at least two miRNAs selected from the group consisting of miR-Let-7a, let-7c, let-7 g, 10b, 100, 101, 125a-5p, 125b, 130a, 134, 140, 143, 145, 186, 195, 196b, 197, 199a, 199b, 204, 214, 218, 222, 320, 424, 497, 154*, and 199a*.

12. primers or probes specific for at least two miRNAs selected from the group consisting of miR-Let-7c, 1, 23b, 24, 27b, 28, 34a, 99a, 100, 125b, 130a, 143, 145, 147b, 187, 188-3p, 199b-5p, 205, 214, 222, 328, 373, 410, 455-5p, and 490-3p.

13. primers or probes specific for at least two miRNAs selected from the group consisting of miR-15b, 34a, 34b, 34c, 127, 134, 135a, 135b, 187, 202, 204, 370, 372, 376a, 382, 424, 449, 465a-5p, 465b-5p, 506, 508, 509, 510, 514, 517a, 517c, 871-5p, 871-3p, 888, 202*, and 888*.

14. primers or probes specific for at least two miRNAs selected from the group consisting of miR-Let-7 family, 10a, 17, 18a, 19a, 19b, 20a, 92, 21, 22, 23a, 24, 27a, 27b, 29a, 31, 34a, 98, 100, 106a, 126, 130a, 133a, 143, 145, 146a, 199a-3p, 210, 221, 222, 345, 365, 382, 409-3p, 431, 484, 495, 532-5p, 939, 27a*, 30a*, 30e*, 93*, 126*, 130b*, and 222*.

15. primers or probes specific for at least two miRNAs selected from the group consisting of miR-15a, 15b, 126, 139, 142-3p, 142-5p, 146, 150, 155, 181a, 181b, 181d, 223, 302b, and 342.

16. primers or probes specific for at least two miRNAs selected from the group consisting of miR-15a, 15b, 17-5p, 20b, 106a, 106b, 142-3p, 142-5p, 146, 149, 150, 155, 181a, 181b, 181c, 182, 183, 205, 213, and 342.

17. primers or probes specific for at least two miRNAs selected from the group consisting of miR-Let-7g, 15a, 20b, 21, 106b, 140, 142-3p, 146, 146b, 150, 181b, 181d, 342, and 431.

18. primers or probes specific for at least two miRNAs selected from the group consisting of miR-Let-7g, 9, 15a, 15b, 17, 19b, 20a, 31, 106a, 124a, 124b, 128a, 137, 142-3p, 146b-5p, 150, 186, 191, 197, 222, 223, 328, 342-3p, 423, 431, 454, 484, 766, 27*, and 223*.

19. primers or probes specific for at least two miRNAs selected from the group consisting of miR-142-3p, 146a, 155, 181a, 205, 223, and 424.

20. primers or probes specific for at least two miRNAs selected from the group consisting of miR-142, 150, and 342.

21. primers or probes specific for at least two miRNAs selected from the group consisting of miR-Let-7i, 1, 7, 135a, 135b, 206, and 345.

22. primers or probes specific for at least two miRNAs selected from the group consisting of miR-Let-7g, 7, 15a, 26b, 27a, 99b, 124, 127, 132, 134, 137, 139, 152, 181a, 187, 195, 192, 202, 299, 302b, 323, 324-3p, 324-5p, 328, 330-3p, 331, 335, 340, 365, 369-3p, 375, 379, 382, 409-5p, 429, 431, 432, 455-5p, 483-5p, 514, 126*, 182*, and 202*.

23. primers or probes specific for at least two miRNAs selected from the group consisting of miR-7, 18a, 21,29a, 34a, 103, 12'7-3p, 129-3p, 130b, 134, 135a, 135b, 136, 141, 148a, 182, 183, 184, 192, 193a-3p, 193a-5p, 195, 199a-3p, 199a-5p, 200b, 200c, 204, 216a, 216b, 217, 224, 340, 365, 367, 374a, 374b, 375, 376a, 376c, 379, 382, 383, 429, 432, 451, 455-5p, 485-5p, 487b, 497, 539, 543, 642, 758, 939, 130b*, 136*, 183*, 200b*, and 493*.

24. primers or probes specific for at least two miRNAs selected from the group consisting of miR-7, 9, 21, 127-3p, 130b, 184, 195, 216a, 216b, 217, 376a, 376c, 497, 939, and 493*.

25. primers or probes specific for at least two miRNAs selected from the group consisting of miR-31, 141, 143, 145, 147b, 192, 194, 200a, 200b, 200bN, 200c, 200cN, 215, 219-2-3p, 321, 375, 378, 422a, 429, 450b-5p, 487a, 490-3p, 492, 504, 565, 574-3p, 622, 650, 801, 143*, and 200b*.

26. primers or probes specific for at least two miRNAs selected from the group consisting of miR-31, 141, 143, 192, 194, 200a, 200b, 200bN, 200c, 200cN, 215, 321, 375, and 429.

27. primers or probes specific for at least two miRNAs selected from the group consisting of miR-31, 106a, 106b, 143, 145, 148a, 203, 205, 210, 211, and 221.

28. primers or probes specific for at least two miRNAs selected from the group consisting of miR-7, 26a, 26b, 29c, 31, 106a, 106b, 124b, 130b, 141, 145, 148a, 182, 188, 192, 197, 203, 375, and 650.

29. primers or probes specific for at least two miRNAs selected from the group consisting of miR-Let-7a, 7, 9, 96, 98, 99a, 103, 107, 124a, 125a, 125b, 127, 128a, 132, 134, 135a, 137, 138, 149, 153, 154, 181a, 181b, 181c, 182, 183, 184, 204, 211, 212, 213, 218, 219, 221, 222, 299-3p, 299-5p, 323-3p, 324-5p, 328, 329, 330, 331, 335, 337, 338, 342, 346, 369-3p, 369-5p, 370, 379, 381, 382, 383, 409-3p, 411, 425, 432, 433-5p, 485-3p, 485-5p, 487b, 488, 491-5p, 494, 495, 496, 504, 539, 541, 543, 584, 656, 668, 758, 874, 889, 935, 939, 1193, 1197, and 9*.

30. primers or probes specific for at least two miRNAs selected from the group consisting of miR-7, 9, 98, 124a, 125a, 125b, 128a, 132, 134, 135a, 137, 138, 154, 182, 183, 213, 218, 323-3p, 329, 337, 369-3p, 369-5p, 370, 381, 382, 409-3p, 425, 433-5p, 483-3p, 485-5p, 487b, 494, 495, 496, 541, 543, 656, 668, 874, 889, 935, 939, and 9*.

31. primers or probes specific for at least two miRNAs selected from the group consisting of miR-9, 124a, 125a, 125b, 128a, 132, 134, 181c, 212, 213, 222, 330-3p, 338-5p, 342, 381, 382, 425, 433, and 491-5p.

32. primers or probes specific for at least two miRNAs selected from the group consisting of miR-9, 96, 99a, 103, 124a, 125b, 128a, 132, 134, 137, 138, 181a, 181b, 212, 219, 221, 222, 324-5p, 328, 330, 331, 335-5p, 338, 369-3p, 381, 382, 383, 425, 433-5p, 485-5p, and 491-5p.

33. primers or probes specific for at least two miRNAs selected from the group consisting of miR-7, 124a, 128a, 132, and 212.

34. primers or probes specific for at least two miRNAs selected from the group consisting of miR-9, 103, 124a, 125b, 128, 132, 134, 137, 138, 181a, 181b, 181c, 204, 212, 213, 218, 338, 381, 382, 425, 432, and 489.

35. primers or probes specific for at least two miRNAs selected from the group consisting of miR-103, 134, 138, 182, 183, 222, 323-3p, 369, 381, and 382.

36. primers or probes specific for at least two miRNAs selected from the group consisting of miR-218, 219, 338, 451, and 486.

37. primers or probes specific for at least two miRNAs selected from the group consisting of miR-7, 132, 212, 213, and 328.

38. primers or probes specific for at least two miRNAs selected from the group consisting of miR-34b, 135b, 146, 146b-5p, 155, 199b-5p, 200c, 205, 223, 302b, and 375.

39. primers or probes specific for at least two miRNAs selected from the group consisting of miR-15b, 18b, 21, 126, 142-3p, 142-5p, 224, 449a, 449b, 450b-5p, 486, 492, 522, 566, 574-3p, 650, 766, and 886-5p.

40. primers or probes specific for at least two miRNAs selected from the group consisting of miR-147b, 200b, and 219-5p.

41. primers or probes specific for at least two miRNAs selected from the group consisting of miR-31, 130b, 136, 141, 143, 145, 148a, 192, 203, 215, 375, 376c, 429, 455-5p, and 650.

42. primers or probes specific for at least two miRNAs selected from the group consisting of miR-106a, 106b, 205, and 210, and 221.

43. primers or probes specific for at least two miRNAs selected from the group consisting of miR-7, 26a, 26b, 26c, 106a, 106b, 124b, 182, 188, and 197.

44. primers or probes specific for at least two miRNAs selected from the group consisting of miR-194, 200a, 200b, 200c, and 321.

45. primers or probes specific for at least two miRNAs selected from the group consisting of miR-147b, 194, 200a, 200b, 200c, 219-3p, 378, 450-5p, 487a, 490-3p, 492, 504, 565, 574-3p, 622, 801, 143*, and 200b*.

46. primers or probes specific for at least two miRNAs selected from the group consisting of miR-122a, 194, 518b, 616, 801, 885-5p, 17*, 30d*, and 194*.

47. primers or probes specific for at least two miRNAs selected from the group consisting of miR-7, 18a, 21, 29a, 34a, 103, 127-3p, 129-3p, 134, 135a, 135b, 182, 183, 184, 193a-3p, 193a-5p, 195, 199a-3p, 199a-5p, 200b, 200c, 204, 216a, 216b, 217, 224, 340, 365, 367, 374a, 374b, 376a, 379, 382, 383, 432, 451, 485-5p, 487b, 497, 539, 543, 642, 758, 939, 130b*, 136*, 183*, 200b*, and 493*.

48. primers or probes specific for at least two miRNAs selected from the group consisting of miR-1, 22, 95, 133a, 133b, 140, and 206.

49. primers or probes specific for at least two miRNAs selected from the group consisting of miR-Let-7a, 7, 9, 124a, 125a, 125b, 128a, 132, 134, 135a, 137, 138, 181a, 181c, 182, 184, 211, 212, 213, 218, 219, 222, 323-3p, 338-5p, 369, 381, 382, 425, 433-5p, 485-5p, 491-5p, 539, 541, 543, 656, 874, 935, and 9*.

50. primers or probes specific for at least two miRNAs selected from the group consisting of miR-7, 9, 98, 124a, 125a, 125b, 128a, 132, 134, 135a, 137, 138, 154, 182, 183, 213, 218, 323-3p, 329, 337, 369-3p, 369-5p, 370, 381, 382, 409-3p, 425, 433-5p, 483-3p, 485-5p, 487b, 494, 495, 496, 541, 543, 656, 668, 874, 889, 935, 939, and 9*.

51. primers or probes specific for miR-330-3p and miR-342.

52. primers or probes specific for at least two miRNAs selected from the group consisting of miR-96, 99a, 103, 181b, 221, 324-5p, 328, 330, 331, 335-5p, and 383.

53. primers or probes specific for at least two miRNAs selected from the group consisting of miR-103, 181b, 204, 432, and 489.

54. primers or probes specific for miR-103 and miR-183.

55. primers or probes specific for miR-451 and miR-486.

56. primers or probes specific for at least two miRNAs selected from the group consisting of miR-22, 133a, 221, 222, and 30e*.

57. primers or probes specific for at least two miRNAs selected from the group consisting of miR-1, 30a-3p, 30e-3p, 133b, 197, 208a, 208b, 302a, 302c, 367, 378, and 499-5p.

58. primers or probes specific for at least two miRNAs selected from the group consisting of miR-Let-7, 10a, 17, 18a, 19a, 19b, 20a, 21, 23a, 24, 27a, 27b, 29a, 31, 34a, 92, 98, 100, 106a, 126, 130a, 143, 145, 146a, 199a-3p, 210, 345, 365, 382, 409-3p, 431, 484, 495, 532-5p, 939, 27a*, 30a*, 93*, 126*, 130b*, and 222*.

59. primers or probes specific for at least two miRNAs selected from the group consisting of miR-Let-7a, Let-7c, 10b, 26a, 100, 125a, 125b, 130a, 140, 143, 145, 195, 196b, 199a, 199b, 204, 214, 222, 424, 517c, and 199a*.

60. primers or probes specific for at least two miRNAs selected from the group consisting of miR-10a, 31, 34b, 34c, 135a, 135b, and 449.

61. primers or probes specific for at least two miRNAs selected from the group consisting of miR-Let-7b, 127, 202, 298, 382, 503, 672, 741, 742, 883-3p, and 202*.

62. primers or probes specific for miR-99a and miR-939.

63. primers or probes specific for at least two miRNAs selected from the group consisting of miR-Let-7g, 101, 134, 186, 197, 218, 320, 497, and 154*.

64. primers or probes specific for at least two miRNAs selected from the group consisting of miR-126, 146, 205, 206, 335, 339-5p, 378, 516-5p, 519c, 520g, 520h, 525, and 1246.

65. primers or probes specific for at least two miRNAs selected from the group consisting of miR-7, 127, and 493*.

66. primers or probes specific for at least two miRNAs selected from the group consisting of miR-Let-7i, 1, 135a, 135b, 206, and 345.

67. primers or probes specific for at least two miRNAs selected from the group consisting of miR-Let-7g, 15a, 26b, 27a, 99b, 124, 132, 134, 137, 139, 152, 181a, 187, 195, 192, 202, 299, 302b, 323, 324-3p, 324-5p, 328, 330-3p, 331, 335, 340, 365, 369-3p, 375, 379, 382, 409-5p, 429, 431, 432, 455-5p, 483-5p, 514, 126*, 182*, and 202*.

68. primers or probes specific for at least two miRNAs selected from the group consisting of miR-9, 21, 130b, 184, 195, 216a, 216b, 217, 376a, 376c, 497, and 939.

69. primers or probes specific for at least two miRNAs selected from the group consisting of miR-15a, 15b, 142-3p, 142-5p, 146, 150, 181a, 181b, 181d, 205, 342, and 423.

70. primers or probes specific for at least two miRNAs selected from the group consisting of miR-126, 139, 155, 223, and 302b.

71. primers or probes specific for at least two miRNAs selected from the group consisting of miR-17-5p, 20b, 106a, 106b, 149, 155, 181c, 182, 183, and 213.

72. primers or probes specific for at least two miRNAs selected from the group consisting of miR-Let-7g, 20b, 21, 106b, 140, 146b, and 431.

73. primers or probes specific for at least two miRNAs selected from the group consisting of miR-Let-7g, 9, 17, 19b, 20a, 31, 106a, 124a, 124b, 128a, 137, 186, 191, 197, 222, 223, 328, 431, 454, 484, 766, 27*, and 223*.

74. primers or probes specific for at least two miRNAs selected from the group consisting of miR-155, 223, and 424.

75. primers or probes specific for at least two miRNAs selected from the group consisting of miR-Let-7 family, 10b, 17-92 family, 21, 29a, 31, 34a,106a,b, 126, 146a,b, 155, 184, 195, 200/141 family, 210, 373, 375, 423-5p, 451, and 486.

76. primers or probes specific for at least two miRNAs selected from the group consisting of miR-21, 31, 34a, 125-5p, 125b, 126, 146a,b, 150, 155, 221, 222, and 223.

77. primers or probes specific for at least two miRNAs selected from the group consisting of miR-270, 373, and 424.

78. (i) primers or probes specific for at least one miRNA selected from the group consisting of miR-128, miR-132, and miR-874, and (ii) primers or probes specific for at least one miRNA selected from the group consisting of miR-9, miR-181a, miR-491-5p, and miR-141.

79. (i) primers or probes specific for at least one miRNA selected from the group consisting of miR-134, miR-323-3p, and miR-382, and (ii) primers or probes specific for at least one miRNA selected from the group consisting of mir-127 and miR-370.

80. (i) primers or probes specific for at least one miRNA selected from the group consisting of miR-34b, miR-486-5p, and miR-192, and (ii) primers or probes specific for at least one miRNA selected from the group consisting of miR-142-5p, miR-146b-5p, miR-155, miR-223, and miR-409-3p.

81. primers or probes specific for miR-34b and miR-155.

82. primers or probes specific for miR-146b-5p and at least one of miR-486b-5p and miR-192.

83. (i) primers or probes specific for at least one miRNA selected from the group consisting of miR-192, miR-194, miR-203, and miR-215, and (ii) primers or probes specific for at least one miRNA selected from the group consisting of miR-30e-3p, miR-145, and miR-148a.

84. (i) primers or probes specific for miR-215 and (ii) primers or probes specific for at least one miRNA selected from the group consisting of miR-30e-3p, miR-194, and miR-203.

85. (i) primers or probes specific for miR-203 and (ii) primers or probes specific for at least one of miR-148a and miR-192.

86. (i) primers or probes specific for miR-194 and (ii) primers or probes specific for at least one of miR-148a and miR192.

87. primers or probes specific for at least one miRNA pair selected from the group consisting of miR-194/miR-145, miR-194/miR148a, miR-194/miR-30e-3p, miR-215/miR-203, miR-203/miR-30e-3p, miR-203/miR148a, miR-192/miR-145, miR-192/miR148a, and miR-192/miR-30e-3p.

88. primers or probes specific for at least one miRNA pair selected from the group consisting of miR-192/miR-126, miR-155/miR-126, miR-145/miR-126, miR-155/miR-3 0e-3p, miR-192/miR-30e-3p, miR-155/miR-409-3p, miR-486-5p/miR-17-5p, miR-155/miR-17-5p, miR-192/miR-17-5p, miR-146b-5p/miR-31, miR-155/miR-31, miR-192/miR-31, miR-486-5p/miR-155, miR-192/miR-155, miR-145/miR-155, miR-146b-5p/miR-155, miR-486-5p/miR-203, miR-192/miR-203, miR-145/miR-203, miR-192/miR-215, and miR-155/miR-215.

89. primers or probes specific for at least one miRNA pair selected from the group consisting of miR-17-5p/miR-155, miR-192/miR-155, miR-215/miR-155, miR-192/miR-30e-3p, miR-155/miR-30e-3p, and miR-146b-5p/miR-30e-3p.

Kits of the invention can further comprise miRNA isolation or purification means. Kits of the invention can further comprise instructions for use.

BRIEF DESCRIPTION OF THE DRAWINGS

FIGS. 4A-G are graphs showing comparison of miRNA concentrations in plasma of MCI and AD patients and age-matched controls. Concentrations of miR-7 (A), miR-128 (B), miR-132 (C), miR-134 (D), miR-323-3p (E), miR-382 (F), and miR-874 (G) were normalized per miR-181a.

DETAILED DESCRIPTION OF THE INVENTION

Figure 1A:
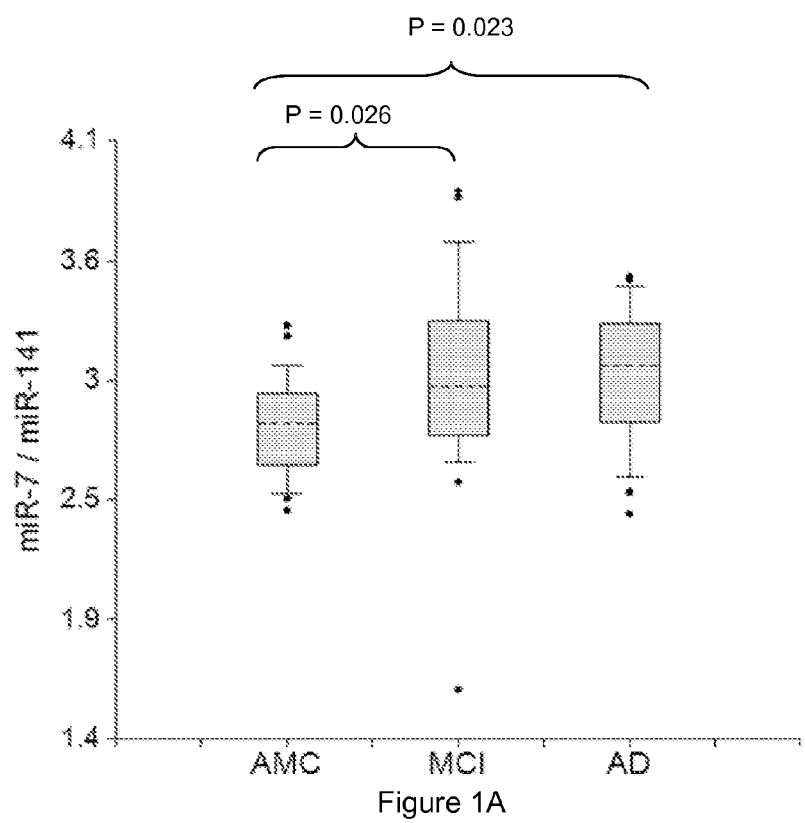
FIGS. 1A-C are graphs showing comparison of miRNA concentrations in plasma of MCI (MCI) and AD patients (AD) and age-matched controls (AMC). Concentrations of miR-7 (A), miR-132 (B), miR-874 (C) were normalized per miR-141. Here and in other box and whisker plots, the box indicates the distribution of 50% of the results and the bar above and below the box indicates 80% of the results. The points indicate assay values located outside of 80% data. Median value of the assays is indicated by the line inside the box. Normalized miRNA concentrations are presented on ordinate axis in relative units (log scale).
Figure 1B:
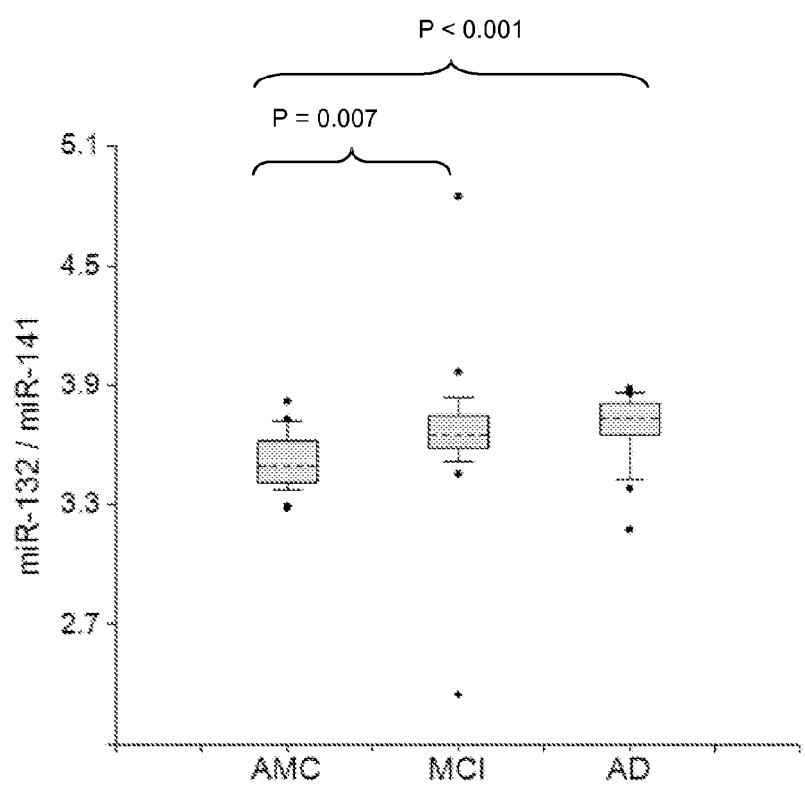
Figure 1C:
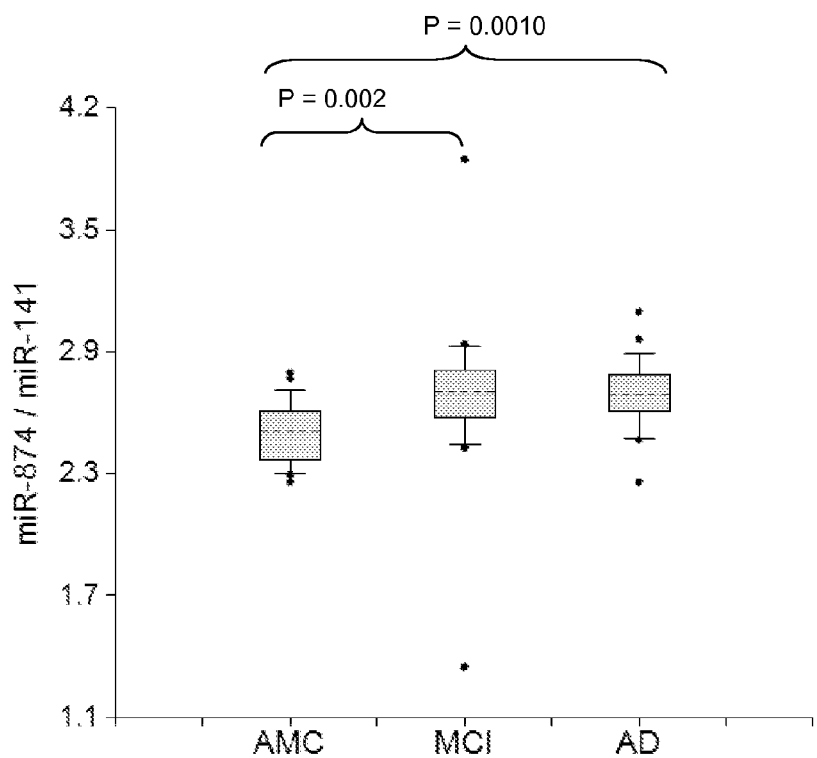
Figure 2A:
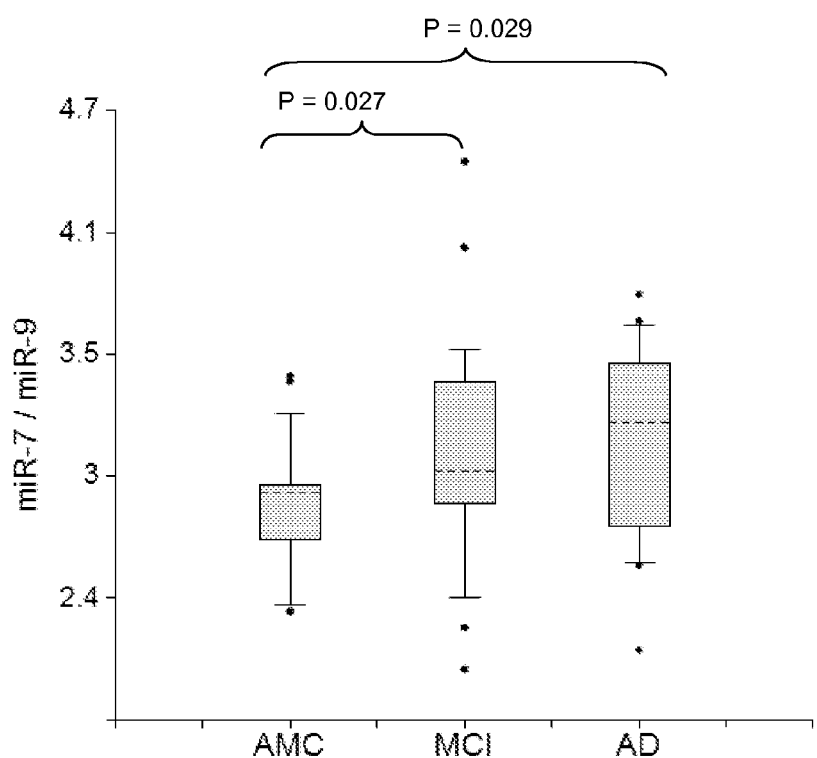
FIGS. 2A-E are graphs showing comparison of miRNA concentrations in plasma of MCI and AD patients (AD) age-matched controls. Concentrations of miR-7 (A), miR-128 (B), miR-132 (C), miR-382 (D), miR-874 (E) were normalized per miR-9.
Figure 2B:
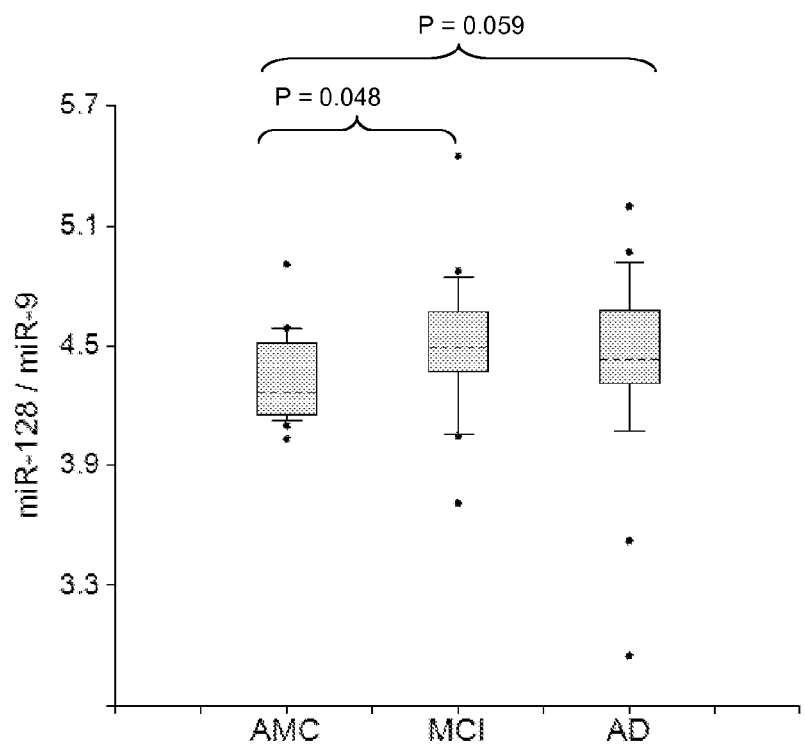
Figure 2C:
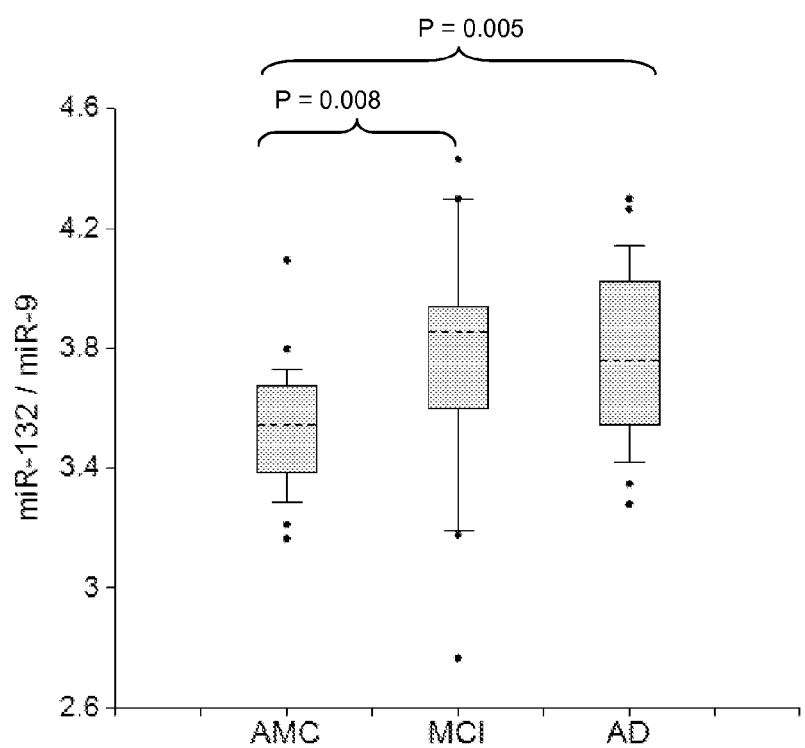
Figure 2D:
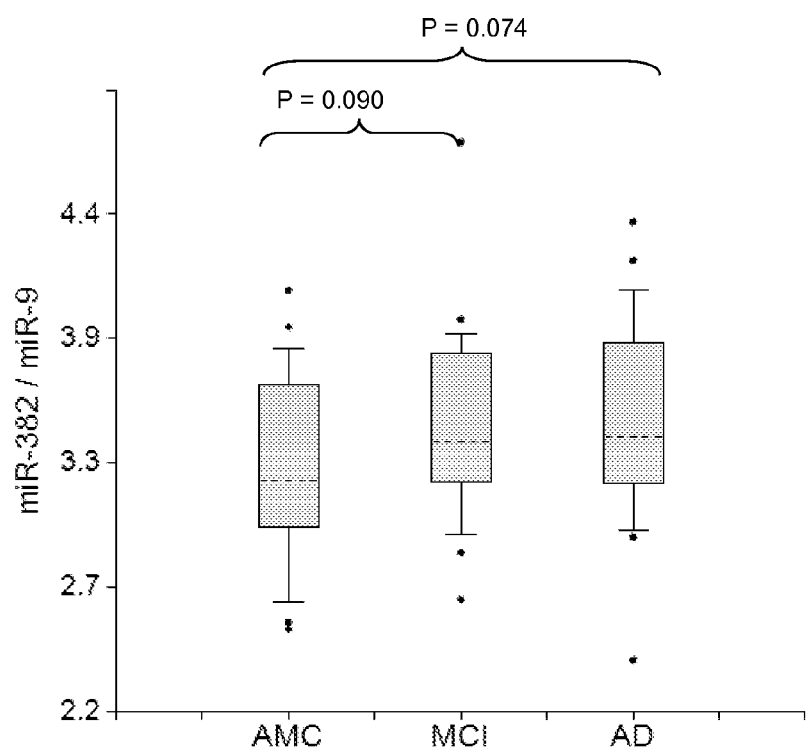
Figure 2E:
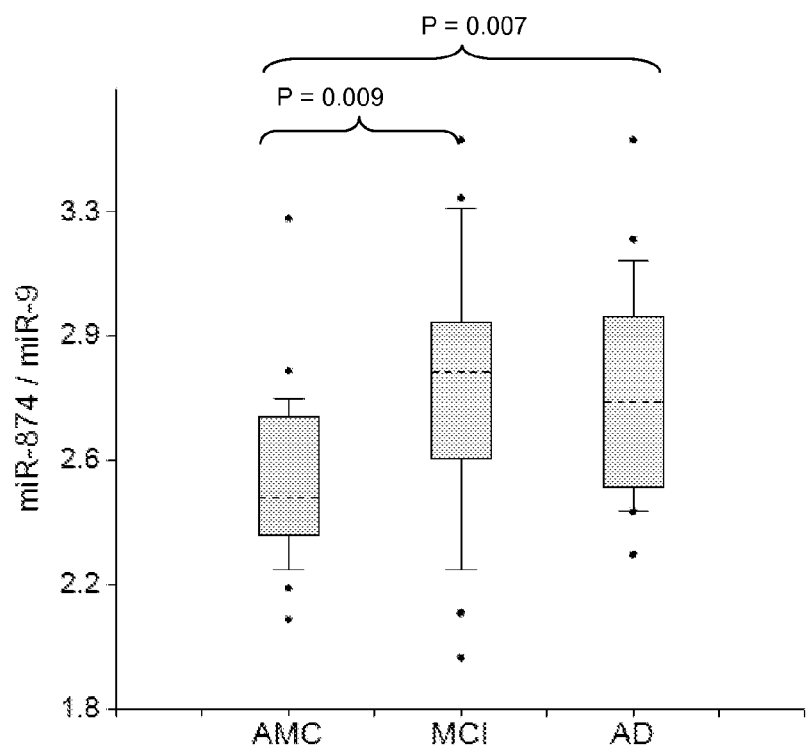
Figure 3A:
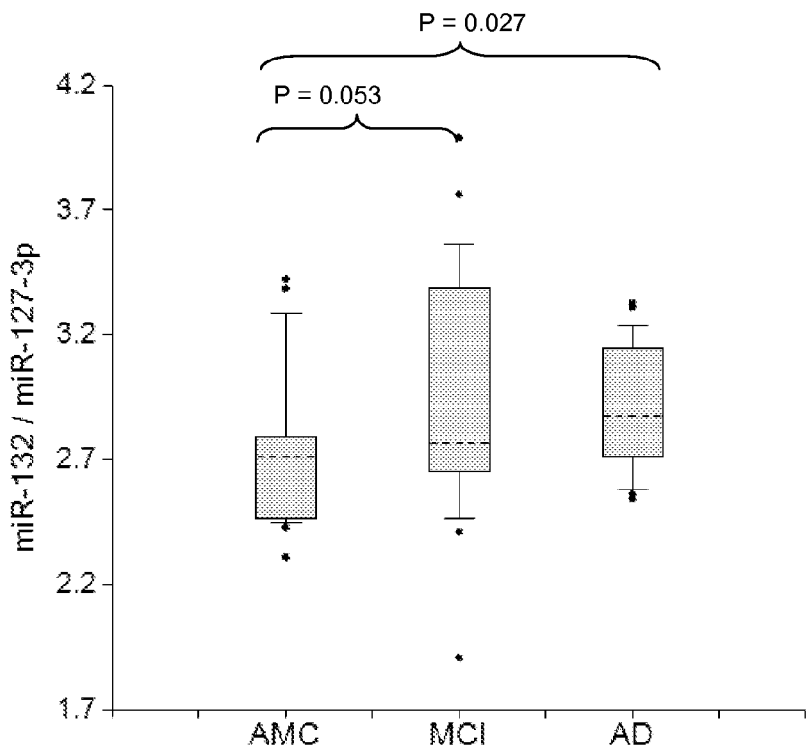
FIGS. 3A-E are graphs showing comparison of miRNA concentrations in plasma of MCI and AD patients and age-matched controls. Concentrations of miR-132 (A), miR-134 (B), miR-323-3p (C), miR-382 (D) and miR-874 (E) were normalized per miR-127-3p.
Figure 3B:
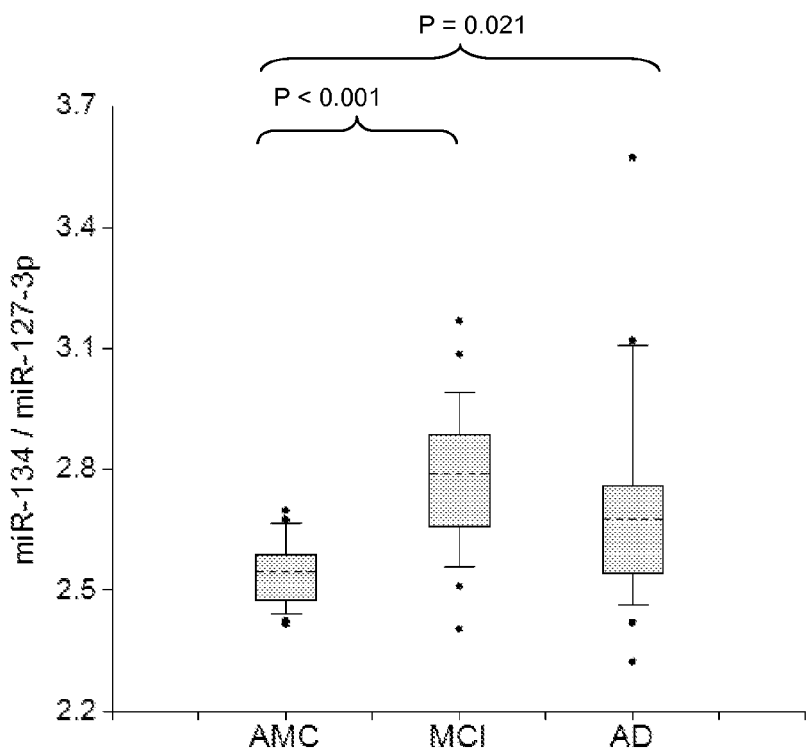
Figure 3C:
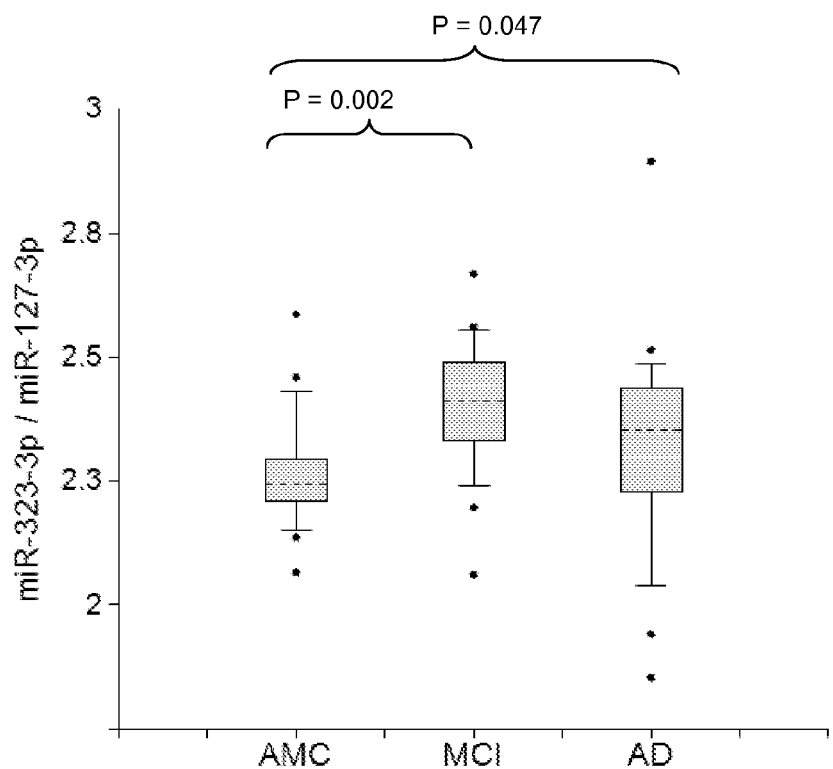
Figure 3D:
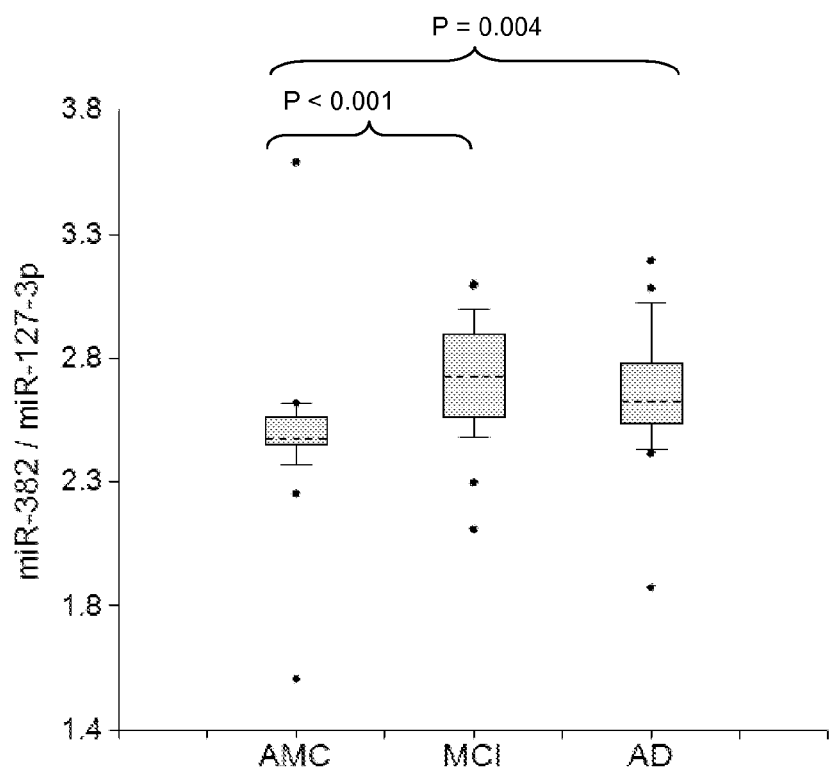
Figure 3E:
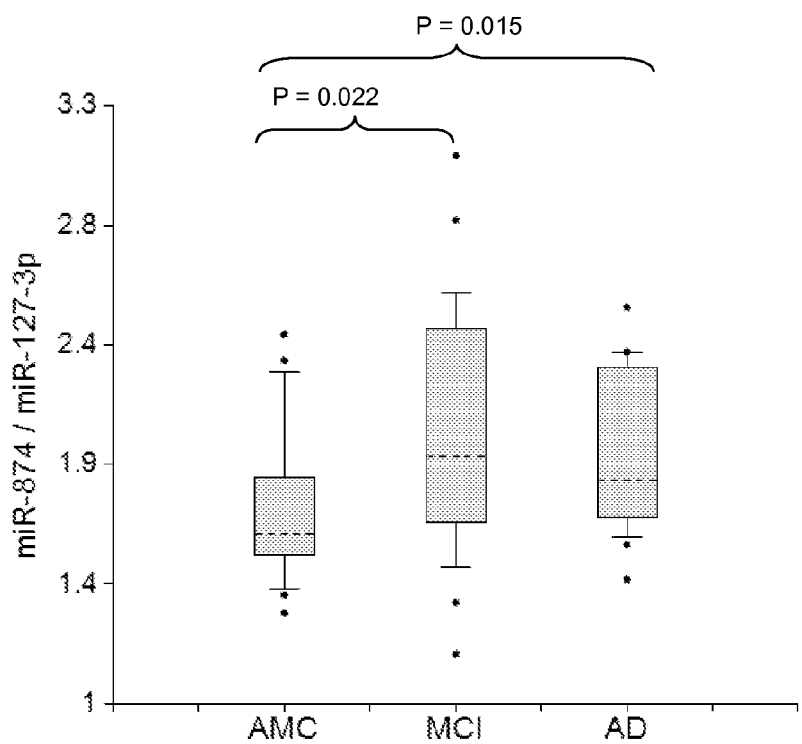
Figure 4A:
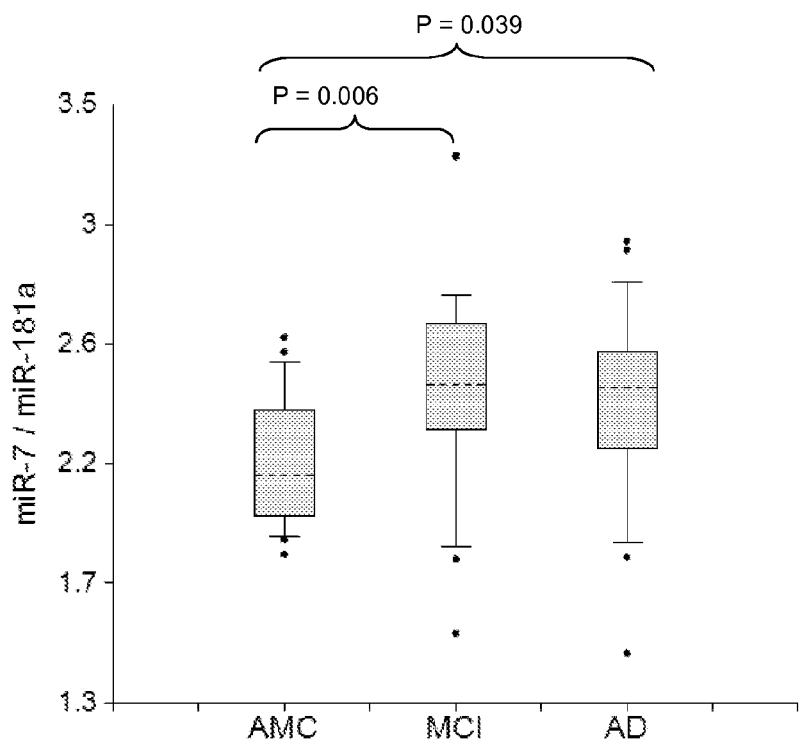
Figure 4B:
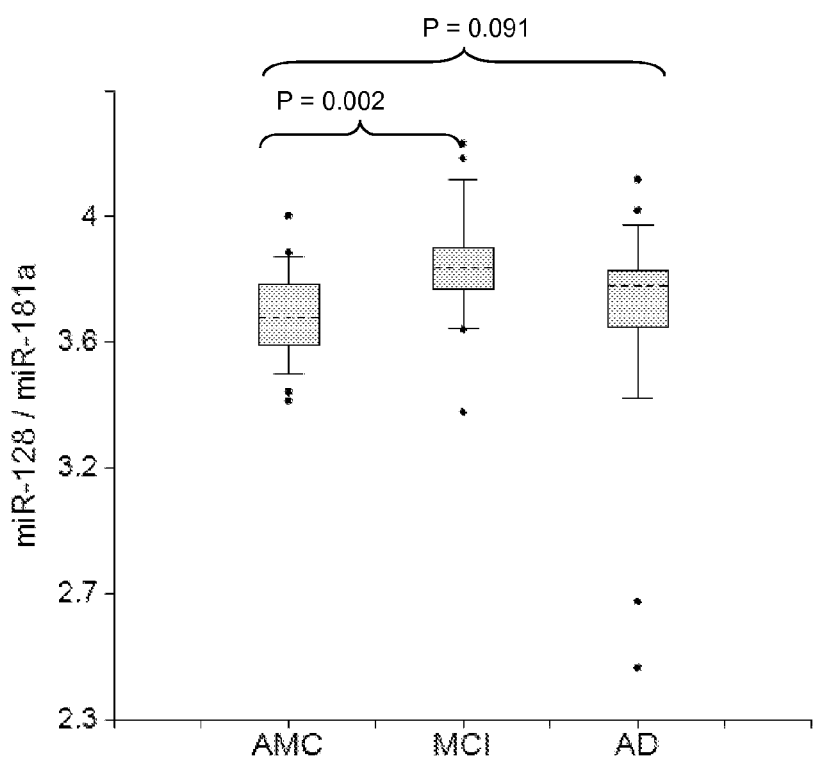
Figure 4C:
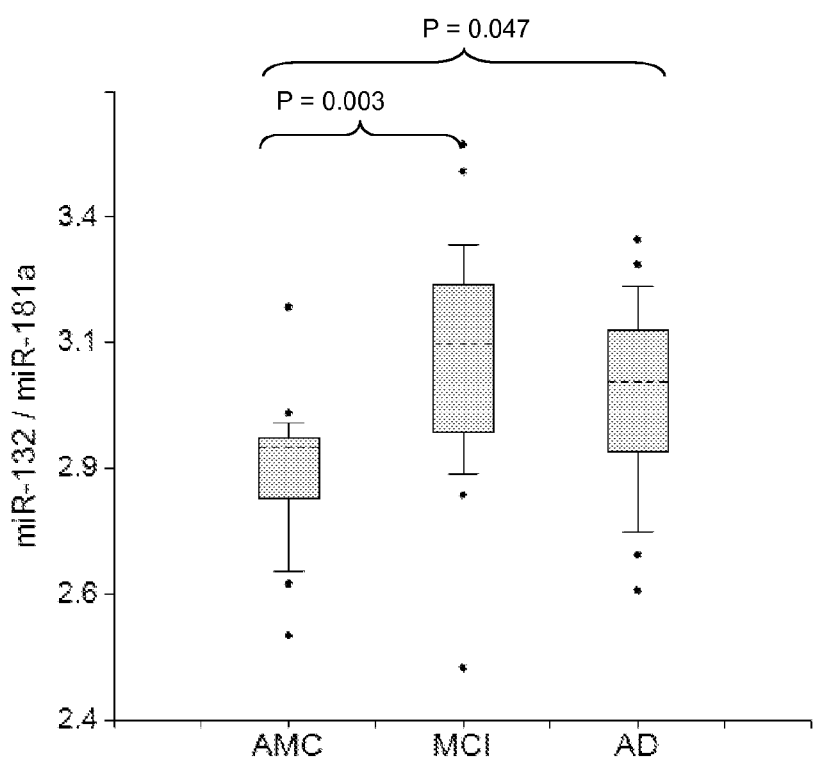
Figure 4D:
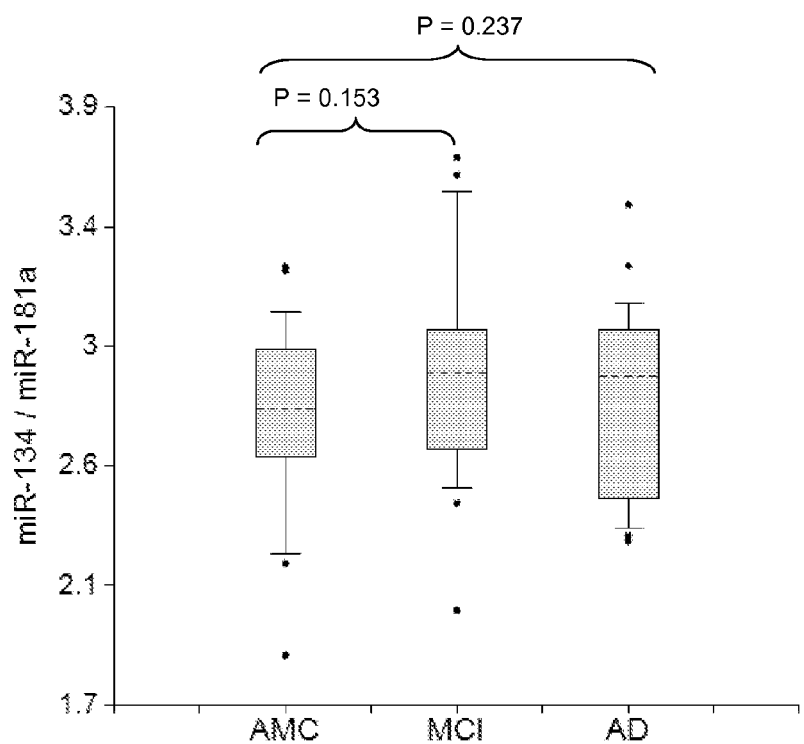
Figure 4E:
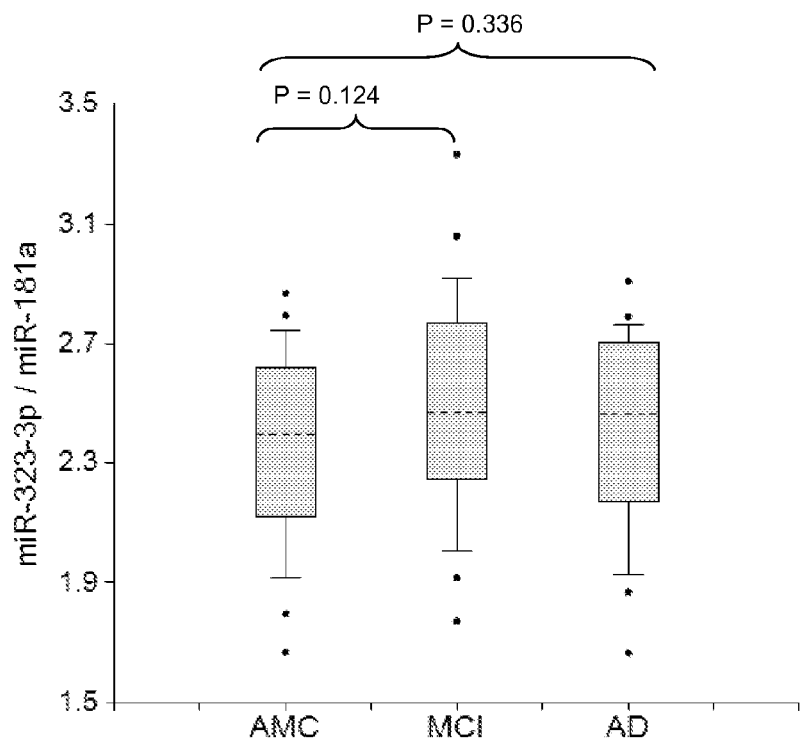
Figure 4F:
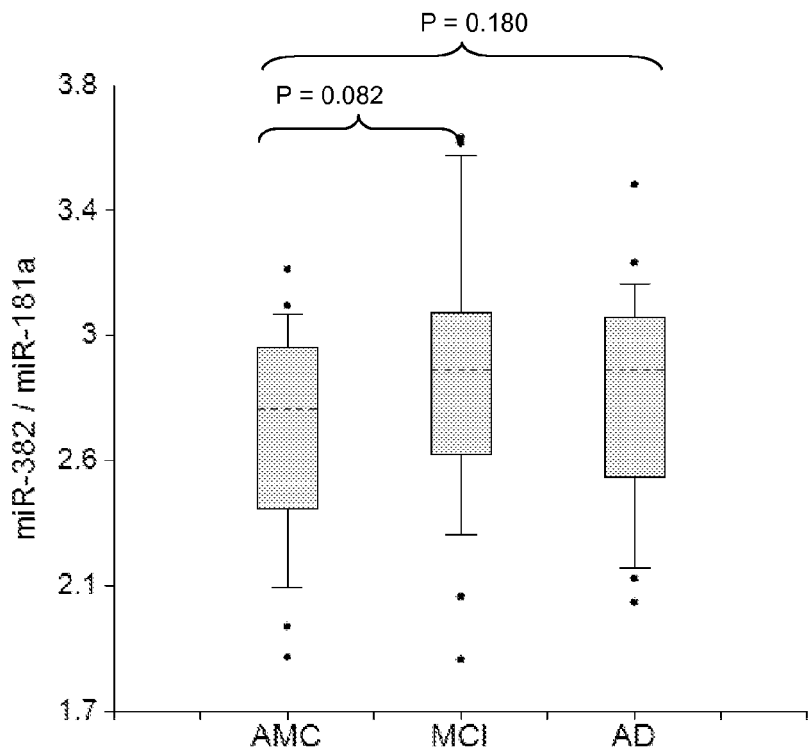
Figure 4G:
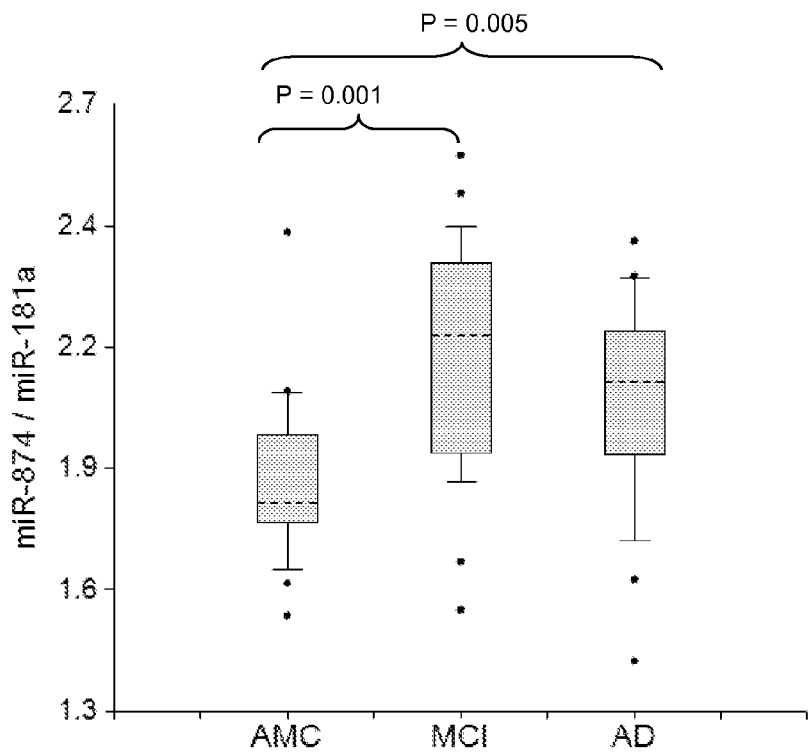
Figure 5A:
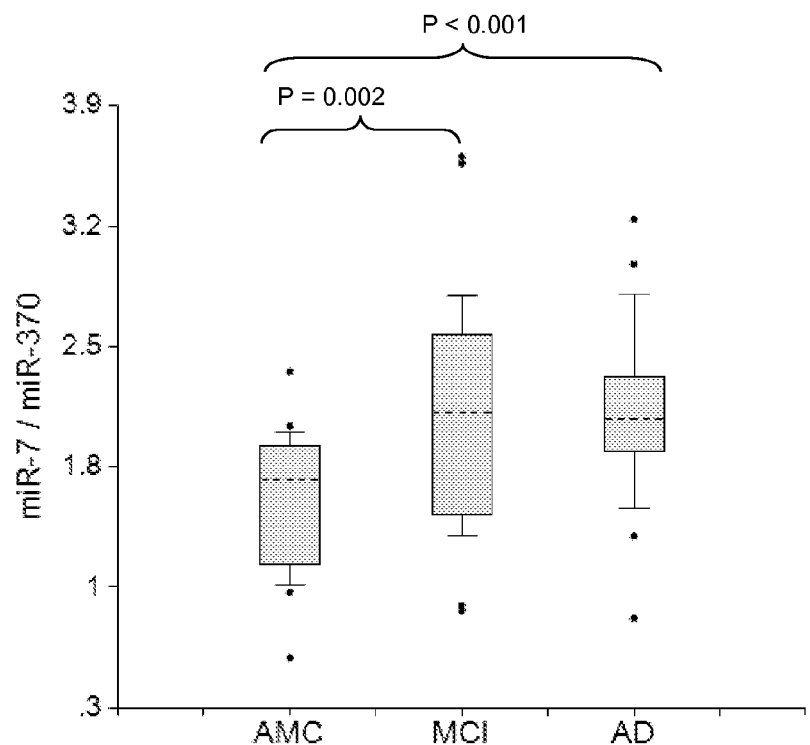
FIGS. 5A-H are graphs showing comparison of miRNA concentrations in plasma of MCI and AD patients and age-matched controls. Concentrations of miR-7 (A), miR-125 (B), miR-128 (C), miR-132 (D), miR-134 (E), miR-323-3p (F), miR-382 (G), and miR-874 (H) were normalized per miR-370.
Figure 5B:
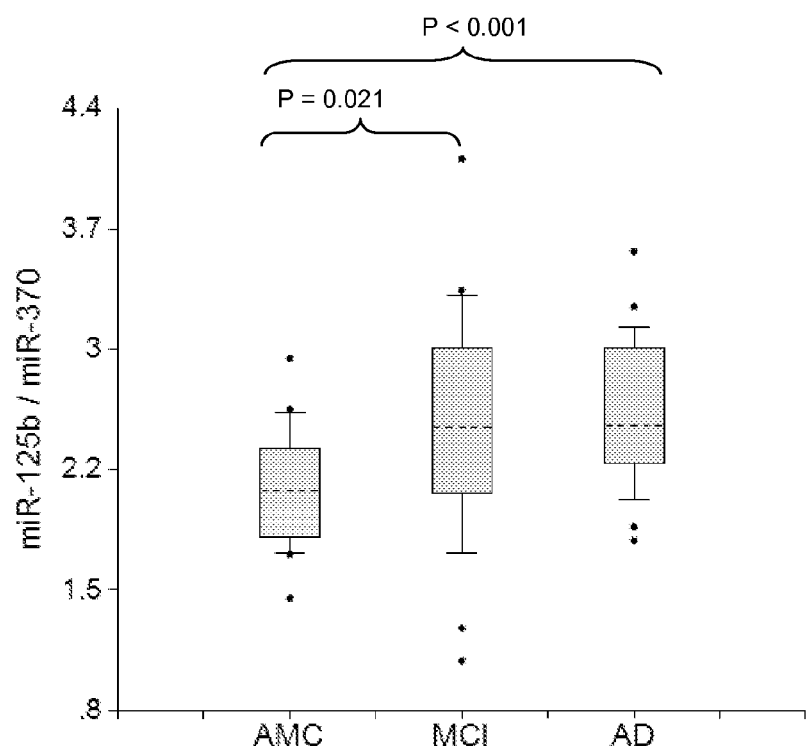
Figure 5C:
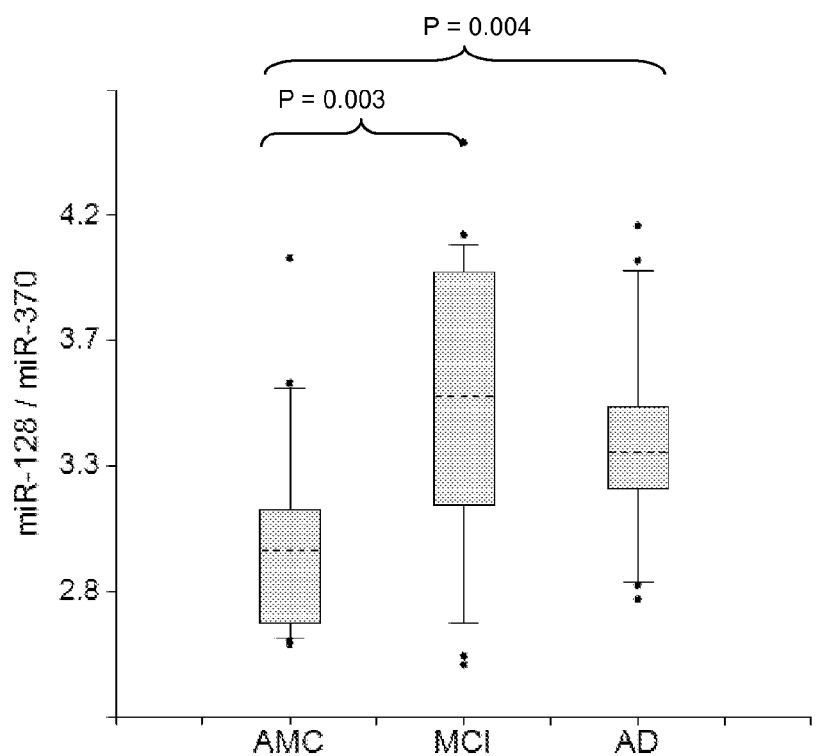
Figure 5D:
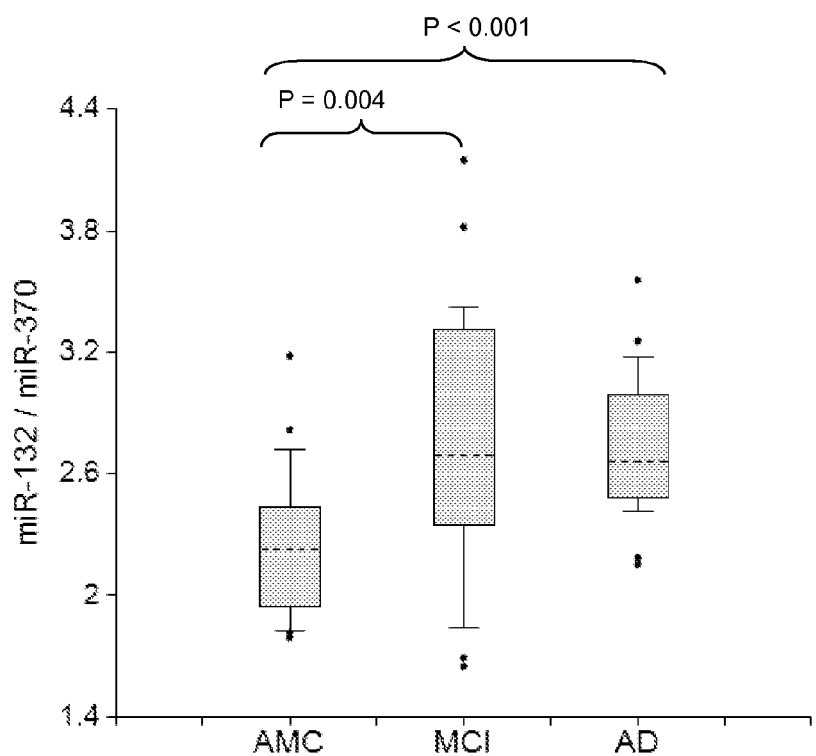
Figure 5E:
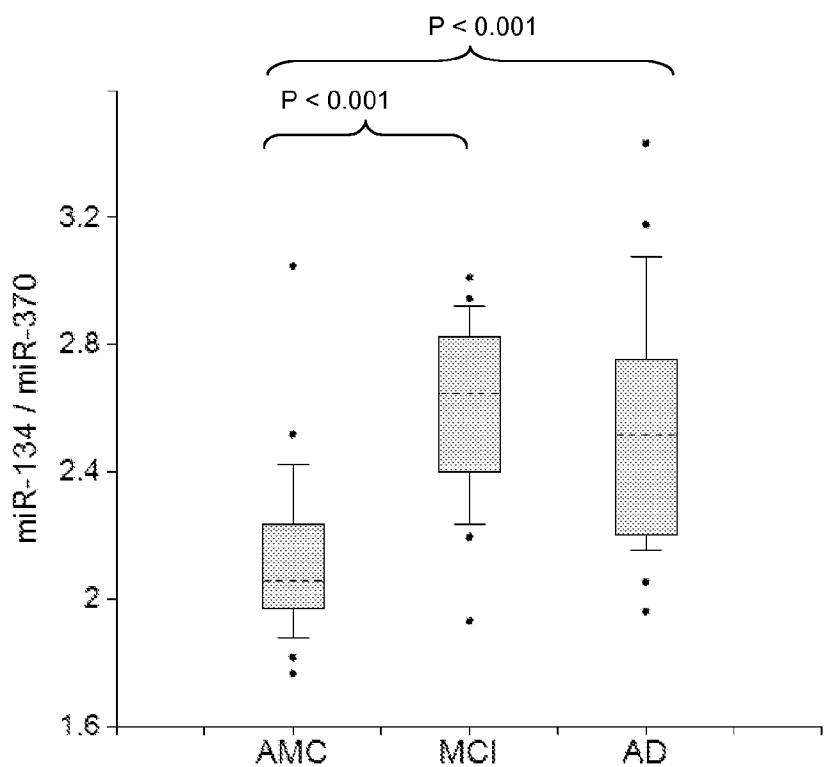
Figure 5F:
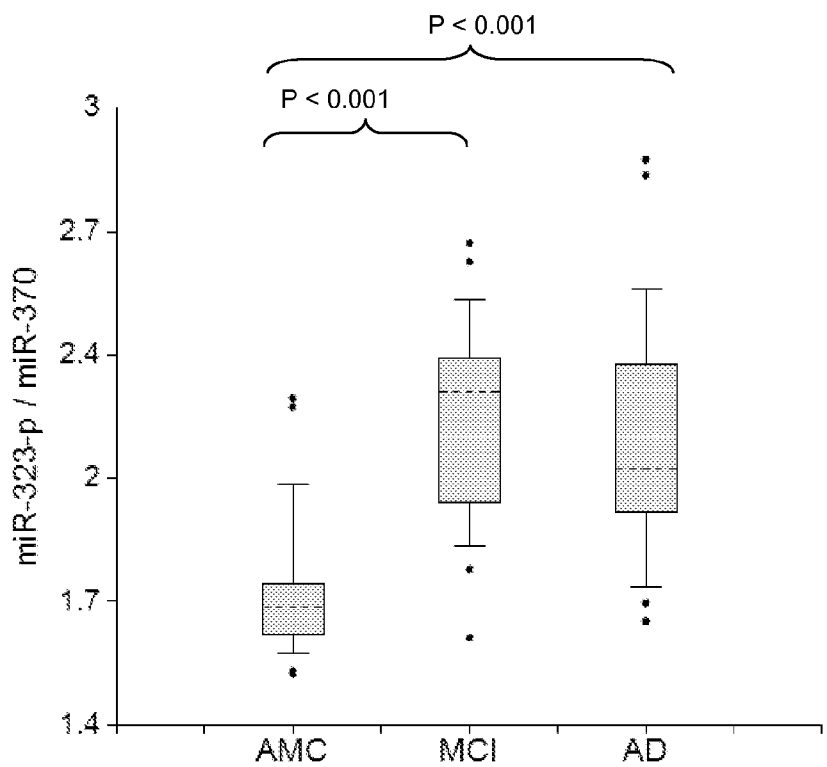
Figure 5G:
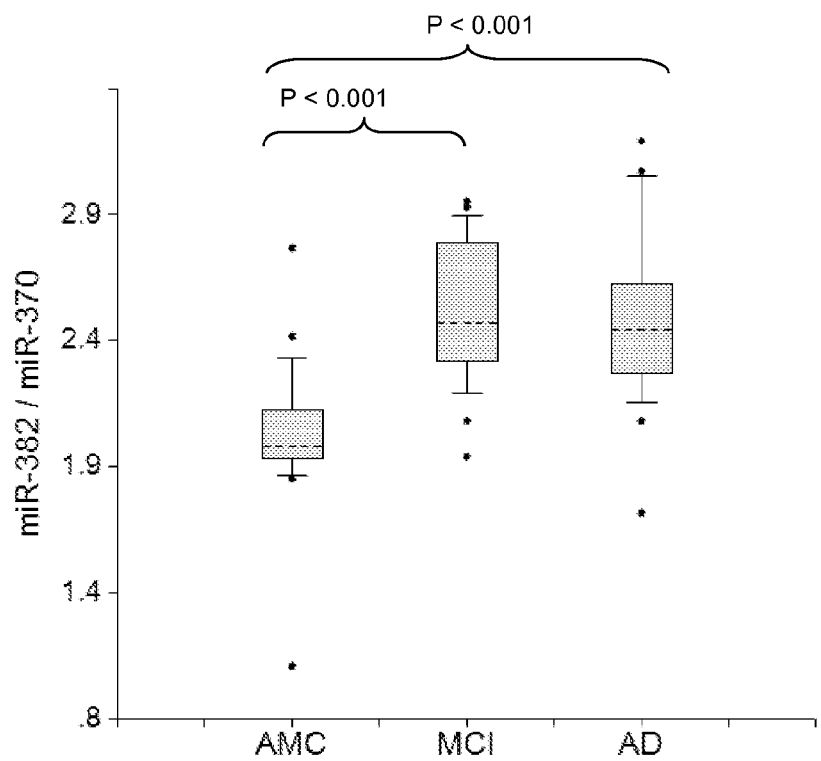
Figure 5H:
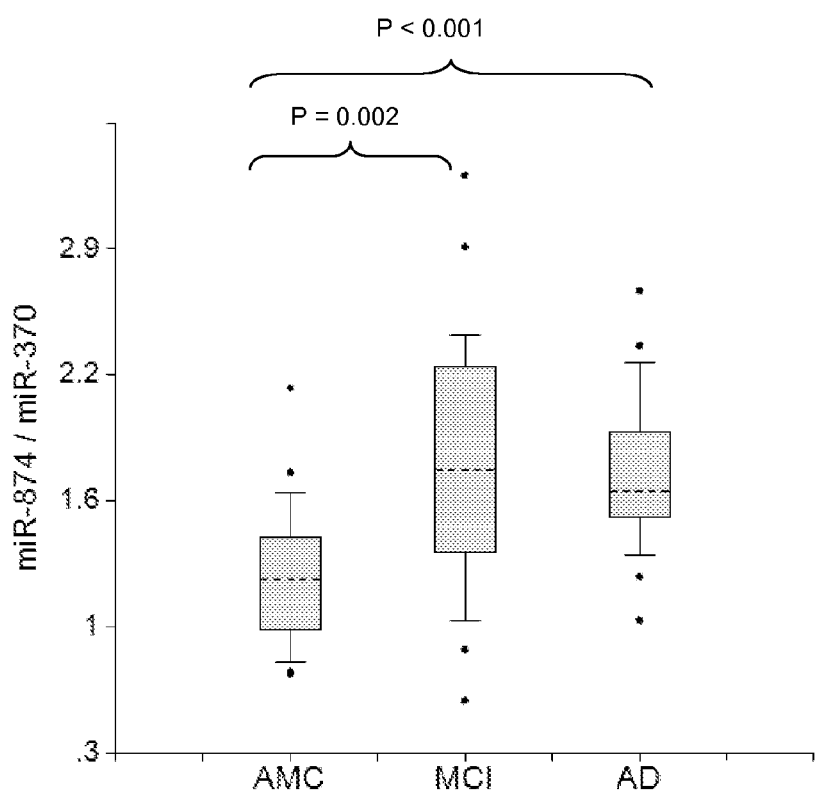
Figure 6A:
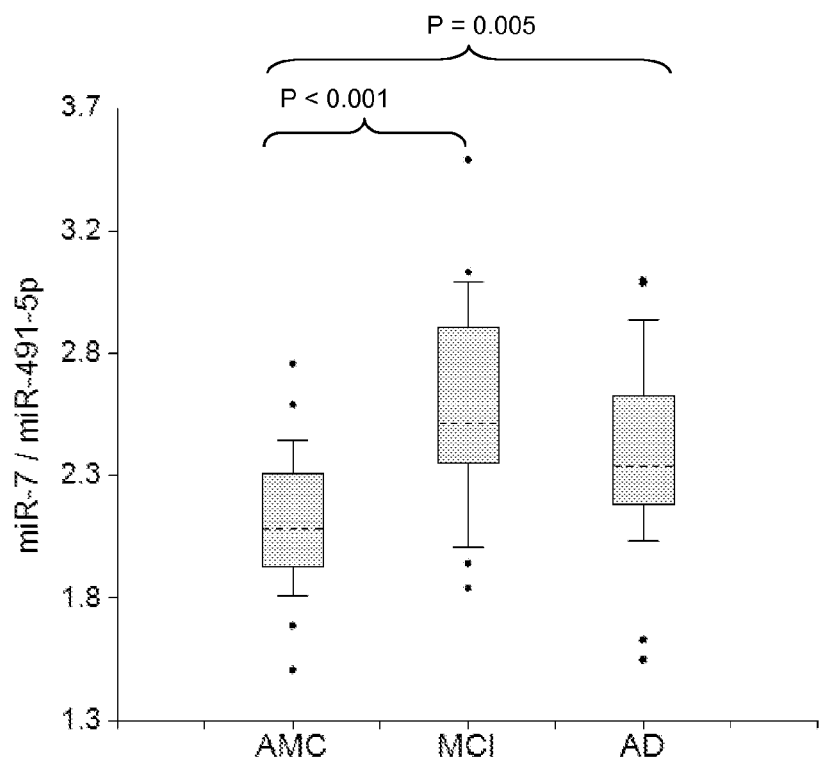
FIGS. 6A-H are graphs showing comparison of miRNA concentrations in plasma of MCI and AD patients and age-matched controls. Concentrations of miR-7 (A), miR-125 (B), miR-128 (C), miR-132 (D), miR-134 (E), miR-323-3p (F), miR-382 (G), and miR-874 (H) were normalized per miR-491-5p.
Figure 6B:
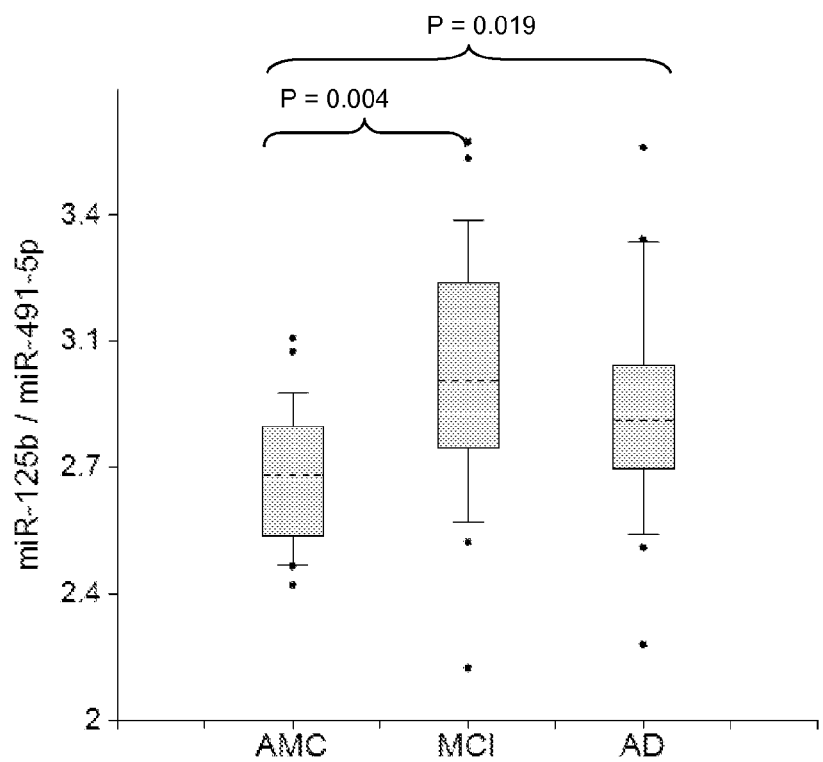
Figure 6C:
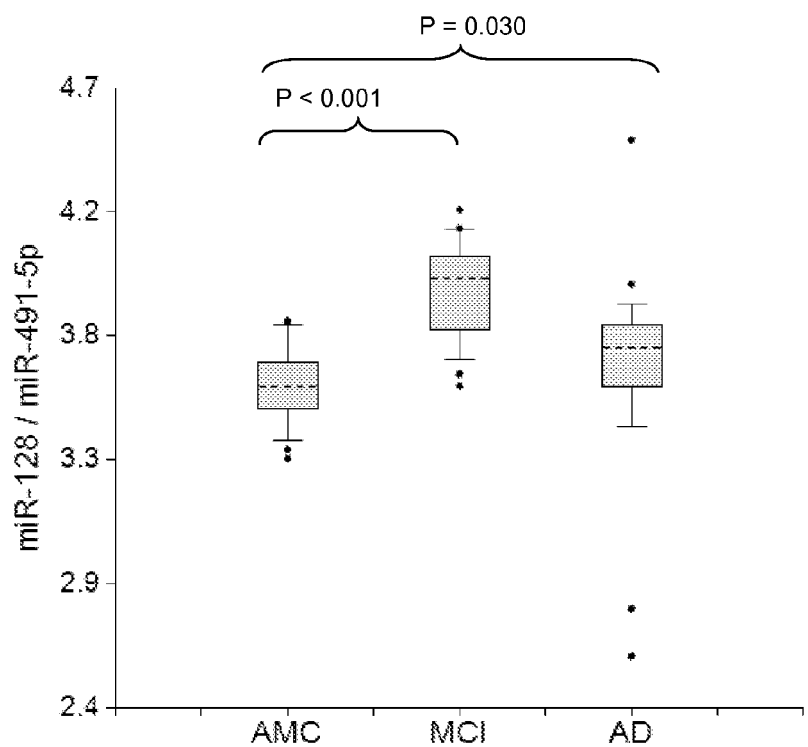
Figure 6D:
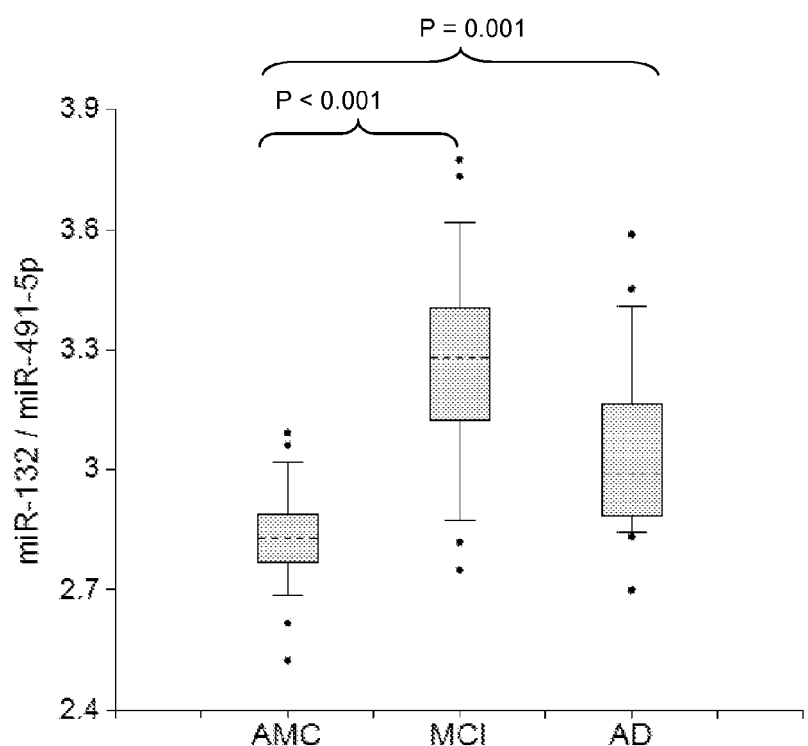
Figure 6E:
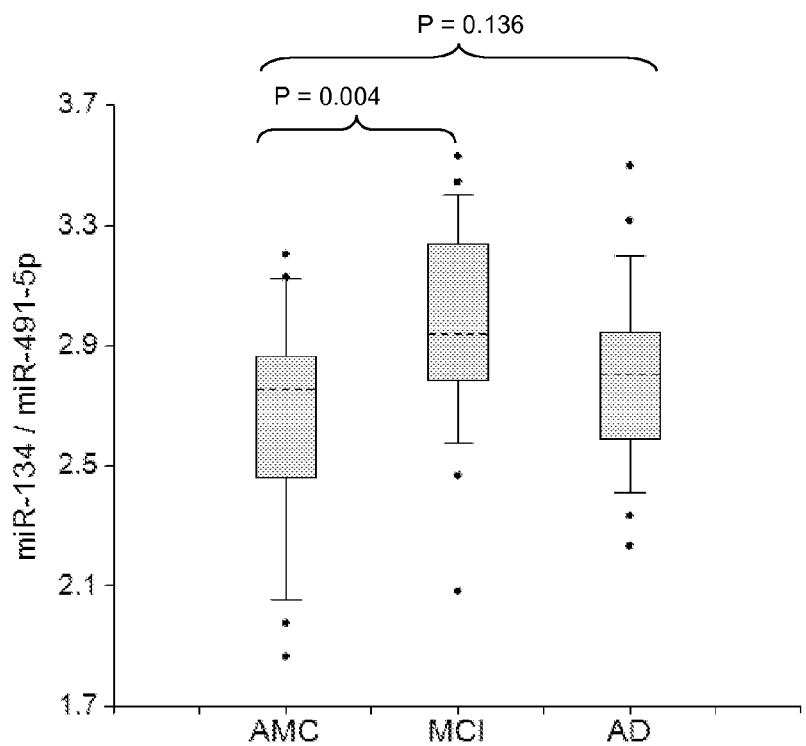
Figure 6F:
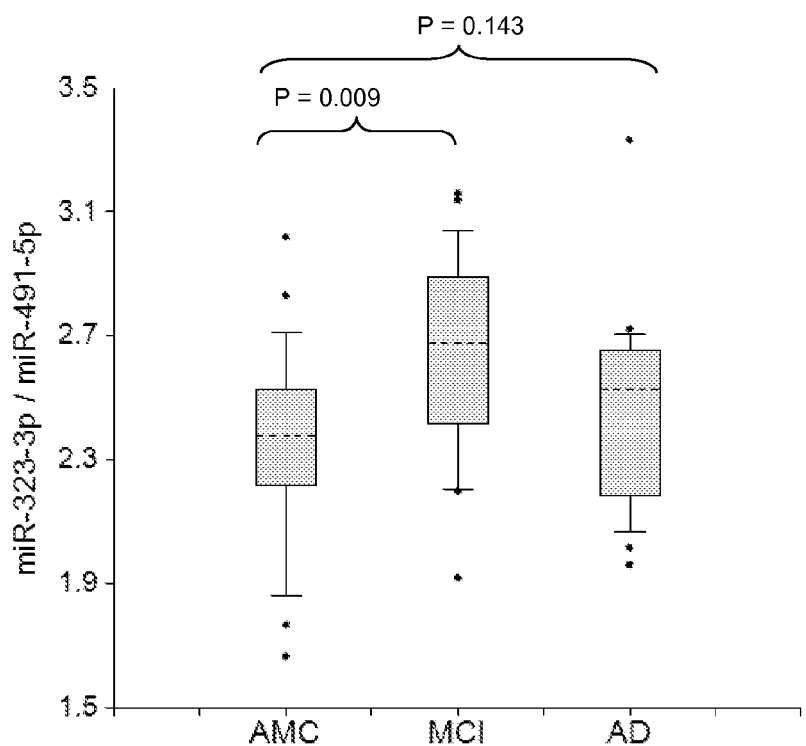
Figure 6G:
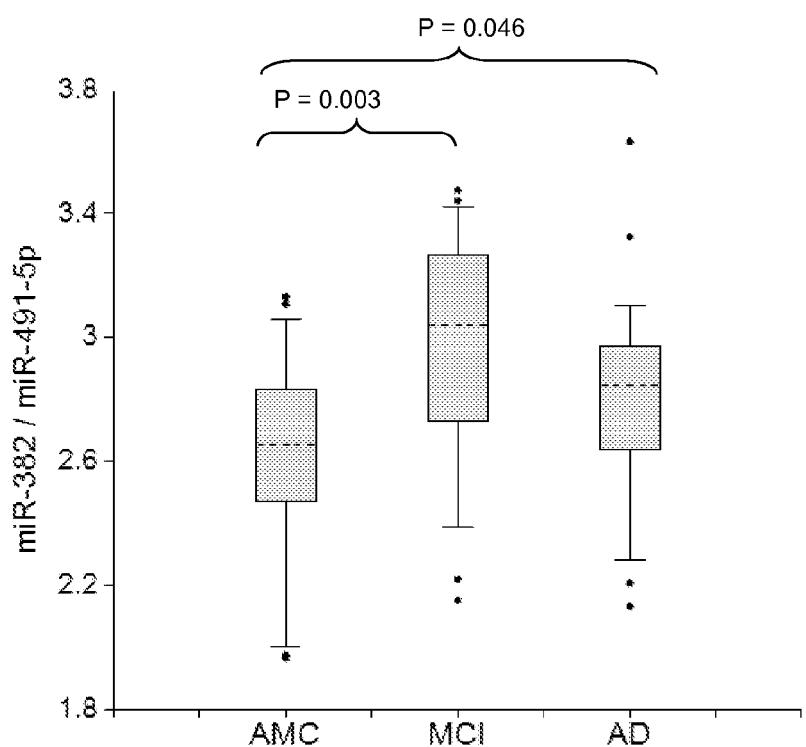
Figure 6H:
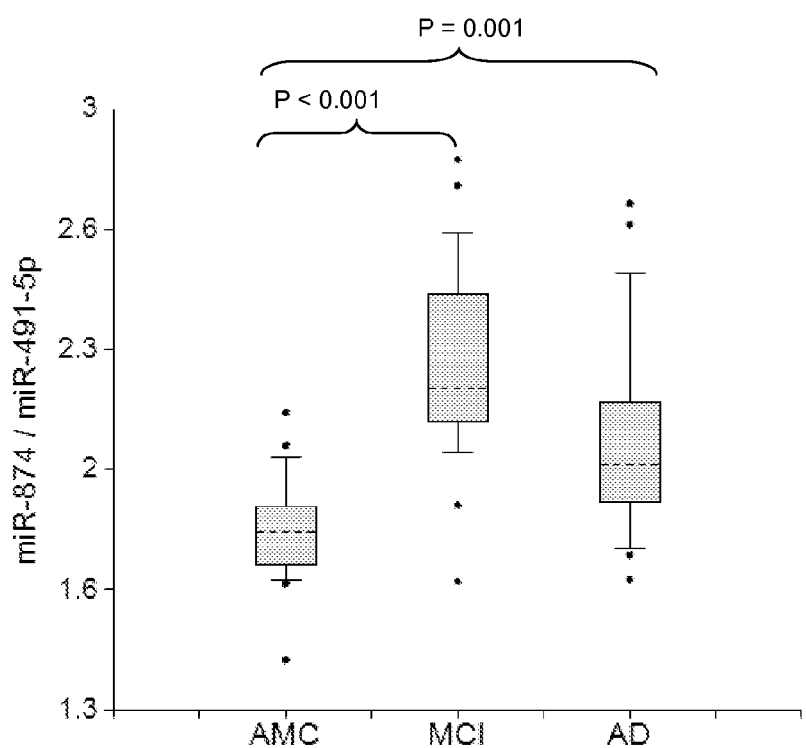
Figure 7A:
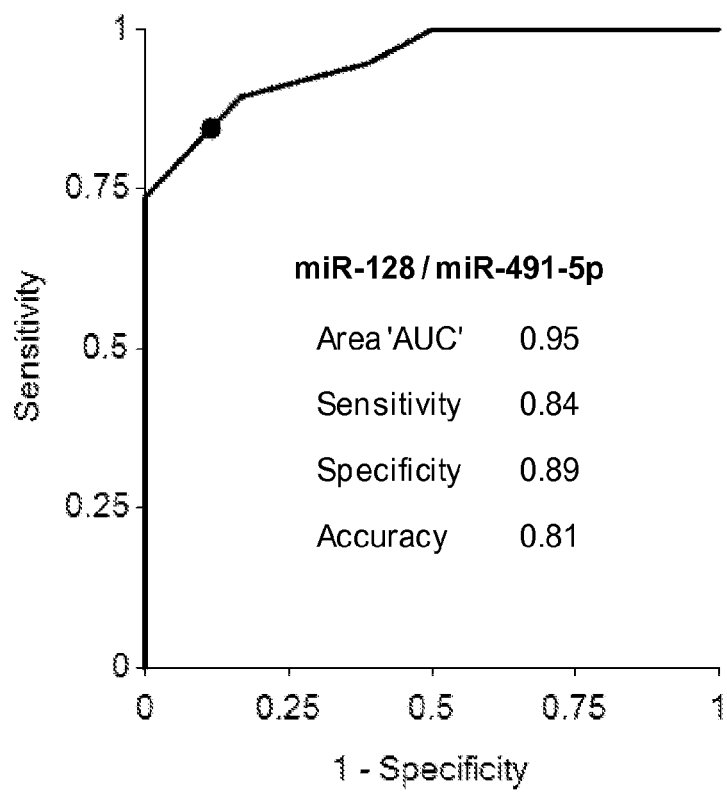
FIGS. 7A-C present Receiver-Operating Characteristic (ROC) curve analysis of differentiation between MCI patients (MCI) and age-matched controls (AMC) obtained with miR-128 (A), miR-132 (B) and miR-874 (C) normalized per miR-491-5p. The areas under the ROC curve (AUC) are reported. Sensitivity, specificity and accuracy for each biomarker/normalizer pair are calculated for the "cut-off" point (indicated as a dot on each plot); the cutoff point is the biomarker/normalizer ratio, at which a sample is equally likely to belong to the AMC or the MCI groups.
Figure 7B:
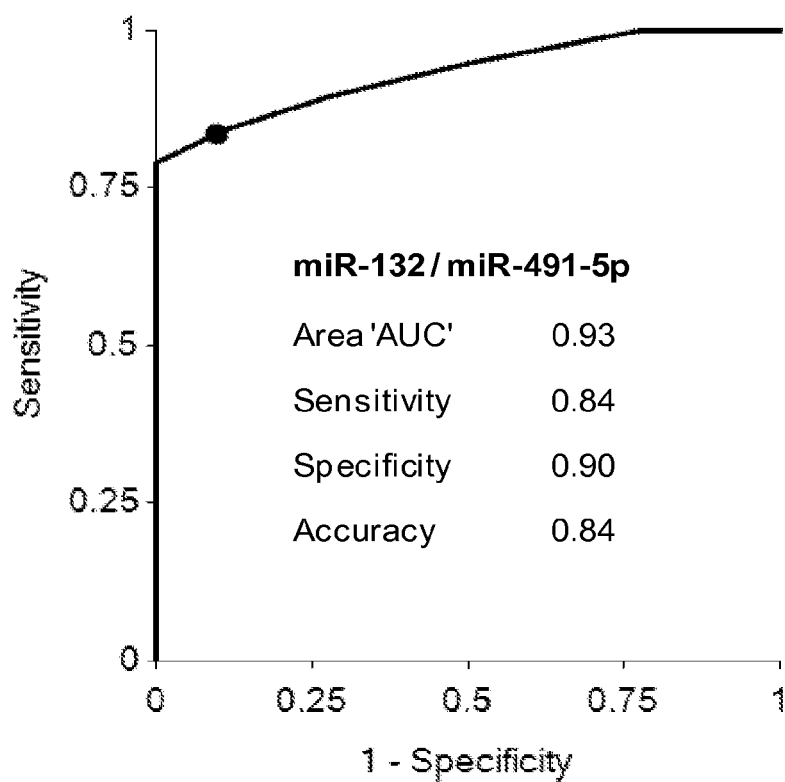
Figure 7C:
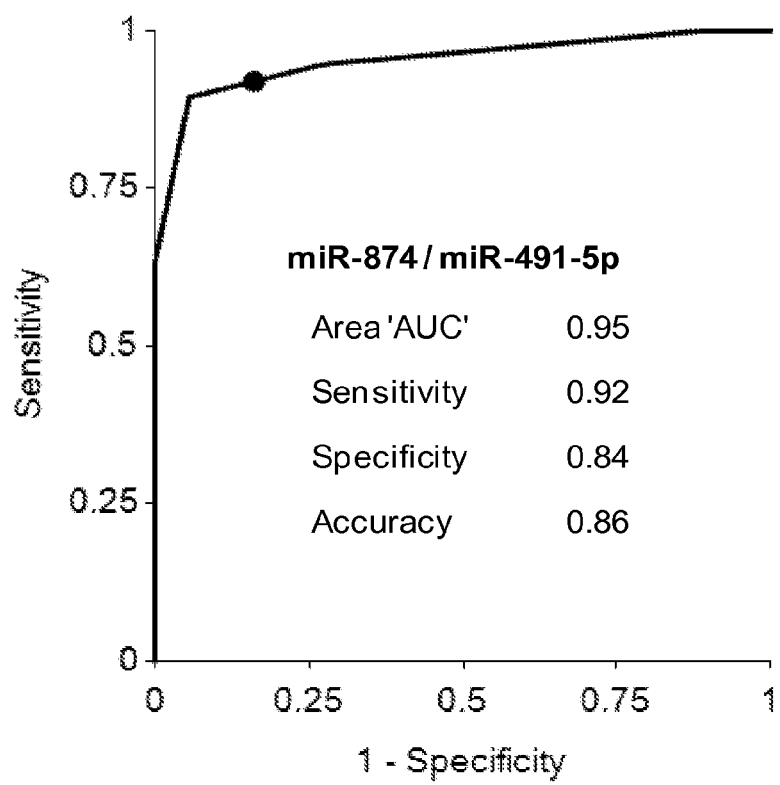
Figure 8A:
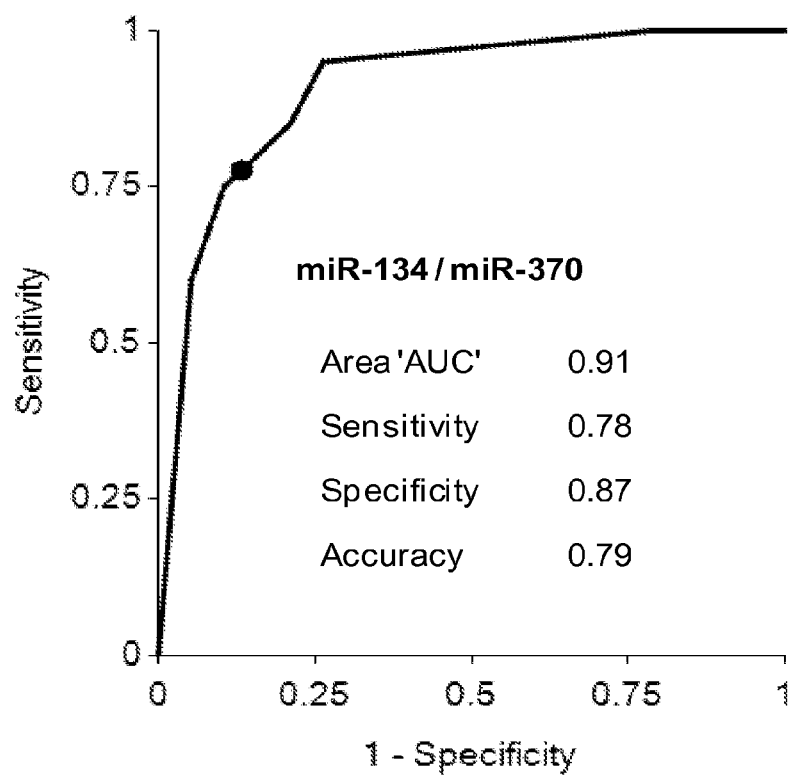
FIGS. 8A-C present Receiver-Operating Characteristic (ROC) curve analysis of differentiation between MCI patients (MCI) and age-matched controls (AMC) obtained with miR-134 (A), miR-323-3p (B) and miR-382 (C) normalized per miR-370. The areas under the ROC curve (AUC) are reported. Sensitivity, specificity and accuracy for each biomarker/normalizer pair are calculated for the "cut-off" point (indicated as a dot on each plot); the cutoff point is the biomarker/normalizer ratio, at which a sample is equally likely to belong to the AMC or the MCI groups.
Figure 8B:
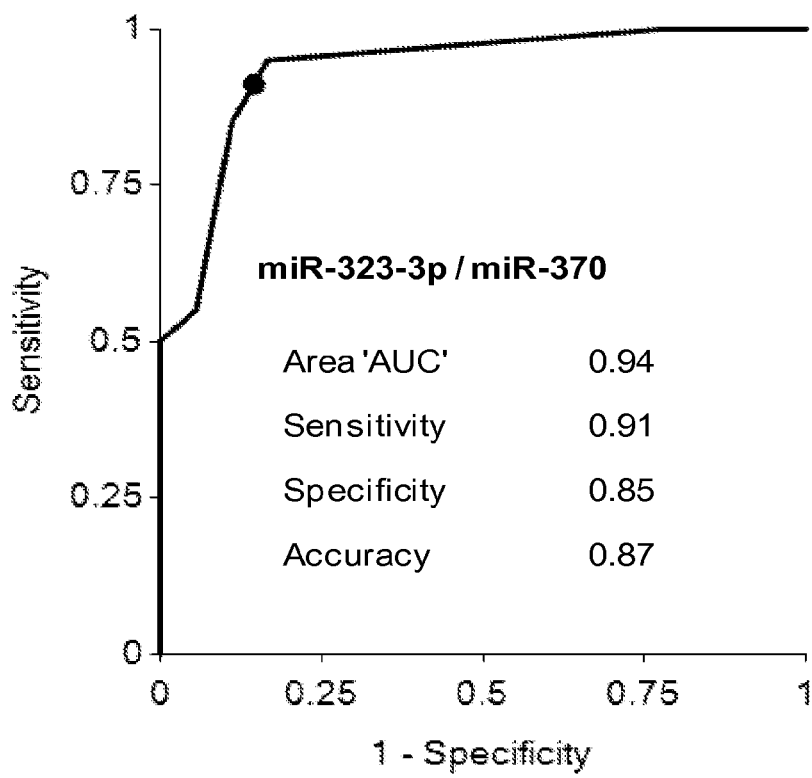
Figure 8C:
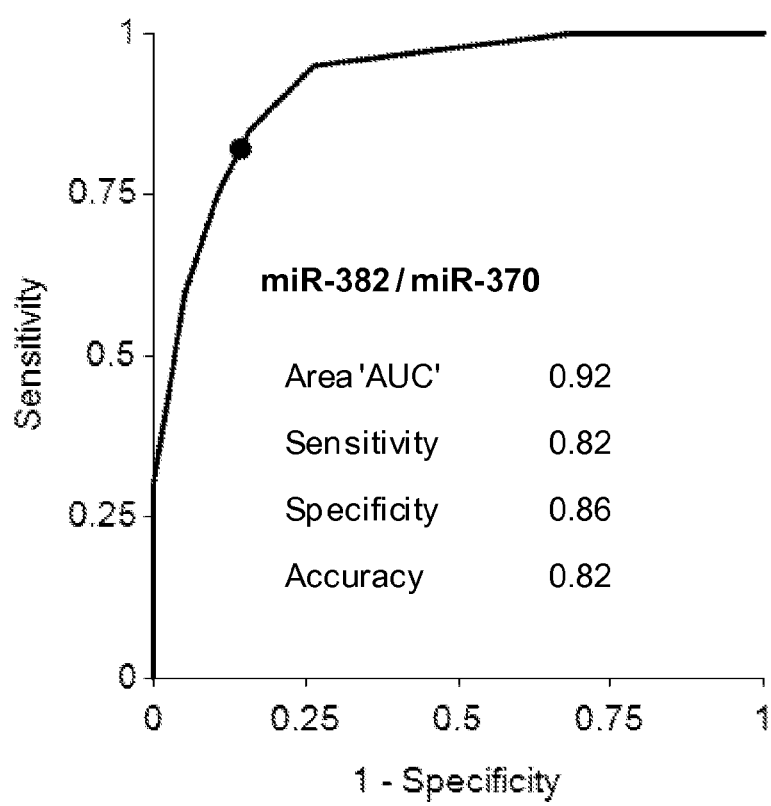
Figures 9A, 9B:
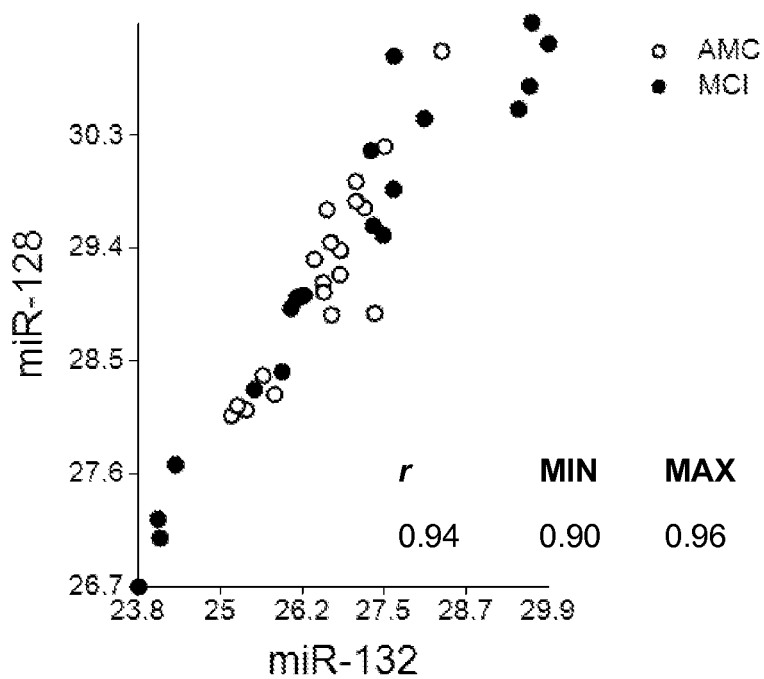
FIGS. 9A-F present analysis of associations between miR-128 and miR-132 (A), miR-128 and miR-874 (B), miR-132 and miR-874 (C), miR-134 and miR-323-3p (D), miR-134 and miR-382 (E), and miR-382 and miR-323-3p (F). The Ct values of various biomarker pairs were compared and Spearman's rank correlation coefficients r along with 95% confidence intervals (MIN & MAX) were calculated.
Figure 9C:
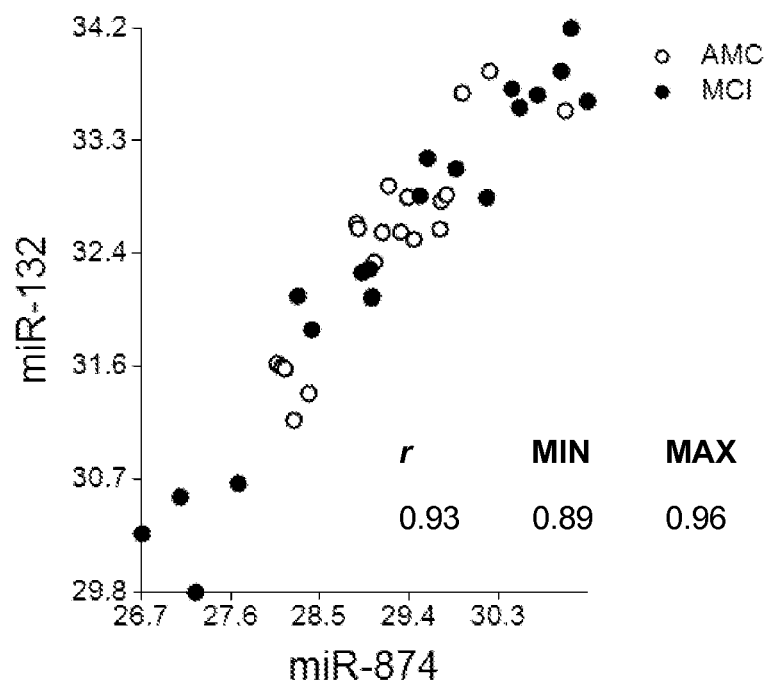
Figure 9D:
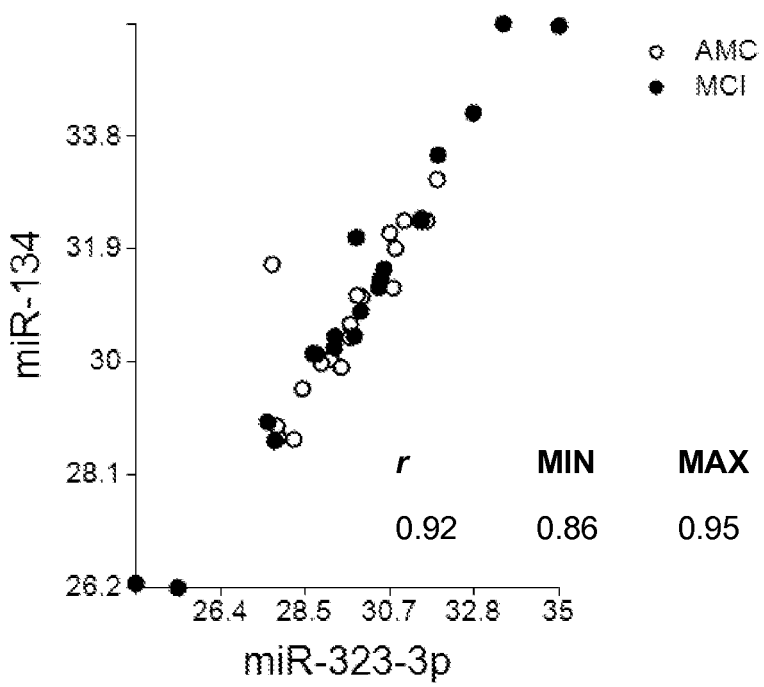
Figure 9E:
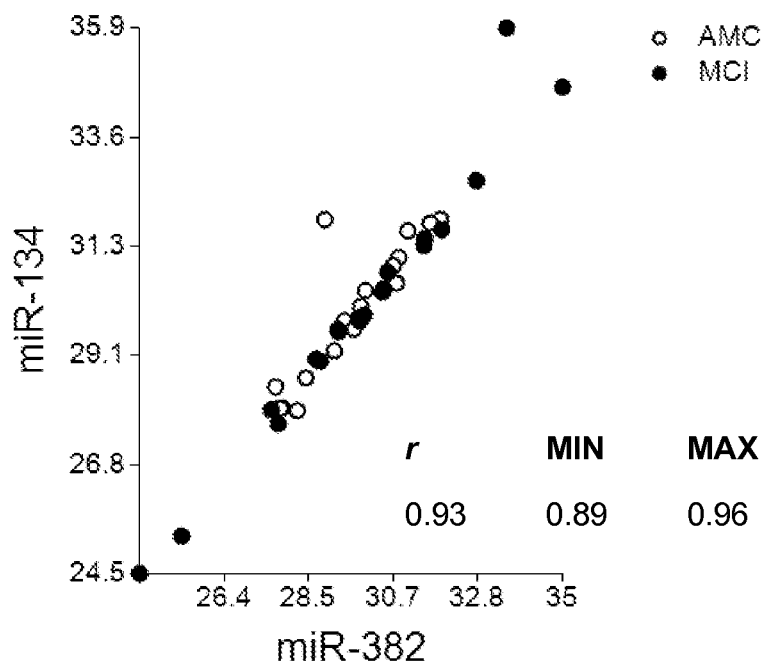
Figure 9F:
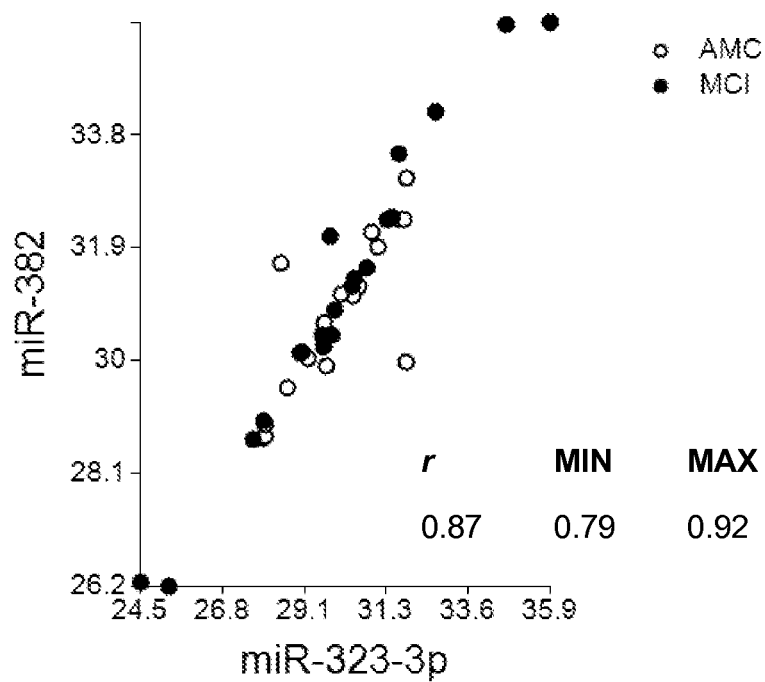
Figure 10A:
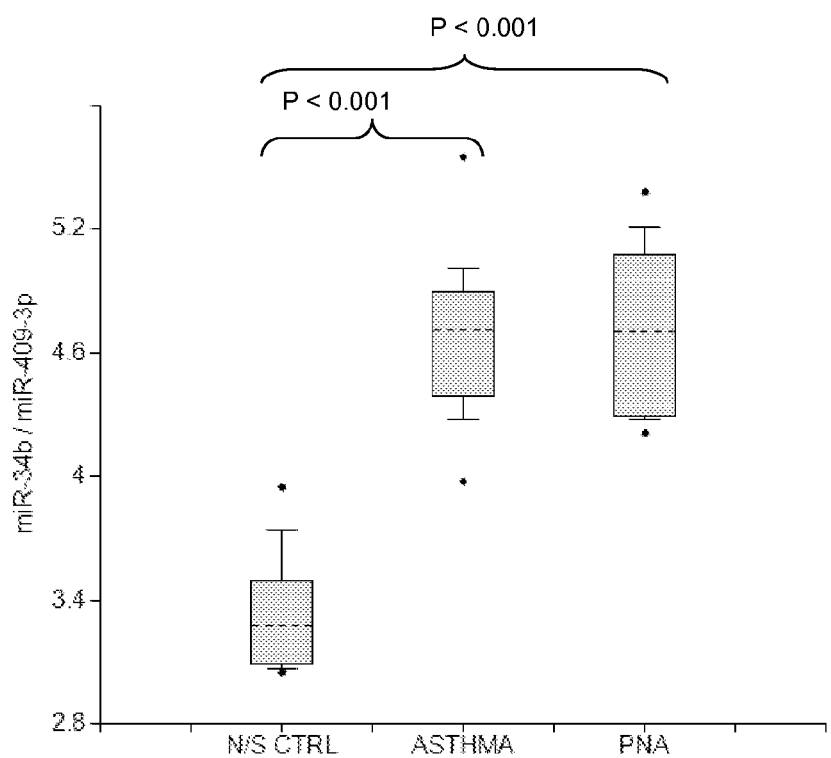
FIGS. 10A-D are graphs showing comparison of lung-enriched biomarkers miR-34b and miR-486-5p concentrations in plasma of asthma and pneumonia patients versus non-smoking controls (A and B) and in plasma of COPD and NSCLC patients versus smoking controls (C and D). Concentrations of biomarker miRNAs were normalized per miR-409-3p, which is expressed in many organs but is under-expressed in the lung.
Figure 10B:
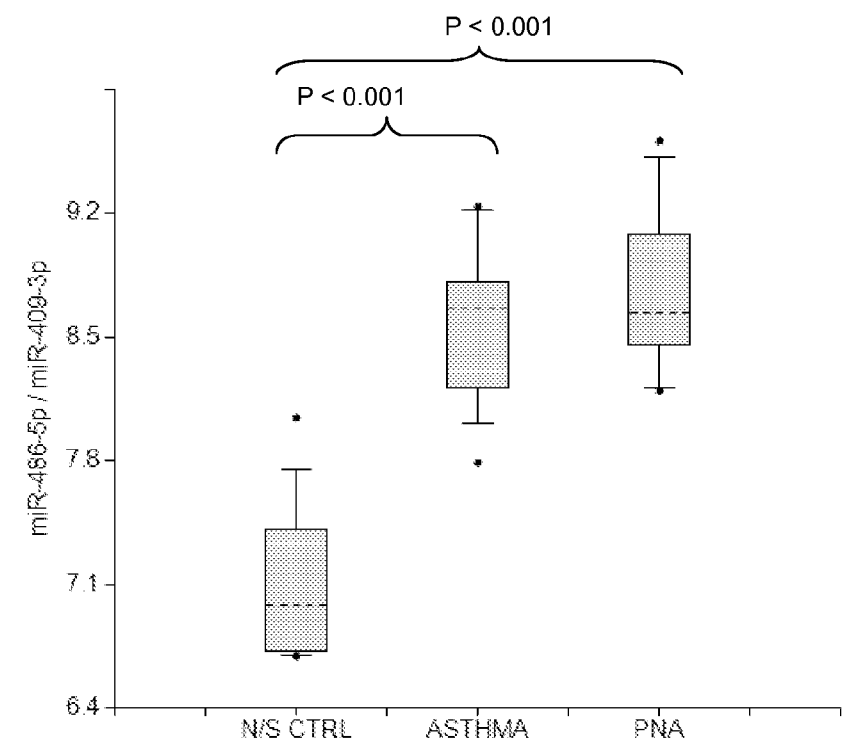
Figure 10C:
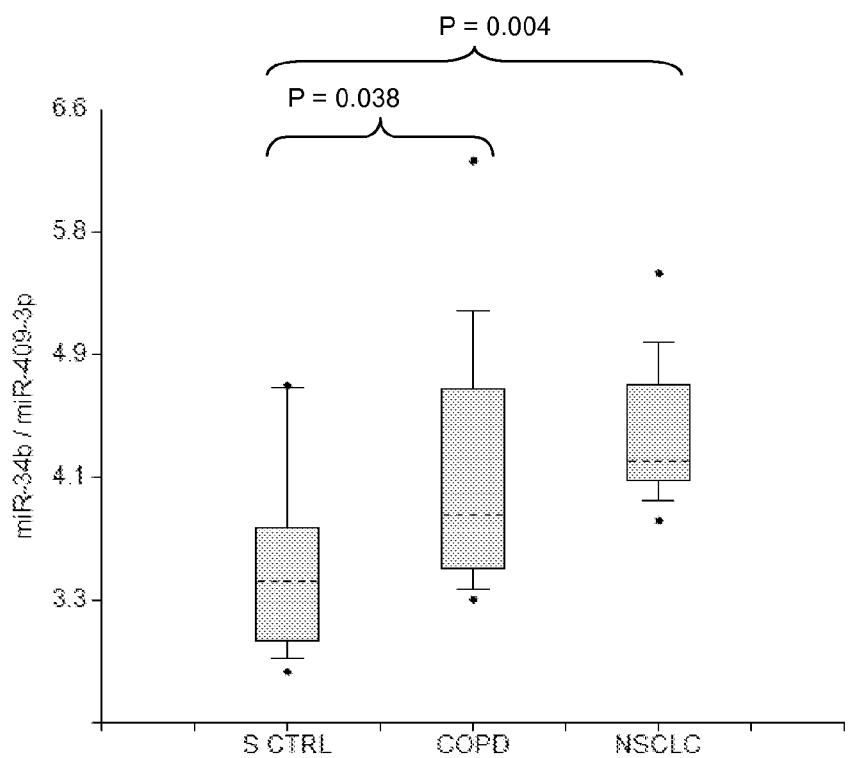
Figure 10D:
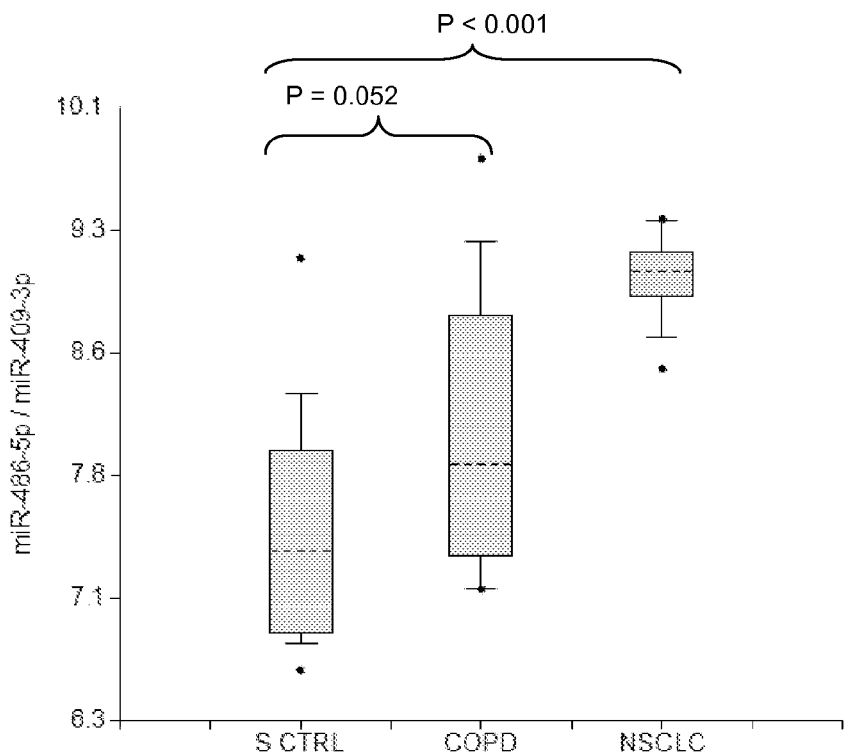
Figure 11A:
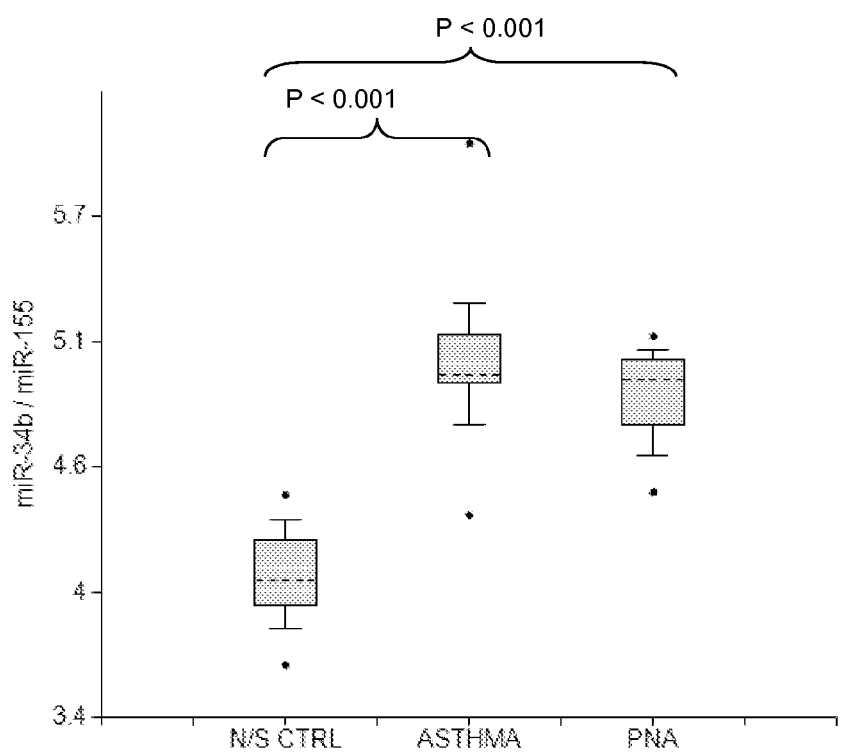
FIGS. 11A-H are graphs showing comparison of lung-enriched biomarkers miR-34b and miR-486-5p concentrations in plasma of asthma and pneumonia (PNA) patients versus non-smoking controls. Concentrations of miRNA biomarkers were normalized per other lung-enriched miRNA: A, B-miR-155; C, D-miR-146b-5p; E, F-miR-223; G, H-miR-142-5p.
Figure 11B:
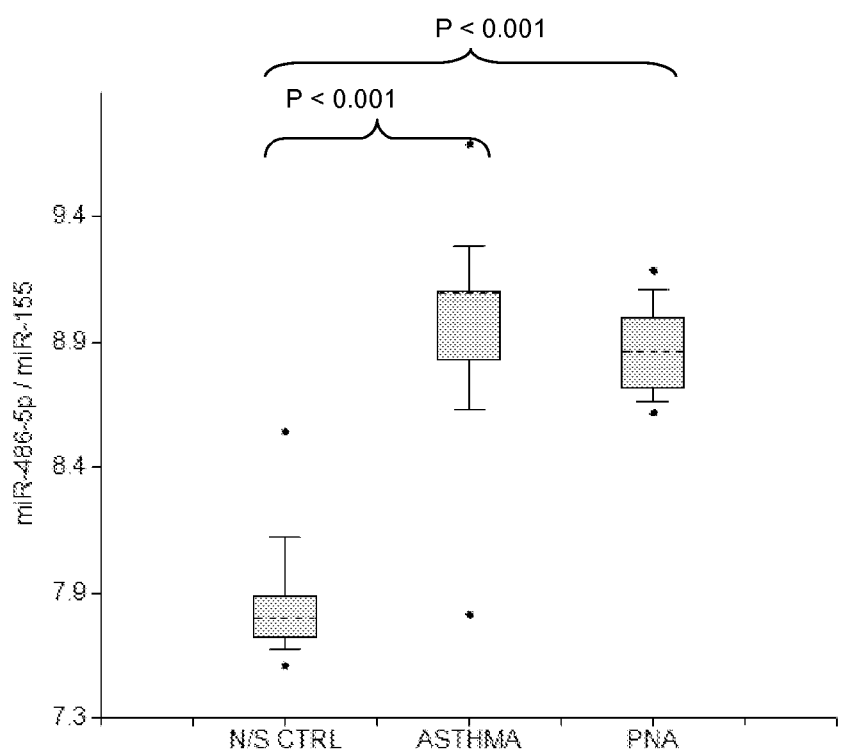
Figure 11C:
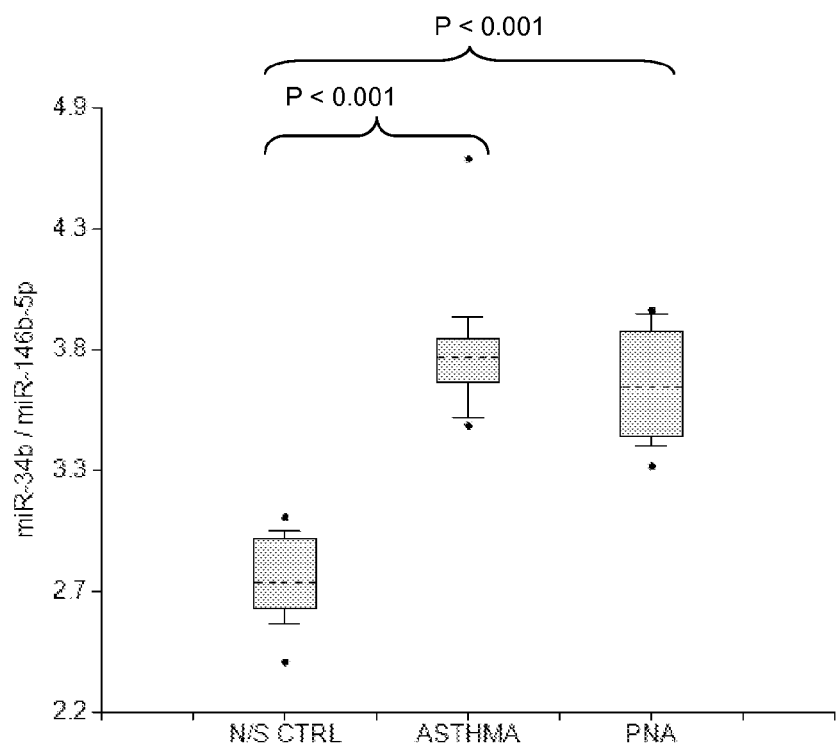
Figure 11D:
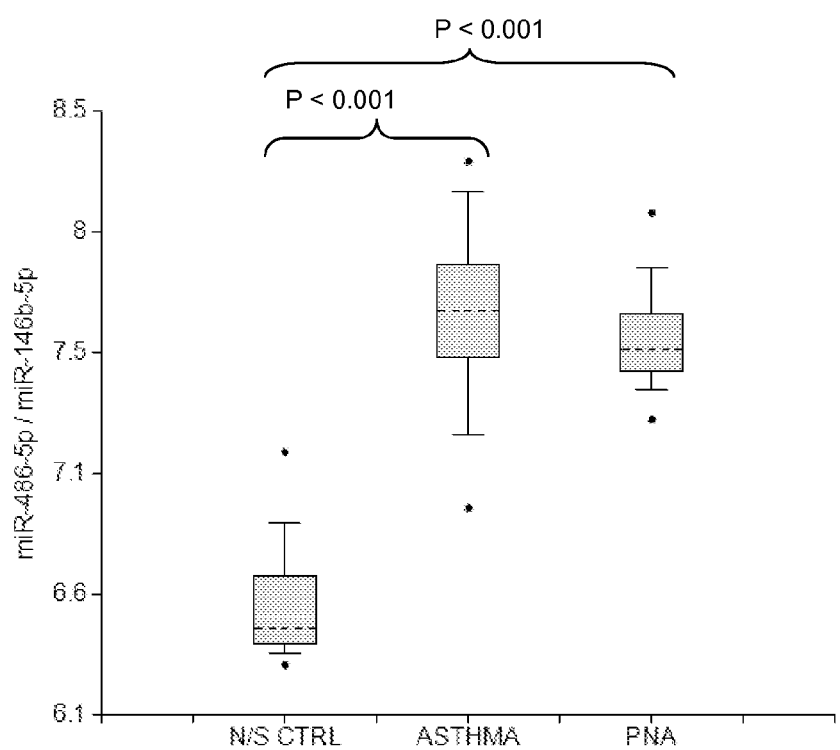
Figure 11E:
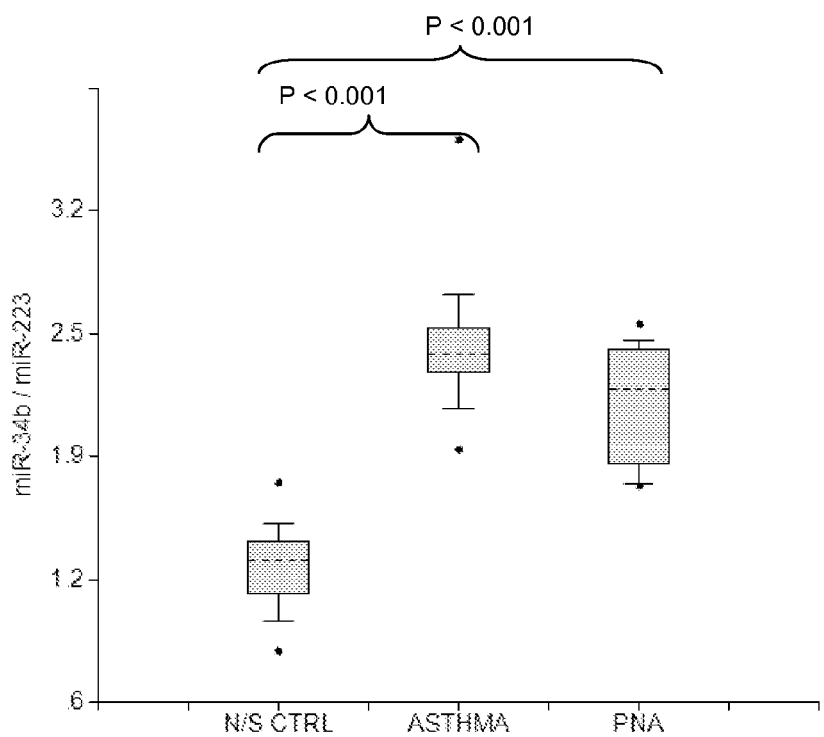
Figure 11F:
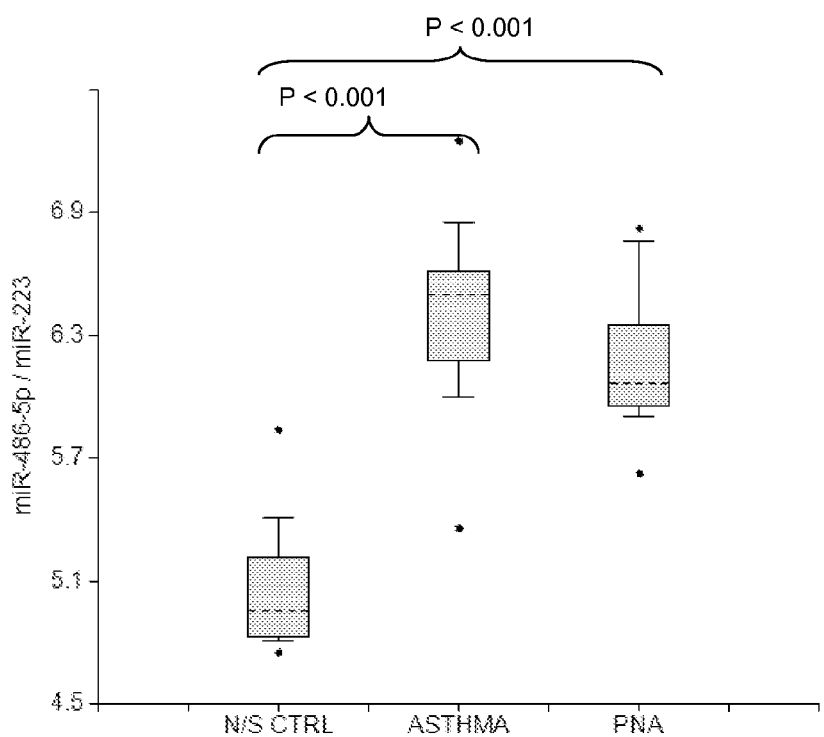
Figure 11G:
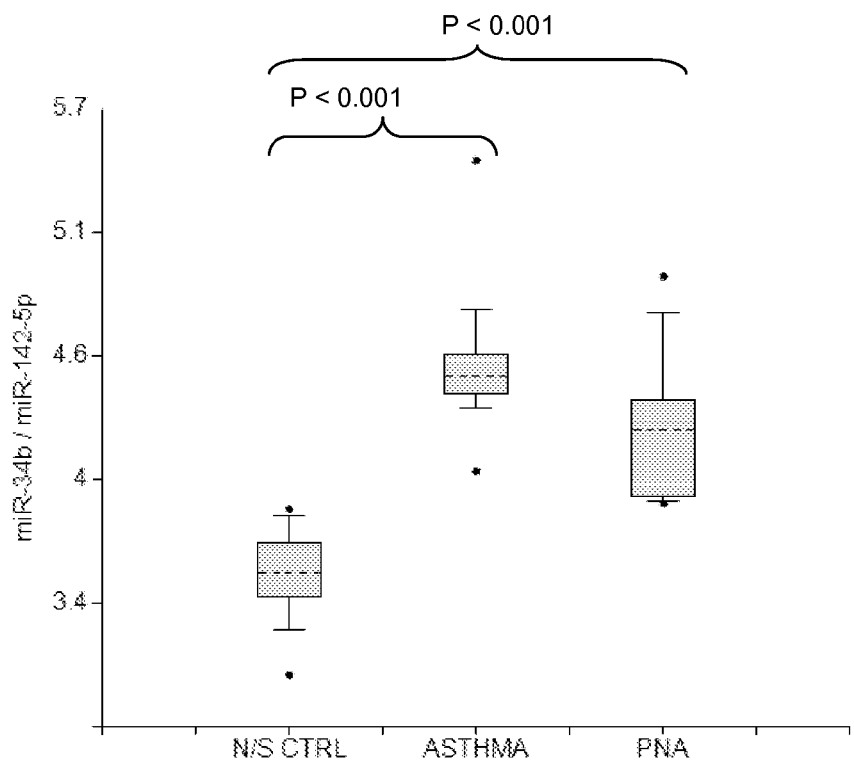
Figure 11H:
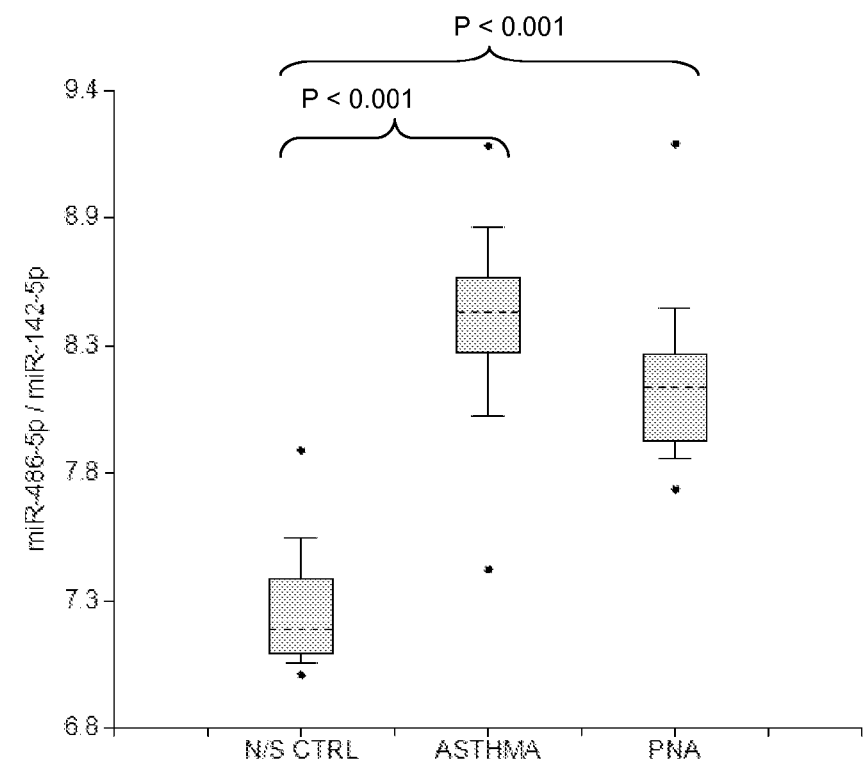
Figure 12A:
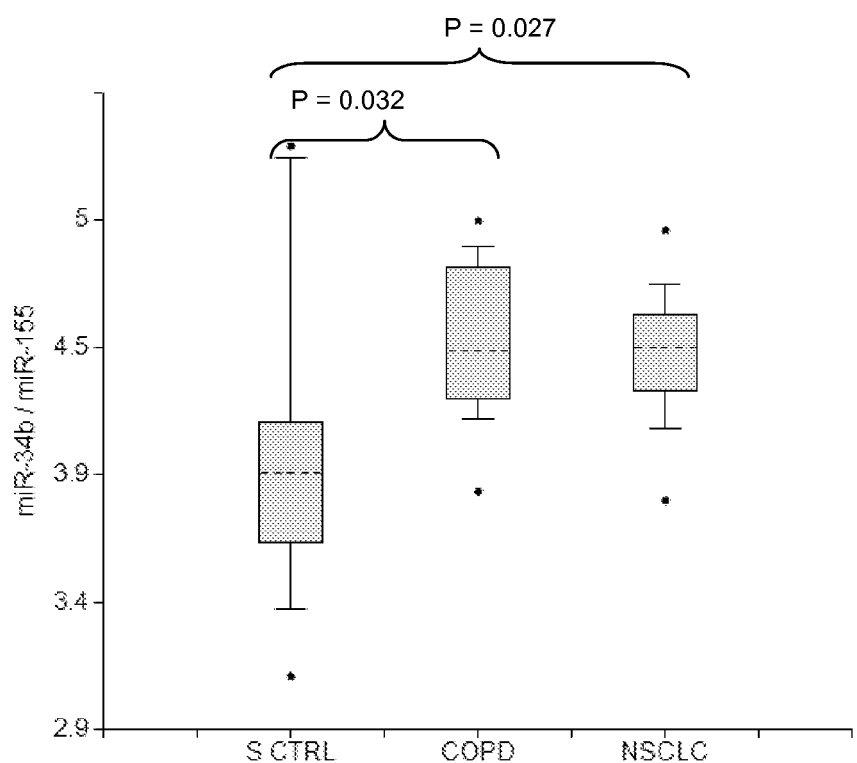
FIGS. 12A-J are graphs showing comparison of lung-enriched biomarkers miR-34b and miR-486-5p concentrations in plasma of COPD and NSCLC patients versus smoking controls. Concentrations of miRNA biomarkers were normalized per miR-409-3p or lung-enriched miRNA: A, B-miR-155; C, D-miR-146b-5p; E, F-miR-223; G, H-miR-142-5p; I, J-miR-409-3p.
Figure 12B:
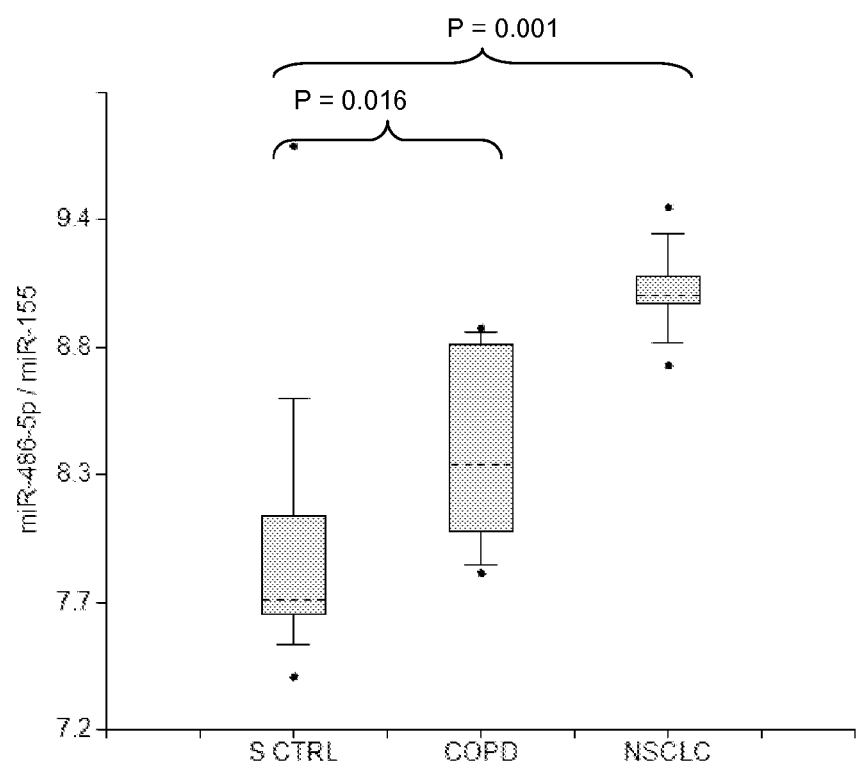
Figure 12C:
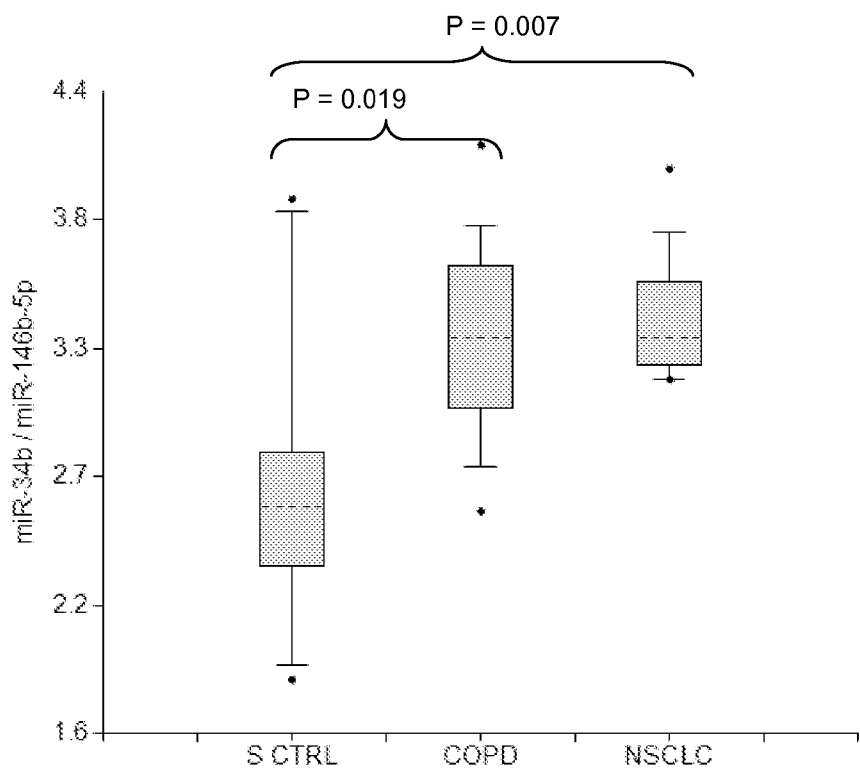
Figure 12D:
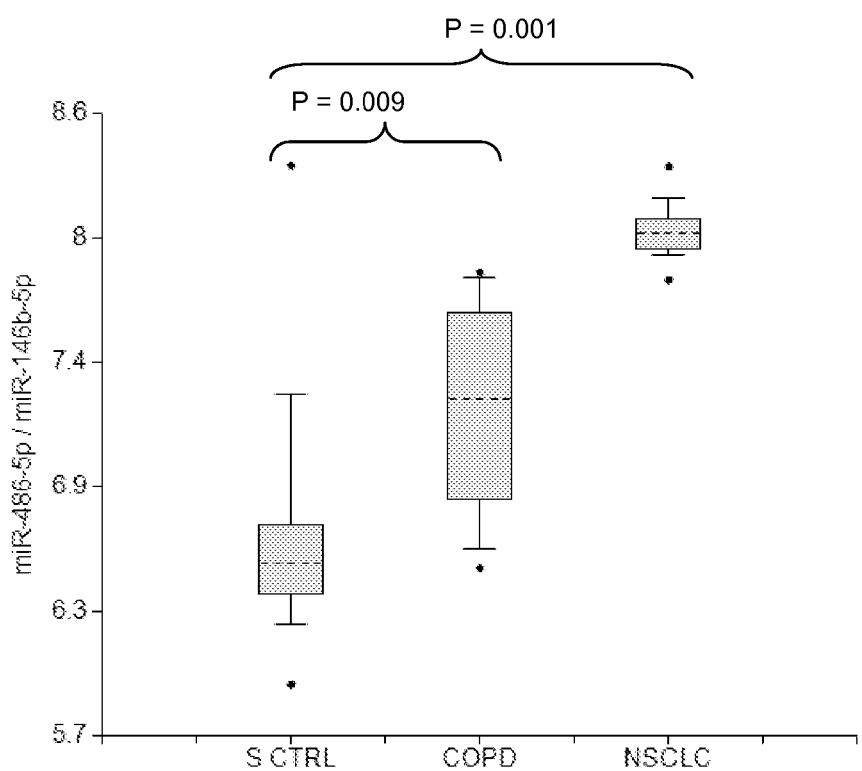
Figure 12E:
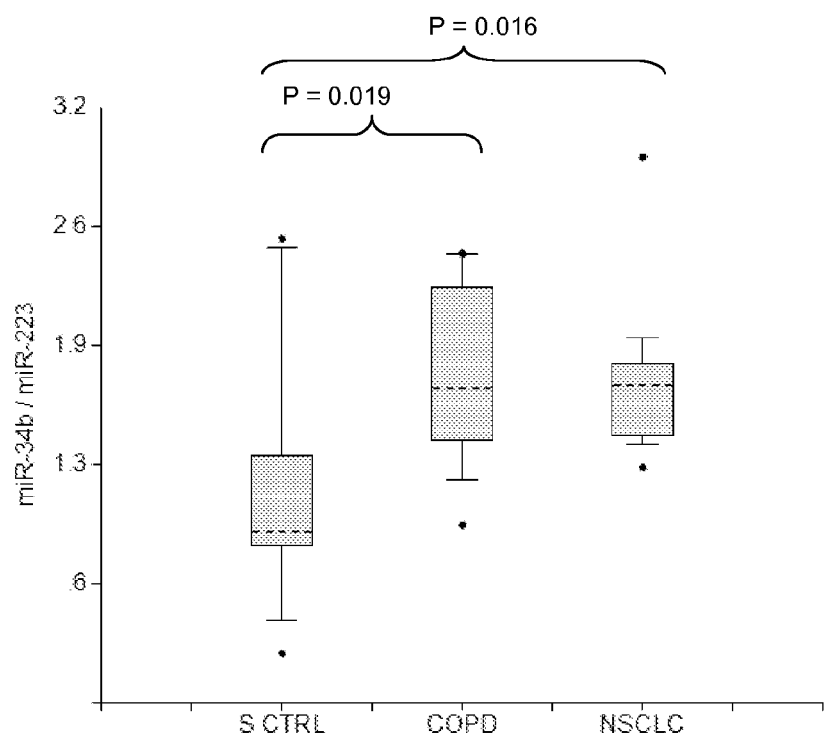
Figure 12F:
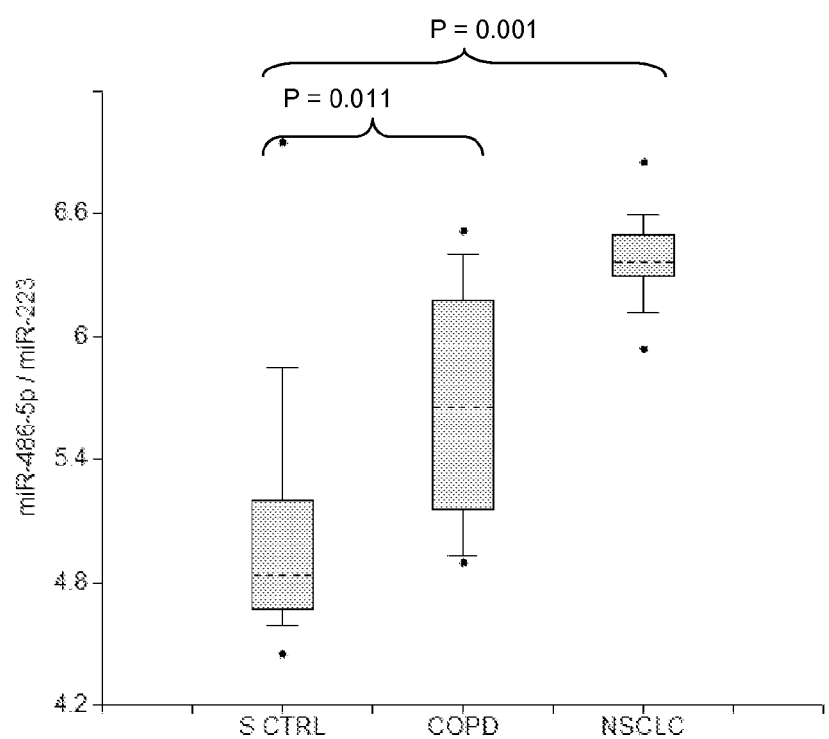
Figure 12G:
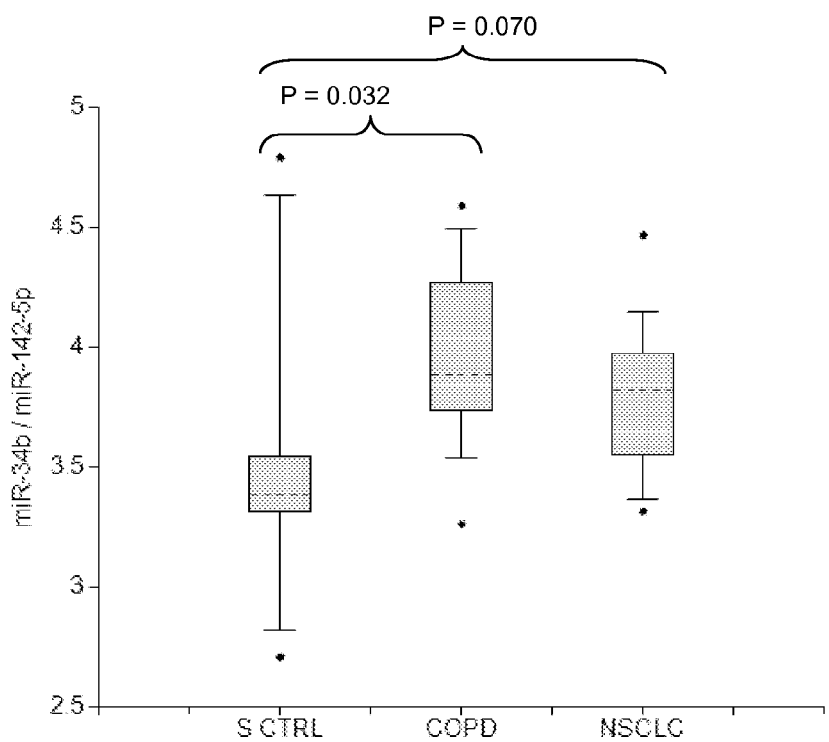
Figure 12H:
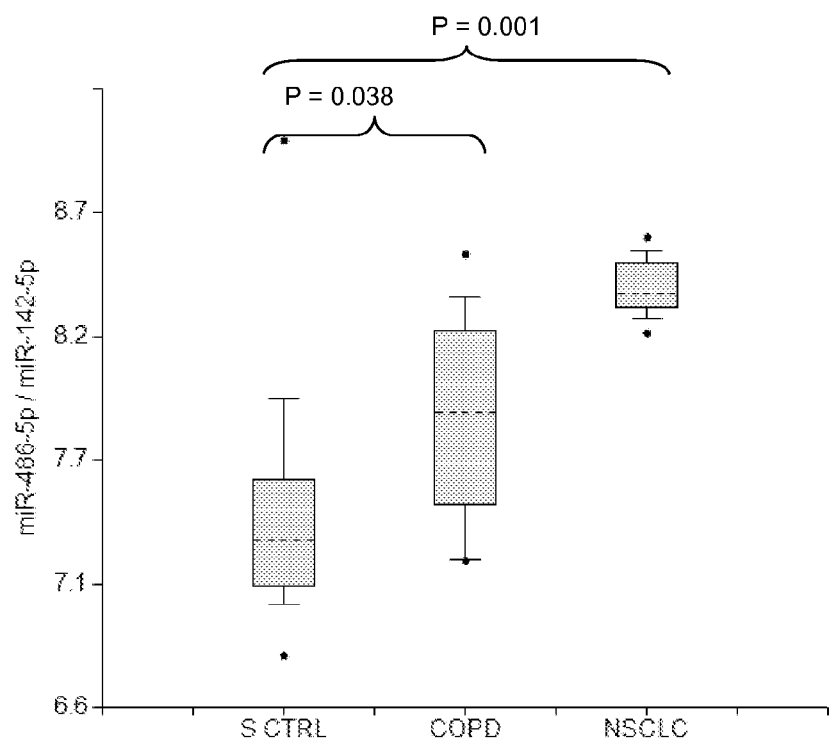
Figure 12I:
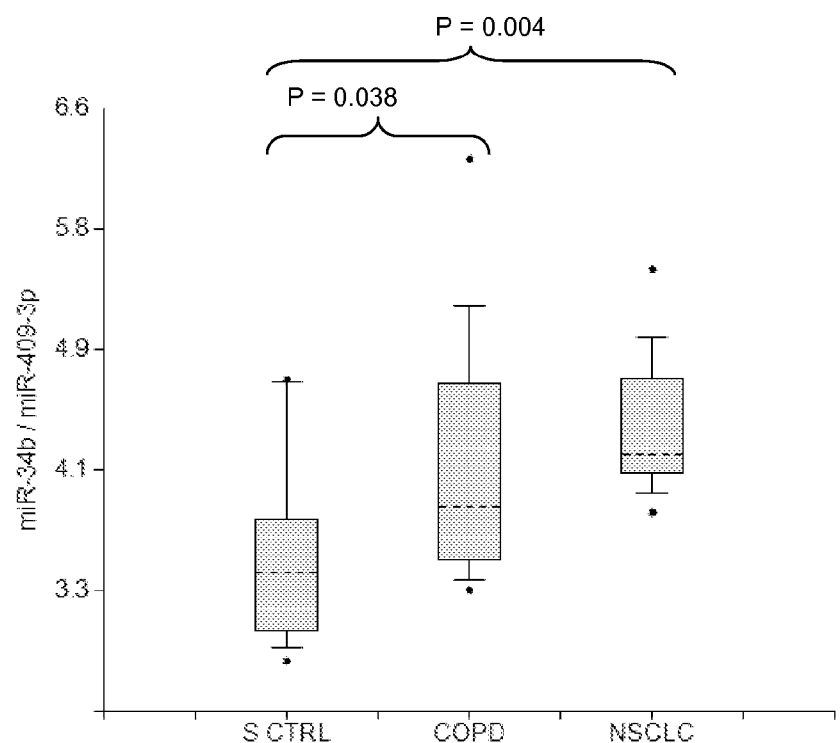
Figure 12J:
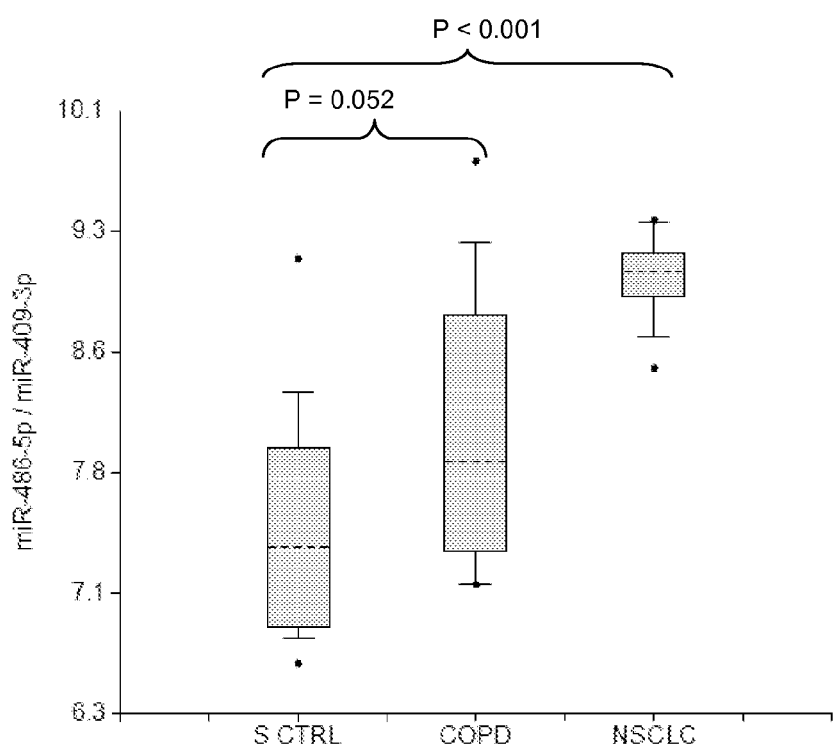
Figure 13A:
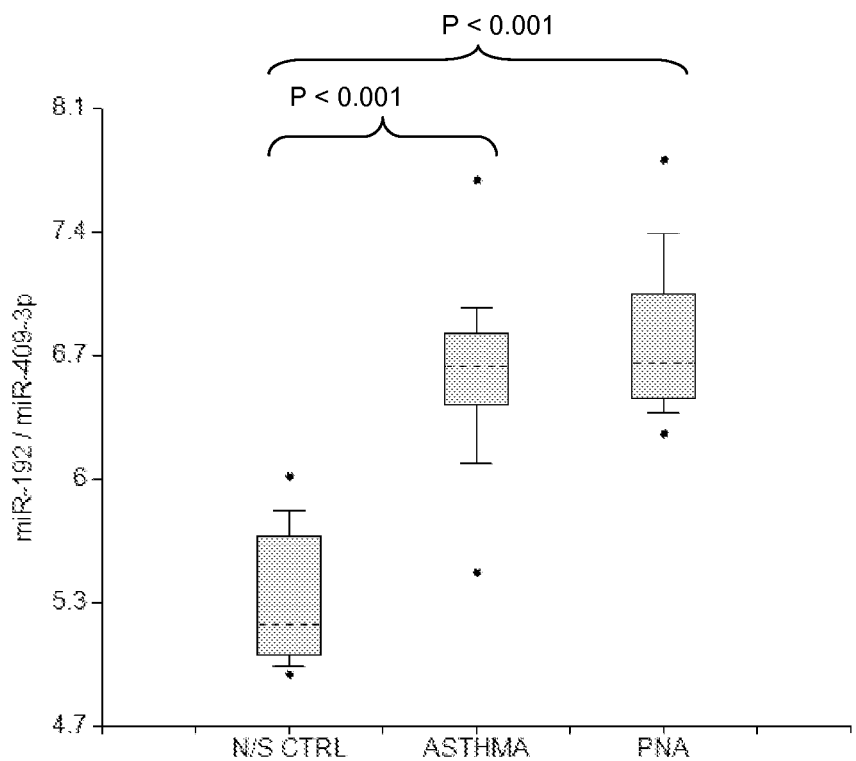
FIGS. 13A-J are graphs showing comparison of miR-192 concentrations in plasma of asthma and pneumonia (PNA) patients versus non-smoking controls (A-E) and in plasma of COPD and NSCLC patients versus smoking controls (F-J). Concentrations of miRNA biomarkers were normalized per miR-409-3p, which is expressed in many organs but is under-expressed in the lung, or per lung-enriched miRNA: A, F-miR-409-3p; B, G-miR-155; C, H-miR-146b-5p; D, I-miR-223; E, J-miR-142-5p.
Figure 13B:
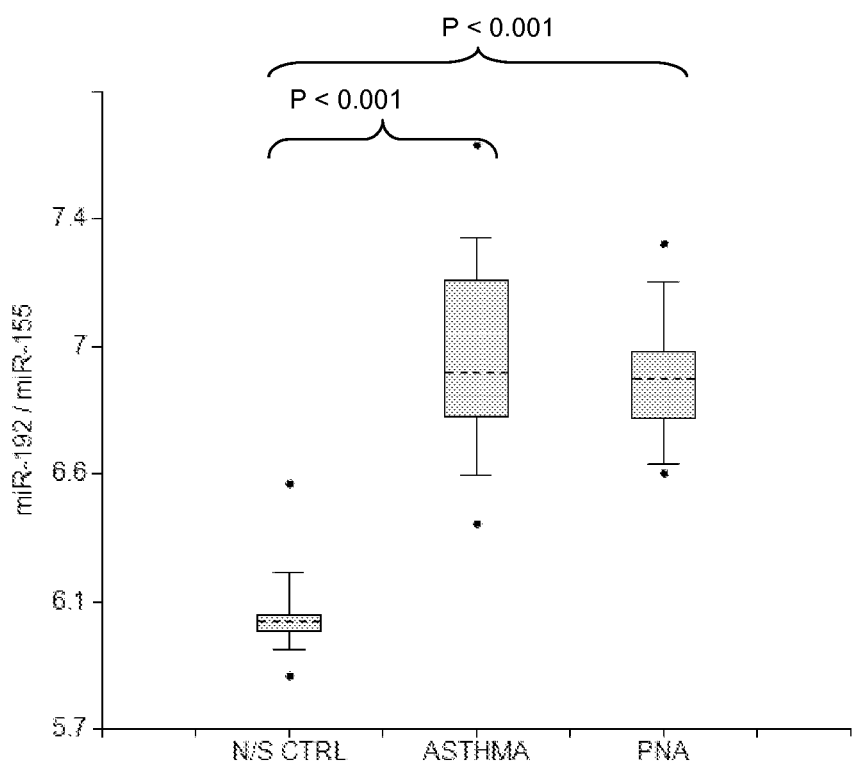
Figure 13C:
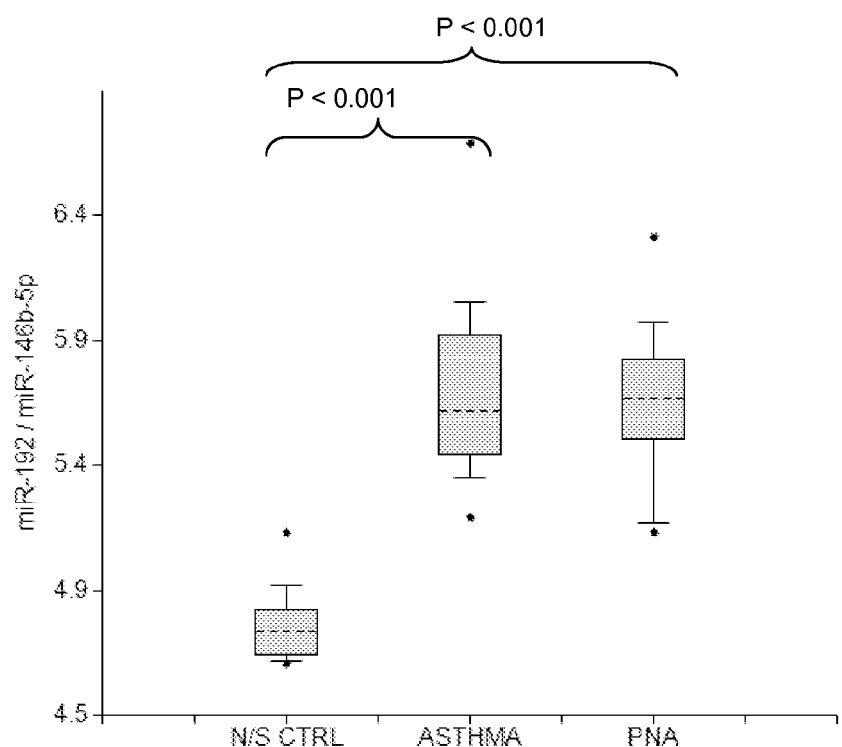
Figure 13D:
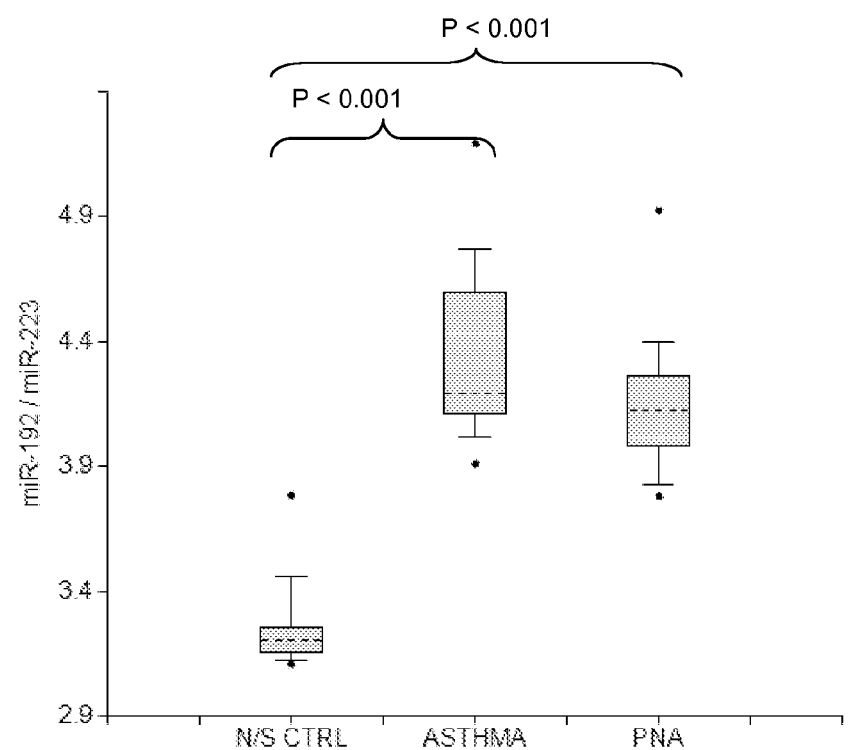
Figure 13E:
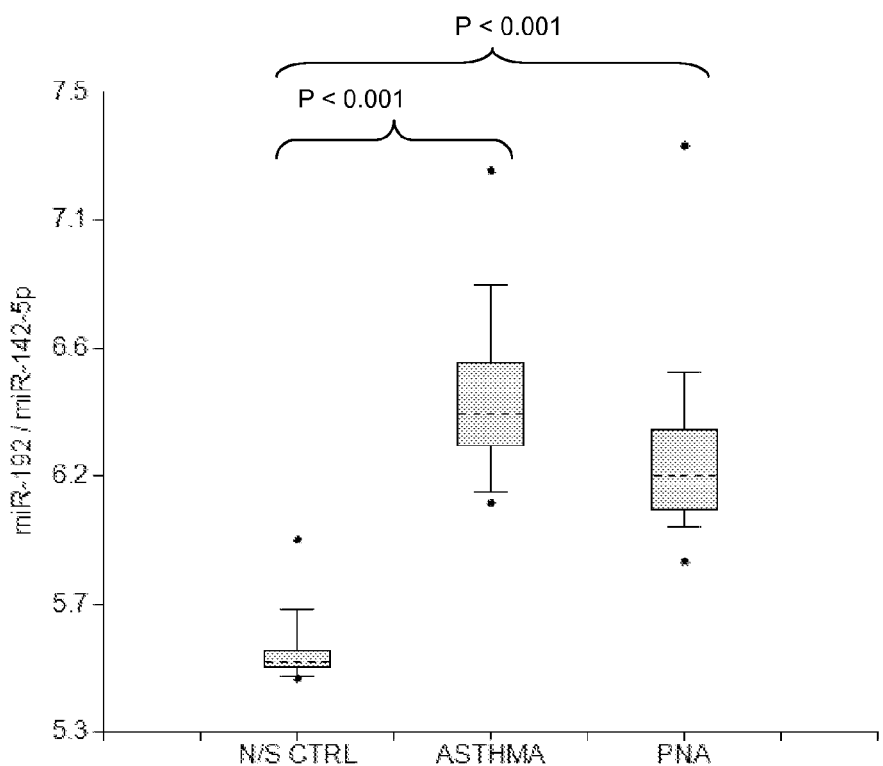
Figure 13F:
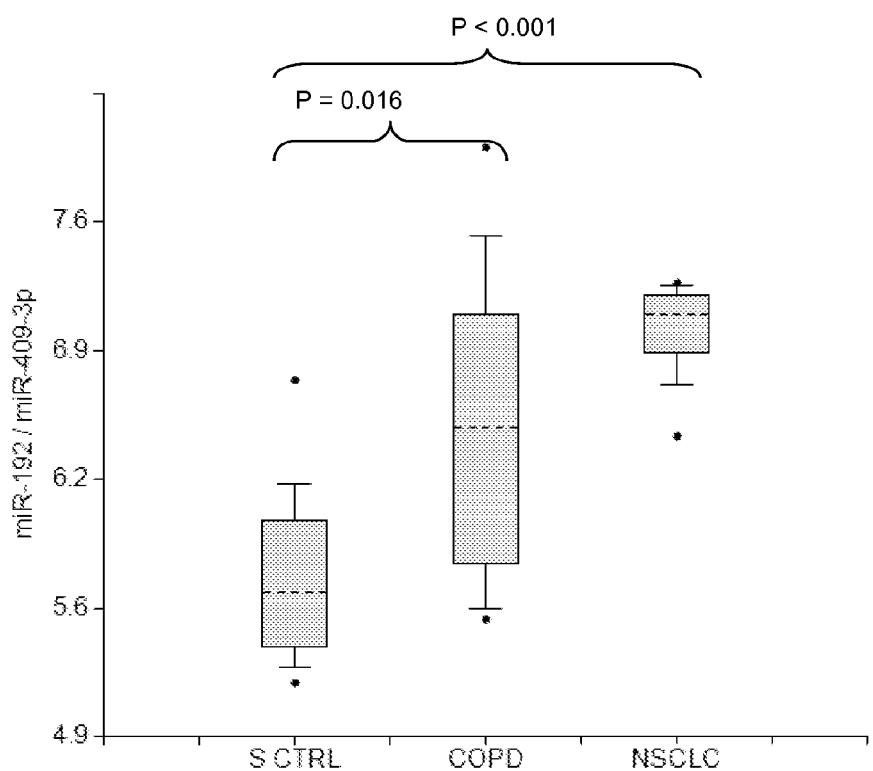
Figure 13G:
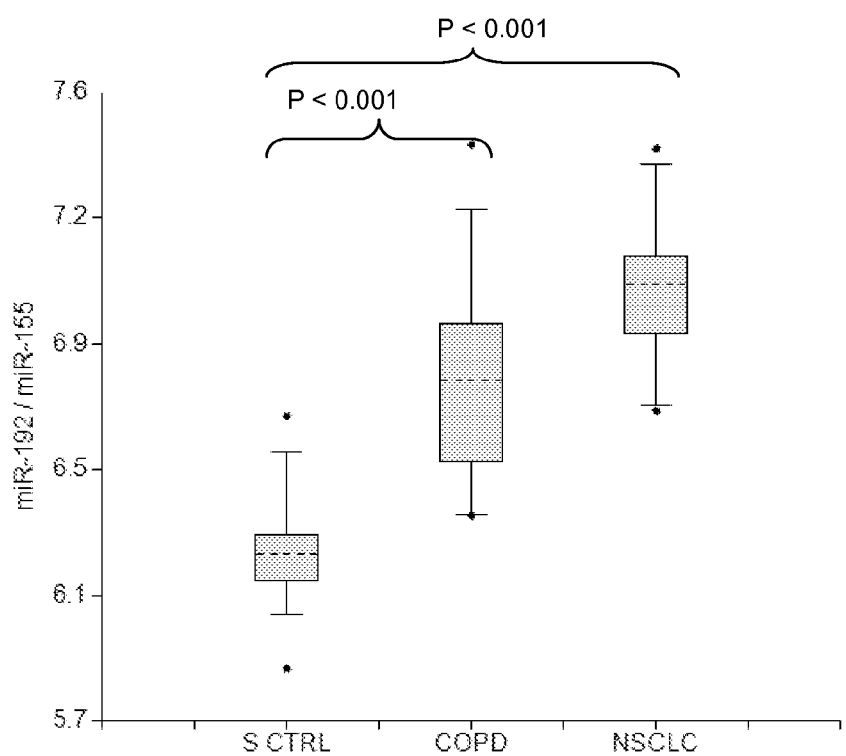
Figure 13H:
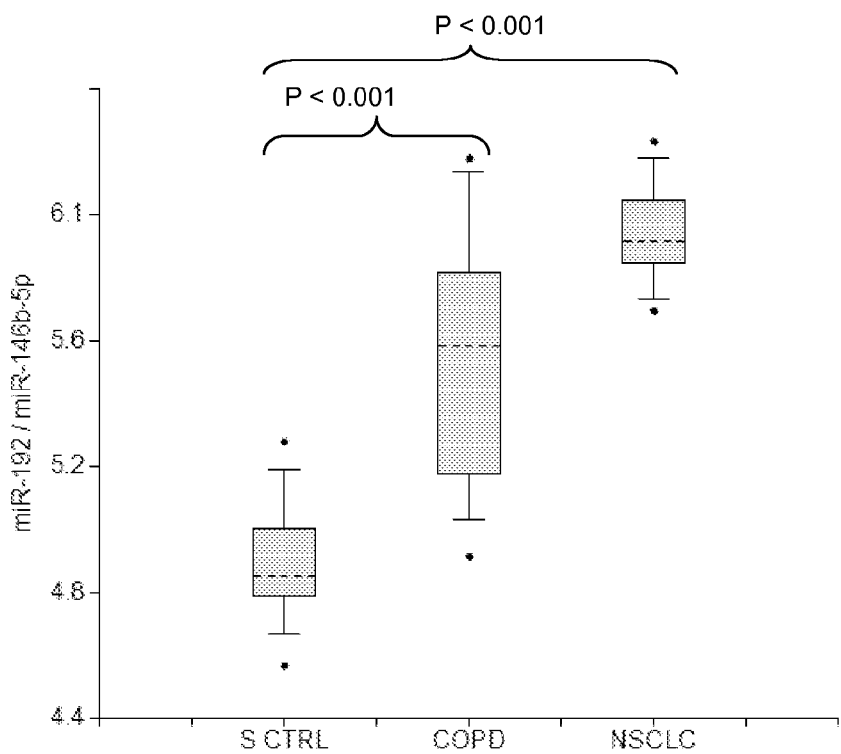
Figure 13I:
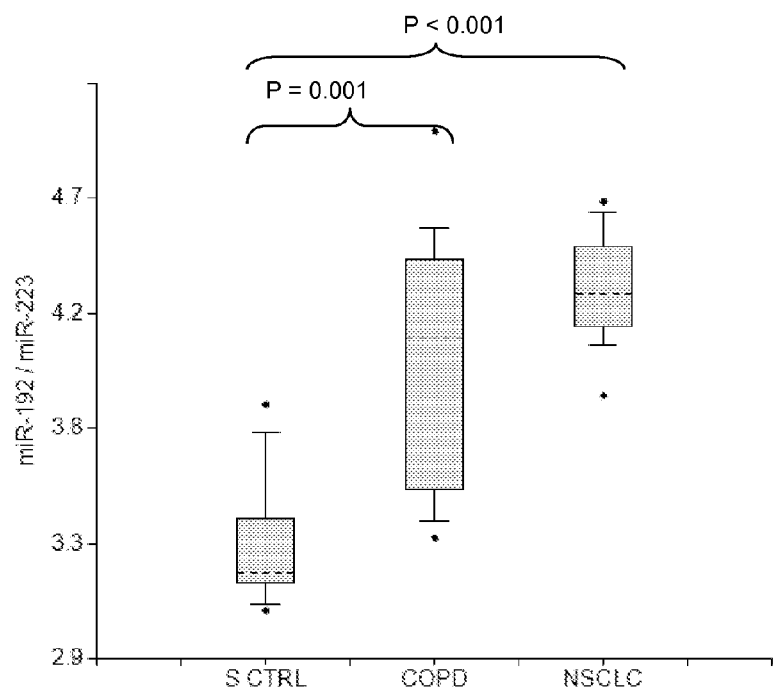
Figure 13J:
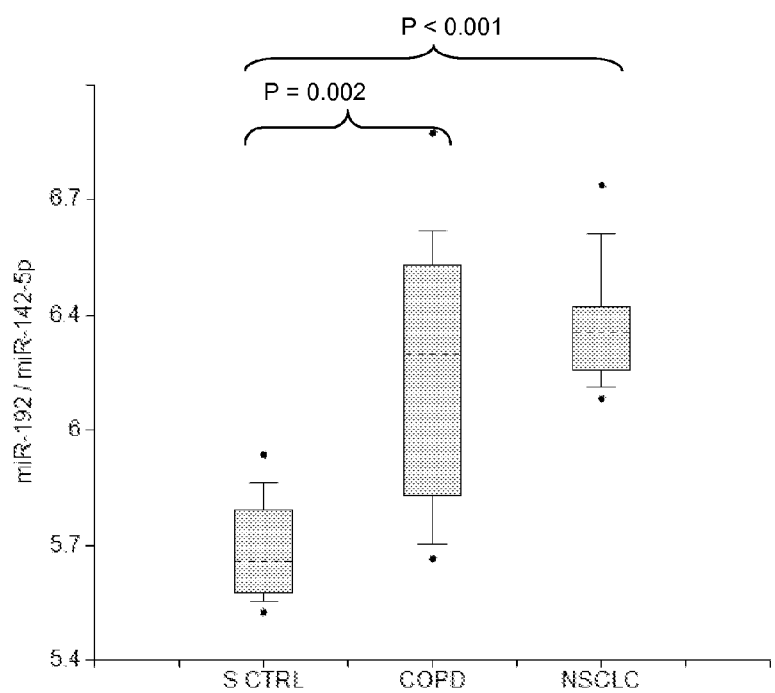

The present invention is based on the idea of shifting the paradigm in the area of clinical screening and diagnostics from disease-specific screening tests to the Universal Screening Test(s) (UST), which will detect pathology of a particular organ system, such as gastrointestinal, nervous, hematological, etc., or of a particular organ or tissue or cell type, but will be disease-non-specific. Additionally such test will be capable to differentiate some broad types of pathologic processes, e.g. inflammatory diseases and tumors. After the pathology is detected, disease-specific tests can be applied for a more specific diagnosis. Such a test(s) can also be used for drug screening as well as for evaluating toxicity of various compounds and environmental factors (e.g. during drug development or clinical trials). The instant invention is based on the use of organ system-, organ-, tissue-, and/or cell type-enriched miRNA in bodily fluids as biomarkers of organ and/or tissue and/or cell pathology, description of the basis for such miRNA selection, and the methods of the UST interpretation. The UST of the invention can also include miRNA biomarkers for some general pathological processes, such as, e.g., hypoxia, inflammation, carcinogenesis, etc.

The present invention provides a novel noninvasive or minimally invasive method for early, preferably before clinical manifestation, detection of pathological changes (without defining a specific disease) in an organ system or in a particular organ/tissue/cell type in a subject, said method comprising determination of the levels of organ system/organ/tissue-enriched miRNA in a bodily fluid (e.g. plasma, serum, urine, saliva, or other bodily fluid) of said subject as compared to a control. Specifically, the method comprises:

a. measuring levels of miRNAs enriched in various organ systems/organs/tissues/cell types in a bodily fluid sample collected from the subject;
b. measuring levels of preselected normalizer miRNAs in the same bodily fluid sample collected from the subject;
c. calculating the ratios of the levels of the miRNAs measured in steps (a) and (b);
d. comparing the ratios of the levels of the miRNAs calculated in step (c) with the corresponding control ratios, and
e. (i) identifying the subject as being afflicted with a pathology of a particular organ system/organ/tissue/cell type when the ratios of the levels of the miRNAs enriched in said organ system to their respective miRNA normalizers calculated in step (c) are higher than the corresponding control ratios or (ii) identifying the subject as not being afflicted with a pathology of said organ system/organ/tissue/cell type when the ratios of the levels of the miRNAs enriched in said organ system to their respective miRNA normalizers calculated in step (c) are not higher than the corresponding control ratios.

If positive for a pathology, such UST should be followed by tests specific for various known pathologies of the organ system/organ/tissue/cell type identified by UST.

The present invention also provides methods for selecting potential miRNA biomarkers. To reflect pathological changes in a particular organ system, organ, tissue, or cell type such biomarkers should be, first, enriched in one of those organ systems, organs, or tissues, and second, their concentrations in bodily fluids should be high enough to be detectable. Although not all miRNA have currently been identified and organ/tissue expression profiles for many of them are not known, published data (See, e.g., Hua et al., BMC Genomics 2009, 10:214; Liang et al., BMC Genomics. 2007, 8:166; Landgraf et al., Cell. 2007, 129:1401-1414; Lee et al., RNA. 2008, 14:35-42; ferrolab.dmi.unict.it/miro/; mips.helmholtz-muenchen.de/phenomir/) are sufficient to formulate major principles for selecting potential biomarkers:

1. Organ system/organ/tissue/cell type-enrichment. Although some miRNA are highly enriched in a particular organ or tissue, e.g. miR-122 in the liver and miR-124 in the brain, there is no known miRNA, which is 100% specific for one organ or tissue. Of course, the higher is miRNA enrichment in a given organ system/organ/tissue/cell type as compared to all other organ systems/organs/tissues/cell types, the better potential as a biomarker it has. Practically, if miRNA concentration in one organ is at least 4-5 times higher than in others, they can be selected as potential biomarkers for UST. For many organs, such miRNA can be found in the literature (See, e.g., Hua et al., BMC Genomics 2009, 10:214; Liang et al., BMC Genomics. 2007, 8:166; Landgraf et al., Cell. 2007, 129:1401-1414; Lee et al., RNA 2008, 14:35-42;

ferrolab.dmi.unict.it/miro/; mips.helmholtz-muenchen.de/phenomir/). Table 1 represents miRNA enriched in various organs according to numerous published data. One can see that some miRNA are enriched in different organs of the same organ system. This is especially characteristic of gastrointestinal, nervous, genital, and hematological organs (Table 2). Using these miRNA allows to design a test that will detect pathology in those systems but not in a particular organ. At the same time, there are miRNA enriched in one-two organs of a system, and these miRNA can be used for tests that can define the location of the pathology more precisely. The list of these miRNA is presented in the third column of Table 2. There are also miRNA enriched in two or even more organs, which usually developed during embryogenesis from the same cell types. In such cases the increase of the miRNA concentration in bodily fluid cannot be interpreted unambiguously. However, combination of several miRNA enriched in different sets of organs resolves this problem, and the present invention also includes a computer implemented method for analysis of data obtained with such several miRNA. It is also important to note that miRNA enrichment in the second organ will not significantly affect the test results, if chances of those miRNA to appear in bodily fluids are low. For example, many miRNA are enriched (in addition to other organs) in the skin, but if those miRNA are located in epidermis their chances of appearing in the bloodstream from the skin are very low, and the method of the invention uses them.

2. miRNA expression level. The test development is easier and its sensitivity is higher if the concentration of a potential miRNA biomarker(s) in the target organ system/organ/tissue/cell type is sufficiently high, since one can expect that more miRNA biomarker molecules appear in bodily fluids. Thus, if there is a choice between many potential miRNA biomarkers, those miRNA should be selected, which not only are enriched in the target but are also highly expressed (e.g., 1000 copies per cell). This is especially important for small organs or their parts or specific cell types within organs, such as pancreatic (β-cell islets. It does not mean that miRNA which are not highly expressed cannot be used for the UST development but the detection of miRNA expressed at low levels may need larger volumes of bodily fluids and more sensitive techniques for miRNA quantitation. At the same time, since miRNA concentration in a bodily fluid also depends on the effectiveness of its secretion from cells into extracellular space and transport to the bodily fluid (see next section), as many as possible organ system/organ/tissue/cell type-enriched miRNA should be analyzed for the experimental selection of the most promising biomarkers.

3. miRNA secretion. There are many ways for cell-free miRNA to appear in bodily fluids (Hunter et al., PLoS ONE. 2008, 3:e3694; Wang et al., Nucleic Acids Res. 2010, 38:7248-7259; Pigati et al., PLoS ONE. 2010, 5:e13515; Gupta et al., Circ. Cardiovasc. Genet. 2010, 3:484-488; Iguchi et al., Commun. Integr. Biol. 2010, 3:478-481; Kosaka et al., J. Biol. Chem. 2010, 285: 17442-17452). miRNA can appear in extracellular space and then in bodily fluids as a result of: (i) cell death and cellular membrane permeabilization; (ii) destruction of some cellular compartments, such as axons, dendrites, and spines in neurons; (iii) exocytosis (Skog et al. Nat Cell Biol., 2008, 10:1470-1476); (iv) blebbing (Charms et al., Biophys. J. 2008, 94:1836-1853; Fackler, Grosse, J. Cell Biol. 2008, 181:879-884); (v) secretion of free or protein-bound miRNA (Wang et al., Nucleic Acids Res. 2010, 38:7248-7259). The latter mechanism provides for more than 50% of cell-free miRNA into extracellular medium from live cells. The secretion of miRNA is selective and the ratios of various miRNA concentrations in cells and extracellular medium are different. The selectivity of the miRNA secretion is very important for selecting potential biomarkers. Since the mechanisms of miRNA secretion from normal cells and during pathology development (Rabinowits et al. Clin Lung Cancer, 2009, 10:42-46) has not been investigated, it is necessary to analyze more miRNA, keeping in mind that some of them, which look promising due to high expression and enrichment in a target organ/tissue can be secreted at a low level and vice versa. Also it was recently demonstrated that some miRNA, e.g., miR-451 and miR-1246, which are secreted at a very low level from normal cells, can be secreted much more effectively from pathological cells (Pigati et al. PLoS ONE, 2010, 5:e13515). These miRNA can also be analyzed as potential biomarkers even if they are not highly enriched in a particular organ system, organ or tissue, since their combination with more organ/tissue-specific miRNA will provide additional information useful for detecting a pathology.

It is important to remember that many miRNA have not been discovered yet and the expression profiles of many recently discovered miRNA in various tissues have not been analyzed. In addition, many organs, tissues, and especially cell types were not tested for expression of already known miRNA. Thus, although UST development can be initiated on the basis of already published data for many organs and tissues, additional search for new biomarkers will increase the informative value of UST. First, the miRNA expression profile of all known miRNA in various organ systems/organs/tissues/cell types should be analyzed to define new organ system-/organ-/tissue-enriched miRNA (e.g., using RT-PCR, which currently is the most sensitive and least variable technique for miRNA quantitative measurement). Second, the expression profiles of all newly discovered miRNA should be analyzed as described above. Third, since all organs are composed of various cell types, the expression of miRNA enriched in particular organs should be additionally analyzed to find out the cell type, in which these miRNA are enriched. Currently, the best technique for such a study is in situ hybridization (ISH). Such information, as currently available for various miRNA, has been included in Tables 1 and 2. For example, information on pancreatic n-cells-enriched miRNA is included in addition to pancreas-enriched miRNA, as well as enrichment of some miRNA in neurons located in various brain areas.

TABLE 1 miRNA enriched in various human organs and tissues.

| Organ/Tissue/Cell | Organ/tissue-enriched miRNA |
|---|---|
| Heart | 1, 22, 30a-3p, 30e-3p, 133a, 133b, 197, 208a, 208b, 221, 222, 302a, 302c, 367, 378, 499-5p, 30e* |
| Musculoskeletal | 1, 22, 95, 133a, 133b, 140, 206 |

TABLE 1-continued miRNA enriched in various human organs and tissues.

| Organ/Tissue/Cell | Organ/tissue-enriched miRNA |
|---|---|
| Lung | 15b, 18b, 21, 34b, 126, 135b, 142-3p, 142-5p, 146, 146b-5p, 155, 199b-5p, 200c, 205, 211, 223, 224, 302b, 375, 449a, 449b, 450b-5p, 486, 492, 522, 566, 574-3p, 620, 650, 766, 886-5p. |
| Trachea | 34b, 135b, 146, 146b, 147b, 155, 199b-5p, 200b, 200c, 205, 219-5p, 223, 302b, 375 |
| Liver | 30e-3p, 122a, 130b, 136, 148a, 194, 376c, 455-3p, 518b, 616, 801, 885-5p, 17*, 30d*, 194* |
| Kidney | 10a, 10b, 30a-3p, 30c, 107, 135a, 135b, 184, 187, 190, 194, 196b, 200a, 204, 211, 324-5p, 489, 500, 501-5p, 502-3p, 502-5p, 503, 506, 508-3p, 508-5p, 509-3p, 509-5p, 510, 532-5p, '768-3p, 886-3p, 886-5p, 891a, 10b*, 30a*, 30c-2*, 30e*, 200a*, 200b*, 424*, 500* |
| Bladder | Let-7g, 18, 23b, 26a, 26b, 27b, 28, 106b, 143, 145, 152, 218, 221, 223, 296, 374, 422b, 451 |
| Adipose | 10b, 30, 99a, 139-3p, 139-5p, 193a-5p, 196a, 224, 335, 365, 378/378*, 422b, 494, 518d-3p, 642a-3p, 708, 10b*, 335* |
| Breast | let-7a, 10b, 26a, 30a-3p, 30a-5p, 125b, 126, 145, 146, 195, 196a-2, 196b, 205, 206, 335, 339-5p, 378, 516-5p, 517c, 519c, 520g, 520h, 525, 1246 |
| Ovary | Let-7a, let-7b, let-7c, 10b, 17-3p, 26a, 100, 125a, 125b, 127, 195, 199a-5p, 202, 214, 298, 382, 503, 672, 741, 742, 883-3p, 199a*, 202* |
| Fallopian tubes | 10a, 10b, 31, 34b, 34c, 135a, 135b, 424, 449 |
| Uterus | Let-7c, 10b, 26a, 99a, 100, 125a-5p, 125b, 130a, 140, 143, 145, 195, 196b, 199b, 204, 214, 222, 939, 199* |
| Cervix | Let-7a, let-7c, let-7g, 10b, 100, 101, 125a-5p, 125b, 130a, 134, 140, 143, 145, 186, 195, 196b, 197, 199a, 199b, 204, 214, 218, 222, 320, 424, 497, 154*, 199a* |
| Prostate | Let-7c, 1, 23b, 24, 27b, 28, 34a, 99a, 100, 125b, 130a, 143, 145, 147b, 187, 188-3p, 199b-5p, 205, 214, 222, 328, 373, 410, 455-5p, 490-3p |
| Testicle | 15b, 34a, 34b, 34c, 127, 134, 135a, 135b, 187, 202, 204, 370, 372, 376a, 382, 424, 449, 465a-5p, 465b-5p, 506, 508, 509, 510, 514, 517a, 517c, 871-5p, 871-3p, 888, 202*, 888* |
| Vascular system | Let-7 family, 10a, 17-92 cluster (17, 18a, 19a, 19b, 20a, 92), 21, 22, 23a, 24, 27a, 27b, 29a, 31, 34a, 98, 100, 106a, 126, 130a, 133a, 143, 145, 146a, 199a-3p, 210, 221, 222, 345, 365, 382, 409-3p, 431, 484, 495, 532-5p, 939, 27a*, 30a*, 30e*, 93*, 126*, 130b*, 222* |
| Spleen | 15a, 15b, 126, 139, 142-3p, 142-5p, 146, 150, 155, 181a, 181b, 181d, 223, 302b, 342 |
| Thymus | 15a, 15b, 17-5p, 20b, 106a, 106b, 142-3p, 142-5p, 146, 149, 150, 155, 181a, 181b, 181c, 182, 183, 205, 213, 342 |
| Lymph nodes | Let-7g, 15a, 20b, 21, 106b, 140, 142-3p, 146, 146b, 150, 181b, 181d, 342, 431 |
| Peripheral lymphocytes | Let-7g, 9, 15a, 15b, 17, 19b, 20a, 31, 106a, 124a, 124b, 128a, 137, 142-3p, 146b-5p, 150, 186, 191, 197, 222, 223, 328, 342-3p, 423, 431, 454, 484, 766, 27*, 223* |
| T-cells | 142-3p, 146a, 155, 181a, 205, 223, 424 |
| B-cells | 142, 150, 342 |
| Thyroid | Let-7i, 1, 7, 135a, 135b, 206, 345 |
| Adrenal gland | Let-7g, 7, 15a, 26b, 27a, 99b, 124, 127, 132, 134, 137, 139, 152, 181a, 187, 195, 192, 202, 299, 302b, 323, 324-3p, 324-5p, 328, 330-3p, 331, 335, 340, 365, 369-3p, 375, 379, 382, 409-5p, 429, 431, 432, 455-5p, 483-5p, 514, 126*, 182*, 202* |
| Pancreas | 7, 18a, 21, 29a, 34a, 103, 127-3p, 129-3p, 130b, 134, 135a, 135b, 136, 141, 148a, 182, 183, 184, 192, 193a-3p, 193a-5p, 195, 199a-3p, 199a-5p, 200b, 200c, 204, 216a, 216b, 217, 224, 340, 365, 367, 374a, 374b, 375, 376a, 376c, 379, 382, 383, 429, 432, 451, 455-5p, 485-5p, 487b, 497, 539, 543, 642, 758, 939, 130b*, 136*, 183*, 200b*, 493* |
| Pancreatic β-cells | 7, 9, 21, 127-3p, 130b, 184, 195, 216a, 216b, 217, 376a, 376c, 497, 939, 493* |
| Large intestine (Colon) | 31, 141, 143, 145, 147b, 192, 194, 200a, 200b, 200bN, 200c, 200cN, 215, 219-2-3p, 321, 375, 378, 422a, 429, 450b-5p, 487a, 490-3p, 492, 504, 565, 5'74-3p, 622, 650, 801, 143*, 200b* |
| Small intestine | 31, 141, 143, 192, 194, 200a, 200b, 200bN, 200c, 200cN, 215, 321, 375, 429 |
| Esophagus | 31, 106a, 106b, 143, 145, 148a, 203, 205, 210, 211, 221 |
| Stomach | 7, 26a, 26b, 29c, 31, 106a, 106b, 124b, 130b, 141, 145, 148a, 182, 188, 192, 197, 203, 375, 650 |

TABLE 1-continued miRNA enriched in various human organs and tissues.

| Organ/Tissue/Cell | Organ/tissue-enriched miRNA |
|---|---|
| Brain | Let-7a, 7, 9, 96, 98, 99a, 103, 107, 124a, 125a, 125b, 127, 128a, 132, 134, 135a, 137, 138, 149, 153, 154, 181a, 181b, 181c, 182, 183, 184, 204, 211, 212, 213, 218, 219, 221, 222, 299-3p, 299-5p, 323-3p, 324-5p, 328, 329, 330, 331, 335, 337, 338, 342, 346, 369-3p, 369-5p, 370, 379, 381, 382, 383, 409-3p, 411, 425, 432, 433-5p, 485-3p, 485-5p, 487b, 488, 491-5p, 494, 495, 496, 504, 539, 541, 543, 584, 656, 668, 758, 874, 889, 935, 939, 1193, 1197, 9* |
| Brain, enriched in synapses, axons, dendrites, spines | 7, 9, 98, 124a, 125a, 125b, 128a, 132, 134, 135a, 137, 138, 154, 182, 183, 213, 218, 323-3p, 329, 337, 369-3p, 369-5p, 370, 381, 382, 409-3p, 425, 433-5p, 483-3p, 485-5p, 487b, 494, 495, 496, 541, 543, 656, 668, 874, 889, 935, 939, 9* |
| Cortex | 9, 124a, 125a, 125b, 128a, 132, 134, 181c, 212, 213, 222, 330-3p, 338-5p, 342, 381, 382, 425, 433, 491-5p |
| Hippocampus | 9, 96, 99a, 103, 124a, 125b, 128a, 132, 134, 137, 138, 181a, 181b, 212, 219, 221, 222, 324-5p, 328, 330, 331, 335-5p, 338, 369-3p, 381, 382, 383, 425, 433-5p, 485-5p, 491-5p |
| Hypothalamus | 7, 124a, 128a, 132, 212 |
| Cerebellum | 9, 103, 124a, 125b, 128, 204, 212, 213, 218, 338, 132, 381, 134, 137, 138, 181a, 181b, 181c, 382, 425, 432, 489 |
| Amygdala | 103, 134, 138, 182, 183, 222, 323-3p, 369, 381, 382, |
| Spinal cord | 218, 219, 338, 451, 486 |
| Pituitary gland | 7, 132, 212, 213, 328 |

Several levels or generations of UST are possible. The first one can be developed for the systems of the human body (gastrointestinal, genitourinary, brain, cardiovascular, etc.). Next level of testing can focus on organs, tissues, cell types, and so on. Depending on clinical demands and economic advantages, there are at least two possible versions of UST and their practical applications: (i) first, the UST for human body systems can be performed and then, if a pathology in one or several systems has been detected, tests for organs/tissues of those systems will be performed; (ii) second, organ/tissue/cell type UST can be directly applied for screening purposes.

All organs and tissues consist of several cell types with different origin, function, and potential pathologies. Although the present invention is mainly focused on the level of organs and tissues, and their systems, the same approach can be used for developing UST covering various cell types, when sufficient information on miRNA expression profiles in various cell types becomes available. Currently, such information has been obtained for pancreatic β-cells (Tables 1 and 2), which makes it feasible to include the β-cell-enriched miRNA in UST, for example, for early detection of type 1 diabetes. miRNA markers for B- and T-lymphocyte are also available and their inclusion into UST will be helpful for early detection of pathologies that involve these cell types.

TABLE 2 miRNA enriched in organ systems and in particular organs only.

| Human body systems | miRNA biomarkers | Organ-enriched |
|---|---|---|
| Respiratory | 34b, 135b, 146, 146b-5p, 155, 199b-5p, 200c, 205, 223, 302b, 375 | Lung: 15b, 18b, 21, 126, 142-3p, 142-5p, 224, 449a, 449b, 450b-5p, 486, 492, 522, 566, 574-3p, 650, 766, 886-5p<br>Trachea: 147b, 200b, 219-5p |
| Digestive (Gastrointestinal) | 31, 130b, 136, 141, 143, 145, 148a, 192, 203, 215, 375, 376c, 429, 455-5p, 650 | Esophagus: 106a, 106b, 205, 210, 221<br>Stomach: 7, 26a, 26b, 26c, 106a, 106b, 124b, 182, 188, 197,<br>Small Intestine: 194, 200a, 200b, 200c, 321<br>Large Intestine: 147b, 194, 200a, 200b, 200c, 219-3p, 378, 450-5p, 487a, 490-3p, 492, 504, 565, 574-3p, 622, 801, 143*, 200b*<br>Liver: 122a, 194, 518b, 616, 801, 885-5p, 17*, 30d*, 194*<br>Pancreas: 7, 18a, 21, 29a, 34a, 103, 127-3p, 129-3p, 134, 135a, 135b, 182, 183, 184, 193a-3p, 193a-5p, 195, 199a-3p, 199a-5p, 200b, 200c, 204, 216a, 216b, 217, 224, |

TABLE 2-continued miRNA enriched in organ systems and in particular organs only.

| Human body systems | miRNA biomarkers | Organ-enriched |
| --- | --- | --- |
| | | 340, 365, 367, 374a, 374b, 376a, 379, 382, 383, 432, 451, 485-5p, 487b, 497, 539, 543, 642, 758, 939, 130b*, 136*, 183*, 200b*, 493* |
| Muscle and Skeletal | 1, 22, 95, 133a, 133b, 140, 206 | |
| Nervous<br>miRNA, enriched in synapses, axons, dendrites, spines | Let-7a, 7, 9, 124a, 125a, 125b, 128a, 132, 134, 135a, 137, 138, 181a, 181c, 182, 184, 211, 212, 213, 218, 219, 222, 323-3p, 338-5p, 369, 381, 382, 425, 433-5p, 485-5p, 491-5p, 539, 541, 543, 656, 874, 935, 9*<br>7, 9, 98, 124a, 125a, 125b, 128a, 132, 134, 135a, 137, 138, 154, 182, 183, 213, 218, 323-3p, 329, 337, 369-3p, 369-5p, 370, 381, 382, 409-3p, 425, 433-5p, 483-3p, 485-5p, 487b, 494, 495, 496, 541, 543, 656, 668, 874, 889, 935, 939, 9* | Cortex: 330-3p, 342<br>Hippocampus: 96, 99a, 103, 181b, 221, 324-5p, 328, 330, 331, 335-5p, 383<br>Hypothalamus: no specific miRNA have been found<br>Cerebellum: 103, 181b, 204, 432, 489<br>Amygdala: 103, 183<br>Spinal cord: 451, 486<br>Pituitary gland: 328 |
| Cardiovascular (Circulatory) | 22, 133a, 221, 222, 30e* | Heart: 1, 30a-3p, 30e-3p, 133b, 197, 208a, 208b, 302a, 302c, 367, 378, 499-5p<br>Vascular system: Let-7, 10a, 17, 18a, 19a, 19b, 20a, 21, 23a, 24, 27a, 27b, 29a, 31, 34a, 92, 98, 100, 106a, 126, 130a, 143, 145, 146a, 199a-3p, 210, 345, 365, 382, 409-3p, 431, 484, 495, 532-5p, 939, 27a*, 30a*, 93*, 126*, 130b*, 222* |
| Urinary | No miRNA enriched in both kidney and bladder have been found | |
| Genital (female) | Let-7a, Let-7c, 10b, 26a, 100, 125a, 125b, 130a, 140, 143, 145, 195, 196b, 199a, 199b, 204, 214, 222, 424, 517c, 199a* | Fallopian tubes: 10a, 31, 34b, 34c, 135a, 135b, 449<br>Ovary: Let-7b, 127, 202, 298, 382, 503, 672, 741, 742, 883-3p, 202*<br>Uterus: 99a, 939<br>Cervix: Let-7g, 101, 134, 186, 197, 218, 320, 497, 154*<br>Breast: 126, 146, 205, 206, 335, 339-5p, 378, 516-5p, 519c, 520g, 520h, 525, 1246 |
| Endocrinal | 7, 127, 493* | Thyroid: Let-7i, 1, 135a, 135b, 206, 345<br>Adrenal gland: Let-7g, 15a, 26b, 27a, 99b, 124, 132, 134, 137, 139, 152, 181a, 187, 195, 192, 202, 299, 302b, 323, 324-3p, 324-5p, 328, 330-3p, 331, 335, 340, 365, 369-3p, 375, 379, 382, 409-5p, 429, 431, 432, 455-5p, 483-5p, 514, 126*, 182*, 202*<br>Pancreatic B-cells:, 9, 21, 130b, 184, 195, 216a, 216b, 217, 376a, 376c, 497, 939, |
| Hematological | 15a, 15b, 142-3p, 142-5p, 146, 150, 181a, 181b, 181d, 205, 342, 423 | Spleen: 126, 139, 155, 223, 302b<br>Thymus: 17-5p, 20b, 106a, 106b, 149, 155, 181c, 182, 183, 213<br>Lymph nodes: Let-7g, 20b, 21, 106b, 140, 146b, 431<br>Peripheral mononuclear cells: Let-7g, 9, 17, 19b, 20a, 31, 106a, 124a, 124b, 128a, 137, |

TABLE 2-continued miRNA enriched in organ systems and in particular organs only.

| Human body systems | miRNA biomarkers | Organ-enriched |
|---|---|---|
| | | 186, 191, 197, 222, 223, 328, 431, 454, 484, 766, 27*, 223* |
| | | T-cells: 155, 223, 424 |
| | | B-cells: no specific miRNA have been found |

Although the present invention is focused on the UST development and its use for early detection of pathologies independent on their nature but specific to a particular organ system, organ, tissue, and/or cell type, such a test(s) can also include miRNA biomarkers, whose expression increase is characteristic of most common general pathologies, such as hypoxia, inflammation, and cancer (Table 3). Many more potential miRNA biomarkers for these pathologies are expected to be described soon.

TABLE 3

List of miRNA whose level changes are characteristic of broad pathologies

| miRNA | Pathology* |
|---|---|
| Let-7 family | Cancer |
| 10b | Cancer |
| 17-92 family | Cancer |
| 21 | Cancer, Inflammation |
| 29a | Cancer |
| 31 | Cancer, Inflammation |
| 34a | Cancer, Inflammation |
| 106a, b | Cancer |
| 125a-5p | Inflammation |
| 125b | Inflammation |
| 126 | Cancer, Inflammation |
| 146a, b | Cancer, Inflammation |
| 150 | Inflammation |
| 155 | Cancer, Inflammation |
| 184 | Cancer |
| 195 | Cancer |
| 200/141 family | Cancer |
| 210 | Cancer |
| 221 | Inflammation |
| 222 | Inflammation |
| 223 | Inflammation |
| 270 | Hypoxia |
| 373 | Cancer, Hypoxia |
| 375 | Cancer |
| 423-5p | Cancer |
| 424 | Hypoxia |
| 451 | Cancer |
| 486 | Cancer |

*References:
1. Osada H., Takahashi T., Carcinogenesis 2007, 28, 2-12.
2. Scholer N. et al., Exptl. Hematology 2010, 38, 1126-1130.
3. Ma L., Weinberg RA., Trends in Genetics, 2008, 24, 448-456.
4. Esquela-Kerscher A, Slack FJ, Nature Rev. Cancer, 2006, 6, 259-269.
5. Krutovskikh VA, Herceg Z., Bioessays, 2010, 32, 894-904.
6. Wang Q. et al., Exptl. Biol. Med., 2012, [Epub Feb 16].
7. Oglesby IK et al., Respiratory Res., 2010, 11, 148.
8. Leidinger P. et al., Frontiers in Genetics, 2012, 2, 104.
9. Lujambio A, Lowe SW., Nature, 2012, 482, 347-355.
10. Yu D.-C., et al., Int. J. Mol. Sci., 2012, 12, 2055-2063.

Various useful miRNA biomarkers and normalizers described in the Examples, below, can be summarized in the following Tables:

TABLE 4 biomarker/normalizer pairs for MCI/AD

| Number | Biomarker | Normalizers |
|---|---|---|
| 1 | miR-128 | miR-9, miR-181a, miR-491-5p, miR-141 |
| 2 | miR-132 | miR-9, miR-181a, miR-491-5p, miR-141 |
| 3 | miR-874 | miR-9, miR-181a, miR-491-5p, miR-141 |
| 4 | miR-134 | mir-127, miR-370 |
| 5 | miR-323-3p | mir-127, miR-370 |
| 6 | miR-382 | mir-127, miR-370 |
| 7 | All biomarker miRNA | Average of several or all normalizer miRNA |

TABLE 5 biomarker/normalizer pairs for pulmonary diseases

| Number | Biomarker | Normalizers |
|---|---|---|
| 1 | miR-34b | miR-142-5p, miR-146b-5p, miR-155, miR-223, miR-409-3p |
| 2 | miR-486-5p | miR-142-5p, miR-146b-5p, miR-155, miR-223, miR-409-3p |
| 3 | miR-192 | miR-142-5p, miR-146b-5p, miR-155, miR-223, miR-409-3p |

TABLE 6 biomarker/normalizer pairs for distinguishing NSCLC from lung inflammatory diseases

| Number | Biomarker | Normalizers |
|---|---|---|
| 1 | miR-34b | miR-155 |
| 2 | miR-486b-5p | miR-146b-5p |
| 3 | miR-192 | miR-146b-5p |

TABLE 7 biomarker/normalizer pairs for GI diseases

| Number | Biomarker | Normalizers |
|---|---|---|
| 1 | miR-192 | miR-30e-3p, miR-145, miR-148a |
| 2 | miR-194 | miR-30e-3p, miR-145, miR-148a |
| 3 | miR-203 | miR-30e-3p, miR-145, miR-148a |
| 4 | miR-215 | miR-30e-3p, miR-145, miR-148a |

TABLE 8 biomarker/normalizer pairs for distinguishing Crohn's disease and GI cancers

| Number | Biomarker | Normalizers |
|---|---|---|
| 1 | miR-215 | miR-30e-3p, miR-194, miR-203 |
| 2 | miR-203 | miR-148a |
| 3 | miR-194 | miR-148a, miR192 |
| 4 | miR-192 | miR-203 |

TABLE 9 miRNA pairs whose ratio distinguishes cancers of various GI organs

| Number | Cancers compared | miRNA pairs |
|---|---|---|
| 1 | Esophageal versus gastric | miR-194/miR-145, miR-194/miR148a, miR-194/miR-30e-3p |
| 2 | Gastric versus colorectal | miR-215/miR-203, miR-203/miR-30e-3p, miR-203/miR148a |
| 3 | Esophageal versus colorectal | miR-192/miR-145, miR-192/miR148a, miR-192/miR-30e-3p |

TABLE 10 miRNA pairs whose ratio distinguishes pathologies of pulmonary and GI systems

| Number | miRNA pairs |
|---|---|
| 1 | miR-192/miR-126 |
| 2 | miR-155/miR-126 |
| 3 | miR-145/miR-126 |
| 4 | miR-155/miR-30e-3p |
| 5 | miR-192/miR-30e-3p |
| 6 | miR-155/miR-409-3p |
| 7 | miR-486-5p/miR-17-5p |
| 8 | miR-155/miR-17-5p |
| 9 | miR-192/miR-17-5p |
| 10 | miR-146b-5p/miR-31 |
| 11 | miR-155/miR-31 |
| 12 | miR-192/miR-31 |
| 13 | miR-486-5p/miR-155 |
| 14 | miR-192/miR-155 |
| 15 | miR-145/miR-155 |
| 16 | miR-146b-5p/miR-155 |
| 17 | miR-486-5p/miR-203 |
| 18 | miR-192/miR-203 |
| 19 | miR-145/miR-203 |
| 20 | miR-192/miR-215 |
| 21 | miR-155/miR-215 |

TABLE 11 miRNA pairs whose ratio distinguishes inflammatory pathologies from cancers of pulmonary plus GI systems

| Number | miRNA pairs |
|---|---|
| 1 | miR-17-5p/miR-155 |
| 2 | miR-192/miR-155 |
| 3 | miR-215/miR-155 |
| 4 | miR-192/miR-30e-3p |
| 5 | miR-155/miR-30e-3p |
| 6 | miR-146b-5p/miR-30e-3p |

Examples of useful methods for measuring miRNA level in bodily fluids include hybridization with selective probes (e.g., using Northern blotting, bead-based flow-cytometry, oligonucleotide microchip [microarray], or solution hybridization assays such as Ambion mirVana mirna Detection Kit), polymerase chain reaction(PCR)-based detection (e.g., stem-loop reverse transcription-polymerase chain reaction [RT-PCR], quantitative RT-PCR based array method [qPCR-array]), or direct sequencing by one of the next generation sequencing technologies (e.g., Helicos small RNA sequencing, miRNA BeadArray (Illumina), Roche 454 (FLX-Titanium), and ABI SOLID). For review of additional applicable techniques see, e.g., Chen et al., BMC Genomics, 2009, 10:407; Kong et al., J Cell Physiol. 2009; 218:22-25. Because many tissue/organ-specific miRNA are present in bodily fluids in much lower concentrations than ubiquitous miRNA, and a screening test should be capable of detecting early disease-associated changes, which can be relatively low, it is important to use, at least at the proof-of-principle stage, the most sensitive and minimally variable technique for measuring miRNA levels. In the present invention RT-PCR, which detects larger numbers of plasma miRNA and is significantly more robust than various array techniques, was used throughout the study. This does not exclude use of other techniques of miRNA analysis in a resulting clinical test.

In some embodiments, miRNA are purified prior to quantification. miRNA can be isolated and purified from bodily fluids by various methods, including the use of commercial kits (e.g., miRNeasy kit [Qiagen], MirVana RNA isolation kit [Ambion/ABI], miRACLE [Agilent], High Pure miRNA isolation kit [Roche], and miRNA Purification kit [Norgen Biotek Corp.]), Trizol extraction(see Example 1, below), concentration and purification on anion-exchangers, magnetic beads covered by RNA-binding substances, or adsorption of certain miRNA on complementary oligonucleotides.

In some embodiments, miRNA degradation in bodily fluid samples and/or during small RNA purification is reduced or eliminated. Useful methods for reducing or eliminating miRNA degradation include, without limitation, adding RNase inhibitors (e.g., RNasin Plus [Promega], SUPERase-In [ABI], etc.), use of guanidine chloride, guanidine isothiocyanate, N-lauroylsarcosine, sodium dodecyl sulphate (SDS), or a combination thereof. Also, when working with urine samples, lower risk of miRNA degradation can be achieved when the sample has been held in the bladder for a shorter time (e.g., less than 4 hours). Reducing miRNA degradation in bodily fluid samples is particularly important when sample storage and transportation is required prior to miRNA quantification.

The present invention also provides several approaches for normalization of miRNA concentrations detected in bodily fluids. To account for possible losses of a given miRNA during purification, potential RT-PCR inhibition, miRNA contaminants derived from dying or damaged blood or urine cells during sample isolation and treatment, variations in kidney filtration, etc., various methods of experimental data normalization can be employed. For example, one or more of the following normalization methods can be used in the present invention:

a) Synthetic miRNA (e.g., miRNA absent in human cells) oligonucleotides can be synthesized and used as controls for losses during purification and RT-PCR inhibition (by adding those to bodily fluid samples before miRNA purification).

b) Concentration of a target miRNA can be normalized to one of ubiquitous miRNA (e.g., miR-16, miR-30e, miR-103 and others), small nucleolar RNAs (snoRNAs), U6 small nuclear RNA (U6 RNA).

c) Another approach is based on normalization of target miRNA concentrations to miRNA that is expressed in numerous tissues but not in a target one. For example miR-10a and miR-141 are expressed in the brain at much lower level than in other organs, and miR-409-3p is expressed in the lung at much lower level than in other tissues. This approach decreases chances a normalizer miRNA being changed due to a target pathology.

d) Concentration of a target miRNA can also be normalized to miRNA in other organ(s) (e.g. miRNA enriched in heart can be normalized to miRNA enriched in colon or brain and vice versa).

e) Normalization of a target miRNA per other miRNA enriched in the same organ, tissue, or organ system can be effective if biomarker and normalizer miRNA are expressed in different cell types or different organs of the same system.

f) Normalization of a target miRNA per another miRNA from the same organ and tissue if their expression and/or secretion are effected differently by a pathology.

g) Normalization of a target miRNA per a tissue-enriched miRNA is useful when, for example, changes in the expression and/or secretion of a target miRNA are characteristic of a particular pathology (cancer, inflammation, etc.) but the miRNA is not enriched in the organ/tissue of interest. In such case normalization per a tissue-enriched miRNA will be helpful for connecting a pathology to a particular organ or organ system.

h) Normalization per the average of several miRNA normalizers or, if many, e.g. >15, miRNA are analyzed normalization per the average of all miRNA tested.

i) To account for variations in kidney filtration (when working with urine samples), miRNA concentration in urine can be normalized on creatinine and/or albumin level.

Normalization calculus along with further data processing can be done by UST software, consisting of three parts:

Data Base Management System (DBMS) used for access and maintenance of K-base and I-base. It can be one of the industry standard systems, like, but not limited to, SQL server, Oracle, MySQL, etc.

Application for Screening Test(s) development used on the research stage. Functions of this application include selection of proper miRNA and construction of D-sets, creation of pathology sets, etc. The application is desktop-type and includes: (i) user interface for entering/inspecting data in K-base and I-base and to control algorithm execution; (ii) Data processing for Learning and Classification on the developmental stage; (iii) Service programs for D-set consistency check, etc.; (iv) Scripts for table creation/verification/modification in K-base and I-base. Algorithm for data processing (Algorithm1) includes Learning and Classification parts.

Application for Screening Test processing in the clinical use of UST. Functions of this application include Training using large amount of data and Classification on actual Screening Test data. The application can be desktop-type, or Web application and includes: (i) user interface for entering/inspecting data in I-base, and to control algorithm execution; (ii) data processing for Learning and/or Classification of subject data; (iii) Scripts for table creation/verification/modification in K-base and I-base; these tables are different from those in application for Screening Test development. Algorithm for data processing (Algorithm2), as in Algorithm 1 includes Learning and Classification and can differ from those in Algorithm1.

As discussed in details below in the Examples, the proposed approach was validated by analysis of plasma miRNA from patients with different diseases of several organs.

1. Nervous System:
   a) MCI (Mild Cognitive Impairment);
   b) Alzheimer's disease (AD).
2. Gastrointestinal System:
   a) Esophageal cancer;
   b) Gastric cancer;
   c) Colon cancer;
   d) Crohn's disease.
3. Respiratory System:
   a) Asthma;
   b) Pneumonia;
   c) COPD (Chronic Obstructive Pulmonary Disease);
   d) Lung cancer.

For selection of biomarkers and normalizer miRNA, plasma concentrations of many miRNA enriched in respective organs or organ systems were analyzed by RT-PCR. Ubiquitous miRNA and miRNA expressed in numerous organs but under-expressed in organs of interest were also analyzed as potential normalizers. All miRNA analyzed for respective organs or organ systems were tested as potential biomarkers and normalizers, and combinations, which provided statistically significant differentiation between a pathology and respective controls, were selected as most promising.

Nervous System

Early detection of Mild Cognitive Imparment (MCI) and Alzheimer's disease (AD) was used for validating the proposed approach to the development of a screening test for the nervous system. AD is the most common neurodegenerative disease, which comprise a large group of pathologies caused by metabolic changes in brain cells, loss of synapses and other compartments of neurons, and finally neuronal death (for review see Neurodegenerative diseases: From Molecular Concepts to Therapeutic Targets. Editors: R. von Bernhardi, N.C. Inestrosa, Nova Publishers, 2008). AD is characterized by neurite retraction, axonal transport defects, synaptic dysfunction, synaptic loss, and finally by neuronal death in several disease-specific areas of the brain, such as hippocampus and cortex (See, e.g., Crews, Masliah, Human Mol Gen., 2010, 19:R12-R20; Bredesen, Molecular Neurodegeneration 2009, 4:27; Nimmrich and Ebert, Rev Neurosci. 2009, 20:1-12; Yoshiyama et al., Neuron. 2007, 53:337-351; Wishart et al., J Neuropathol Exp Neurol. 2006, 65:733-739; Gylys et al., Neurochem Int. 2004; 44:125-131; Conforti et al., Trends Neurosci. 2007, 30:159-166; Revuelta, et al. Am J Alzheimers Dis Other Demen 2008, 23: 97-102).

The first symptomatic stage of AD that is manifested by mild clinical symptoms is MCI, which is usually defined as an intermediate state between normal aging and dementia (DeCarli, Lancet Neurol., 2003, 2:15-21; Stephan et al., Alzheimer's Res Therapy, 2009, 1:1-9; Apostolova et al., Human Brain Mapping, 2010, 31:786-797). MCI is a heterogeneous syndrome that may lead to different outcomes. Up to 40% of MCI patients revert to normal status (Larrieu et al., Neurology, 2002, 59:1594-1599; Brooks, Loewenstein, Alzheimer's Res Therapy, 2010, 2:28-36), and autopsy studies demonstrate that a substantial percentage of MCI patients do not have evidence of AD pathology (Jicha et al., Arch Neurol, 2006, 63:674-681; Khan, Alkon, Neurobiol. Aging, 2010, 31:889-900). About 60% of MCI patients convert to dementia at a rate of 10-15% annually (Petersen et al., Arch Neurol. 2001, 58:1985-1992; Apostolova et al., Human Brain Mapping, 2010, 31:786-797). Although AD is the most common cause of dementia, about 20% of MCI patients who progress to dementia are diagnosed not with AD but other neurodegenerative diseases, such as vascular, Lewy body, Huntington, Parkinson, and other dementias (Jicha et al., Arch Neurol, 2006, 63:674-681; Stephan et al., Alzheimer's Res Therapy, 2009, 1:1-9).

Thus, detection of MCI and AD by analysis of circulating miRNA supports the idea of developing an organ/system-specific test for various pathologies. As discussed in detail in the Examples for selection of biomarker and normalizer miRNA, concentrations of many brain-enriched miRNA, including neurite/synapse-enriched ones, in plasma of MCI and AD patients and age-matched control group were analyzed by RT-PCR. All selected miRNA were tested as potential biomarkers and normalizers and combinations, which provided statistically significant differentiation between MCI patients and age-matched controls, were identified as most promising. The data have demonstrated that the most effective potential biomarkers are neurite/synapse miRNA and the most effective normalizers are other brain-enriched miRNA, although other miRNA can also be used for normalization. Two families of biomarkers, miR-132 family and miR-134 family, and several normalizers have demonstrated the highest sensitivity (84%-92%) and specificity (84%-90%) in MCI detection. High correlation between members of miR-134 family can be easily explained by the fact that all members of this family, namely miR-134, miR-323-3p and miR-382, belong to the same cluster and are expressed in the same cell types. Close relationships between members of miR-132 family, namely miR-128, miR-132 and miR-874, have not been described before. It is also interesting that miR-132 and miR-134 biomarker families yield better results with different normalizers. miR-132 family works better than miR-134 family with normalizers miR-491-5p, miR-181a, miR-9, and miR-141. On the other hand, miR-134 family demonstrates better results than miR-132 family with normalizers miR-370 and miR-127.

Thus, the heterogeneous MCI syndrome and AD can be detected by analysis of cell-free circulating brain-enriched miRNA in the plasma.

Since different brain areas are involved in various neurodegenerative diseases leading to the development of dementia (Geldmacher & Whitehouse, Neurology. 1997, 48:S2-9; Levy & Chelune, J Geriatr Psychiatry Neurol. 2007 20:227-23 8; Gong & Lippa, Am J Alzheimer's Dis Other Demen, 2010, 25:547-555) and due to diverse miRNA expression profile in various brain areas (Landgraf et al., Cell. 2007, 129:1401-1414; The miR-Ontology Data Base: ferrolab.dmi.unict.it/miro/), analysis of other brain-enriched miRNA would be helpful for distinguishing changes and processes caused by distinct neuronal pathologies in the brain.

Gastrointestinal System

Plasma samples of patients with stages 1 and 2 cancers of three gastrointestinal (GI) organs (esophagus. stomach, and colon) and with the Crohn's disease (an inflammatory bowel disease that may affect any part of the GI tract) were used for validating the proposed approach to the development of a screening test for the GI system. Plasma concentrations of miRNA enriched in GI system or in particular GI organs, e.g. miR-215 highly enriched in colon and small intestine and miR-203, enriched in esophagus and to a lesser degree in stomach, as well as of ubiquitous miR-30e-3p were measured. Ratios of all possible miRNA pairs were calculated to find the most promising biomarker/normalizer combinations. The obtained data have demonstrated that miR-192, miR-194, miR-203 and miR-215 are the most effective biomarkers, and miR-145, miR-148a and miR-30e-3p are the most effective normalizers. Biomarker/normalizer ratios effectively differentiate patients with all studied diseases from controls. miR-203, highly enriched in esophagus and stomach, is especially effective in detecting cancers of these organs, and miR-215, highly enriched in column is most effective in differentiating patients with colon cancer and Crohn's disease from controls. Combination of two or more biomarker/normalizer ratios can be used to increase specificity and sensitivity. For example, miR-192 and miR-203 normalized per miR-30e-3p effectively distinguished patients with all pathologies of GI system from controls with 94% sensitivity and 100% specificity. It is important that all tested tumors were stage 1 or 2, which means that the proposed approach can be effectively used for screening and early diagnosis. Then pairs of different cancers as well as Crohn's disease versus all cancers of the GI system were compared in greater details. As a result the following biomarker/normalizer ratios capable of distinguishing particular pathologies have been found:

1. Crohn's disease versus esophageal, gastric and colorectal cancers: miR-194/miR-148; miR-215/miR-30e-3p; miR-215/miR-194; miR-203/miR-148a; miR-192/miR-203; miR-215/miR-203 and miR-194/miR-192.
2. Esophageal cancer versus gastric cancer: miR-194/miR-145; miR194/miR-148 a; miR194/miR-30e-3p.
3. Esophageal cancer versus colorectal cancer: miR-192/miR-145; miR192/miR-148 a; miR192/miR-30e-3p.
4. Gastric cancer versus colorectal cancer: miR-203/30e-3p; miR-203/miR-148a; miR-215/miR-203.

Thus, analysis of plasma concentrations of miRNA enriched in organs of the GI system is effective for: (i) detection of tumors and inflammatory conditions, such as Crohn's disease, in esophagus, stomach and colon; (ii) differentiation of an inflammatory disease from cancers; (iii) differentiation of cancers located in various organs of the GI system.

Respiratory System

Plasma samples of patients with four diseases, namely asthma, pneumonia, Chronic Obstructive Pulmonary Disease (COPD), and Non-Small Cell Lung Cancer (NSCLC, stages 1-4), were used for validating the proposed approach to the development of a screening test for the respiratory system. Since enrolled patients with asthma and pneumonia were non-smokers and patients with COPD and NSCLC were smokers, plasma samples were also collected from two distinct control groups—smokers and non-smokers. Plasma concentrations of lung-enriched miRNA and of miR-409-3p, which is present in many organs but is under-expressed in the lung, were measured. Again, as described above for the GI system, ratios of all possible miRNA pairs were calculated to find the most promising biomarker/normalizer combinations.

miR-34b and miR-486-5p, which are highly enriched in the lung, have been found to be effective biomarkers that normalized per miR-409-3p differentiated patients with asthma and pneumonia from non-smoking controls and patients with COPD and NSCLC from smoking controls. Other effective normalizers are lung-enriched miR-142-5p, miR-146b-5p, miR-155 and miR-223, potentially due to their downregulation in lung pathologies (Liu X. et al. Clin. Cancer Res. 2009, 15:1177-1183; Miko E. et al., Exp. Lung Res. 2009, 35:646-664; Halappanavar S. et al. Toxicology 2011, 285: 133-141; Heegaard N H et al. Int. J. Cancer, 2012, 130:1378-1386). Unexpectedly, miR-192 also behaved as an effective biomarker for pulmonary pathologies. Since this miRNA was also shown to be an effective biomarker for diseases of the GI system, it is reasonable to suggest that expression or/and secretion of miR-192 is increased due to inflammation or tumor development processes (Benjamin H et al., J. Mol. Diagn. 2010, 12:771-779; Lan H Y. Clin. Exp. Pharmacol. Physiol. 2011 Dec. 28 [Epub ahead of print]; Luzna P. et al. Diagn. Pathol. 2011, 6:114; Wu Q. et al. J. Biomed. Biotechnol. 2011, Epub May 26; Zhou J. et al., J. Clin. Oncol. 2011, 29:4781-4788).

Since miRNA biomarker/miRNA normalizer ratios were not different for smoking and non-smoking controls, the four pathologies were compared with the combined controls (smoking and non-smoking subjects). Obtained data demonstrated that patients with all four analyzed pathologies can be effectively distinguished from such combined controls by various sets of miRNA biomarkers and normalizers, e.g. miR-34b normalized per miR-409-3p, miR-486-5p normalized per miR-223, or miR-192 normalized per miR-155. There were also other effective sets of miRNA biomarkers and normalizers.

The ability of various combinations of miRNA biomarkers and normalizers to distinguish NSCLC from such inflammatory diseases as asthma, pneumonia and COPD was also analyzed. The results demonstrated that patients with NSCLC were effectively differentiated from patients with inflammatory diseases using ratios of miR-34b to miR-155, miR-486-5p to miR-146b-5p or to miR-142-5p, miR-192 to miR-146b-5p. There were other effective combinations of miRNA biomarkers and normalizers.

Thus, pathologies of the pulmonary system can be effectively detected by analysis cell-free circulating miRNA in plasma, if lung-enriched miRNA are used as biomarkers, or normalizers, or both. Some biomarker/normalizer combinations can also effectively differentiate cancer patients from patients with inflammatory pulmonary diseases.

Distinction of Pathologies in Different Organ Systems

To validate the idea that a test based on analysis of organ-enriched miRNA in bodily fluids is capable of detecting subjects with a pathology of a particular organ system, it is necessary to demonstrate that there are miRNA combinations capable to distinguish pathologies of distinct organ systems. As described in details in Examples, miRNA were purified from the plasma samples obtained from patients with diseases of the GI system (Crohn's disease and esophageal, gastric and colorectal cancers) and of the pulmonary system (asthma, pneumonia, COPD and NSCLC). Concentrations of lung-enriched and GI system-enriched miRNA as well as, several miRNA, involved in pathological processes of various organs, were analyzed. Additionally, ubiquitous miR-30e-3p and miR-409-3p were included in the study as potential normalizers. Concentrations of each miRNA were normalized per miR-30e-3p and miR-409-3p, as well as on each other, converted into Relative Quantity (RQ) of miRNA according the ABI protocol ($2^{-\Delta Ct}$), and miRNA profiles characteristic of patients with the diseases of pulmonary and GI systems were compared. The data demonstrated that many miRNA pairs effectively distinguish patients with diseases of pulmonary and GI systems: miR-192/miR-126; miR-155/miR-126; miR-145/miR-126; miR-155/miR-30e-3p; miR-192/miR-30e-3p; miR-155/miR-409-3p; miR-486-5p/miR-17-5p; miR-155/miR-17-5p; miR-192/miR-17-5p; miR-146b-5p/miR-31; miR-155/miR-31; miR-192/miR-31; miR-486-5p/miR-155; miR-192/miR-155; miR-145/miR-155; miR-146b-5p/miR-155; 486-5p/miR-203; miR-192/miR-203; miR-145/miR-203; miR-192/miR-215; miR-155/miR-215. Combination of two miRNA pairs increases the test accuracy. For example, the combination of miR-145/miR-155 and miR-486-5p/miR-155 ratios distinguished patients with all pathologies of the GI system from patients with pulmonary diseases with 95% sensitivity, 90% specificity, and 93% accuracy.

Distinction of Different Pathologies in Various Organ Systems

Due to characteristic changes in expression and secretion of some miRNA during inflammatory diseases and cancer development in various organs, it was hypothesized that analysis of their concentrations in bodily fluids could be used for distinguishing among these pathologies. The same plasma samples were used for miRNA purification and the same miRNA that were described in the previous section were analyzed. In this study the ability of various miRNA combinations to differentiate patients with inflammatory diseases (asthma, pneumonia, COPD and Crohn's disease) from patients with various cancers (esophageal, gastric, colorectal and non-small cell lung cancers) was investigated. The data demonstrate that several miRNA pairs effectively distinguish patients with inflammatory diseases from cancer patients: miR-17-5p/miR-155; mir-192/miR-155; miR-215/miR-155; miR146b-5p/miR155; miR192/miR-30e; miR-146b-5p/miR-30e-3p; miR155/miR-30e-3p. There are less miRNA pairs that differentiate inflammation diseases from cancers than miRNA pairs capable to differentiate diseases of the pulmonary system from diseases of GI system. First, changes in expression of many miRNA are characteristic to both pathology types. Second, in many cases carcinogenesis is accompanied by relatively prominent inflammation. Combination of two miRNA pairs increases the test accuracy. For example the combination of miR-146b-5p/miR-155 and miR-146b-5p/miR-30e-3p ratios distinguished all patients with inflammatory diseases from cancer patients with 80% sensitivity, 98% specificity, and 89% accuracy.

Thus, the results of the experiments presented in present invention support its main ideas. The analysis of plasma concentration of miRNA, enriched in a particular organ system or in an organ, differentiates: (i) organ system diseases from controls; (ii) pathologies of three organs of the gastrointestinal system; (iii) diseases of pulmonary and gastrointestinal system; (iv) cancers and inflammatory diseases.

Kits

In conjunction with the above diagnostic and screening methods, the present invention provides various kits comprising one or more primer and/or probe sets specific for the detection of target miRNA. Such kits can further include primer and/or probe sets specific for the detection of normalizer miRNA. Primer or probe combinations in kits can be based, for example, on various combinations of the molecules listed in Tables 1-11.

Such kits can be useful for direct miRNA detection in bodily fluid samples isolated from patients or can be used on purified RNA samples.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs). Alternatively (or in addition), a kit can include reagents for performing a hybridization assay. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include miRNA isolation or purification means as well as positive and negative controls. A kit can also include a notice associated therewith in a form prescribed by a governmental agency regulating the manufacture, use or sale of diagnostic kits. Detailed instructions for use, storage and trouble shooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit.

Definitions

The term "screening test" is used herein to refer to a test, which is used for early detection of a disease, preferably prior to its clinical manifestation. Two types of screening tests are mainly described herein: (i) the screening tests that detect a pathology in a particular organ system/organ/tissue/cell type, and (ii) the screening tests that detect particular general pathological changes, such as, e.g., hypoxia, inflammation, or carcinogenesis, but do not localize this pathology to a particular organ system/organ/tissue/cell type. The term "universal screening test (UST)" refers to one or both of the above screening tests.

The term "organ system" refers to a group of related organs that work together to perform a certain task. For example, esophagus, stomach, duodenum, small and large intestines are organs of the digestive system. Salivary glands, pancreas, and liver als are components of the digestive system. At the same time, pancreatic (3-islets, which secrete hormones, are also related to the endocrinal system.

Within the meaning of the present invention, the term "organ/tissue/cell type-enriched miRNA" refers to miRNA, which is present in increased amounts (e.g., at least 5-times higher concentrations) in a respective organ, tissue, or cell type, as compared to other organs, tissues or cell types, and can be a source of detectable amounts of miRNA in a bodily fluid being tested. The term "organ system-enriched miRNA" refers to miRNA, which is present in increased amounts (e.g., at least 5-times higher concentrations) in all or at least several organs of the respective organ system, as compared to other organ systems, organs, tissues or cell types, and can be a source of detectable amounts of miRNA in a bodily fluid being tested. To be useful in the diagnostic methods of the present invention, such organ system-/organ-/tissue-/cell type-enriched miRNA should be detectable in bodily fluids as a result of its release from cells and transport to said bodily fluids.

The term "a pathology" is used herein to refer to a non-specified pathology involving metabolic and/or structural changes in a respective organ, tissue or cell type associated with their dysfunction and/or partial destruction and/or loss. The term "associated with" is used to encompass any correlation, co-occurrence and any cause-and-effect relationship.

The terms "microRNA" or "miRNA" as used herein refer to a class of small approximately 22 nt long non-coding mature RNA molecules. They play important roles in the regulation of target genes by binding to complementary regions of messenger transcripts (mRNA) to repress their translation or regulate degradation(Griffiths-Jones Nucleic Acids Research, 2006, 34, Database issue: D140-D144). Frequently, one miRNA can target multiple mRNAs and one mRNA can be regulated by multiple miRNA targeting different regions of the 3' UTR. Once bound to an mRNA, miRNA can modulate gene expression and protein production by affecting, e.g., mRNA translation and stability (Baek et al., Nature 455(7209):64 (2008); Selbach et al., Nature 455(7209):58 (2008); Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; and Ying et al., 2004, Gene, 342, 25-28). Examples of organ/tissue/cell-enriched miRNA useful in the methods of the present invention include, without limitation, miRNA listed in Table 1. Examples of organ system-enriched miRNA useful in the methods of the present invention include, without limitation, miRNA listed in Table 2, column 2. Examples of organ/tissue/cell type-enriched miRNA useful for more precise localization of a pathology in the methods of the present invention include, without limitation, miRNA enlisted in Table 2, column 3.

Information on most currently known miRNA can be found in the miRNA database miRBase (available at the world wide web at mirbase.org). See also Burside et al., BMC Genomics 9:185 (2008); Williams et al., BMC Genomics 8:172 (2007); Landgraf et al., Cell 129:1401 (2007).

The term "miRNA array" as used herein refers to a multiplex technology used in molecular biology and in medicine. It consists of an arrayed series of multiple (e.g., thousands) microscopic spots of oligonucleotides, each containing a specific sequence (probe)complementary to a particular target miRNA. After probe-target hybridization under high-stringency conditions the resulting hybrids are usually detected and quantified by quantifying fluorophore-, silver-, or chemiluminescence-labeled targets to determine relative abundance of miRNA. In the methods of the present invention, both custom made and commercially available miRNA arrays can be used. Non-limiting examples of useful commercially available miRNA arrays (based on various methods of target labeling, hybrid detection and analysis) include arrays produced by Agilent, Illumina, Exiqon, Invitrogen, Febit, and LC Sciences.

The term "next generation sequencing technologies" as used herein broadly refers to sequencing methods which generate multiple sequencing reactions in parallel. This allows vastly increased throughput and yield of data. Non-limiting examples of commonly used next generation sequencing platforms include Helicos small RNA sequencing, miRNA BeadArray (Illumina), Roche 454 (FLX-Titanium), and ABI SOLID.

An "individual" or "subject" or "animal", as used herein, refers to humans, veterinary animals (e.g., cats, dogs, cows, horses, sheep, pigs, etc.) and experimental animal models of neurodegenerative diseases or other neuronal pathologies (see Examples, below). In a preferred embodiment, the subject is a human.

The term "urinary tract" refers to the organs and ducts, which participate in the secretion and elimination of urine from the body.

The term "purified" as used herein refers to material that has been isolated under conditions that reduce or eliminate the presence of unrelated materials, i.e., contaminants, including native materials from which the material is obtained. For example, RNA purification includes elimination of proteins, lipids, salts and other unrelated compounds present in bodily fluids.

As used herein, the term "substantially free" is used operationally, in the context of analytical testing of the material. Preferably, purified material substantially free of contaminants is at least 50% pure; more preferably, at least 90% pure, and still more preferably at least 99% pure. Purity can be evaluated by chromatography, gel electrophoresis, composition analysis, biological assay, and other methods known in the art.

As used herein, the term "similarly processed" refers to samples (e.g., bodily fluid samples or purified RNAs) which have been obtained using the same protocol.

The term "a control level" as used herein encompasses predetermined standards (e.g., a published value in a reference) as well as levels determined experimentally in similarly processed samples from control subjects (e.g., age and gender matched healthy subjects). Since the present invention describes screening tests that can be performed for the same patient periodically, prior data from the same individual can be used as "a control level".

For differentiation between two pathologies, such as cancer versus inflammation or esophageal cancer versus colorectal cancer, the ratios of levels of miRNA in plasma will be compared not with predetermined control ratios but with predetermined ranges of ratios of miRNA levels in plasma, which is characteristic of the respective pathologies. To define these ratios, several hundred patients will be enrolled and levels of miRNAs of interest will be measured in their plasma samples. Then ratios of levels of various miRNA pairs will be calculated, which will provide the range of ratios characteristic of the respective pathology and covering, for example, 100%, 99% or 95% of pathology cases. The predetermined range used in the real clinical setting will be determined by demands to test sensitivity and specificity.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198(2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999),U.S. Pat. Nos. 5,789,166 and 5,932,419, Hogrefe, Strategies 14. 3: 74-75 (2001),U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198(1995), Barrenttino et al., Nucl. Acids. Res. 22: 541-542 (1993), Tessier and Thomas, Meths. Molec. Biol. 57: 229-237, and Pons et al., Meth. Molec. Biol. 67: 209-218.

The term "Labeled Data" used for Training Data Set refers to results of analysis obtained on clinical samples from persons with known diagnosis. For example, for Labeled Data for miRNA targeting Liver, data should be collected from people with liver pathologies (label "Liver" and, e.g., "hepatitis" or "hepatocellular carcinoma"), and without any liver pathology (label "Control").

As used herein, the term "D-Set" refers to a set of miRNA (biomarkers) selected for detection of a pathology in a particular organ system/organ/tissue/cell type. Each D-set is comprised of at least one but typically more than one biomarker, and some biomarkers are members of more than one D-set.

The term "K-base" refers to a database, containing knowledge about all Screening Test types and their components. The information is grouped in the set of different tables, such as:
  list of all Screening tests developed up to date;
  list of all pathologies, covered by those tests;
  list of used (and supposed for using) miRNA;
  list of D-Sets used in all Screening Tests;
  relationships Screening Tests type—D-sets—miRNA;
  tables containing constants for each miRNA used in corresponding D-sets. These tables have to be populated on the Learning step of the algorithms, and used for calculations in the Classification part of the algorithm.

This database is modified and expanded with arrival of new verified research data.

The term "I-base" refers to a database, containing actual data of Screening Tests on individuals, including lists of subjects and pertinent information, history of Screening Tests, their raw data and processed results, etc.

Both databases, along with programs, implementing algorithms for Learning/Classification, are part of the present invention.

The term "Iteration" is used at algorithm description. It refers to the body of the program loop, which is cyclically executed.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Comparison of Different Methods Used for miRNA Purification from Serum and Plasma There are many commercial kits for miRNA isolation, including the miRNeasy kit (Qiagen), the MirVana RNA isolation kit (Ambion/ABI), miRACLE (Agilent), High Pure miRNA isolation kit (Roche), and miRNA Purification kit (Norgen Biotek Corp.). In addition, the in-house techniques based on the use of Trizol (Invitrogen) are commonly used. After Trizol deproteinization, RNA is precipitated with isopropyl alcohol or additionally purified on silica columns. In some experiments, purified RNA is treated with RNAse-free DNAse (Qiagen, ABI, Invitrogen or other). miRNA preparations obtained by different methods are compared using RT PCR.

miRNA was purified from plasma and serum samples obtained from the same 5 healthy donors. 10⁷ copies of *Arabidopsis thaliana* miR-159a (ath-miR-159a) were spiked per 1 ml plasma or serum after addition of guanidine-containing solution for evaluation of miRNA yield. Two techniques, one based on MirVana Paris kit (Ambion/ABI), and another based on Trizol (Invitrogen) deproteinization, and subsequent purification on silica columns, were compared. After RNA purification, concentrations of spiked miRNA and human endogenous miR-9, miR-16, and miR-134 were measured in final preps by RT-PCR. MirVana Paris kit was more effective in miRNA isolation then the Trizol-based technique and was selected for future experiments. Although all analyzed miRNA were detectable in serum and plasma and both sample types are suitable for miRNA testing, the final PCR Ct values were about 2 cycles lower for plasma, and the latter was used in subsequent experiments. Based on the quantitative measurement of spiked ath-miR-159a, average yield of miRNA isolated from plasma with MirVana kit was 71.4%.

Example 2: Selection of miRNA for Testing

Potential miRNA biomarkers (Table 1) were initially selected based on literature data on their enrichment in various organs and tissues (See, e.g., Hua et al., BMC Genomics 2009, 10:214; Liang et al., BMC Genomics. 2007, 8:166; Landgraf et al., Cell. 2007, 129:1401-1414; Lee et al., RNA. 2008, 14:35-42; ferrolab.dmi.unict.it/miro/; mips.helmholtz-muenchen.delphenomir/). Then miRNA common for several organs of the same organ system were selected as potential biomarkers for the respective system (Table 2, column 2). Those miRNA that are enriched in one organ but not in other organs of the system were identified as potential biomarkers for more precise pathology localization (Table 2, column 3). For normalization, in addition to spiked synthetic non-human miRNA, e.g., ath-mir-159a, and ubiquitous miRNA, such as miR-16 and miR-30e-3p, miRNA expressed in numerous tissues but not in a target tissue were selected. For example, miR-10b and miR-141 can be used for normalizing brain biomarkers, and miR-409-3p for pulmonary system biomarkers, etc. Other promising normalizers, which are enriched in the analyzed tissues, organs and systems analyzed, were selected experimentally.

All these biomarkers have to be included as a corresponding D-set to K-base per Example 8, below.

Example 3: Detection of an Increase in Levels of Brain-Enriched miRNA in Serum/Plasma of Patients Diagnosed with Neurological Diseases Plasma samples from amnestic MCI and AD patients and AMC, 20 in each group, were used in the study. RNA was isolated from two 200 [1.1 aliquots of plasma samples by the Trizol-silica method according to an Asuragen procedure. Single target qRT-PCR was performed using the TaqMan® Reverse Transcription Kit and miRNA-specific stem-loop primers (Applied Biosystems). RT step was performed in triplicate and 2 ! al plasma equivalents were present in final PCR.

Data presented in FIGS. 1-6 demonstrate the 2-5 times increase in median concentrations of neurite/synaps e miRNAs (miR-7, miR-125b, miR-128, miR-132, miR-134, miR-323-3p, miR-382, miR-874) in plasma of MCI and AD patients when compared to age-matched controls. The effect is more prominent when normalization is performed per brain-enriched miRNA, such as miR-9, miR-127, miR-181a, miR-370, and miR-491-5p.

Two families of biomarkers, miR-132 and miR-134 families, and several normalizers have demonstrated the highest sensitivity and specificity. Receiver-Operating Characteristic (ROC) curves for these combinations of biomarkers and a normalizer are presented in FIGS. 7A-C and 8A-C. Biomarkers miR-128, miR-132 and mir-874 ("miR-132 family") demonstrated 84%-92% sensitivity and 84%-90% specificity when normalized per miR-491-5p. The area under the ROC curve (AUC) for miR-128, miR-132 and miR-874 is 0.95, 0.93 and 0.95, respectively. The second promising set of biomarkers consists of miR-134, miR-323-3p and miR-382 ("miR-134 family") and demonstrates 78%-91% sensitivity and 85-87% specificity when normalized per miR-370. AUC for miR-134, miR-323-3p and miR-382 are 091, 0.94 and 0.92, respectively.

Correlation analysis shown in FIG. 9A-F demonstrates that miR-128, miR-132 and miR-874 form one family of biomarkers (Spearman test r values in the pair comparison are in the 0.93-0.95 range) and miR-134, miR-323-p and miR-382 form another family of biomarkers (Spearman test r values in the pair comparison are in the 0.87-0.93 range). High correlation between members of miR-134 family can be easily explained by the fact that all members of this family, namely miR-134, miR-323-3p and miR-382, belong to the same cluster and are expressed in the same cell types (www.diana.pcbi.upenn.edu/cgi-binimiRGen/v3/Cluster.cgi). Close relationships between members of miR-132 family, namely miR-128, miR-132 and miR-874, have not been described before. It is also interesting that biomarker families miR-132 and miR-134 produce better results with different normalizers. miR-132 family works better than miR-134 family with normalizers miR-491-5p, miR-181a, miR-9, and miR-141. On the other hand, miR-134 family demonstrates better results than miR-132 family with normalizers miR-370 and miR-127. Correlation between miR-132 and miR-134 biomarker families is relatively low (r values in the pair comparison Spearman test are in the 0.56-0.79 range) indicating that they either reflect distinct pathological processes or are located in different brain areas.

Example 4: Detection of an Increase in Levels of Lung-Enriched miRNA in Serum/Plasma of Patients with Lung Diseases Plasma samples were obtained from patients diagnosed with various lung diseases, such as asthma, pneumonia, Chronic Pulmonary Obstructive Disease (COPD), and non-small cell lung cancer (NSCLC), 10 in each group. Since enrolled patients with asthma and pneumonia were non-smokers and patients with COPD and NSCLC were smokers, plasma samples were also collected from two groups of controls, smokers and non-smokers, 10 in each group. RNA was isolated from two 200 μl aliquots of plasma samples by the Trizol-silica method according to an Asuragen procedure. Single target qRT-PCR was performed using the TaqMan® Reverse Transcription Kit and miRNA-specific stem-loop primers (Applied Biosystems). RT step was performed in triplicate and 2 p.1 plasma equivalents were present in final PCR to measure concentration of miR-34b, miR-142-5p, miR-146-5p, miR-155, miR-223, miR-486-5p, enriched in the lung, as well as the levels of ubiquitous and enriched in gastrointestinal system miR-192 and miR-409-3p. The latter is essentially ubiquitous but under-expressed in the lung. Concentrations of each lung-enriched miRNA were normalized per miR-409-3p and miR-192, as well as on each other, converted into Relative Quantity (RQ) of miRNA according the ABI protocol ($2^{-\Delta Ct}$), and compared with miRNA profiles from controls.

Figure 14A:
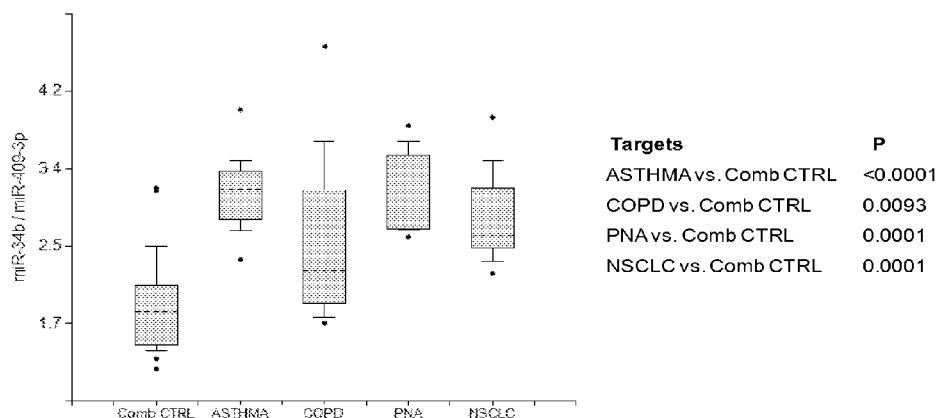
FIGS. 14A-C are graphs showing comparison of biomarkers miR-34b (A), miR-486-5p (B) and miR-192 (C) concentrations in plasma of asthma, pneumonia (PNA), COPD and NSCLC patients versus combined (non-smoking and smoking) controls. Concentrations of miRNA biomarkers were normalized per miR-409-3p (A) or per lung-enriched miR-223 (B) and miR-146b-5p (C).
Figure 14B:
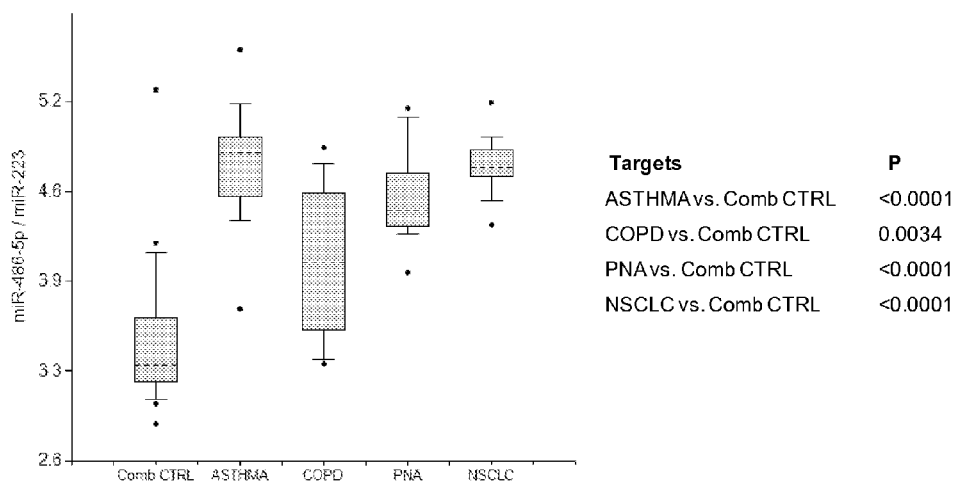
Figure 14C:
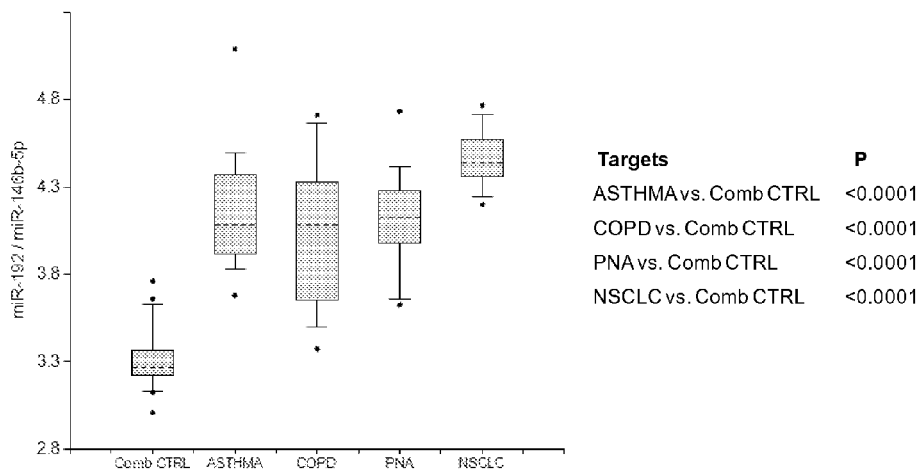

As expected miR-34b and miR-486-5p, which are highly enriched in the lung, were found to be effective biomarkers and miR-409-3p is an effective normalizer (FIG. 10A-D). Other effective normalizers are lung-enriched miR-142-5p, miR-146b-5p, miR-155 and miR-223 (FIGS. 11A-H and 12A-H), which, at least in some cases, could be explained by their downregulation in lung pathologies (Liu X. et al. Clin. Cancer Res. 2009, 15:1177-1183; Miko E. et al., Exp. Lung Res. 2009, 35:646-664; Halappanavar S. et al. Toxicology 2011, 285: 133-141; Heegaard N H et al. Int. J. Cancer, 2012, 130:1378-1386). Unexpectedly, miR-192 also behaved as an effective biomarker (FIG. 13A-J). Since this miRNA was also shown to be a biomarker for diseases of the GI system, it is reasonable to suggest that expression and/or secretion of this miRNA is increased due to inflammation or tumor development (Benjamin H. et al., J. Mol. Diagn. 2010, 12:771-779; Lan H Y. Clin. Exp. Pharmacol. Physiol. 2011 Dec. 28 [Epub ahead of print]; Luzna P. et al. Diagn. Pathol. 2011, 6:114; Wu Q. et al. J. Biomed. Biotechnol. 2011, Epub May 26; Zhou J. et al., J. Clin. Oncol. 2011, 29:4781-4788). miRNA biomarker miRNA/miRNA normalizer ratios were not different for smoking and non-smoking controls. Thus, various pathologies could be compared to the combined controls (smoking and non-smoking subjects). FIG. 14A-C demonstrates that the four analyzed pathologies are effectively distinguished from such combined controls by various sets of miRNA biomarkers and normalizers, e.g. miR-34b normalized per miR-409-3p, miR-486-5p normalized per miR-223, or miR-192 normalized per miR-155. There were also other effective sets of miRNA biomarkers and normalizers.

Figure 15A:
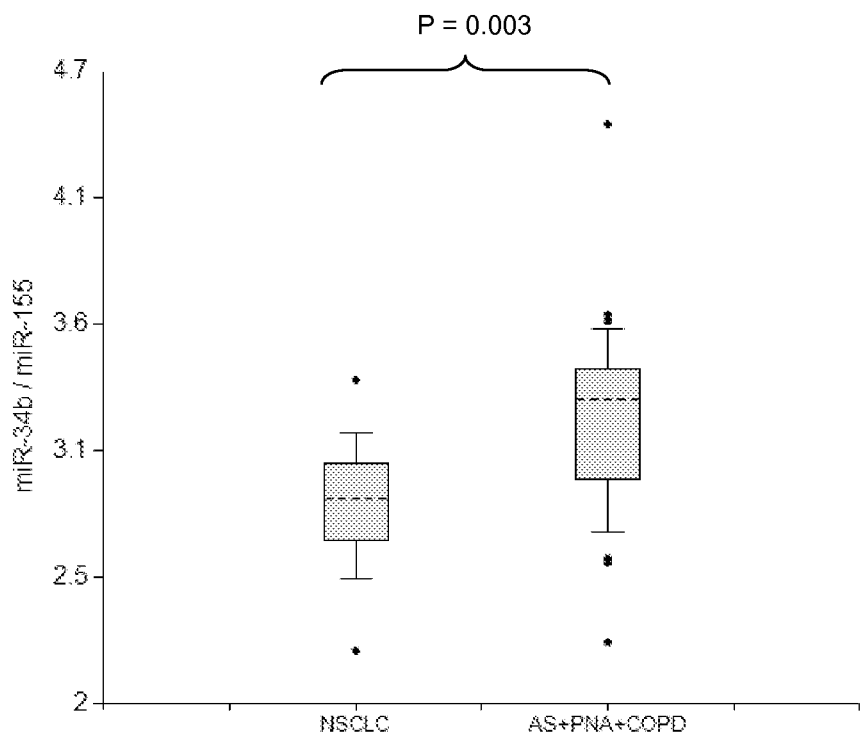
FIGS. 15A-C are graphs showing comparison of biomarkers miR-34b, miR-486-5p and miR-192 concentrations in plasma of all patients with inflammatory lung diseases (asthma, pneumonia and COPD) versus patients with NSCLC. Concentrations of miRNA biomarkers were normalized per various lung-enriched miRNA: A-miR-155; B, C-miR-146b-5p.
Figure 15B:
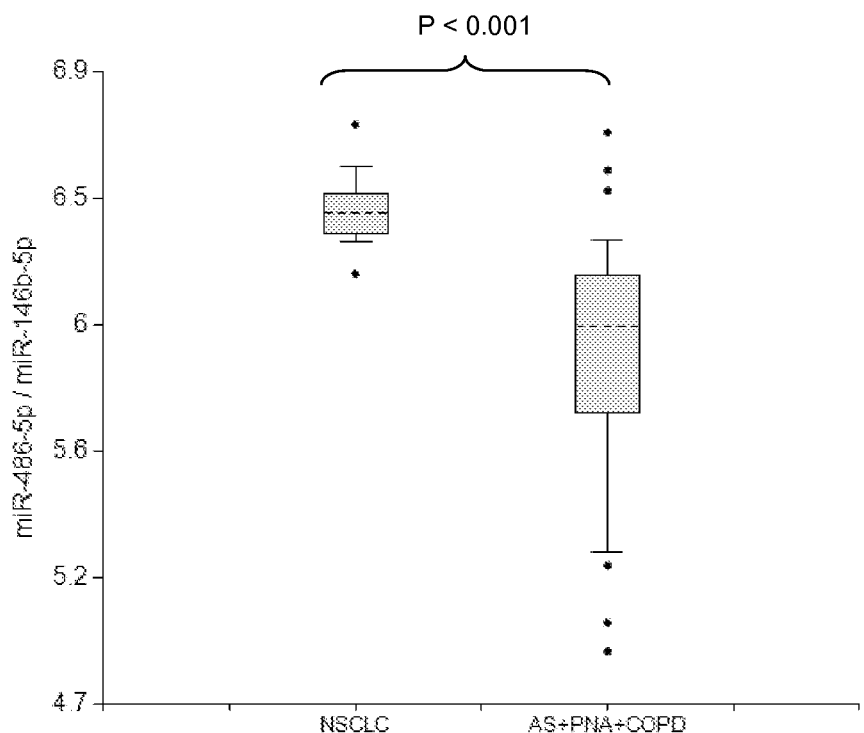
Figure 15C:
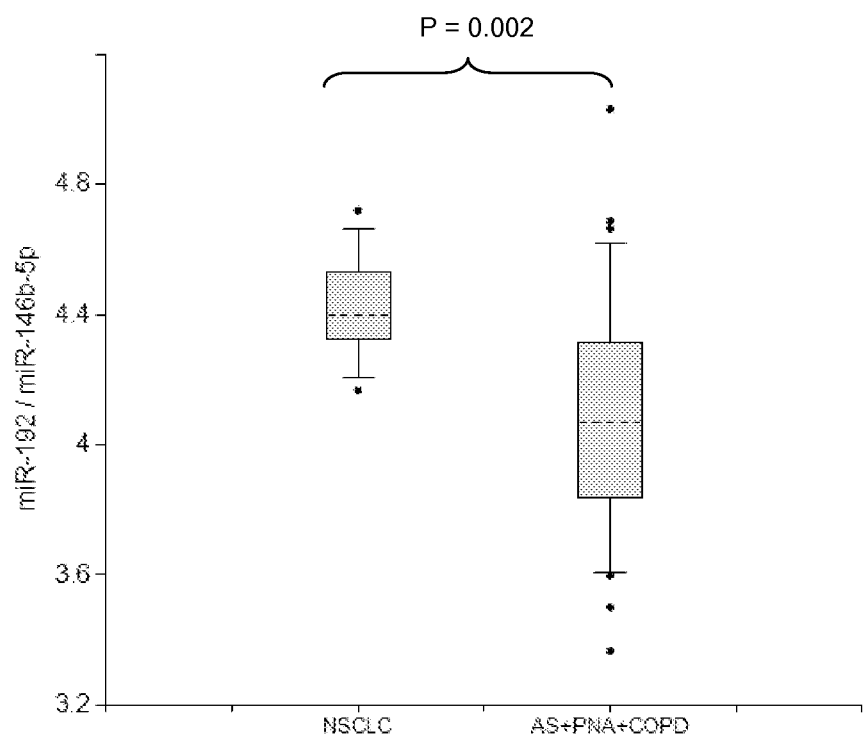

The ability of various combinations of miRNA biomarkers and normalizers to distinguish NSCLC from such inflammatory diseases as asthma, pneumonia and COPD was also analyzed. FIG. 15A-C shows that patients with NSCLC are differentiated from patients with inflammatory diseases using ratios of miR-34b to miR-155, miR-486-5p to miR-146b-5p or miR-192 to miR-146b-5p. There were other effective combinations of miRNA biomarkers and normalizers.

Figure 16A:
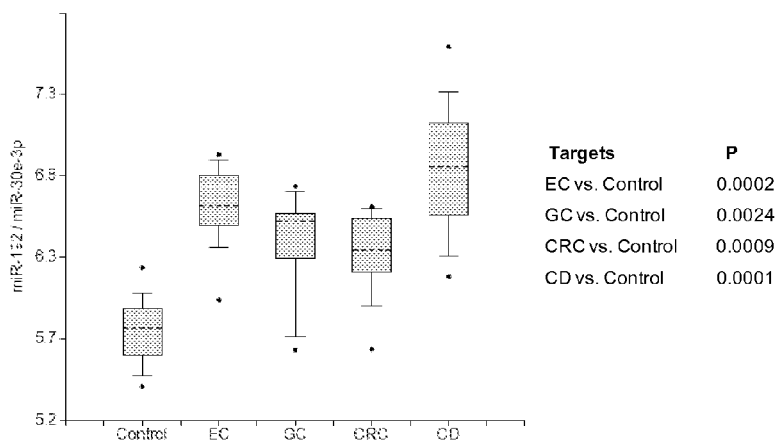
FIGS. 16A-M are graphs showing comparison of concentrations of miR-192 (A, E, I), miR-194 (B, F, J), miR-203 (C, G, K) and miR-215 (D, H, L), enriched in organs of gastrointestinal (GI) system, in plasma of patients with esophageal (EC), gastric (CC) and colorectal (CRC) cancers and Crohn's disease (CD) versus controls. Concentrations of miRNA biomarkers were normalized per ubiquitous miR-30e-3p or per other GI-enriched miRNA: A-D-miR-30e-3p; E-H-miR-148a; I-L-miR-145. A-L: patients with the indicated diseases versus controls; M: a graph showing comparison of miR-203 and miR-192 concentrations in plasma of patients with all GI pathologies studied (Pathology) versus controls. All concentrations were normalized per ubiquitous miR-30e-3p and presented in relative units (log scale).
Figure 16B:
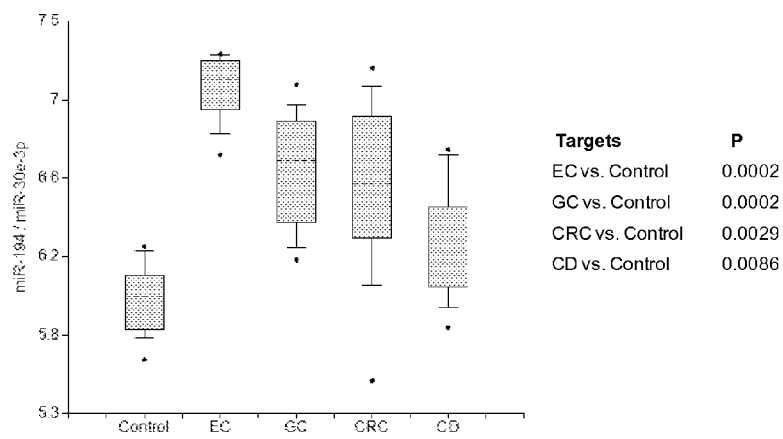
Figure 16C:
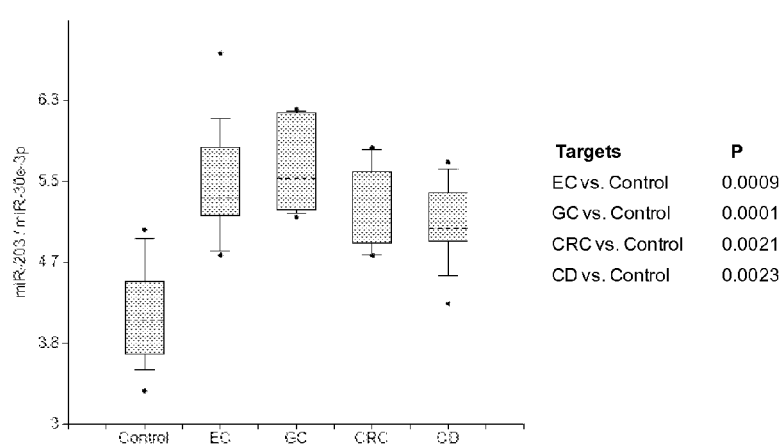
Figure 16D:
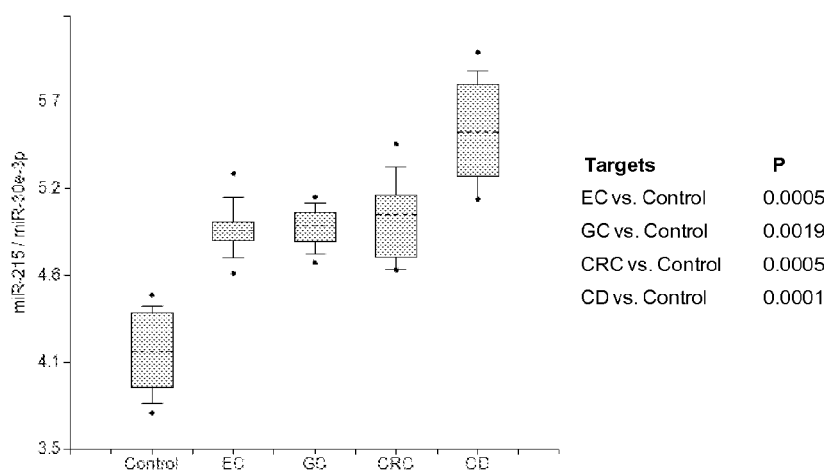
Figure 16E:
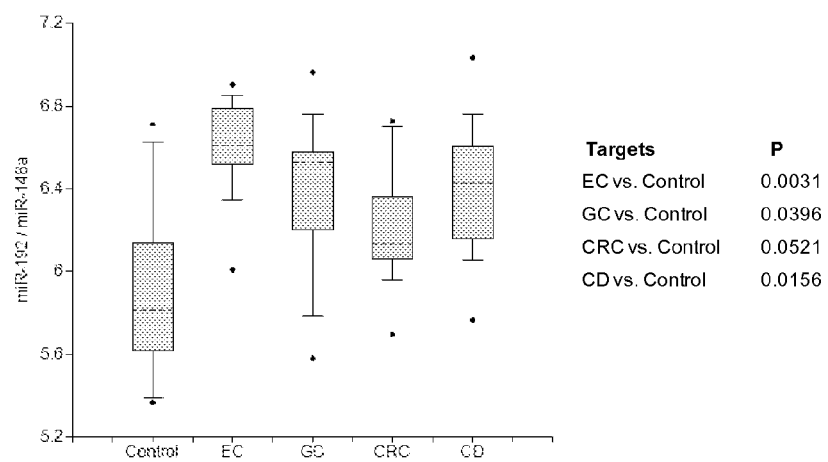
Figure 16F:
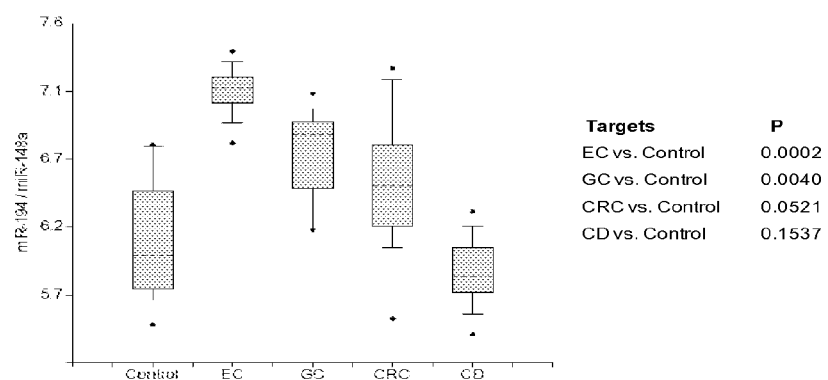
Figure 16G:
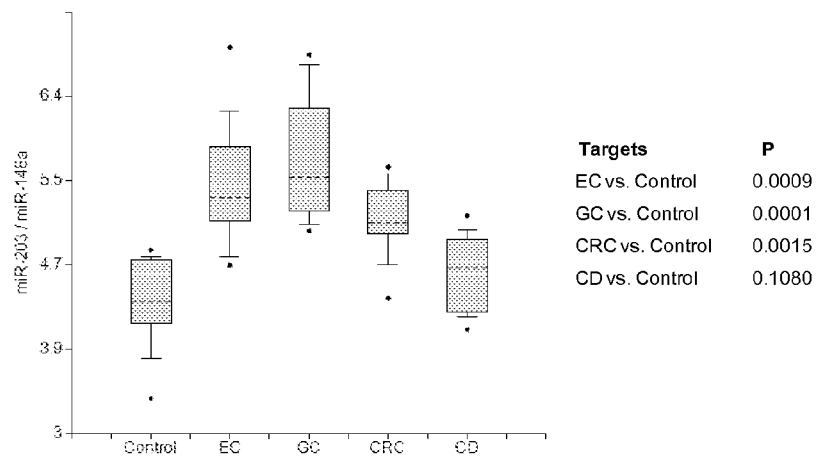
Figure 16H:
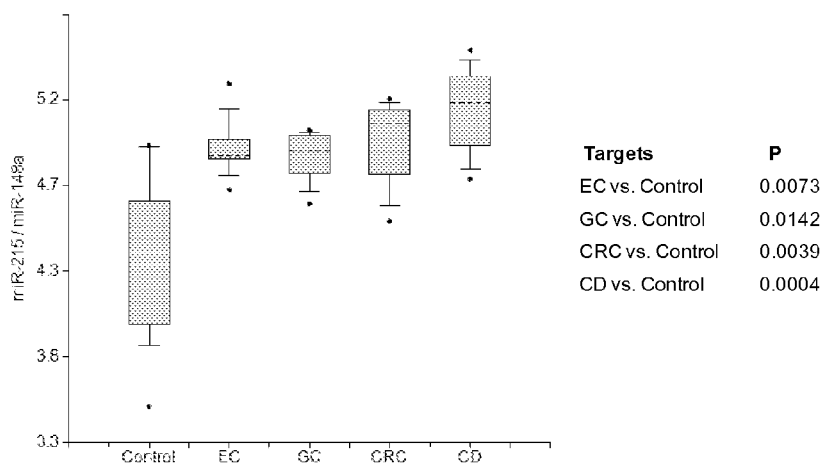
Figure 16I:
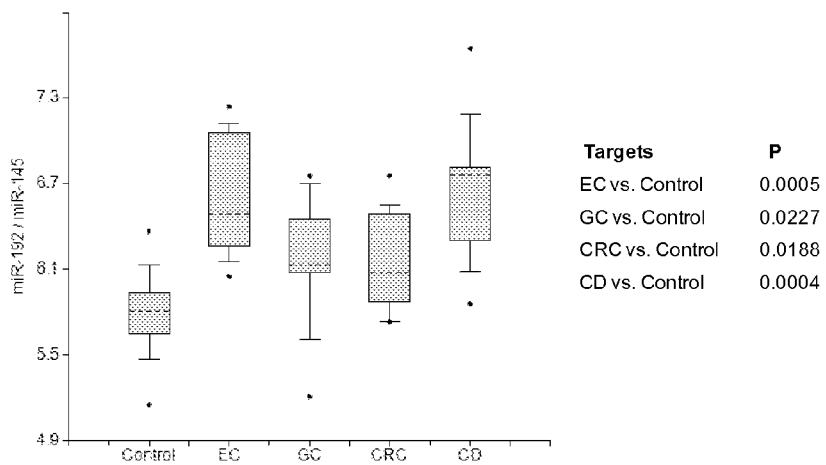
Figure 16J:
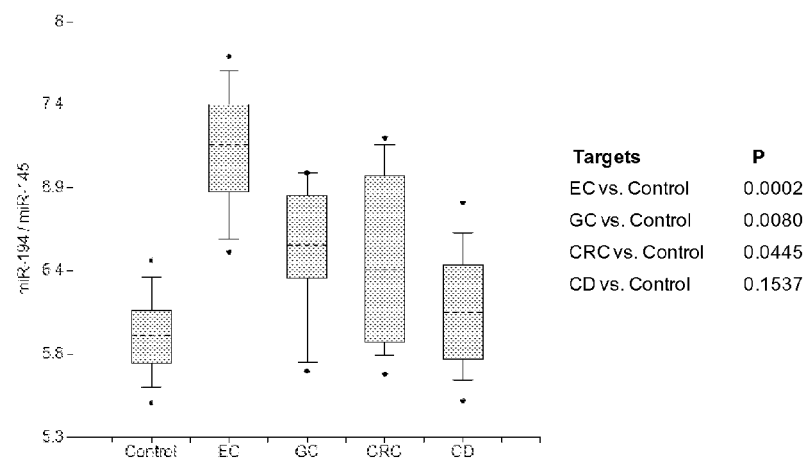
Figure 16K:
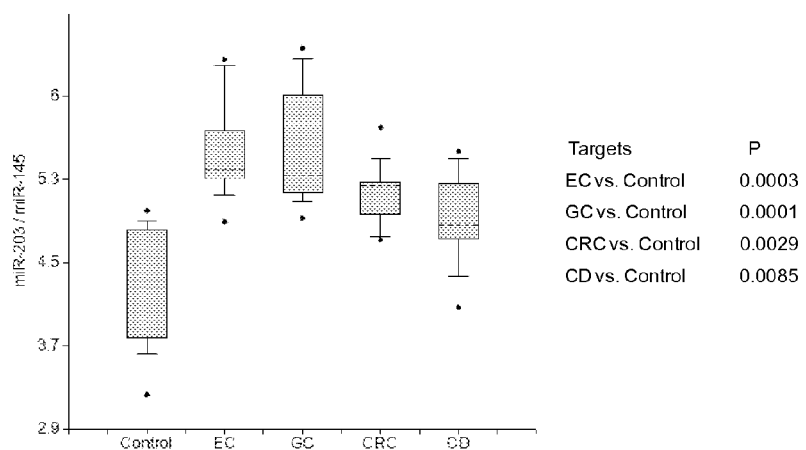
Figure 16L:
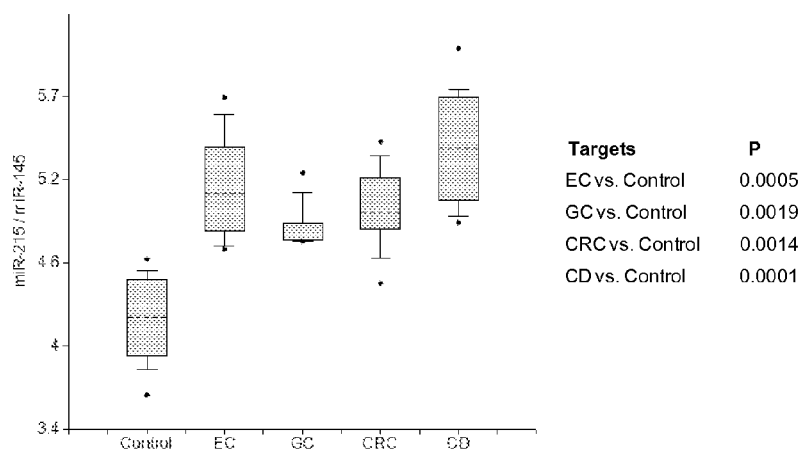
Figure 16M:
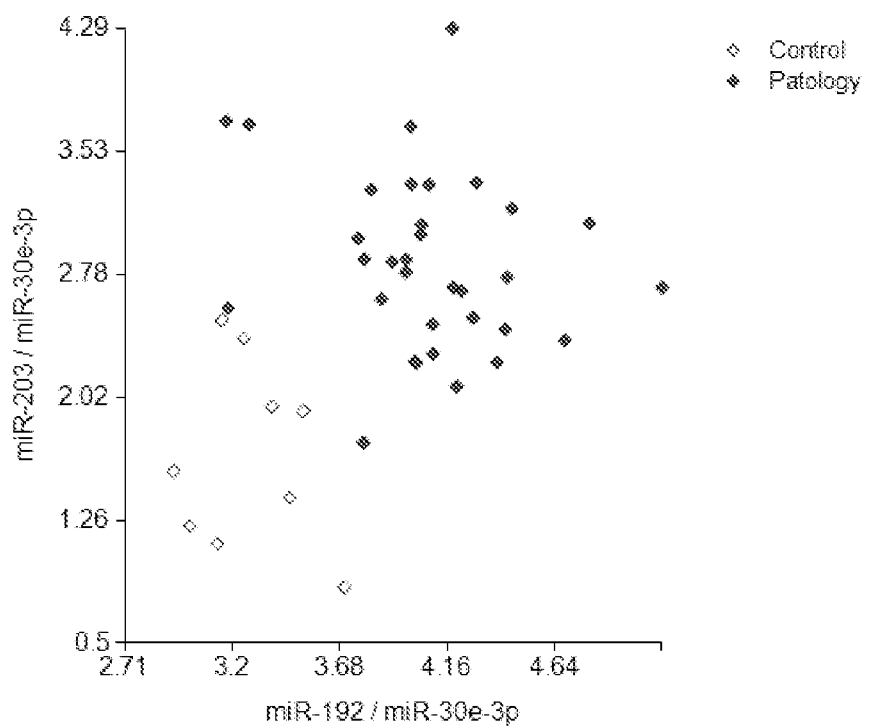
Figure 17A:
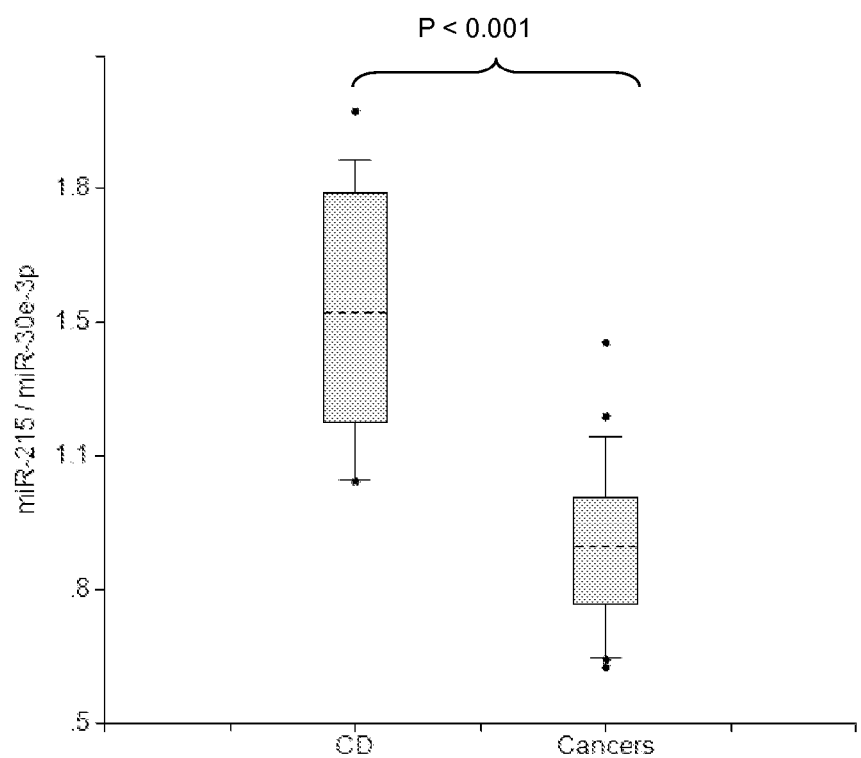
FIGS. 17A-G are graphs showing comparison of various miRNA concentration ratios in plasma of all cancer patients (esophageal, gastric and colorectal cancers) versus patients with Crohn's disease. A: miR-215/miR-30e-3p; B: miR-203/miR-148a; C: miR-194/miR-148a; D: miR-192/miR-203; E: miR-215/miR-203; F: miR-215/miR-194; G: miR-194/miR-192.
Figure 17B:
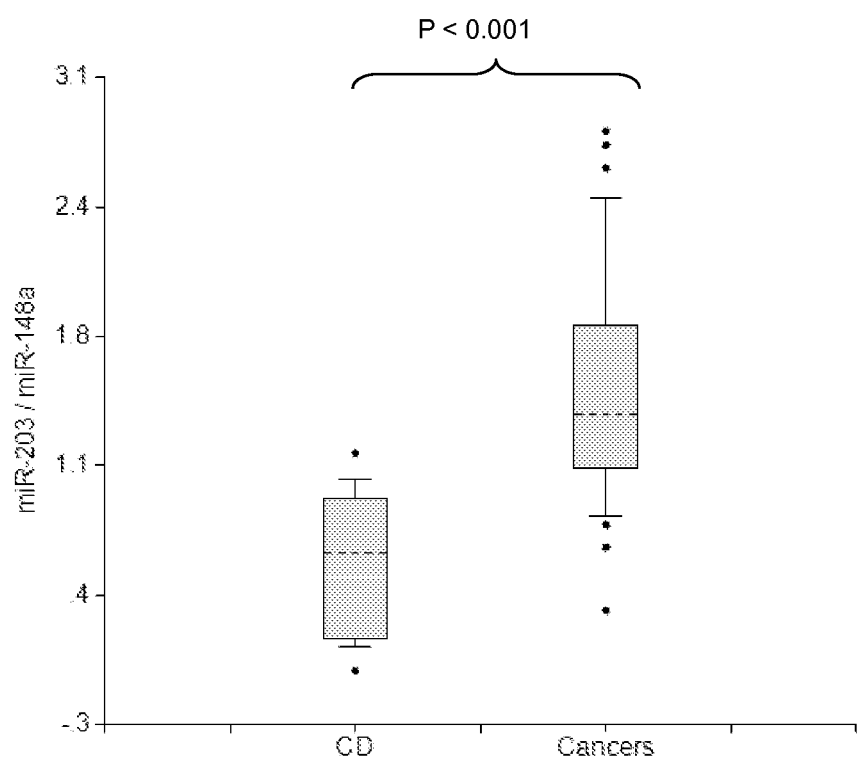
Figure 17C:
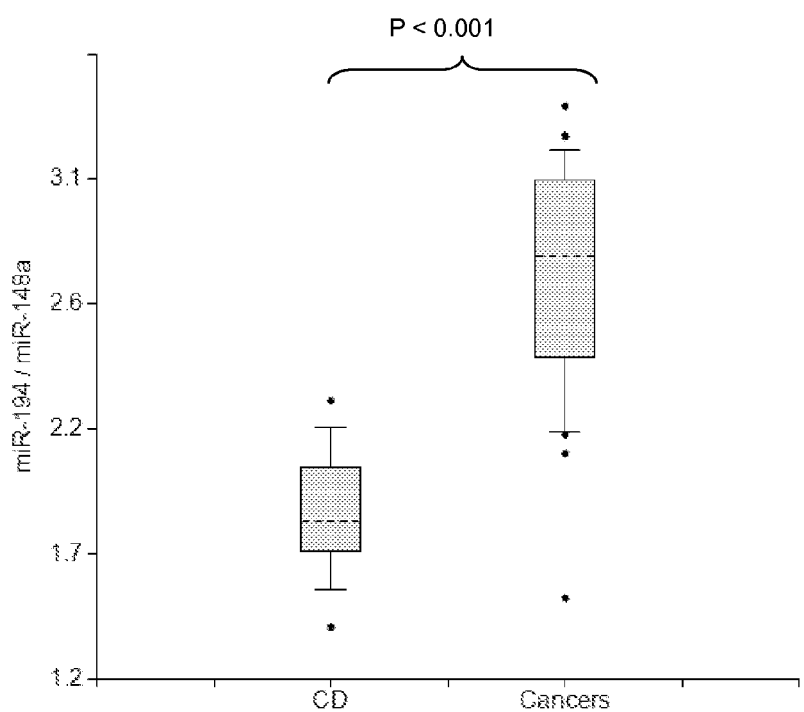
Figure 17D:
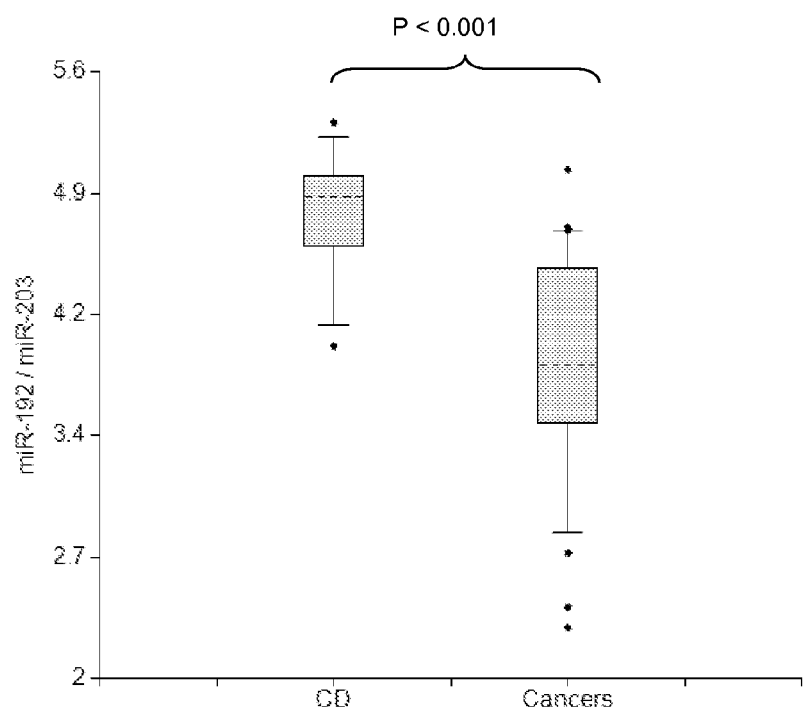
Figure 17E:
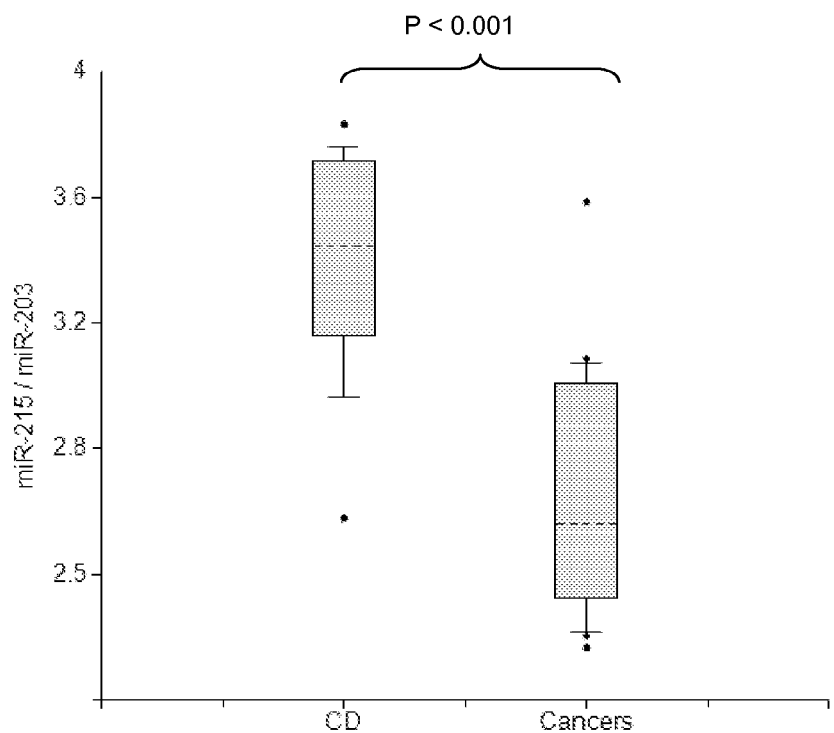
Figure 17F:
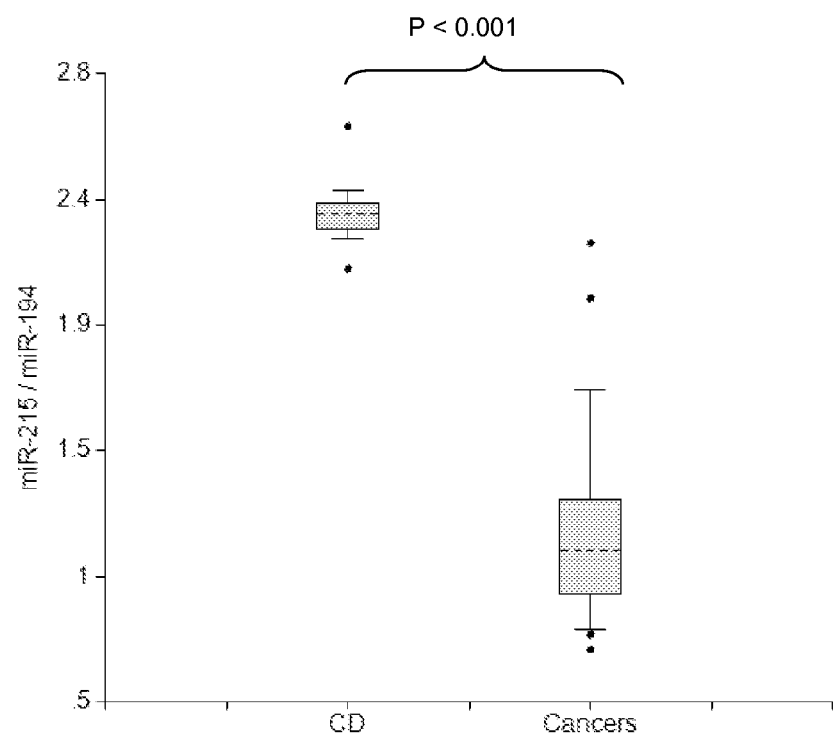
Figure 17G:
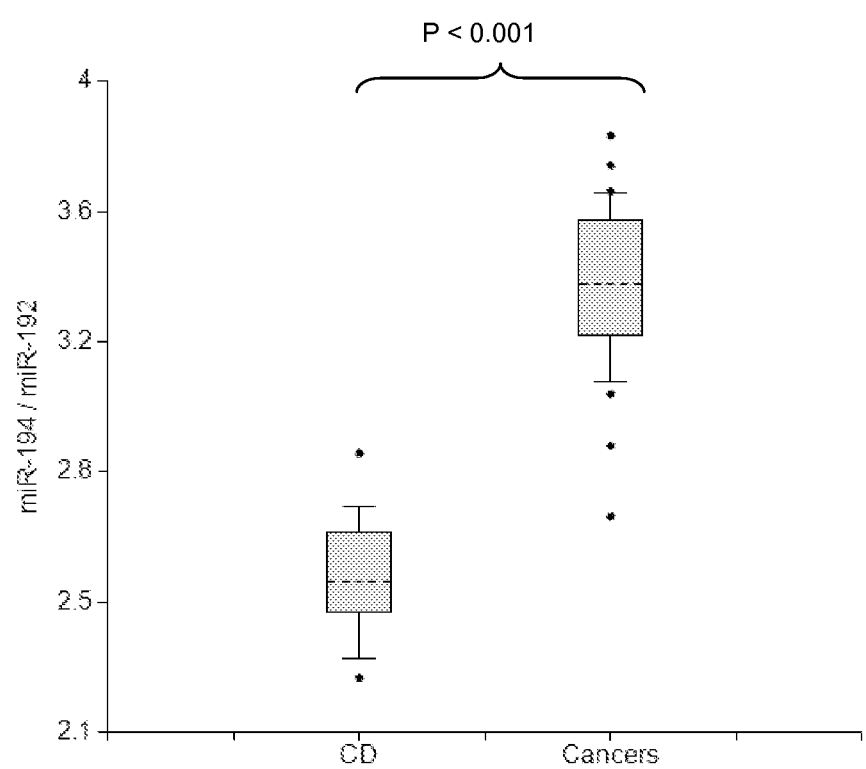

Example 5: Detection of an Increase in Levels of Gastrointestinal System-Enriched miRNA in Serum/Plasma of Patients with Diseases of Gastrointestinal System Plasma samples were obtained from patients diagnosed with various diseases of the GI system, such as esophageal, gastric and colon cancers, and an inflammatory condition, Crohn's disease, 10 in each group. RNA was isolated from two 200 p,1 aliquots of plasma samples by the Trizol-silica method according to an Asuragen procedure. Single target qRT-PCR was performed using the TaqMan® Reverse Transcription Kit and miRNA-specific stem-loop primers (Applied Biosystems). RT step was performed in triplicate and 2 pi plasma equivalents were present in final PCR to measure concentration of miR-145, miR-148a, miR-192, miR-194, miR-203, miR-215, enriched in organs of GI system, as well as the level of ubiquitous miR-30e-3p. Concentrations of each GI system-enriched miRNA were normalized per miR-30e-3p, as well as on each other, converted into Relative Quantity (RQ) of miRNA according the ABI protocol ($2^{-\Delta Ct}$), and compared with miRNA profiles from controls. FIG. 16A-L clearly shows miR-192, miR-194, miR-203 and miR-215 as effective biomarkers, and miR-145, miR-148a and miR-30e-3p as effective normalizers. Biomarker/normalizer ratios effectively differentiate patients with all studied diseases from controls. miR-203, highly enriched in esophagus and stomach, is especially effective in detecting cancers of these organs, and miR-215, highly enriched in column is most effective in differentiating patients with colon cancer and Crohn's disease from controls. Combination of miR-192 and miR-203 normalized per miR-30e-3p effectively distinguishes patients with all pathologies of the GI system from controls (FIG. 16M) with 94% sensitivity and 100% specificity calculated as described in Example 8. It is important that all tumors were stage 1 or 2 cancers, which means that the proposed approach can be effectively used for screening and early diagnosis.

Figure 18A:
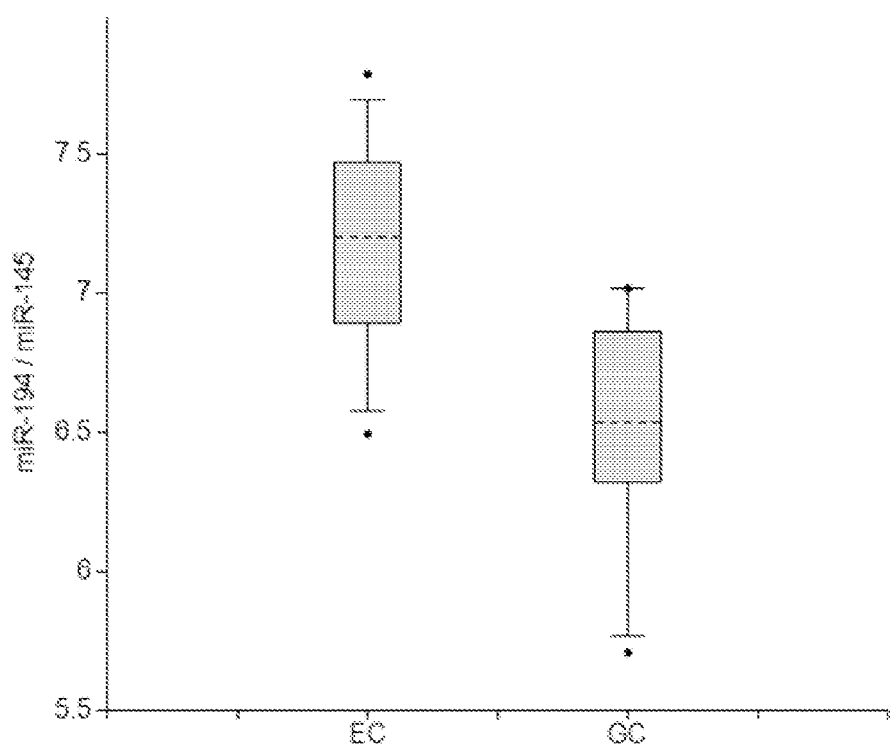
FIGS. 18A-I are showing comparison of various miRNA concentration ratios in plasma of patients with cancers of particular gastrointestinal organs. A-C: esophageal cancer (EC) versus gastric cancer (GC); D-F: gastric cancer (GC) versus colorectal cancer (CRC); G-I: esophageal cancer (EC) versus colorectal cancer (CRC). A: miR-194/miR-145; B: miR-194/miR-148a; C: miR-194/miR-30e-3p; D: miR-215/miR-203; E: miR-203/miR-30e-3p; F: miR-203/miR-148a; G: miR-192/miR-145; H: miR-192/miR-148a; I: miR-192/miR-30e-3p.
Figure 18B:
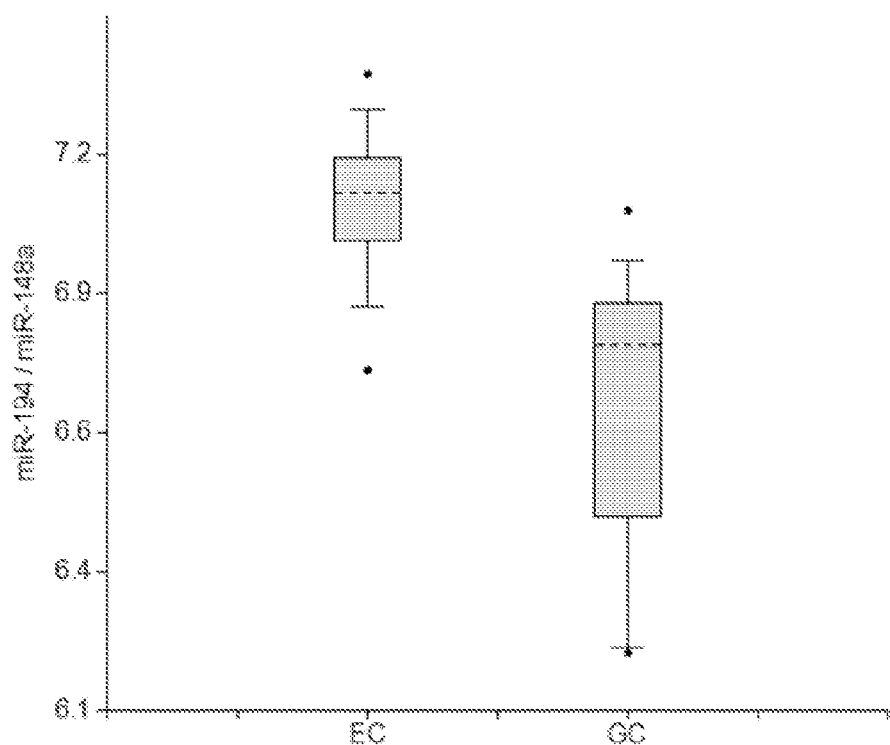
Figure 18C:
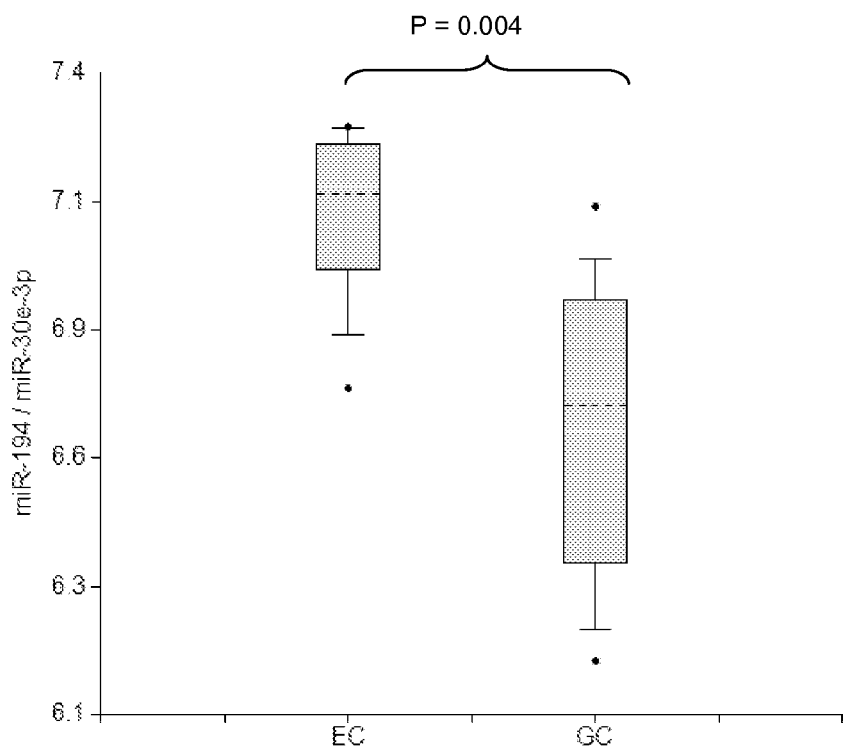
Figure 18D:
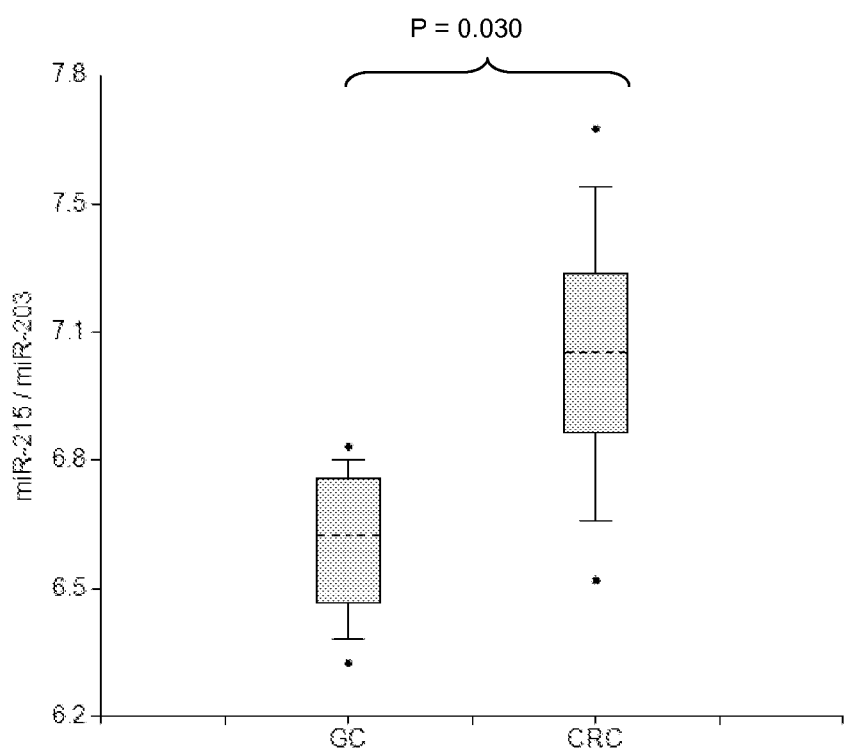
Figure 18E:
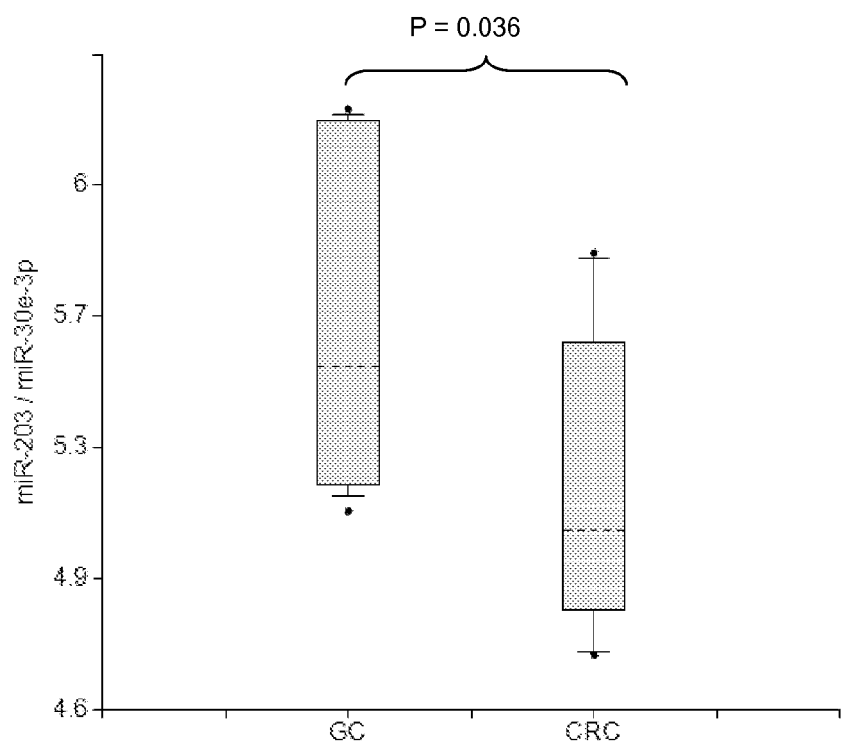
Figure 18F:
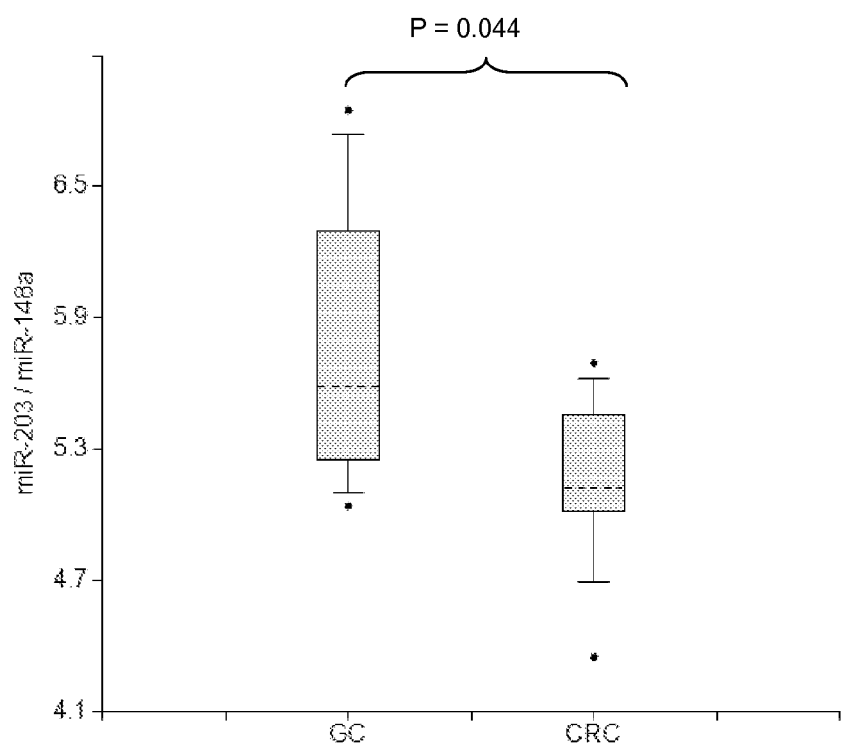

Further, various cancers were compared with each other, and Crohn's disease was compared with all cancers of the GI system. As a result the following biomarker/normalizer ratios capable of distinguishing particular pathologies have been found:

1. Crohn's disease versus esophageal, gastric and colorectal cancers: miR-194/miR-148a; miR-215/miR-30e-3p; miR-215/miR-194; miR-203/miR-148a; miR-192/miR-203; miR-215/miR-203 and miR-194/miR-192 (FIG. 17A-G).
2. Esophageal cancer versus gastric cancer: miR-194/miR-145; miR194/miR-148 a; miR194/miR-30e-3p (FIG. 18A-C).
3. Gastric cancer versus colorectal cancer: miR-203/30e-3p; miR-203/miR-148a; miR-215/miR-203 (FIG. 18D-F).

Figure 18G:
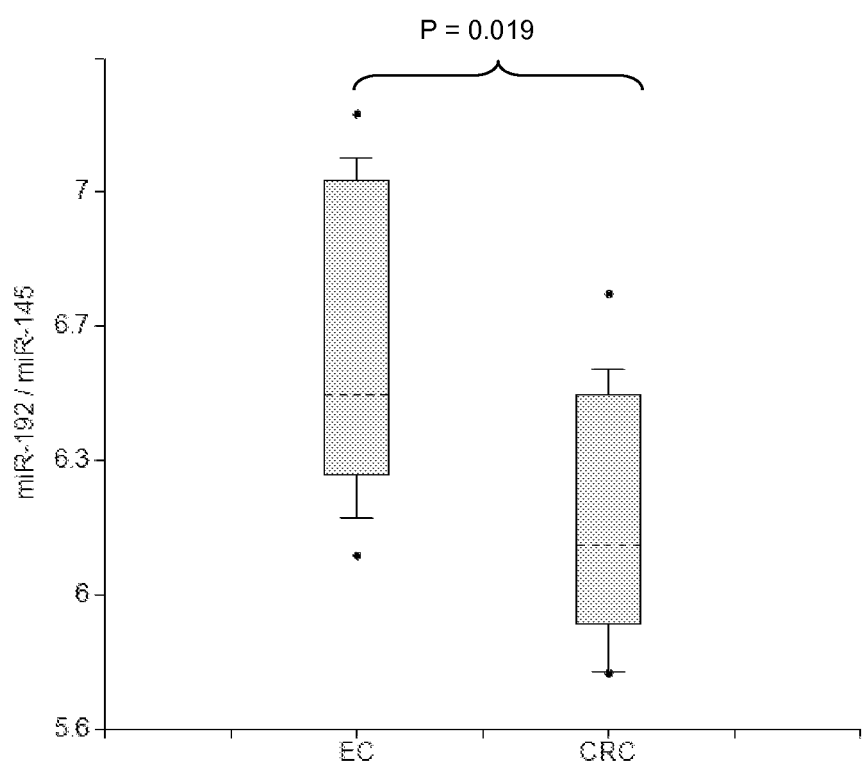
Figure 18H:
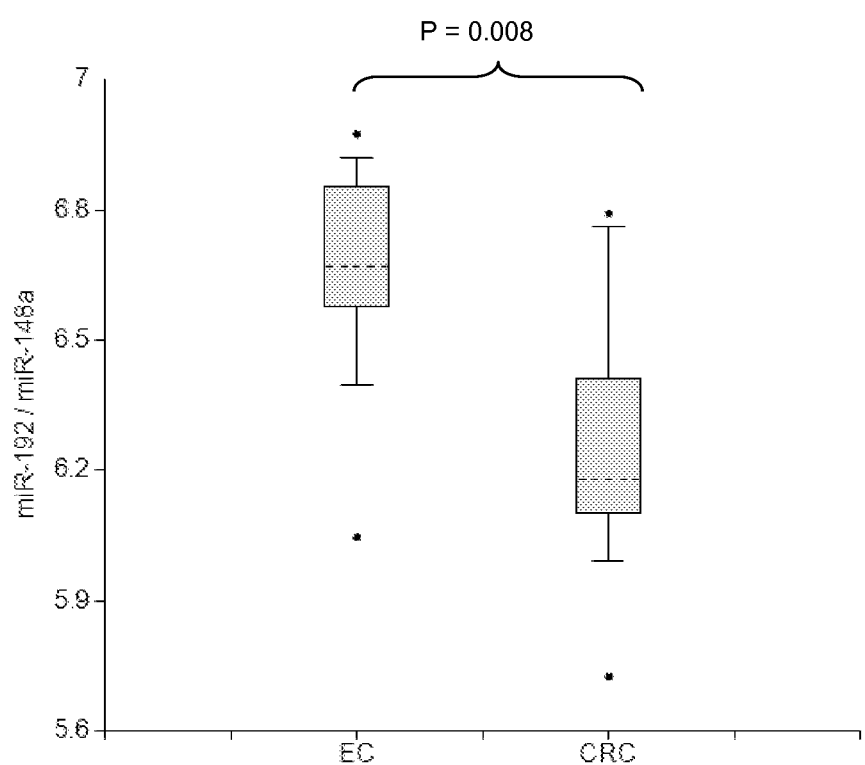
Figure 18I:
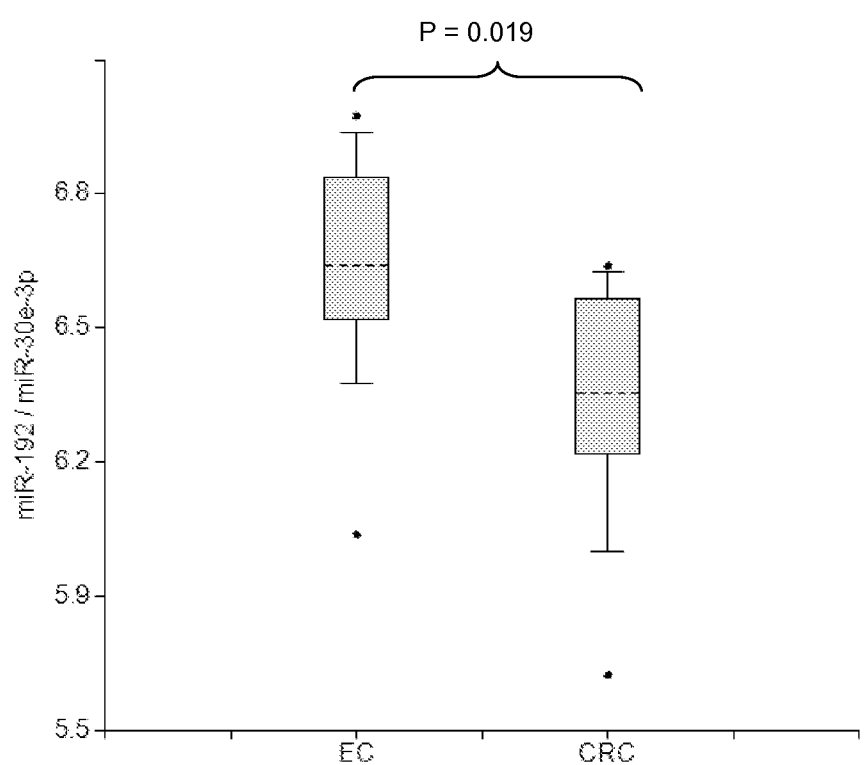

4. Esophageal cancer versus colorectal cancer: miR-192/miR-145; miR192/miR-148a; miR192/miR-30e-3p (FIG. 18G-I).

Thus, analysis of plasma concentrations of miRNA enriched in organs of the GI system is effective for: (i) detection of Crohn's disease and tumors in esophagus, stomach and colon; (ii) differentiation of an inflammatory disease from cancers; (iii) differentiation of cancers located in various organs of the GI system.

Figure 19A:
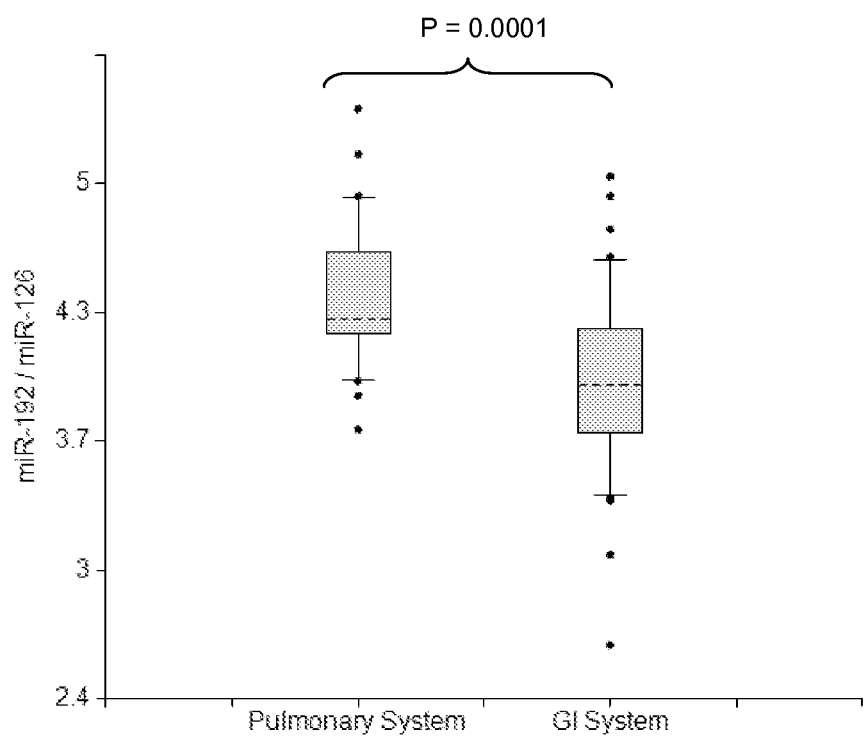
FIGS. 19A-W are graphs showing comparison of various miRNA concentration ratios in plasma of all patients with diseases of gastrointestinal (GI) system (Crohn's disease and esophageal, gastric and colorectal cancers) versus patients with diseases of pulmonary system (asthma, pneumonia, COPD, NSCLC). A-U: one biomarker/normalizer miRNA pair (A-miR-192/miR-126; B-miR-155/miR-126; C-miR-145/miR-126; D-miR-155/miR-30e-3p; E-miR-192/miR-30e-3p; F-miR-155/miR-409-3p; G-miR-486-5p/miR-17-5p; H-miR-155/miR-17-5p; I-miR-192/miR-17-5p; J-miR-146b-5p/miR-31; K-miR-155/miR-31; L-miR-192/miR-31; M-miR-486-5p/miR-155; N-miR-192/miR-155; O-miR-145/miR-155; P-miR-146b-5p/miR-155; Q-miR-486-5p/miR-203; R-miR-192/miR-203; S-miR-145/miR-203; T-miR-192/miR-215; U-miR-155/miR-215). V: a graph showing comparison of the ratios miR-486-5p/miR-155 and miR-145/miR-155 in plasma of patients with all CI pathologies versus all pulmonary diseases. W: Receiver-Operating Characteristic (ROC) curve analysis of differentiation between patients with GI and pulmonary diseases using miRNA pairs presented on Fig. V. The areas under the ROC curve (AUC) are reported. Sensitivity, specificity and accuracy for each biomarker/normalizer pair are calculated for the "cutoff" point, which is the biomarker/normalizer ratio, at which a sample is equally likely to belong to the GI or the pulmonary groups.
Figure 19B:
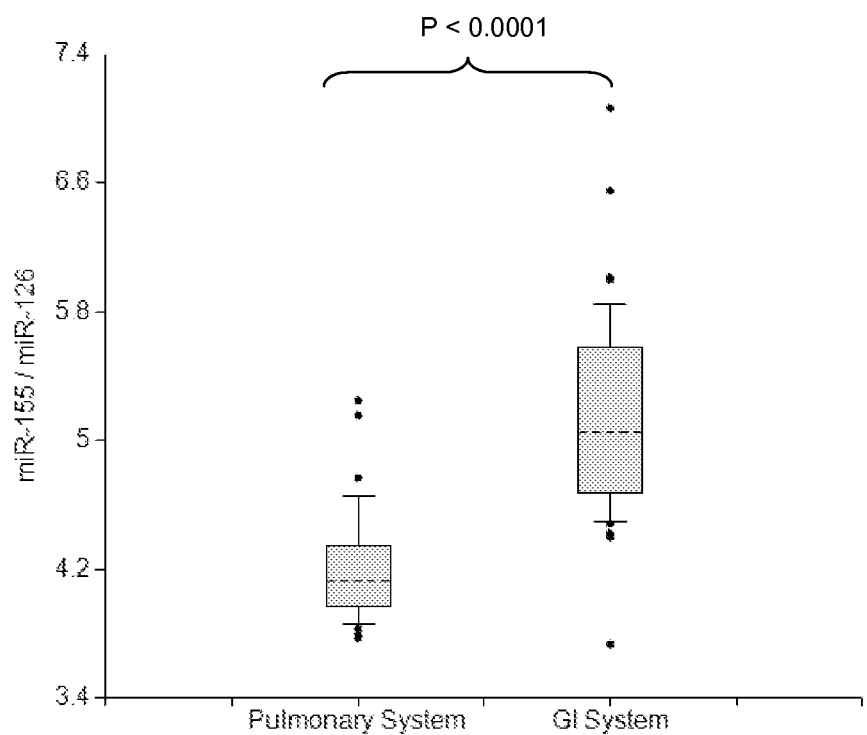
Figure 19C:
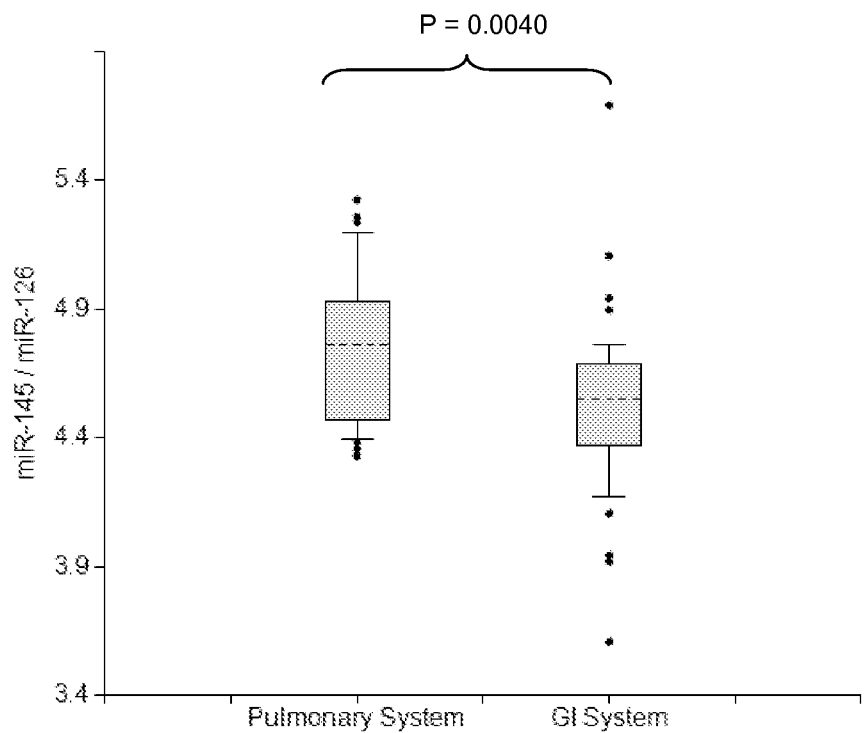
Figure 19D:
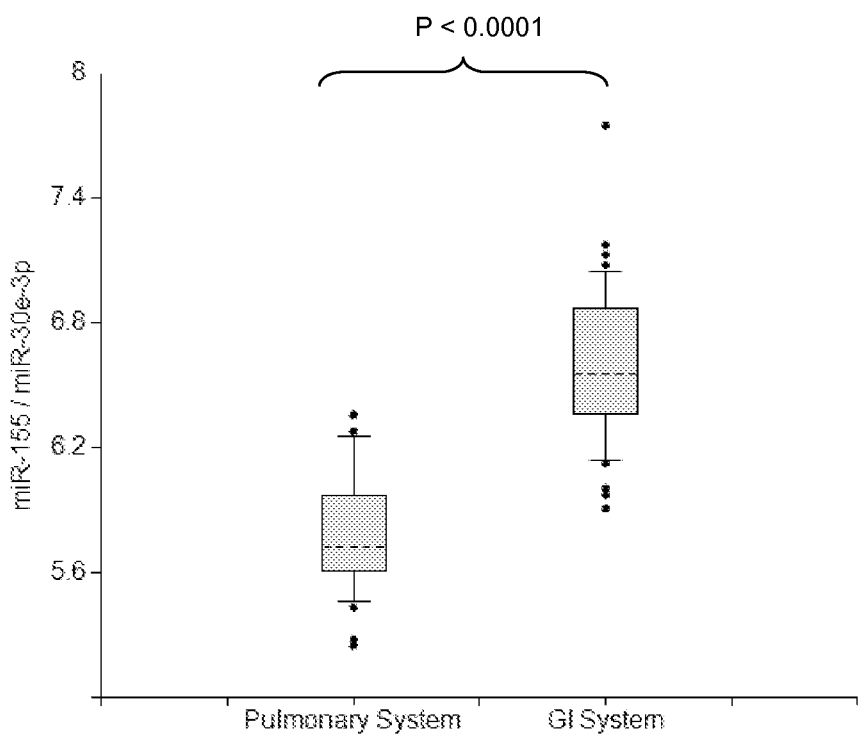
Figure 19E:
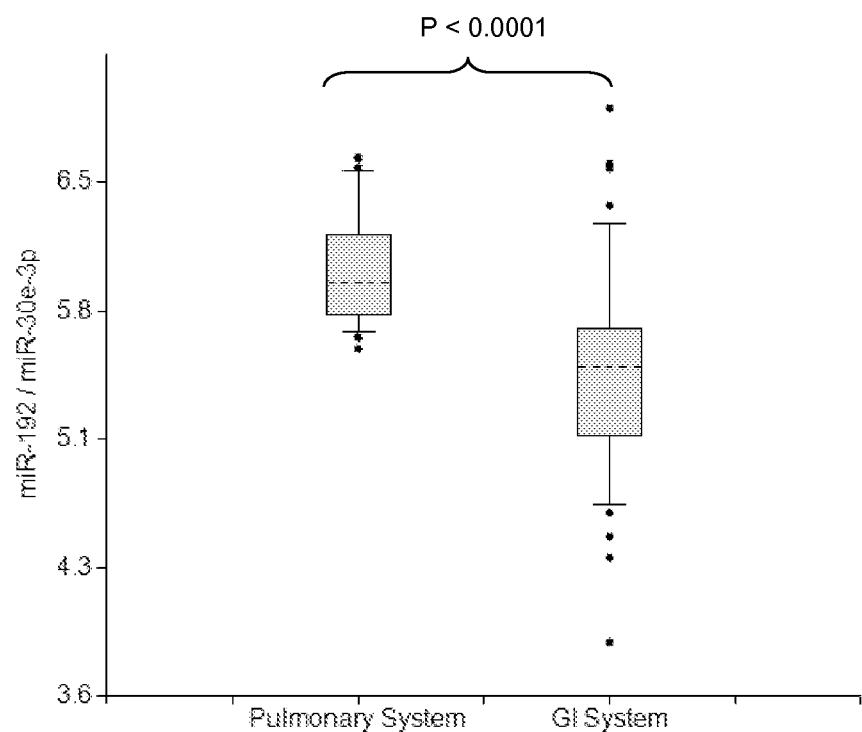
Figure 19F:
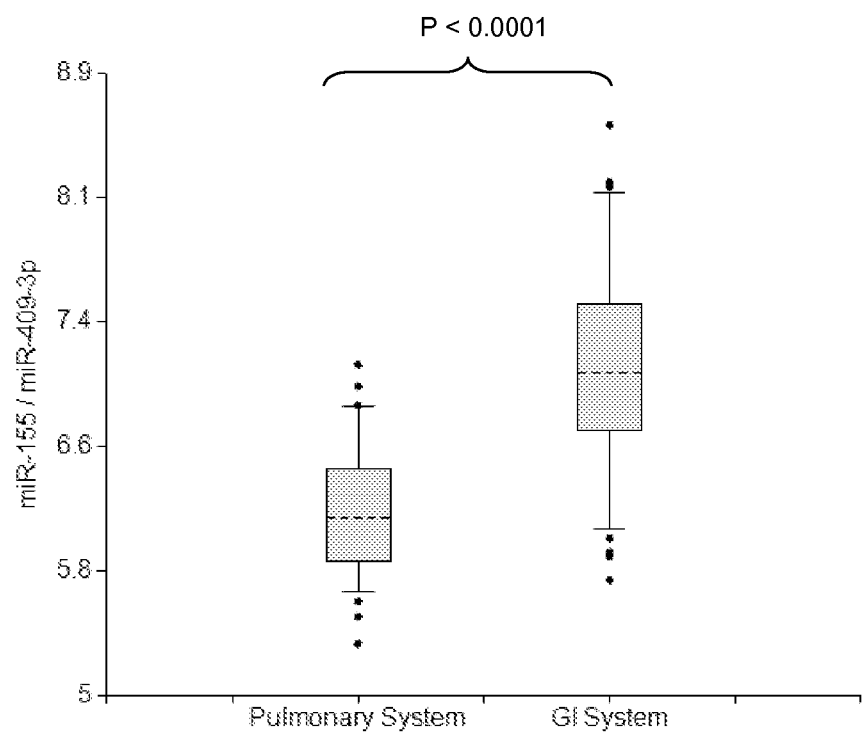
Figure 19G:
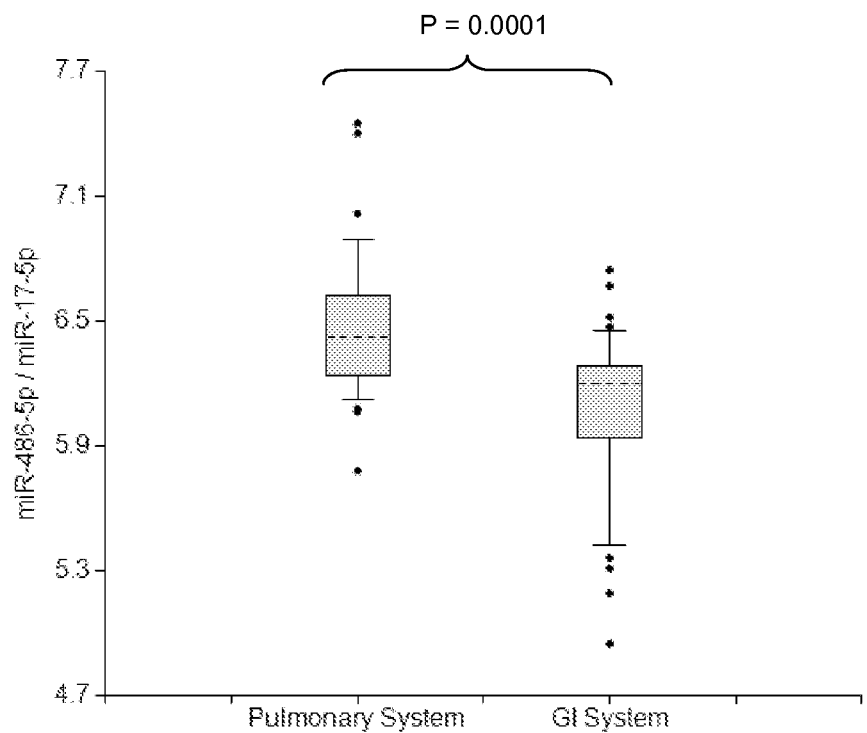
Figure 19H:
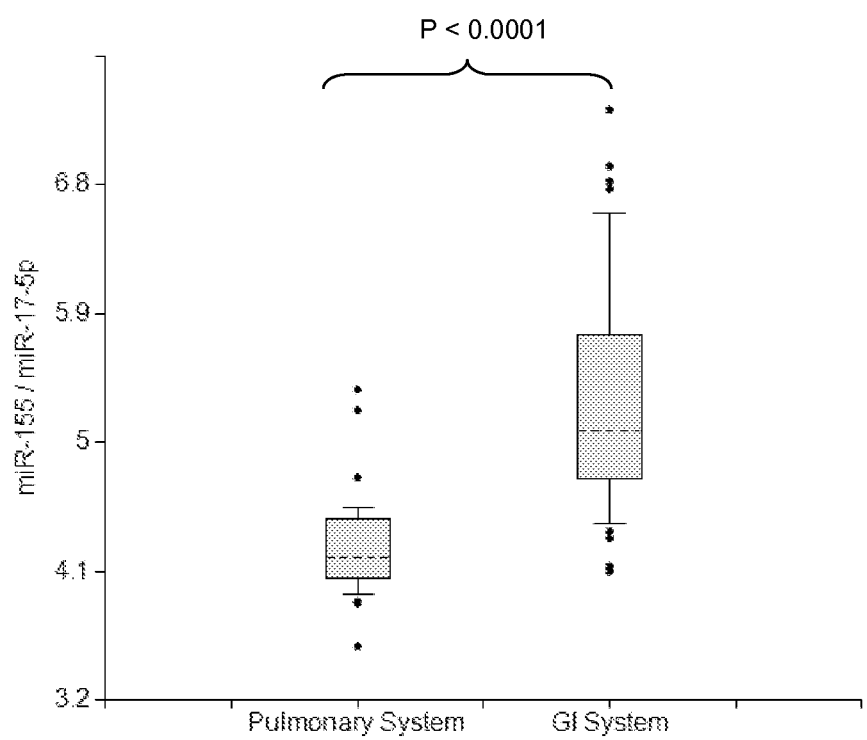
Figure 19I:
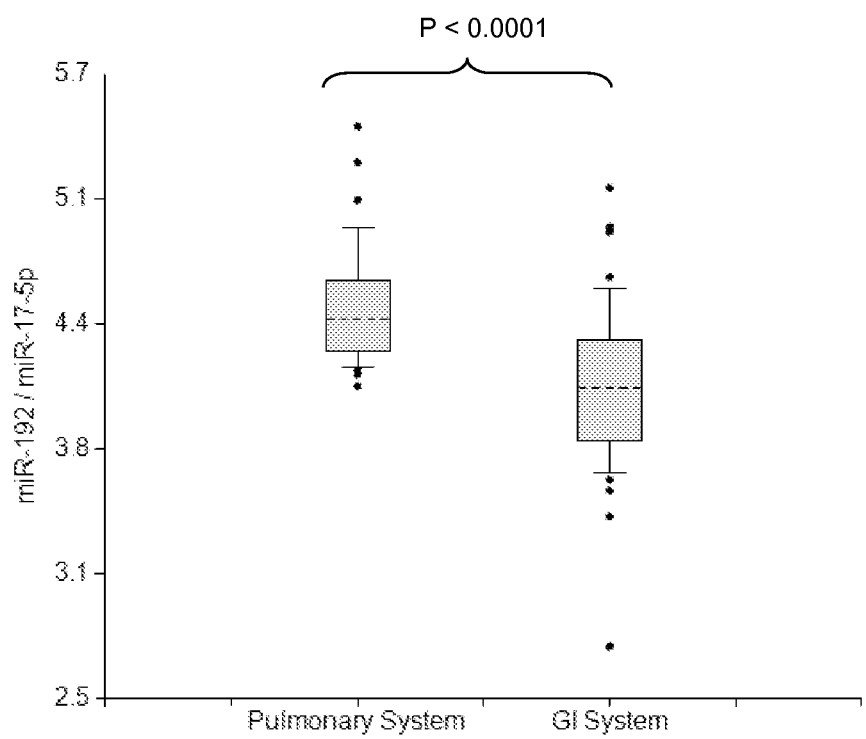
Figure 19J:
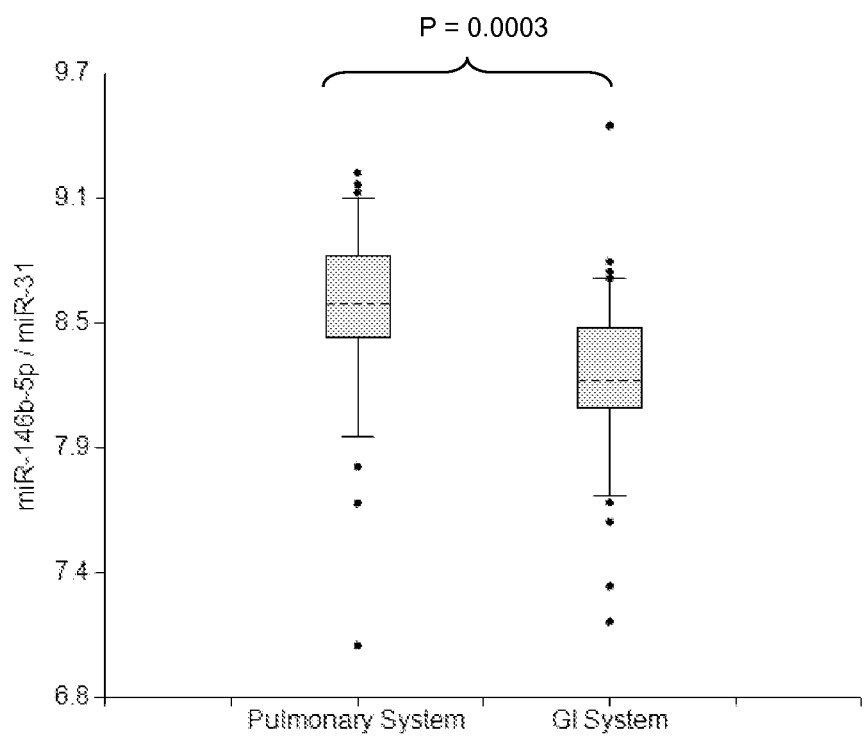
Figure 19K:
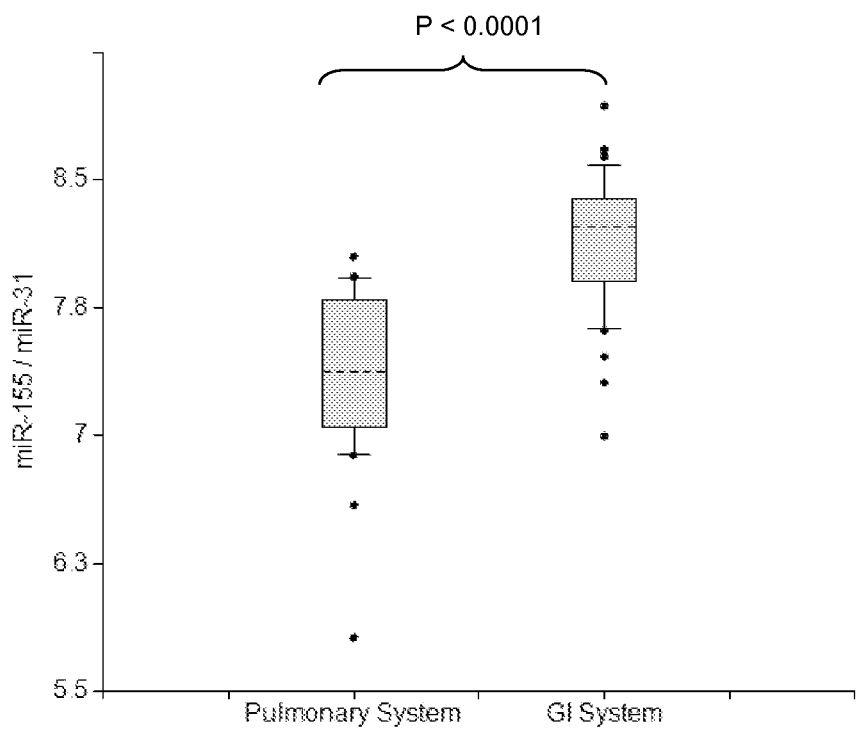
Figure 19L:
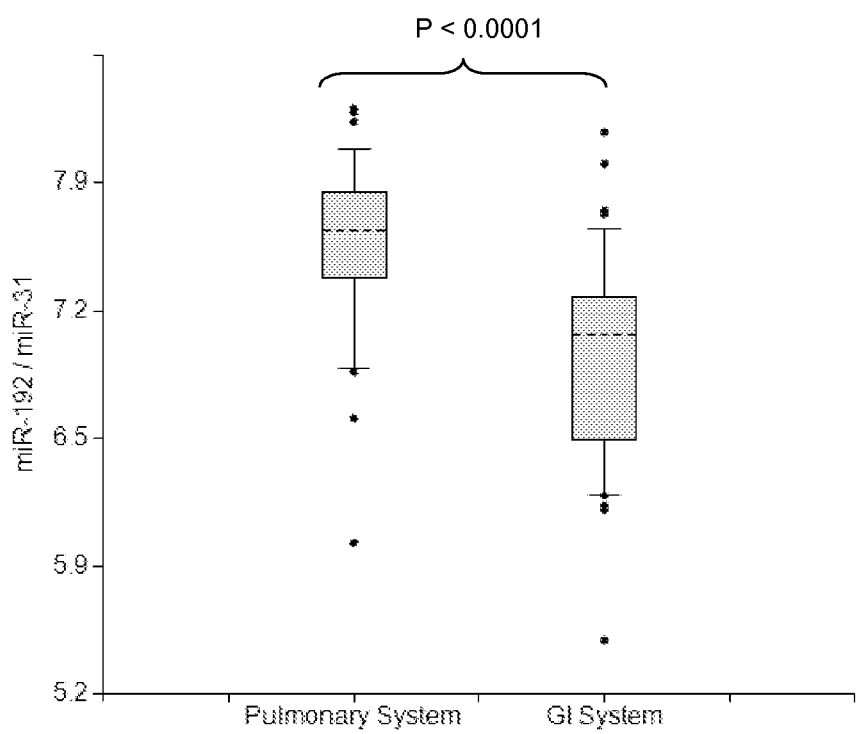
Figure 19M:
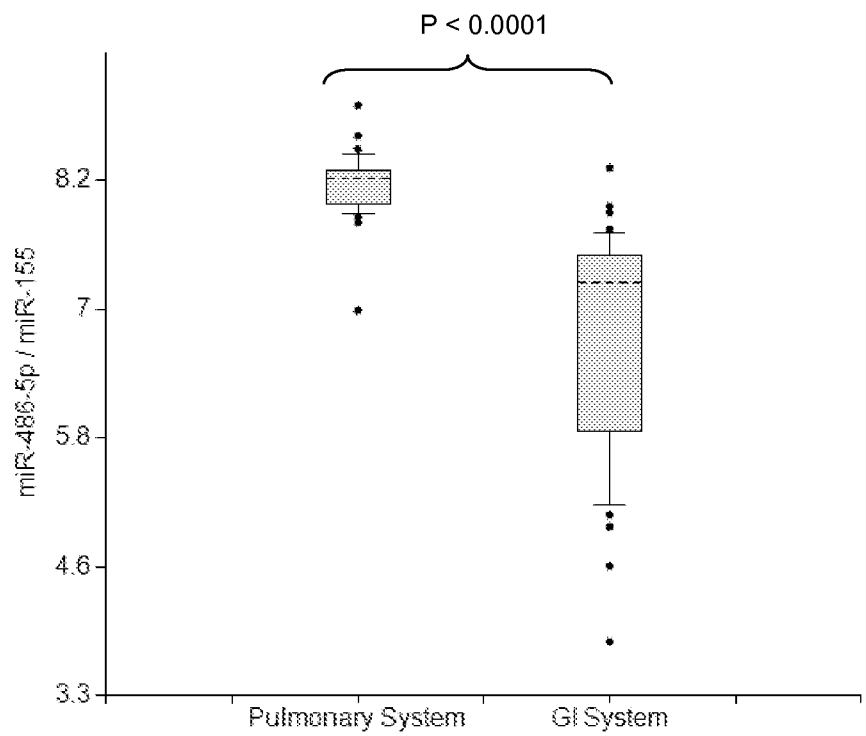
Figure 19N:
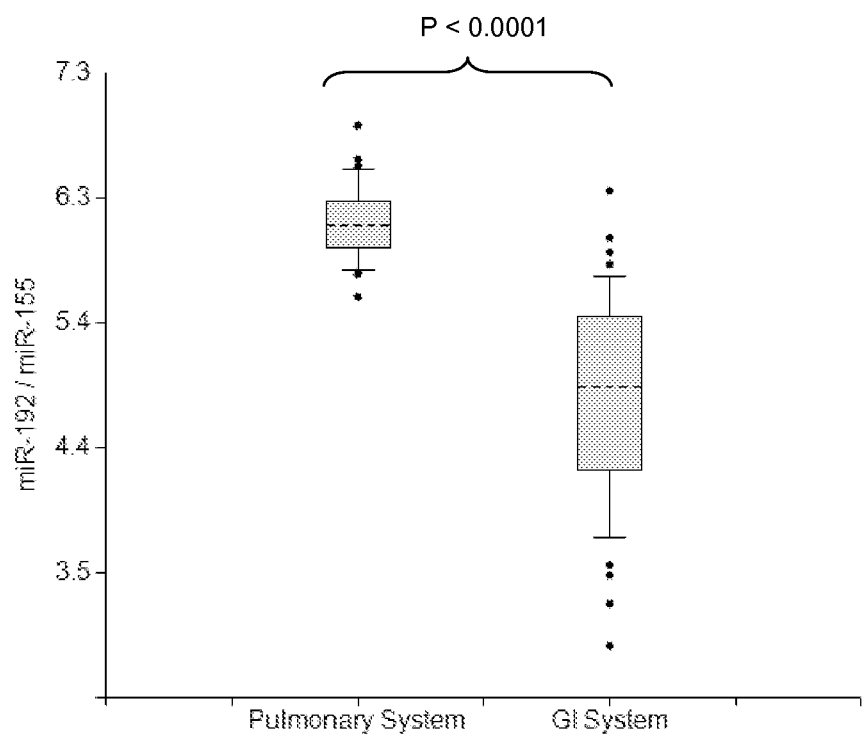
Figure 19O:
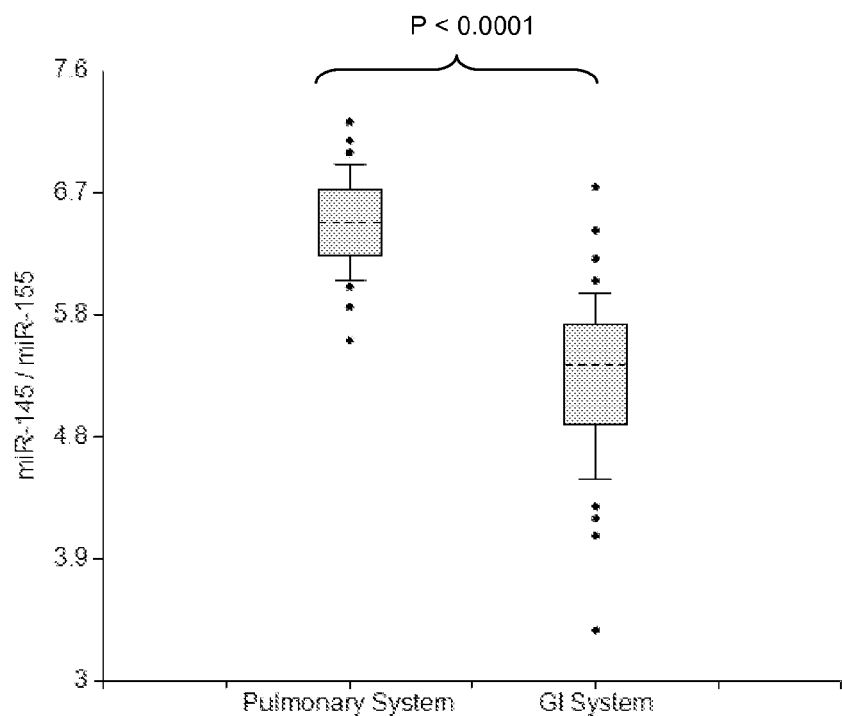
Figure 19P:
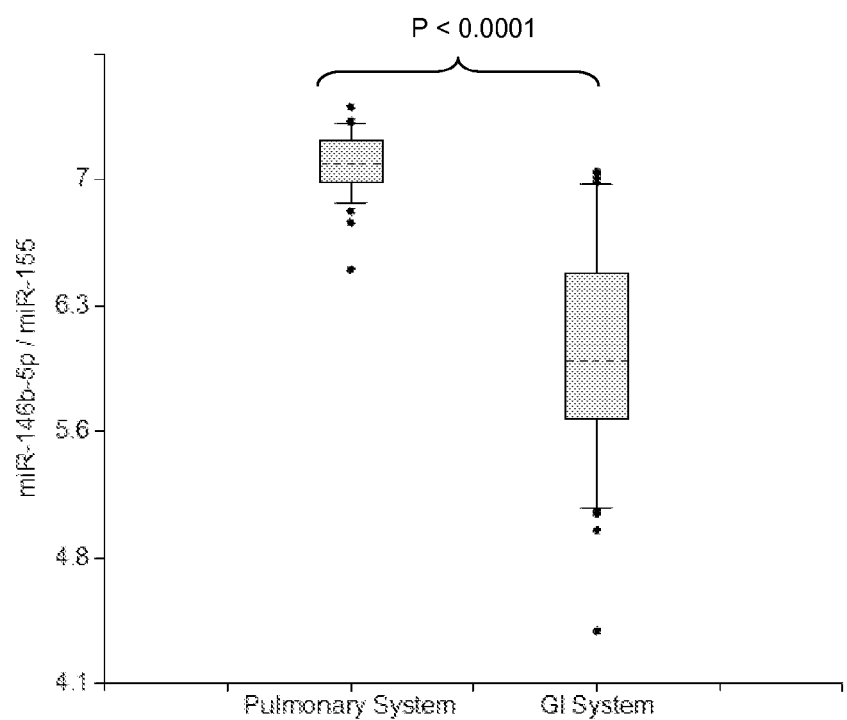
Figure 19Q:
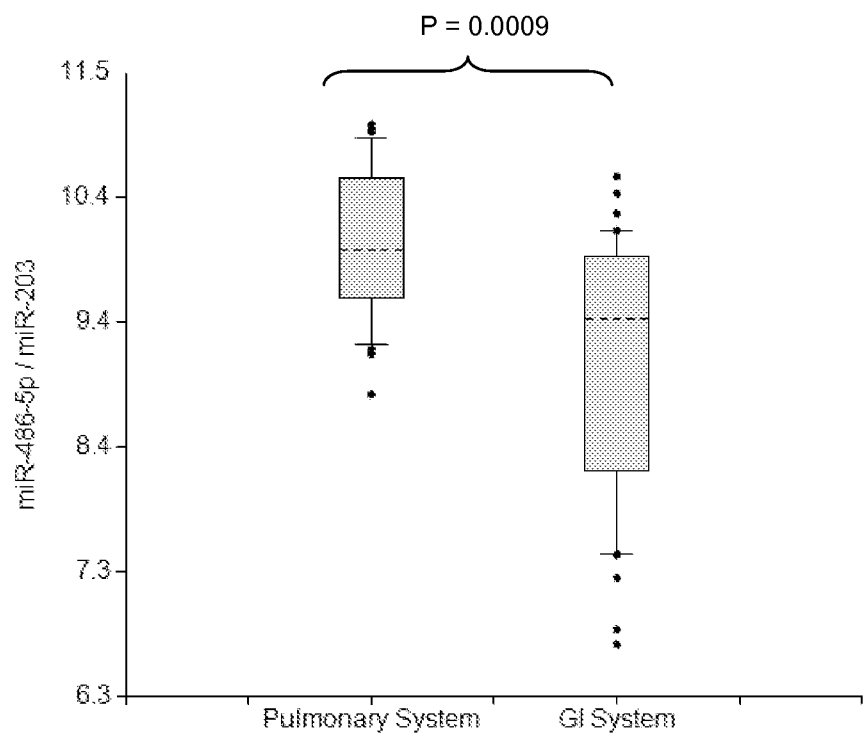
Figure 19R:
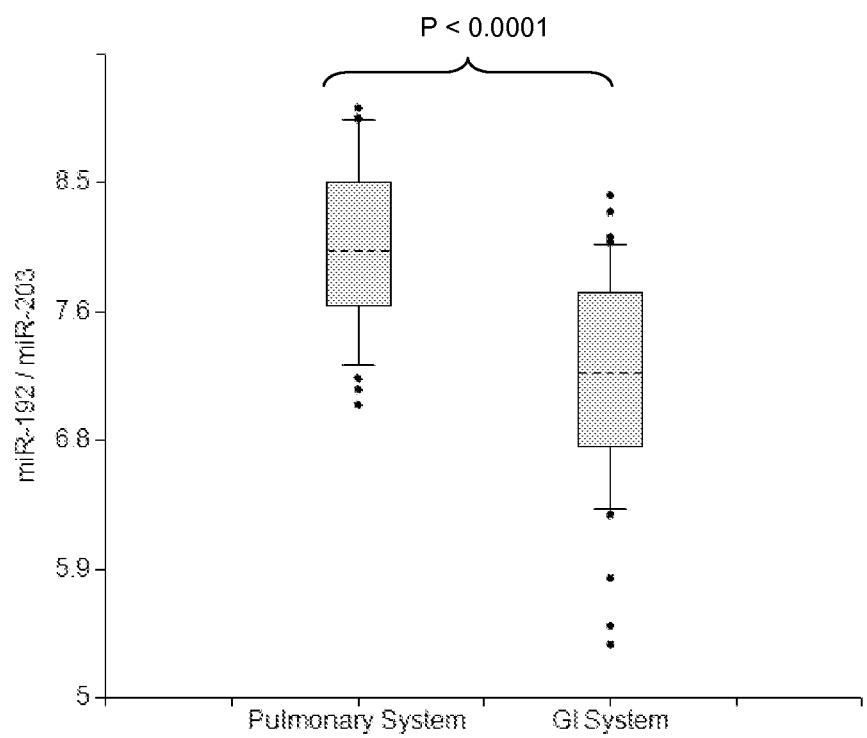
Figure 19S:
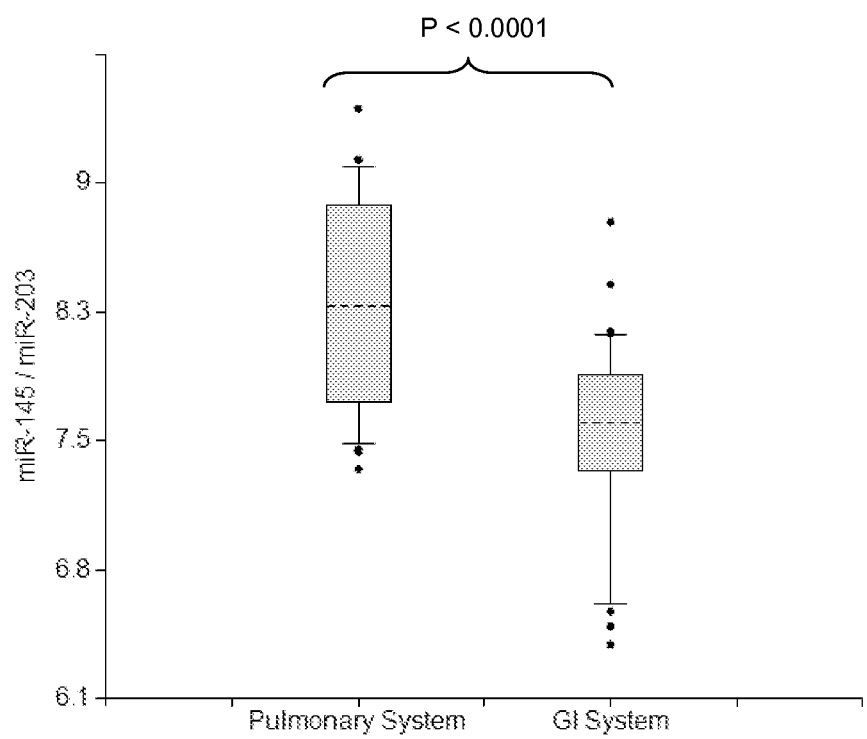
Figure 19T:
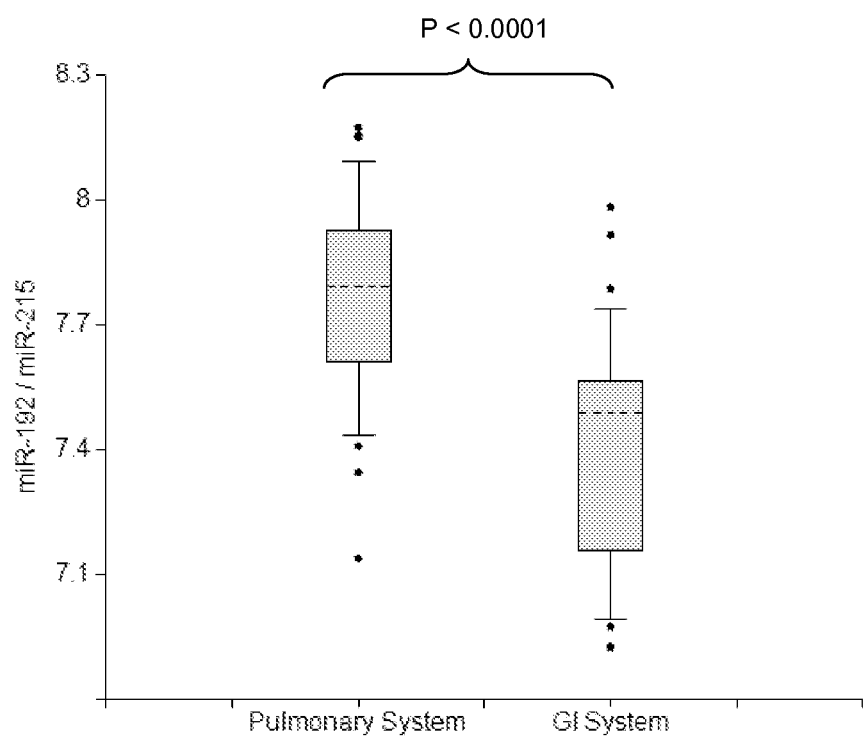
Figure 19U:
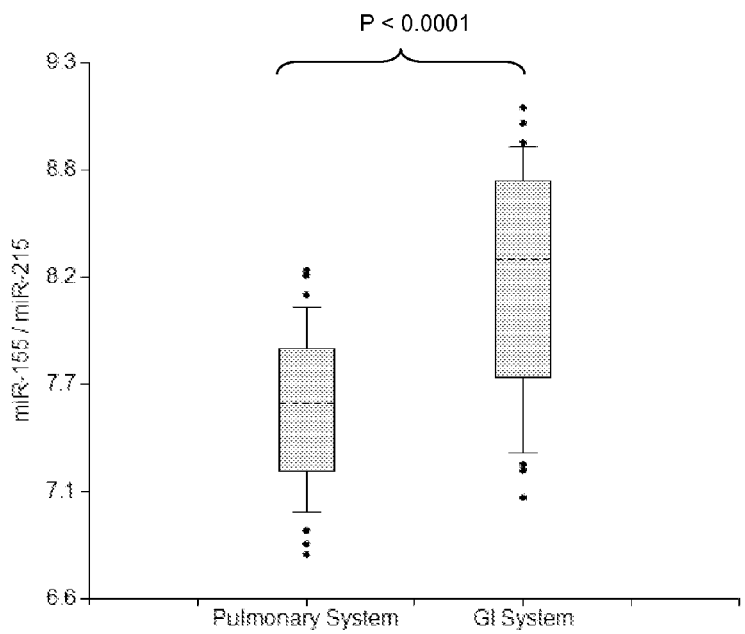

Example 6: Differentiation of Pathologies of Various Organ Systems miRNA preparations purified from the plasma samples obtained from patients described in Examples 4 and 5 were used in the study. The ability of various miRNA combinations to differentiate patients with diseases of the GI system (Crohn's disease and esophageal, gastric and colorectal cancers) from patients with diseases of the pulmonary system (asthma, pneumonia, COPD and NSCLC) was investigated. Lung-enriched miR-126, miR-146b-5p, miR-155, and miR-486-5p, and GI-enriched miR-145, miR-192, miR-203 and miR-215 were included in the study. Expression of some of these miRNA (Table 3) is known to be deregulated in pathologies of various organs. Additionally, miR-17-5p and mir-31, involved in pathological processes of various organs, as well as miR-30e-3p and miR-409-3p, which were used as normalizers in Experiments 4 and 5, were analyzed. RNA was isolated from two 200 µl aliquots of plasma samples by the Trizol-silica method according to an Asuragen procedure. Single target TaqMan® miRNA qRT-PCR assays (Applied Biosystems) were run using 2 µl plasma equivalents in triplicate in a reaction volume of 10 µl for final PCR. Concentrations of each miRNA were normalized per miR-30e-3p and miR-409-3p, as well as on each other, converted into Relative Quantity (RQ) of miRNA according the ABI protocol ($2^{-\Delta Ct}$), and miRNA profiles characteristic of patients with the diseases of the pulmonary and GI systems were compared. FIGS. 19A-U demonstrate that many miRNA pairs effectively distinguish patients with diseases of pulmonary and GI systems: miR-192/miR-126; miR-155/miR-126; miR-145/miR-126; miR-155/miR-30e-3p; miR-192/miR-30e-3p; miR-155/miR-409-3p; miR-486-5p/miR-17-5p; miR-155/miR-17-5p; miR-192/miR-17-5p; miR-146b-5p/miR-31; miR-155/miR-31; miR-192/miR-31; miR-486-5p/miR-155; miR-192/miR-155; miR-145/miR-155; miR-146b-5p/miR-155; 486-5p/miR-203; miR-192/miR-203; miR-145/miR-203; miR-192/miR-215; miR-155/miR-215.

Figure 19V:
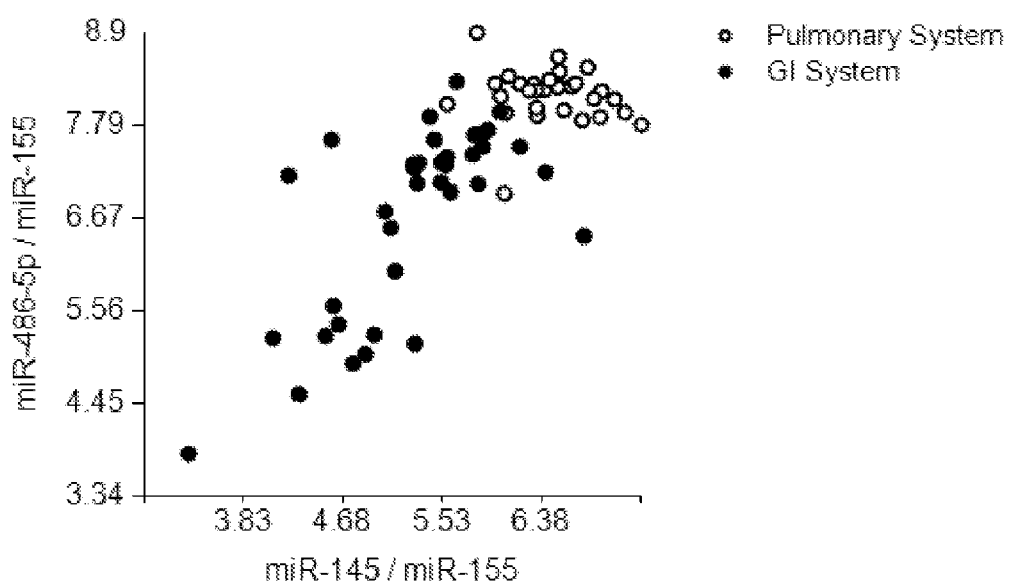
Figure 19W:
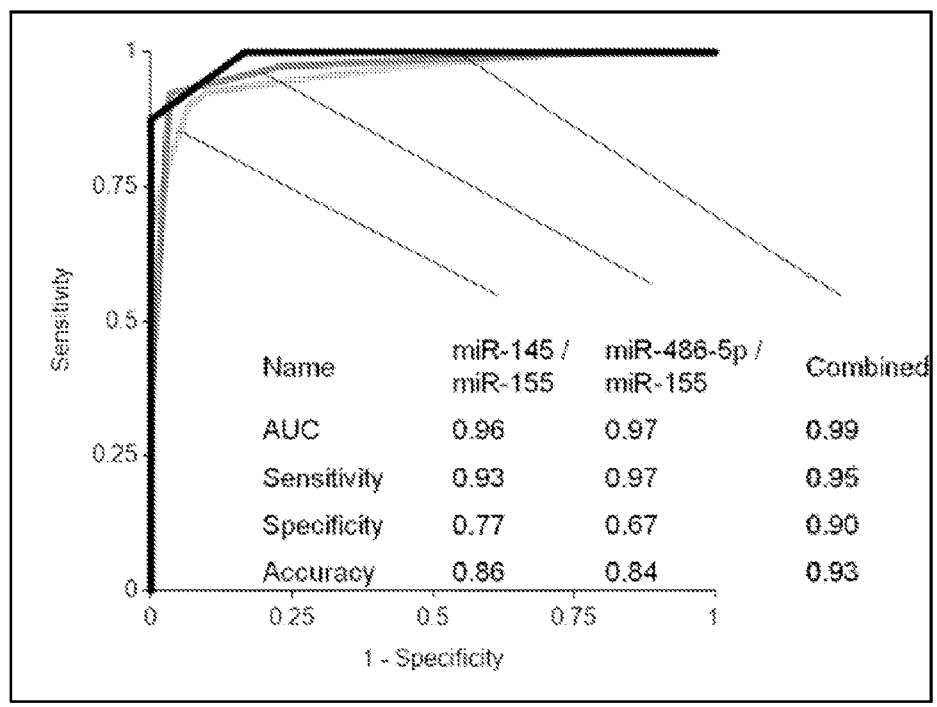

Combination of two miRNA pairs increases the test accuracy. FIGS. 19V and 19W provide an example with the combination of miR-145/miR-155 and miR-486-5p/miR-155 ratios, which distinguishes patients with all pathologies of the GT system from patients with pulmonary diseases with 95% sensitivity, 90% specificity, and 93% accuracy.

Example 7: Differentiation of Cancers from Inflammatory Diseases

The same plasma samples were used for RNA purification and the same miRNA were analyzed that were studied in the Example 6. In this study the ability of various miRNA combinations to differentiate patients with inflammatory diseases (asthma, pneumonia, COPD and Crohn's disease) from patients with various cancers (esophageal, gastric, colorectal and non-small cell lung cancers) was investigated. FIGS. 20A-F demonstrate that several miRNA pairs effectively distinguish patients with inflammatory diseases from patients with various cancers: miR-17-5p/miR-155; mir-192/miR-155; miR-215/miR-155; miR192/miR-30e; miR-146b-5p/miR-30e-3p; miR155/miR-30e-3p. There are less miRNA pairs differentiating inflammation diseases from cancers than miRNA pairs capable of differentiating diseases of the pulmonary system from diseases of the GI system. First, changes in expression of many miRNA are characteristic of both pathology types. Second, in many cases carcinogenesis is accompanied by relatively prominent inflammation.

Figure 20A:
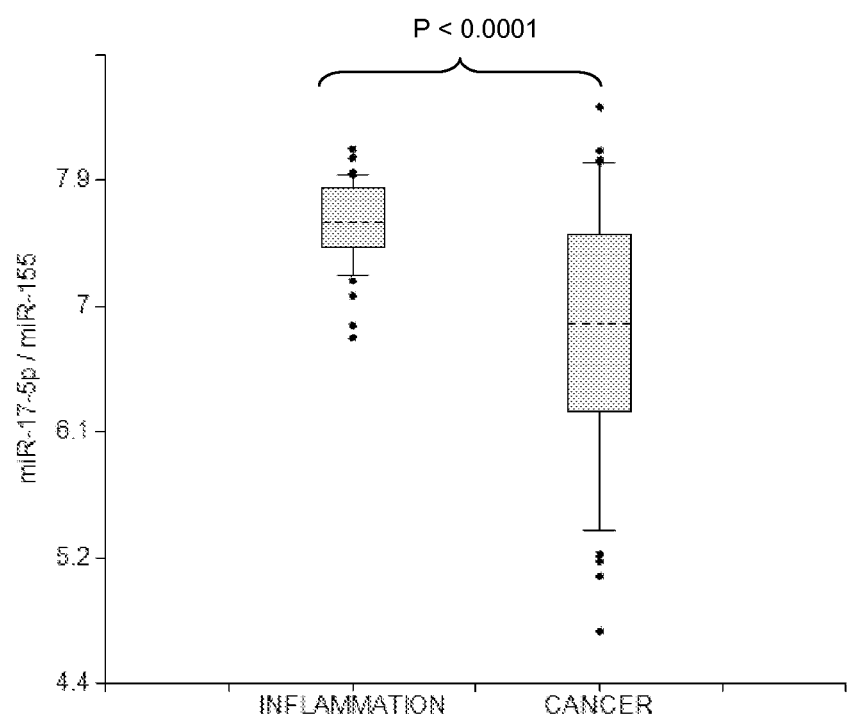
FIGS. 20A-H are graphs showing comparison of various miRNA concentration ratios in plasma of all patients with inflammatory diseases (asthma, pneumonia, COPD and Crohn's disease) versus cancer patients (esophageal, gastric, colorectal and non-small cell lung cancers). A-F: one biomarker/normalizer miRNA pair (A-miR-17-5p/miR-155; B-miR-192/miR-155; C-miR-215/miR-155; D-miR-192/miR-30e-3p; E-miR-155/miR-30e-3p; F-miR-146b-5p/miR-30e-3p. G: a graph showing comparison of the ratios miR-146b-5p/miR-155 and miR-146b-5p/miR-30e-3p in plasma of patients with all inflammatory diseases versus all cancers. H: Receiver-Operating Characteristic (ROC) curve analysis of differentiation between patients with cancers and inflammatory diseases using miRNA pairs presented on Fig. G. The areas under the ROC curve (AUC) are reported. Sensitivity, specificity and accuracy for each biomarker/normalizer pair are calculated for the "cutoff" point, which is the biomarker/normalizer ratio, at which a sample is equally likely to belong to the inflammatory disease or the cancer patient groups.
Figure 20B:
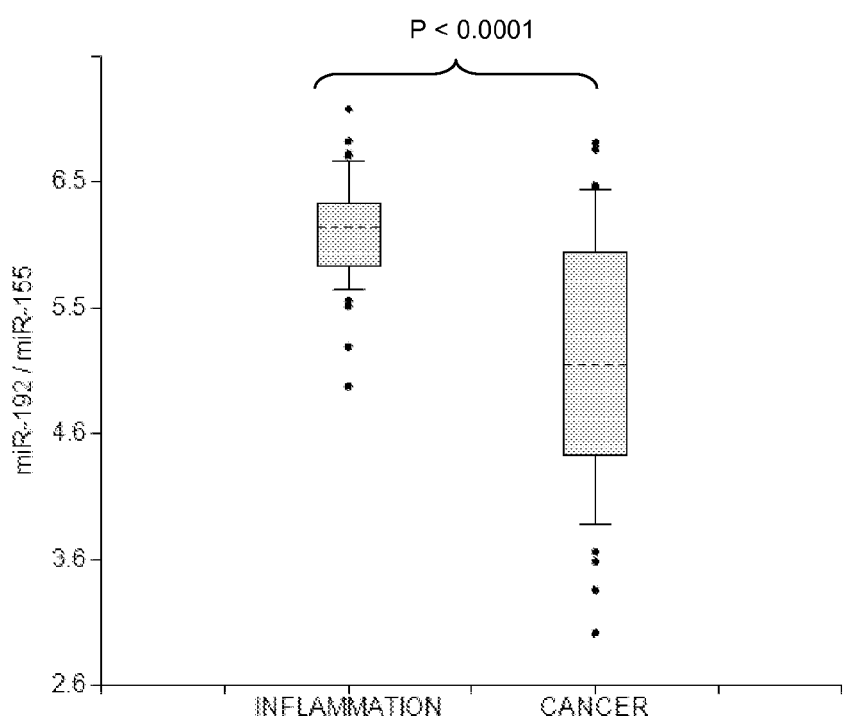
Figure 20C:
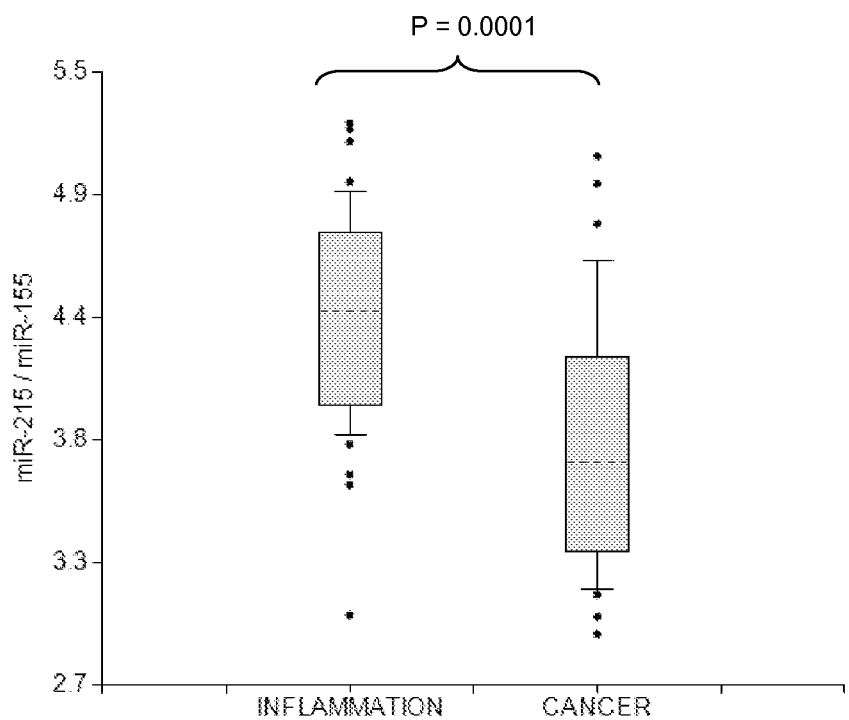
Figure 20D:
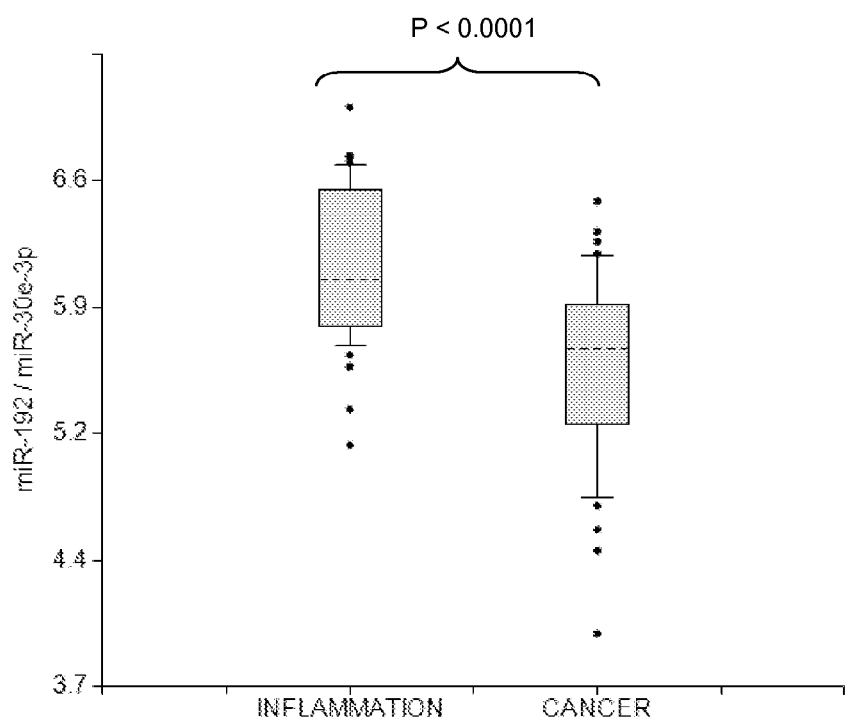
Figure 20E:
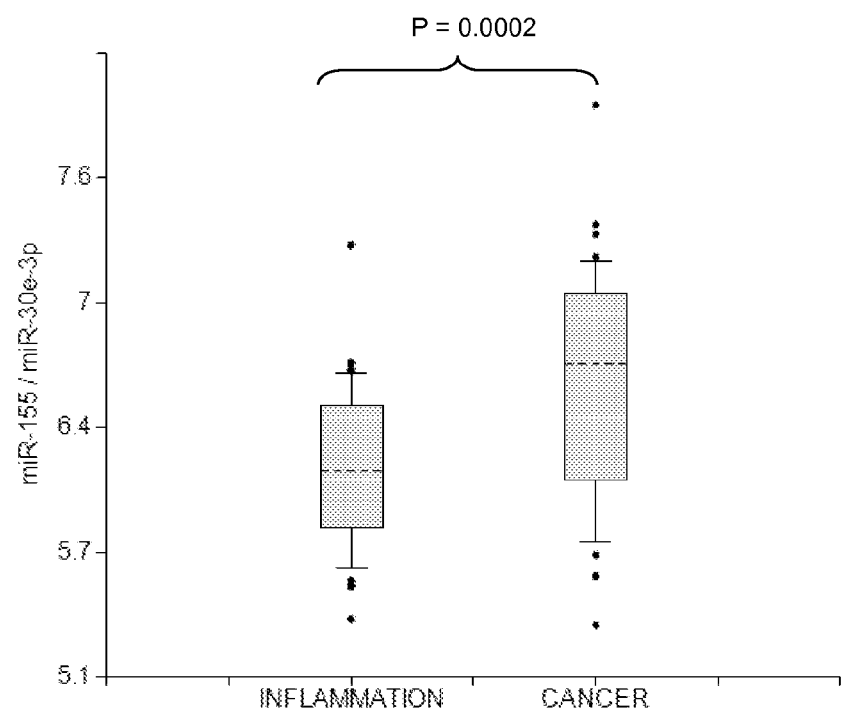
Figure 20F:
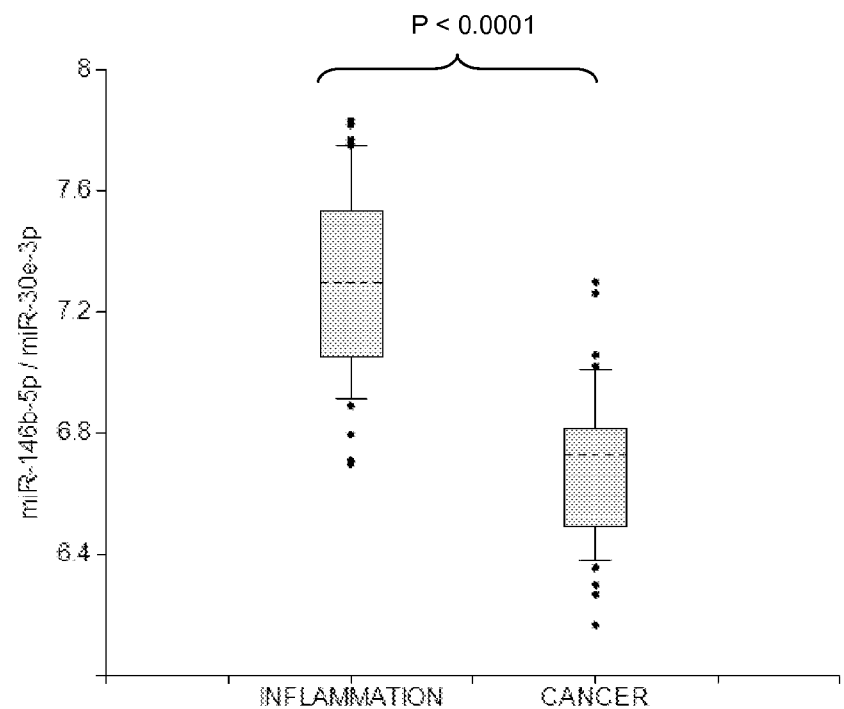
Figure 20G:
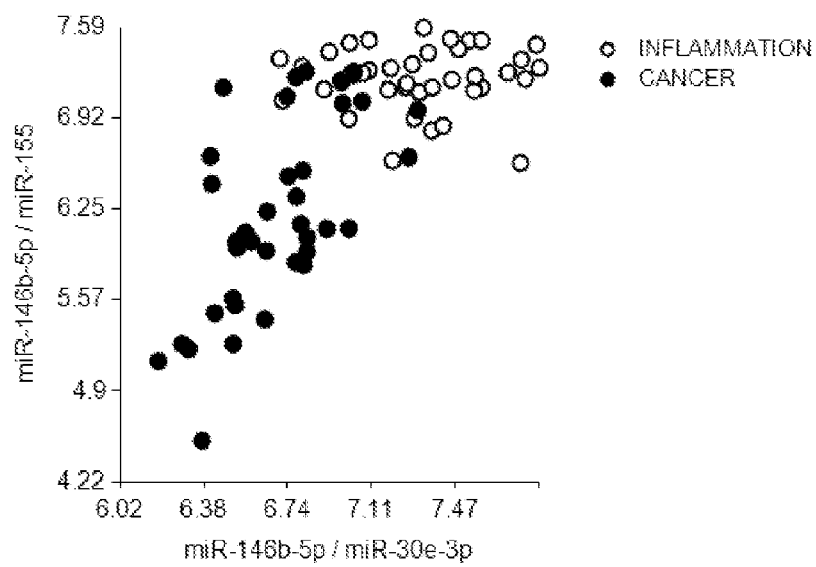
Figure 20H:
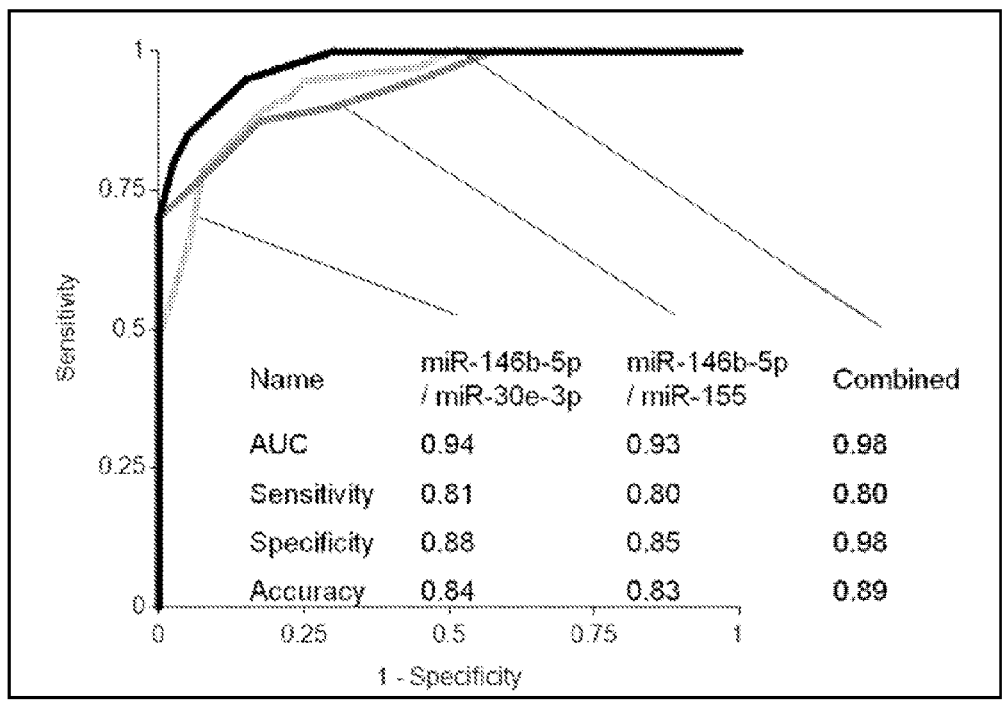

Combination of two miRNA pairs increases the test accuracy. FIGS. 20G and 20H provide an example with the combination of miR-146b-5p/miR-155 and miR-146b-5p/miR-30e-3p ratios, which distinguishes all patients with inflammatory diseases from cancer patients with 80% sensitivity, 98% specificity, and 89% accuracy.

Thus, the results of the experiments presented above support the main ideas of the present invention. The analysis of concentration of miRNA, enriched in a particular organ system or in an organ, in plasma differentiates: (i) organ system diseases from controls; (ii) pathologies of three organs of the GI system; (iii) diseases of the pulmonary and CI system; (iv) cancers and inflammatory diseases.

Example 8: A Method for Multiple miRNA Analysis and its Use for Biomarker Selection and Detection of an Organ System or Particular Organ with Pathological Changes Two different applications are used for the UST development (research stage) and its clinical usage (Screening Data Processing). Algorithms in both applications contain Training and Classification parts, but they are significantly different.

The Algorithm Used for Screening Test Development

In the following algorithm description and related figures, the term "Biomarker" defines a miRNA pair, Marker and Normalizer, used for pathology diagnosis and more generally for distinguishing various groups of subjects. The term "ROC" stands for Receiver-Operating Characteristic, the statistics used in Classification.

The proposed algorithm is based on the following simplified assumptions:
  For any biomarker or combinations of biomarkers, a limited number, e.g. of experiments are available;
  Response of any biomarker to a particular pathology can be explored independently and should not be linked to the "final" combination of biomarkers assigned to a particular D-s et;
  Algorithms should be probabilistic, which allows better result estimate.

Figure 21A:
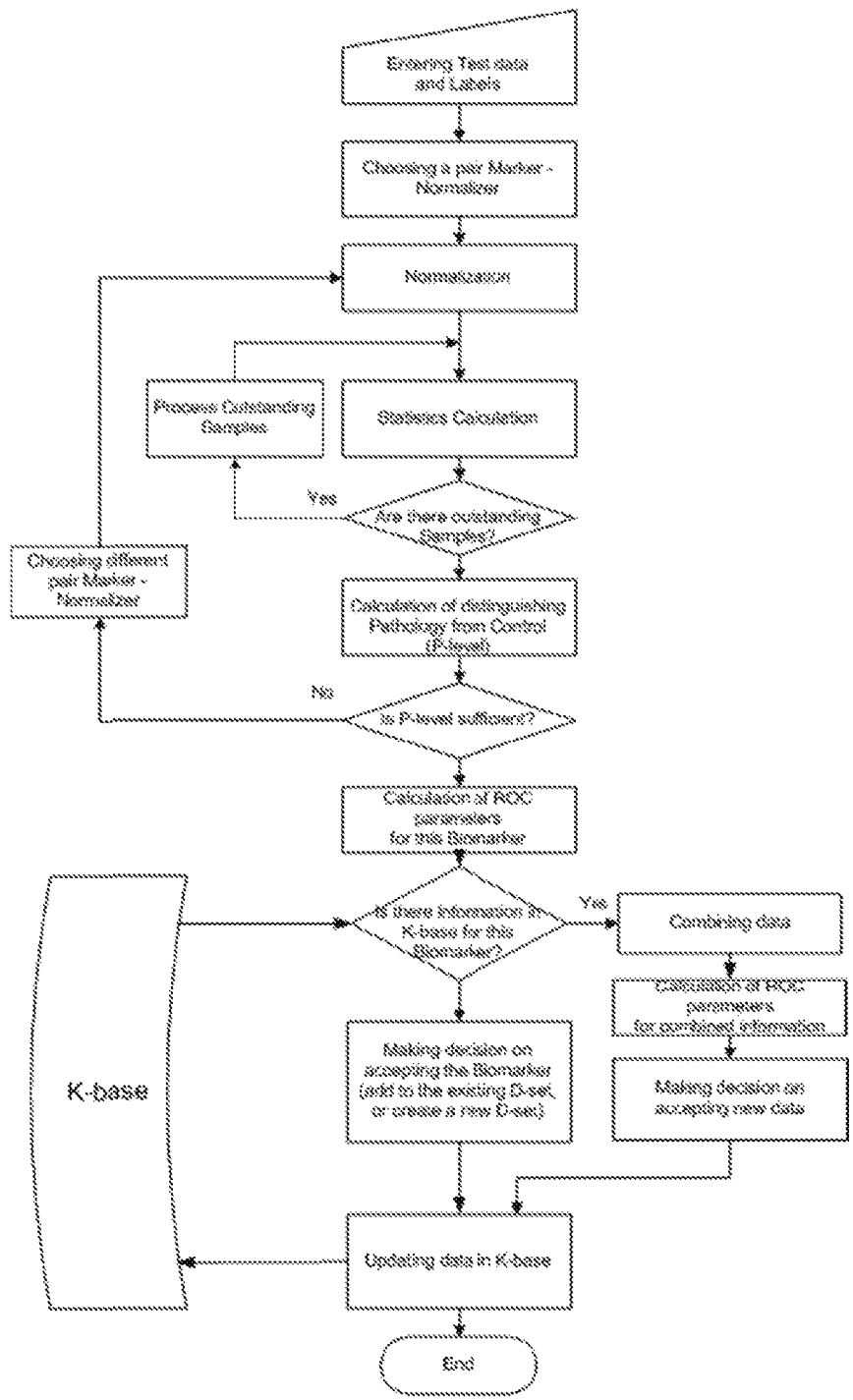
FIGS. 21A-B are flowcharts showing biomarker training (A) and classification (B) procedures for pathologies.
Figure 21:
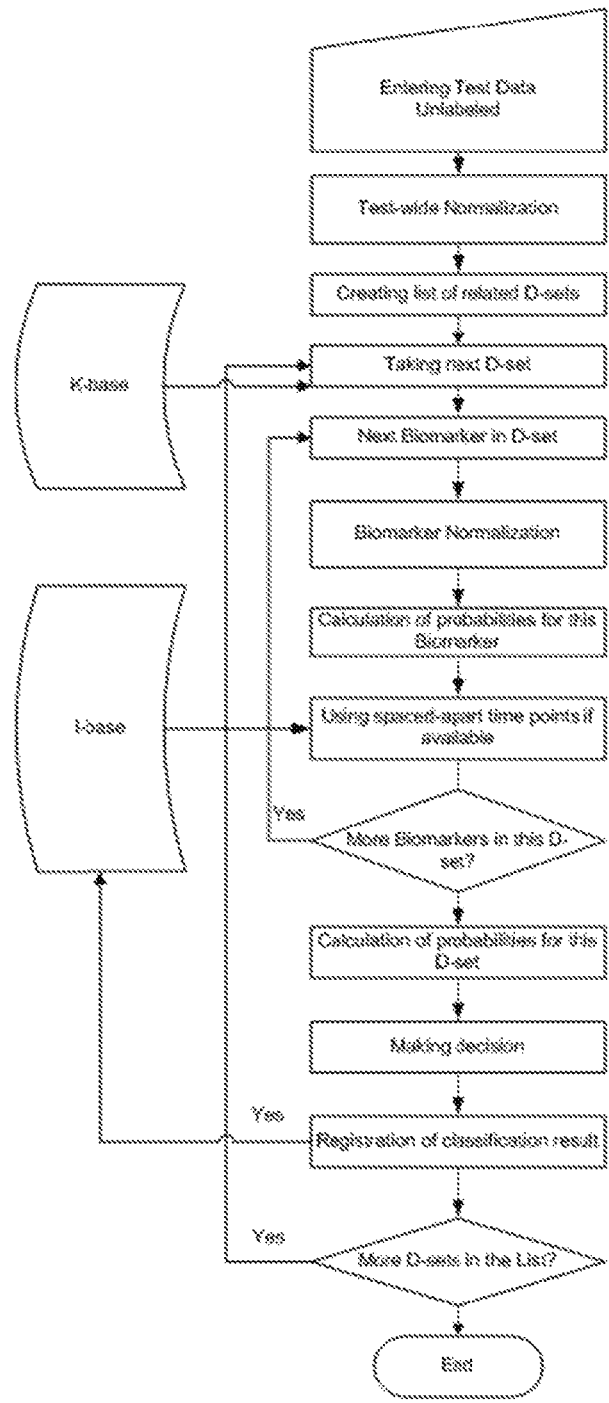

The first part of the algorithm is related to Training using Labeled data, for a pathology of a respective organ system, organ, tissue, or cell type. FIG. 21A outlines operations in this part of the algorithm.

This part assumes intensive dialog, practically on every step, with the person who performs experiments. The very first step always includes some manual operation—or typing sample values, or performing operations to import data—partially or completely—from some standard documents. The type of the document can be, but is not limited to, Excel spreadsheet, or text delimited file. All other steps can be performed automatically, with only manual confirmation like "Next", or can have some manual corrections. For example, on the Normalization stage one should provide the best type of Normalization, or make all processing for several types of it. Some samples can have values outside of certain statistically reasonable range. As a rule, this range is multiple of standard deviation, for example, but not limited to, two or three times standard deviation, depending on value distribution (how close is it to the Normal one, etc.), a decision can be made as to whether to exclude these samples from statistics, and so on. Statistical analysis includes calculation of P-level of Target—Control separation and ROC (Receiver-Operating Characteristic) curve parameters. The last step of the algorithm—making a decision to add the marker—can include parts (internal loop) of the Classification algorithm, described below. In this step, calculated parameters are applied to the Training set. The decision to use this marker is based on the level of Classification success. This decision can be revisited at the Classification stage.

Classification part of the algorithm is shown in FIG. 21B.

The second part of the algorithm, Classification, is used mostly for Validation data processing. Also, part of it, internal loop, can be used in the last step of Training algorithm. In general, at the research stage, these parts—Training Procedure and Classification procedure are used in iterative manner, i.e., are repeated several times, to reach clinically acceptable testing accuracy.

The Classification procedure contains two nested iteration loops, through D-sets (outer loop) and Biomarkers in every D-set (internal loop).
Iteration steps through internal Biomarker loop include:
Step 1. Normalization of D-Set Biomarkers Normalization can include one general Screening test normalization (one per test), based on spiked miRNA, and normalization specific for a particular D-set—type b), c) or d) (see the Detailed Description of the Invention section, above), or more than one of them. The version of specific normalization used for each Biomarker is included into K-base as a description of the D-set. Thus, if one Biomarker is a member of more than one D-sets, it should be normalized accordingly, in every set.
Steps 2. Biomarker Probability Calculation Biomarker concentration for a particular person has to be mapped to two probabilities: of having pathology or not having it. The mapping operation uses two probability functions, based on processing Biomarker data of two populations: with pathology and without it (Control). Each probability function is a linearly approximated curve, which goes from 1 to 0 for Control population, and from 0 to 1 for population with the Target pathology. Description of every curve is stored, retrieved and updated in K-base. Step 3. Using history (time-spaced points)

Significant parts of Target and Control curves are overlapping. If an actual value is within this overlapping area, it is necessary to make a decision how to interpret the result. This is based on, but not limited to, comparison of probabilities of having the pathology and being free of it; analyzing existing Biomarker data for the same person if such data have been taken and stored in I-base.
This is the end of Biomarker iterations.
Iteration Steps for the D-Set Loop (Outer D-Steps)
Step 1. Target Probability Calculation.

In most cases, Biomarkers, which are included in a particular D-set, are statistically independent, i.e. probabilities of the particular concentration value to belong to the Control or Target Group do not significantly depend on the value(s) of other Biomarkers in the D-set. In this case, the weighted sum of probabilities for Biomarkers, comprising this D-set, has been calculated. By default, all weights are equal, e.g., for three biomarkers each weight is ⅓. However, individual weights can be stored in K-base, for every biomarker within this D-set. They can be based on some Biomarker ROC parameters, like sensitivity, specificity or AUC (area under curve). The sum of weights for all biomarkers in any D-set should be 1.

In the case of significant interdependency of some Biomarkers in a particular D-set, K-base contains a description of multidimensional probability surface for this group, where dimension equals to the number of dependent Biomarkers in the group. Using this description, each combination of Biomarker values is mapped to two probabilities. If the D-set contains also independent Biomarkers, probabilities of the D-set are calculated using weighted sum of probabilities for the group(s) of dependent Biomarkers, and individual independent Biomarkers.
D-Step 2. Making a Decision.

As a rule, the result should be presented as POSITIVE or NEGATIVE towards Target pathology. In special cases, the result UNDETERMINED with percentage attached can be also used. Decision making parameters must be previously defined and stored in K-base. They can be Screening-wide, or target (organ system/organ/tissue) specific and applied to probabilities, calculated in the previous step (D-Step 1). These parameters can be applied to each of two probabilities (PP–pathology probability, PC–control probability), or, more common, to the difference of two. Examples: (i) difference parameter is 0, i.e. PP>PC means POSITIVE, PP<PC means NEGATIVE; (ii) PP–PC 0.25 is NEGATIVE, PP–PC≥0.35 POSITIVE and UNDETERMINED in between; (iii) PP>0.6 is POSITIVE, PC>0.7 is NEGATIVE, everything else is UDETERMINED.
D-Step 3. Registration The results are displayed and saved to I-base, together with identification data, such as test#, date/time stamps, patient identification, etc.
The Algorithm for Clinical Trial and Usage When research stage is complete, K-base contains all components of UST and its versions: biomarkers, D-sets, and constants for Classification. In the next stage larger clinical studies are conducted using these tools.

Based on obtained result, verification and evaluation of the biomarkers and D-sets as well as some modifications of the algorithm or/and constants are performed. For example, different classification algorithm, like Multinomial Logistic Regression (Hosmer D W, Lemeshow S. Applied logistic regression. Wiley, 2000; Allison P D. Logistic regression using the SAS system: theory and application. Wiley, 2008) or Support Vector Machines (Cristianini N, Shawe-Taylor J. An Introduction to Support Vector Machines and Other Kernel-based Learning Methods. Cambridge Press, 2000; Abe S. Support Vector Machines for Pattern Classification. Springer, 2010) can be used. K-base gets some changes accordingly. After such changes, clinical trials will be performed.

In the clinical usage, Classification algorithm uses constants and parameters from K-base, and actual test data are stored to I-base. K-base remains unchanged until next revision, i.e. arrival of new research verified data.

In general, any of the algorithms, functional operations, or subject matter described in this specification can be implemented in digital electronic circuitry, or in computer software, firmware, or hardware, including the structures disclosed in this specification and their structural equivalents, or in combinations of one or more of them. For example, in some embodiments, one or more data processing apparatuses can be part of a module that can be installed in a computer and configured to perform algorithms to select and/or detect biomarkers for pathologies as well as perform algorithms for classification of one or more pathologies. In some embodiments, the one or more data processing apparatuses can be part of a module that can be installed in a computer and configured to perform the Classification algorithm set forth in Example 8 including the nested iteration loops (e.g., Biomarker loop and the D-set loop). For example, the one or more data processing apparatuses can be configured to perform one or more of the operations shown in FIGS. 21A and 21B. In some embodiments, the algorithms can be implemented as one or more computer program products, i.e., one or more modules of computer program instructions encoded on a computer readable medium for execution by, or to control the operation of, data processing apparatus.

The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment or a combination of one or more of them. The apparatus includes code for creating, verifying, and/or modifying the K-base or I-base tables. In some embodiments, the K-base and 1-base can be maintained on a database management system such as, SQL server, Oracle, MySQL, among others.

A computer program (also known as a program, software, software application, script, or code) can be written in any form of programming language, including compiled or interpreted languages, and it can be deployed in any commonly used deployment form, presenting a unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes described in this specification can be performed by one or more programmable processors executing one or more computer programs to perform functions by operating on input data and generating output. Processors suitable for the execution of a computer program include, by way of example, both general and special purpose microprocessors, and any one or more processors of any kind of digital computer.

In some embodiments, a user manually enters, through the one or more devices, data obtained from screening tests in the research stage or clinical stage. In some embodiments, a user can observe or receive, from one or more devices, output data such as, but not limited to, biomarker classification data and data relating to detections of biomarker concentration changes. Other kinds of devices can be used to provide for interaction with a user as well; for example, feedback provided to the user can be any form of sensory feedback, e.g., visual feedback or auditory feedback; and input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. For example, in some embodiments, the system can include a graphical user interface/Web interface that allows a user to enter and/or inspect data in the K-base and I-base. Alternatively, or in addition, the interface can allow the user to control, modify, or manipulate an algorithm's execution. In some embodiments, the system can retrieve or output data from other systems and/or components coupled to the network.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for selecting subjects for administering one or more disease-specific diagnostic tests to identify a specific pathology in the gastrointestinal (GI) system and/or the respiratory system and/or the nervous system, which method comprises:
   a. for each of the gastrointestinal (GI) system, the respiratory system and the nervous system, measuring the level of one or more biomarker miRNAs in a bodily fluid sample collected from a subject of interest, wherein the bodily fluid is selected from the group consisting of blood plasma, serum, urine, and saliva;
   b. for each of the biomarker miRNAs measured in step (a), measuring the level of a normalizer miRNA in the same bodily fluid sample collected from the subject of interest;
   c. calculating the ratio of the level of the biomarker miRNA measured in step (a) to the level of the normalizer miRNA measured in step (b) for each of said organ systems;
   d. comparing the ratio calculated in step (c) with a corresponding control ratio for each of said organ systems, wherein the corresponding control ratio was determined in a corresponding bodily fluid collected from the subject of interest in the past, or from a different subject or a population of subjects without pathology of the respective organ systems, and
   e. determining for at least one biomarker miRNA measured in step (a) that the ratio calculated in step (c) is greater in the bodily fluid sample collected from the subject of interest than the corresponding control ratio, and administering one or more disease-specific diagnostic tests to the subject of interest,
      wherein the biomarker miRNA for the gastrointestinal (GI) system measured in step (a) is selected from the group consisting of miR-31, miR-130b, miR-136, miR-141, miR-143, miR-145, miR-148a, miR-192, miR-203, miR-215, miR-375, miR-376c, miR-429, miR-455-5p, miR-650, miR-106a, miR-106b, miR-205, miR-210, miR-221, miR-7, miR-26a, miR-26b, miR-26c, miR-124b, miR-182, miR-188, miR-197, miR-194, miR-200a, miR-200b, miR-200c, miR-321, and the normalizer miRNA measured in step (b) is selected from the group consisting of miR-30e-3p, miR-145, and miR-148a;

the biomarker miRNA for the respiratory system measured in step (a) is selected from the group consisting of miR-486-5p, miR-34b, miR-192, miR-135b, miR-146, miR-146b-5p, miR-155, miR-199b-5p, miR-200c, miR-205, miR-223, miR-302b, and miR-375, and the normalizer miRNA measured in step (b) is selected from the group consisting of miR-142-5p, miR-146b-5p, miR-155, miR-223, and miR-409-3p; and the biomarker miRNA for the nervous system measured in step (a) is selected from the group consisting of miR-128, miR-132, miR-874, miR-134, miR-323-3p, miR-382, miR-Let-7a, miR-7, miR-9, miR-124a, miR-125a, miR-125b, miR-135a, miR-137, miR-138, miR-181a, miR-181c, miR-182, miR-184, miR-211, miR-212, miR-213, miR-218, miR-219, miR-222, miR-338-5p, miR-369, miR-381, miR-409-3p, miR-425, miR-433-5p, miR-485-5p, miR-491-5p, miR-539, miR-541, miR-543, miR-656, miR-935, miR-939, and miR-9*, and the normalizer miRNAs measured in step (b) is selected from the group consisting of miR-9, miR-181a, miR-491-5p, miR-141, miR-127, miR-370, and miR-433-5p.

2. The method of claim 1, wherein
the biomarker miRNA for the gastrointestinal (GI) system measured in step (a) is selected from the group consisting of miR-215, miR-203, miR-192, and miR-194, and the normalizer miRNA measured in step (b) is selected from the group consisting of miR-30e-3p, miR-145 and miR-148a;

the biomarker miRNA for the respiratory system measured in step (a) is selected from the group consisting of miR-486-5p, miR-34b, or miR-192, and the normalizer miRNA measured in step (b) is selected from the group consisting of miR-142-5p, miR-146b-5p, miR-155, miR-223, and miR-409-3p; and the biomarker miRNA for the nervous system measured in step (a) is selected from the group consisting of miR-128, miR-132, miR-874, miR-134, miR-323-3p, and miR-382, and the normalizer miRNA measured in step (b) is selected from the group consisting of miR-9, miR-181a, miR-491-5p, miR-141, miR-127, and miR-370.

3. The method of claim 1, further comprising determining for at least one of said organ systems whether the pathology is a cancer or an inflammation, which method comprises:

f. calculating the ratio of the level of one or more biomarker miRNAs to the level of one or more normalizer miRNAs in a bodily fluid sample collected from the subject of interest, wherein the bodily fluid is selected from the group consisting of blood plasma, serum, urine, and saliva;

g. comparing the ratio(s) calculated in step (f) with corresponding predetermined ranges of ratios characteristic of cancer and inflammation, and h. (i) determining that the pathology is a cancer when the ratio(s) calculated in step (f) is within the predetermined range characteristic of cancer, or (ii) determining that the pathology is an inflammation when the ratio(s) calculated in step (f) is within the predetermined range characteristic of inflammation, wherein (i) said organ system is the respiratory system and the biomarker/normalizer miRNA pair(s) is selected from the group consisting of miR-34b/miR-155, miR-486b-5p/miR-146b-5p, and miR-192/miR-146b-5p, or (ii) said organ system is the gastrointestinal (GI) system and the biomarker/normalizer miRNA pair(s) is selected from the group consisting of miR-215/miR-30e-3p, miR-215/miR-194, miR-215/miR-203, miR-203/miR-148a, miR-194/miR-148a, miR-194/miR-192, miR-192/miR-203, or (iii) said organ system is the respiratory system or the gastrointestinal (GI) system and the biomarker/normalizer miRNA pair(s) is selected from the group consisting of miR-17-5p/miR-155, miR-192/miR-155, miR-215/miR-155, miR-146b-5p/miR-155, miR-192/miR-30e-3p, miR-155/miR-30e-3p, and miR-146b-5p/miR-30e-3p.

4. The method of claim 1, wherein the corresponding control ratio is the ratio of the levels of the same biomarker and normalizer mRNAs in a similarly processed bodily fluid sample from the same subject collected in the past.

5. The method of claim 1, which method comprises a step of collecting the bodily fluid sample from the subject of interest prior to step (a).

6. The method of claim 1, wherein the level of the biomarker and normalizer mRNAs is determined using RT-PCR.

7. The method of claim 1, wherein, prior to measuring the biomarker and normalizer miRNA levels, miRNAs are purified from the bodily fluid sample.

8. The method of claim 1, further comprising the step of reducing or eliminating degradation of miRNA in the bodily fluid sample.

9. The method of claim 1, wherein the bodily fluid is blood plasma.

10. The method of claim 1, further comprising administering a treatment to the subject of interest.

11. The method of claim 1, wherein
step (c) involves:

(1) calculating, using a suitably programmed processor, the ratio of the level of the biomarker miRNA measured in step (a) to the level of the normalizer miRNA measured in step (b) for each of the gastrointestinal (GI) system, the respiratory system and the nervous system;

(2) calculating, by the processor and based on the ratio determined in step (1), a first probability based on a first predefined probability distribution curve, wherein the first predefined probability distribution curve corresponds to pathologies of each of said organ systems;

(3) calculating, by the processor and based on the ratio determined in step (1), a second probability based on a second predefined probability distribution curve, wherein the second predefined probability distribution curve corresponds to a control for each of said organ systems;

step (d) involves determining, by the processor, a difference between the first probability calculated in step (c)(2) and the second probability calculated in step (c)(3) for each of said organ systems, and step (e) involves determining that the difference between the first probability and the second probability calculated in step (c) is positive.

* * * * *